(12) United States Patent
Winslow et al.

(10) Patent No.: US 10,801,021 B2
(45) Date of Patent: Oct. 13, 2020

(54) COMPOSITIONS AND METHODS FOR MULTIPLEXED QUANTITATIVE ANALYSIS OF CELL LINEAGES

(71) Applicant: The Board of Trustees of the Leland Stanford Junior University, Stanford, CA (US)

(72) Inventors: Monte M. Winslow, Stanford, CA (US); Dmitri Petrov, Stanford, CA (US); Ian P. Winters, Stanford, CA (US); Christopher McFarland, Stanford, CA (US); Zoe N. Rogers, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/940,818

(22) Filed: Mar. 29, 2018

(65) Prior Publication Data
US 2018/0282720 A1 Oct. 4, 2018

Related U.S. Application Data

(60) Provisional application No. 62/481,067, filed on Apr. 3, 2017.

(51) Int. Cl.
*C12N 15/10* (2006.01)
*C12Q 1/6886* (2018.01)

(52) U.S. Cl.
CPC ........ *C12N 15/1065* (2013.01); *C12Q 1/6886* (2013.01)

(58) Field of Classification Search
CPC .............................. C12N 15/10; C12Q 1/6886
See application file for complete search history.

(56) References Cited

U.S. PATENT DOCUMENTS

| 7,238,854 B2 | 7/2007 | Yadav et al. |
| 2015/0031556 A1 | 1/2015 | Barrett et al. |

FOREIGN PATENT DOCUMENTS

| WO | WO2000/05393 | 2/2000 |
| WO | 2012/083069 A2 | 6/2012 |
| WO | 2016040594 A1 | 3/2016 |
| WO | 2016049024 A2 | 3/2016 |
| WO | WO2018/031864 | 2/2018 |
| WO | WO2018/187156 | 10/2018 |

OTHER PUBLICATIONS

Perdigoto et al., "Distinct Levels of Notch Activity for Commitment and Terminal Differentiation of Stem Cells in the Adult Fly Intestine", Development, Sep. 28, 2011, pp. 4585-4595, 138, The Company of Biologists Ltd., Cambridge, United Kingdom.
Bhang et al., "Studying clonal dynamics in response to cancer therapy using high-complexity barcoding", Nature Medicine, May 2015, pp. 440-452, vol. 21, No. 5, Macmillan Publishers Limited, Basingstoke, United Kingdom.
Caswell et al., "Obligate Progression Precedes Lung Adenocarcinoma Dissemination", Cancer Discovery, Jul. 2014, pp. 781-789, vol. 4, Issue 7, American Association for Cancer Research, Philadelphia, PA.
Chuang et al., "Molecular definition of a metastatic lung cancer state reveals a targetable CD109—Janus kinase—Stat axis", Nature Medicine, Feb. 13, 2017, pp. 291-300, 23, Macmillan Publishers Limited, Basingstoke, United Kingdom.
Cornils et al., "Multiplexing clonality: combining RGB marking and genetic barcoding", Nucleic Acids Research, Apr. 1, 2014, pp. 1-10, vol. 42, No. 7, e56, Oxford University Press, Oxford, United Kingdom.
Lu et al., "Tracking single hematopoietic stem cells in vivo using high-throughput sequencing in conjunction with viral genetic barcoding", Nat Biotechnol., Oct. 2, 2011, pp. 928-933, 29(10), Macmillan Publishers Limited, Basingstoke, United Kingdom.
Nguyen et al., "Barcoding reveals complex clonal dynamics of de novo transformed human mammary cells", Nature, Dec. 10, 2015, pp. 267-283, vol. 528, Macmillan Publishers Limited, Basingstoke, United Kingdom.
Sun et al., "Clonal dynamics of native haematopoiesis", Nature, Oct. 16, 2014, pp. 322-327, 514, vol. 528, Macmillan Publishers Limited, Basingstoke, United Kingdom.
Winslow et al., "Suppression of lung adenocarcinoma progression by Nkx2-1", Nature, May 5, 2011, pp. 101-104 and Supp Info 1-13, vol. 473, Macmillan Publishers Limited, Basingstoke, United Kingdom.
Mazumdar et al., "Clonal dynamics following p53 loss of heterozygosity in Kras-driven cancers", Sep. 2, 2016, Nature Communications, 13 pages.
Nolan-Stevaux et al., "Measurement of Cancer Cell Growth Heterogeneity through Lentiviral Barcoding Identifies Clonal Dominance as a Characteristic of In Vivo Tumor Engraftment", Jun. 2013, PLoS One, vol. 8, Issue 6, 11 pages.

(Continued)

*Primary Examiner* — Antonio Galisteo Gonzalez
(74) *Attorney, Agent, or Firm* — Kyle A. Gurley; Bozicevic, Field & Francis LLP

(57) ABSTRACT

Compositions and methods are provided for measuring population size for a plurality of clonal cell populations in the same individual, e.g., for measuring tumor size for a plurality of clonally independent tumors within the same individual. A subject method can include: (a) contacting an individual with a plurality of cell markers that are heritable and distinguishable from one another, to generate a plurality of distinguishable lineages of heritably marked cells; (b) after sufficient time has passed for the heritably marked cells to undergo at least one round of division, detecting and measuring quantities of at least two of the plurality of cell markers present in the contacted tissue, thereby generating a set of measured values; and (c) using the set of measured values to calculate the number of heritably marked cells that are present (e.g., for at least two of the distinguishable lineages of heritably marked cells).

24 Claims, 48 Drawing Sheets
(45 of 48 Drawing Sheet(s) Filed in Color)
Specification includes a Sequence Listing.

(56) References Cited

OTHER PUBLICATIONS

Seibler et al., "Double-Reciprocal Crossover Mediated by FLP-Recombinase: A Concept and an Assay", 1997, Biochemistry, vol. 36, No. 7, pp. 1740-1747.
Zanatta et al., "Genetic barcode sequencing for screening altered population dynamics of hematopoietic stem cells transduced with lentivirus", 2014, The American Society of Gene & Cell Therapy, 11 pages.
Barretina, J. et al. The Cancer Cell Line Encyclopedia enables predictive modelling of anticancer drug sensitivity. Nature 483, 603-607, doi:10.1038/nature11003 (2012).
Bollard, J. et al. Palbociclib (PD-0332991), a selective CDK4/6 inhibitor, restricts tumour growth in preclinical models of hepatocellular carcinoma. Gut 66, 1286-1296, doi:10.1136/gutjnl-2016-312268 (2017).
Chen, Z. et al. A murine lung cancer co-clinical trial identifies genetic modifiers of therapeutic response. Nature 483, 613-617, doi:10.1038/nature10937 (2012).
Cheng, D. T. et al. Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. J Mol Diagn 17, 251-264, doi:10.1016/j.jmoldx.2014.12.006 (2015).
Chiou, S. H. et al. Pancreatic cancer modeling using retrograde viral vector delivery and in vivo CRISPR/Cas9-mediated somatic genome editing. Genes Dev 29, 15761585, doi:10.1101/gad.264861.115 (2015).
Gao, H. et al. High-throughput screening using patient-derived tumor xenografts to predict clinical trial drug response. Nature Med 21(11), 1318-25 (2015).
Garnett, M. J. et al. Systematic identification of genomic markers of drug sensitivity in cancer cells. Nature 483, 570-575, doi:10.1038/nature11005 (2012).
Haibe-Kains, B. et al. Inconsistency in large pharmacogenomic studies. Nature 504, 389-393, doi:10.1038/nature12831 (2013).
Hidalgo, M. et al. Patient-Derived Xenograft Models: An Emerging Platform for Translational Cancer Research. Cancer discovery 4, 998-1013, doi:10.1158/2159-8290.CD-14/0001 (2014).
Hoffman, R. M. J. N. R. C. Patient-derived orthotopic xenografts: better mimic of metastasis than subcutaneous xenografts: better mimic of metastasis than subcutaneous xenografts. Nat Rev Cancer 15(8), 451-2 (2015).
Iorio, F. et al. A Landscape of Pharmacogenomic Interactions in Cancer. Cell 166, 740-754, doi:10.1016/j.cell.2016.06.017 (2016).
Jackson, E. L. et al. Analysis of lung tumor initiation and progression using conditional expression of oncogenic K-ras. Genes Dev 15(24), 3243-3248 (2001).
Kersten, K., de Visser, K. E., van Miltenburg, M. H. & Jonkers, J. Genetically engineered mouse models in oncology research and cancer medicine. EMBO Mol Med 9, 137-153, doi:10.15252/emmm.201606857 (2017).
Madisen, L. et al. A robust and high-throughput Cre reporting and characterization system for the whole mouse brain. Nat Neurosci 13, 133-140, doi:10.1038/nn.2467 (2010).
Papageorgis, P. & Stylianopoulos, T. Role of TGFbeta in regulation of the tumor microenvironment and drug delivery (review). Int J Oncol 46, 933-943, doi:10.3892/ijo.2015.2816 (2015).
Pezza, J. A., Kucera, R. & Sun, L. J. N. E. B. Polymerase fidelity: what is it, and what does it mean for your PCR. (2014).
Roper, N., Stensland, K. D., Hendricks, R. & Galsky, M. D. The landscape of precision cancer medicine clinical trials in the United States. Cancer Treat Rev 41, 385-390, doi:10.1016/j.ctrv.2015.02.009 (2015).
Roychowdhury, S. & Chinnaiyan, A. M. Translating genomics for precision cancer medicine. Annu Rev Genomics Hum Genet 15, 395-415, doi:10.1146/annurev-genom-090413-025552 (2014).
Singh, M., Murriel, C. L. & Johnson, L. J. C. r. Genetically engineered mouse models: closing the gap between preclinical data and trial outcomes. Cancer Res 72 (11), 2695-2700 (2012).
Li, C. et. al., Quantitative in vivo analyses reveal a complex pharmacogenomic landscape in lung adenocarcinoma. bioRxiv Posted Jan. 29, 2020 (doi: https://doi.org/10.1101/2020.01.28.923912).
Venkataram, et al., Development of a Comprehensive Genotype-to-Fitness Map of Adaptation-Driving Mutations in Yeast, Cell 167, 1585-1596, Sep. 8, 2016 (http://dx.doi.org/10.1016/j.cell.2016.08.002).
Levy, et al., Quantitative evolutionary dynamics using high-resolution lineage tracking, Nature, vol. 519, Mar. 12, 2015, 9 pgs.

Figure 7 a

| | Human Lung Adenocarcinoma | | | |
|---|---|---|---|---|
| | TCGA, 2014 | | Imielinski et al., 2012 | |
| | All N=230 | KRAS$^{mut}$ N=75 (33%) | All N=183 | KRAS$^{mut}$ N=49 (27%) |
| P53(TP53) | 46% | 32% | 51% | 45% |
| LKB1(STK11) | 19% | 30% | 15% | 22% |
| SETD2 | 9% | 7% | 5% | 6% |
| RB1 | 7% | 5% | 4% | 0% |
| RBM10 | 9% | 16% | 8% | 6% |
| APC | 4% | 3% | 7% | 10% |
| CDKN2A | 24% | 19% | 14% | 12% |
| ARID1A | 8% | 7% | 9% | 12% |
| KEAP1 | 19% | 21% | 12% | 12% |
| SMAD4 | 4% | 3% | 5% | 4% |
| ATM | 12% | 15% | 12% | 20% | b

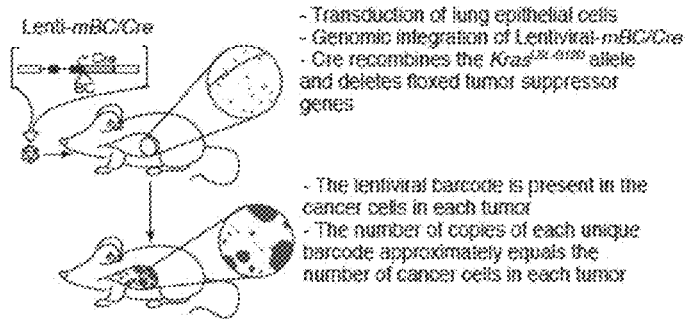

- Transduction of lung epithelial cells
- Genomic integration of Lentiviral-mBC/Cre
- Cre recombines the Kras$^{LSL-G12D}$ allele and deletes floxed tumor suppressor genes

- The lentiviral barcode is present in the cancer cells in each tumor
- The number of copies of each unique barcode approximately equals the number of cancer cells in each tumor c

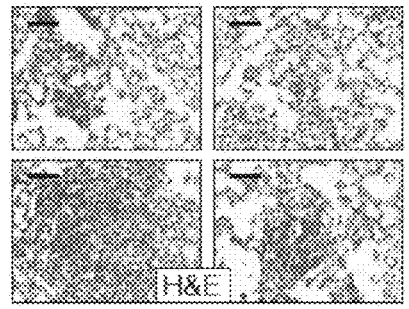

| Sample | Mouse genotype | Viral dilution | Lung weight (g) | Tumor # under scope | # of tumors dissected | Bulk lung DNA in PCR (μg) | # of pooled PCR reactions |
|---|---|---|---|---|---|---|---|
| 1740 | $PT;H11^{LSL-Cas9}$ | undil. | 1.339 | 43 | 1 | 115.2 | 29 |
| 1740repeat | $PT;H11^{LSL-Cas9}$ | undil. | 1.339 | 43 | 1 | 115.2 | 29 |
| 2014 | $PT;H11^{LSL-Cas9}$ | undil. | 0.195 | 5 | 0 | 16.8 | 5 |
| 2014repeat | $PT;H11^{LSL-Cas9}$ | undil. | 0.195 | 5 | 0 | 16.8 | 5 |
| 1734 | $PT;H11^{LSL-Cas9}$ | undil. | 0.266 | 14 | 0 | 22.9 | 6 |
| 1772 | $PT;H11^{LSL-Cas9}$ | undil. | 0.899 | 16 | 3 | 77.3 | 20 |
| 2084 | $PT;H11^{LSL-Cas9}$ | undil. | 0.290 | 20 | 4 | 24.9 | 7 |
| 2091 | $PT;H11^{LSL-Cas9}$ | undil. | 0.466 | 14 | 3 | 40.1 | 11 |
| 1741 | $PT;H11^{LSL-Cas9}$ | undil. | 0.350 | 8 | 3 | 30.1 | 8 |
| 1778 | $PT;H11^{LSL-Cas9}$ | 1/10 | 0.188 | 0 | 0 | 16.2 | 5 |
| 1776 | $PT;H11^{LSL-Cas9}$ | 1/10 | 0.162 | 0 | 0 | 13.9 | 4 |
| 1767 | $PT;H11^{LSL-Cas9}$ | 1/10 | 0.196 | 2 | 0 | 16.9 | 5 |
| 1894 | $PT;H11^{LSL-Cas9}$ | 1/10 | 0.156 | 3 | 0 | 13.4 | 4 |
| 1894repeat | $PT;H11^{LSL-Cas9}$ | 1/10 | 0.156 | 3 | 0 | 13.4 | 4 |
| 2193 | $LT;H11^{LSL-Cas9}$ | undil. | ND | 14 | 5 | 34.4 | 9 |
| 2228 | $LT;H11^{LSL-Cas9}$ | undil. | ND | 7 | 5 | 18.3 | 5 |
| 2379 | $LT;H11^{LSL-Cas9}$ | undil. | 0.927 | 19 | 6 | 79.7 | 20 |
| 2366 | $LT;H11^{LSL-Cas9}$ | undil. | 1.183 | 36 | 11 | 101.7 | 26 |
| 2324 | $LT;H11^{LSL-Cas9}$ | undil. | 1.814 | 40 | 10 | 156.0 | 40 |
| 2324repeat | $LT;H11^{LSL-Cas9}$ | undil. | 1.814 | 40 | 10 | 156.0 | 40 |
| 2358 | $LT;H11^{LSL-Cas9}$ | undil. | 0.154 | 7 | 0 | 13.2 | 4 |
| 2080 | $T;H11^{LSL-Cas9}$ | undil. | 0.316 | 14 | 0 | 27.2 | 7 |
| 2078 | $T;H11^{LSL-Cas9}$ | undil. | 0.382 | 22 | 1 | 32.9 | 9 |
| 2095 | $T;H11^{LSL-Cas9}$ | undil. | 0.257 | 21 | 0 | 22.1 | 6 | b

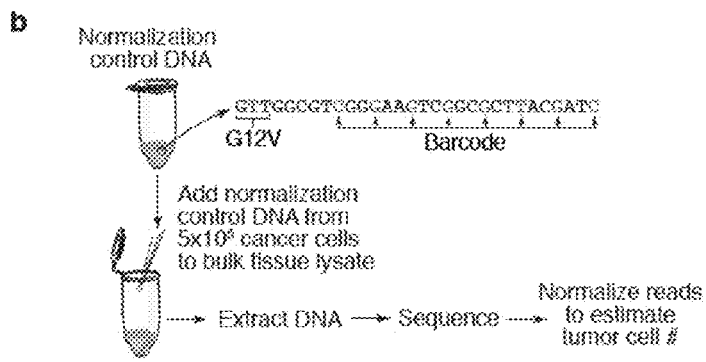

Figure 41 a

|  | $Kras^{LSL-G12D}$ | $Kras^{LSL-G12D};$ $p53^{flox/flox}$ | $Kras^{LSL-G12D};$ $Lkb1^{flox/flox}$ |
|---|---|---|---|
| p53 | Increased tumor burden Shorter survival (Jackson, 2005) | N/A | No Published Data |
| Lkb1 | Increased tumor burden Shorter survival (Ji, 2007) | No Published Data | N/A |
| Rb1 | Slightly increased tumor burden slightly shorter survival (Ho, 2009) | No Published Data | No Published Data |
| Atm | Possible slight reduction in survival (with $Kras^{LA-2 (non-LSL-G12D)}$ allele) (Efeyan, 2009) | No Published Data | No Published Data |
| Cdkn2a | Slightly increased tumor burden Slightly shorter survival (Schuster, 2014) | No Published Data | No Published Data |
| Apc | Increase in tumor burden (Sanchez-Rivera, 2014) | Non-significant increase in tumor burden (Sanchez-Rivera, 2014) | No Published Data |
| Arid1a | Non-significant increase in tumor burden (Rogers, 2017 and Walter, 2017) | Non-significant increase in tumor burden (Walter, 2017) | No Published Data |
| Setd2 | Increase in tumor burden (Rogers, 2017 and Walter, 2017) | Increase in tumor burden (Walter, 2017) | No Published Data |
| Keap1 | Increase in tumor burden (Romero, 2017) No increase in tumor burden (Rogers, 2017) | No Published Data | No Published Data |
| Smad4 | No increase in tumor burden (Rogers, 2017) | No Published Data | No Published Data |
| Rbm10 | Increase in tumor burden (Rogers, 2017) | No Published Data | No Published Data | b

|  | TCGA, 2014 | | | GENIE, 2017 | | |
|---|---|---|---|---|---|---|
|  | All | $TP53^{mut}$ | $LKB1^{mut}$ | All | $TP53^{mut}$ | $LKB1^{mut}$ |
| # of Samples (%) | 230 | 107 (47%) | 43 (19%) | 1563 | 775 (53%) | 274 (15%) |
| P53(TP53) | 47% | N/A | 30% | 50% | N/A | 38% |
| LKB1(STK11) | 19% | 12% | N/A | 18% | 13% | N/A |
| SETD2 | 9% | 7% | 2% | 7% | 6% | 5% |
| RB1 | 7% | 10% | 9% | 8% | 9% | 4% |
| RBM10 | 9% | 7% | 17% | 5% | 5% | 5% |
| APC | 4% | 5% | 7% | 6% | 6% | 7% |
| CDKN2A | 24% | 26% | 21% | 11% | 14% | 14% |
| ARID1A | 8% | 8% | 3% | 8% | 10% | 8% |
| KEAP1 | 19% | 17% | 40% | 13% | 12% | 42% |
| SMAD4 | 4% | 5% | 2% | 4% | 5% | 4% |
| ATM | 12% | 5% | 23% | 10% | 7% | 15% |

Figure 47 a

| Background Mutation | Co-occurring Mutation | GENIE OR* | P-value | TCGA OR | P-value | Combined OR | P-value | LN Mean Ratio raw | weighted |
|---|---|---|---|---|---|---|---|---|---|
| LKB1 (STK11) | APC | 1.28 | 0.8633 | 0.56 | 0.7747 | 1.20 | 0.9379 | 1.21 | 1.35 |
|  | ARID1A | 1.04 | 0.9761 | 0.69 | 0.8258 | 1.00 | 0.9798 | 1.12 | 1.20 |
|  | ATM | 1.85 | 0.4653 | 5.19 | 0.0554 | 2.13 | 0.1201 | 1.04 | 1.06 |
|  | CDKN2A | 1.35 | 0.8796 | 1.29 | 0.6800 | 1.35 | 0.9055 | 1.11 | 1.17 |
|  | KEAP1 | 10.24 | 0.0000 | 2.84 | 0.2062 | 8.29 | 0.0000 | 1.13 | 1.20 |
|  | RB1 | 0.60 | 0.9990 | 1.06 | 0.7042 | 0.67 | 0.9509 | 1.03 | 1.05 |
|  | RBM10 | 1.00 | 0.9586 | 3.02 | 0.2429 | 1.28 | 0.5722 | 1.01 | 1.02 |
|  | SETD2 | 0.62 | 0.9996 | 0.22 | 0.9807 | 0.55 | 0.9998 | 0.73 | 0.64 |
|  | SMAD4 | 0.97 | 0.9546 | 0.65 | 0.7262 | 0.94 | 0.9472 | 1.12 | 1.18 |
|  | TP53 | 0.55 | 1.0000 | 0.41 | 0.9979 | 0.53 | 1.0000 | 1.00 | 1.00 |
| TP53 | APC | 1.07 | 0.9312 | 0.93 | 0.6906 | 1.06 | 0.9270 | 0.89 | 0.93 |
|  | ARID1A | 1.69 | 0.5613 | 1.02 | 0.7275 | 1.60 | 0.7741 | 0.97 | 1.03 |
|  | ATM | 0.49 | 1.0000 | 0.24 | 0.9972 | 0.46 | 1.0000 | 1.04 | 1.10 |
|  | CDKN2A | 1.70 | 0.5559 | 1.64 | 0.5411 | 1.69 | 0.6622 | 0.97 | 1.02 |
|  | KEAP1 | 0.93 | 0.9971 | 0.71 | 0.9641 | 0.88 | 0.9992 | 0.93 | 0.95 |
|  | RB1 | 4.79 | 0.0179 | 5.59 | 0.1544 | 4.88 | 0.0190 | 1.05 | 1.11 |
|  | RBM10 | 0.97 | 0.9550 | 0.51 | 0.9537 | 0.85 | 0.9959 | 0.93 | 0.89 |
|  | SETD2 | 0.76 | 0.9977 | 0.76 | 0.8762 | 0.75 | 0.9917 | 0.93 | 0.75 |
|  | SMAD4 | 1.22 | 0.8290 | 1.17 | 0.6005 | 1.22 | 0.8451 | 0.98 | 1.05 |
|  | LKB1 | 0.55 | 1.0000 | 0.41 | 0.9979 | 0.53 | 1.0000 | 0.93 | 0.71 |

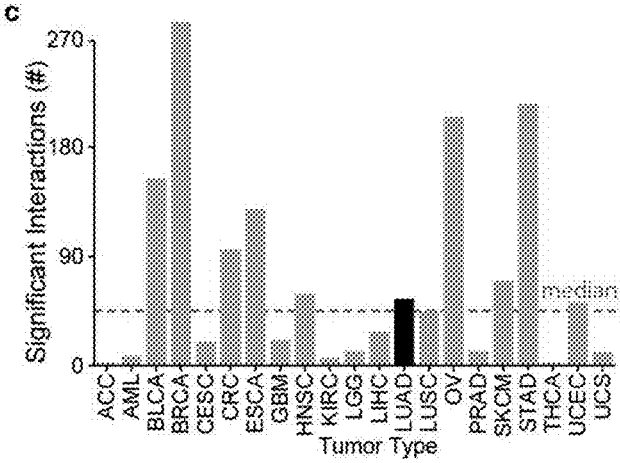

b

|  | Human Genetics | |
|---|---|---|
|  | Redundant | Cooperate |
| Tuba-seq Cooperate | Atm–p53<br>Smad4–Lkb1<br>Arid1a–Lkb1 | Rb1–p53<br>Arid1a–p53<br>Smad4–p53<br>Cdkn2a–p53<br>Apc–Lkb1<br>Cdkn2a–Lkb1<br>Keap1–Lkb1 |
| Tuba-seq Redundant | Lkb1–p53<br>Rbm10–p53<br>Keap1–p53<br>Setd2–p53<br>Rb1–Lkb1<br>Setd2–Lkb1 | Apc–p53<br>Atm–Lkb1<br>Rbm10–Lkb1 |

SEQUENCE LISTING

<160> NUMBER OF SEQ ID NOS: 148

<210> SEQ ID NO 1
<211> LENGTH: 22
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 1
nggnaartcn gcnctnacna th                                        22

<210> SEQ ID NO 2
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 2
gctgaaaatg actgagtata aactagtagt c                              31

<210> SEQ ID NO 3
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 3
ttagcagttg gcctttaatt gg                                        22

<210> SEQ ID NO 4
<211> LENGTH: 101
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (30)..(37)
<223> OTHER INFORMATION: n is a, c, g, or t

<400> SEQUENCE: 4
aatgatacgg cgaccaccga gatctacacn nnnnnnnaca ctctttccct acacgacgct    60
cttccgatct gctgaaaatg actgagtata aactagtagt c                      101

```
<210> SEQ ID NO 5
<211> LENGTH: 87
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (25)..(32)
<223> OTHER INFORMATION: n is a, c, g, or t

<400> SEQUENCE: 5
caagcagaag acggcatacg agatnnnnnn nngtgactgg acttcagacg tgtgctcttc      60
cgatccgtag ggtcatactc atccaca                                         87

<210> SEQ ID NO 6
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 6
aatgatacgg cgaccaccga gatctacac                                       29

<210> SEQ ID NO 7
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 7
caagcagaag acggcatacg agat                                            24

<210> SEQ ID NO 8
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 8
tgactttgca gggcaagttt                                                 20

<210> SEQ ID NO 9
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 9
cagcagtccc caactccata                                                 20

<210> SEQ ID NO 10
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 10
gccccaagtg agaatcagtg                                                 20
```

```
<210> SEQ ID NO 11
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 11
ggcttctttc ttgggtcctg                                                   20

<210> SEQ ID NO 12
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 12
ctgagccagc aactctgtga                                                   20

<210> SEQ ID NO 13
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 13
aactgtgctg gtgtgtgcaa                                                   20

<210> SEQ ID NO 14
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 14
caaagctgga agcgagactg                                                   20

<210> SEQ ID NO 15
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 15
tctgcaagtt caagcgatga                                                   20

<210> SEQ ID NO 16
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 16
cctccagccg ctcctcat                                                     18

<210> SEQ ID NO 17
<211> LENGTH: 20
<212> TYPE: DNA
<213> ORGANISM: Artificial sequence
<220> FEATURE:
<223> OTHER INFORMATION: synthetic polynucleotide
```

<400> SEQUENCE: 17
gcctttctgt ggaaatggaa                                          20

<210> SEQ ID NO 18
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 18
ttgtcaagac cgacctgtcc                                          20

<210> SEQ ID NO 19
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 19
tctggacgaa gagcatcagg                                          20

<210> SEQ ID NO 20
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 20
cgctgttctc ctcttcctca                                          20

<210> SEQ ID NO 21
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 21
cccactcccc tgttaccttt                                          20

<210> SEQ ID NO 22
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 22
ggagccattt cttggggtta                                          20

<210> SEQ ID NO 23
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 23
agctctggct ccttgtggat                                          20

<210> SEQ ID NO 24

```
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 24
ggctcatttg ggttgcttct                                              20

<210> SEQ ID NO 25
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 25
ggcctatccc acttctgagc                                              20

<210> SEQ ID NO 26
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 26
acaccaccac caccatcatc                                              20

<210> SEQ ID NO 27
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 27
ctggctggag ctgtgagagt                                              20

<210> SEQ ID NO 28
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 28
tggattcagg tgacctagat gg                                           22

<210> SEQ ID NO 29
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 29
gaacgccgaa cctaagcag                                               19

<210> SEQ ID NO 30
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 30
```
ttccaggctg agtggtaagg                                                    20

<210> SEQ ID NO 31
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 31
ccaccatgat attcggcaag                                                    20

<210> SEQ ID NO 32
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 32
gctccaatcc ttccattcaa                                                    20

<210> SEQ ID NO 33
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 33
tggatacttt ctcggcagga                                                    20

<210> SEQ ID NO 34
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 34
agctagggat ccgccgcata accagtg                                            27

<210> SEQ ID NO 35
<211> LENGTH: 66
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (12)..(19)
<223> OTHER INFORMATION: n is a, c, g, or t
<220> FEATURE:
<221> NAME/KEY: misc_feature
<222> LOCATION: (22)..(26)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: misc_feature
<222> LOCATION: (36)..(40)
<223> OTHER INFORMATION: n is a, c, g, or t

<400> SEQUENCE: 35
agctagtccg gnnnnnnnna annnnnttnn nnnaannnnn atgcccaaga agaagaggaa        60

```
ggtgtc                                                                          66

<210> SEQ ID NO 36
<211> LENGTH: 77
<212> TYPE: DNA
<213> ORGANISM: Artificial sequence
<220> FEATURE:
<223> OTHER INFORMATION: synthetic polynucleotide

<400> SEQUENCE: 36
aatgatacgg cgaccaccga gatctacact ctttccctac acgacgctct tccgatctgc      60
gcacgtctgc cgcgctg                                                    77

<210> SEQ ID NO 37
<211> LENGTH: 83
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (25)..(30)
<223> OTHER INFORMATION: n is a, c, g, or t

<400> SEQUENCE: 37
caagcagaag acggcatacg agatnnnnnn gtgactggac ttcagacgtg tgctcttccg      60
atccaggttc ttgcgaacct cat                                             83

<210> SEQ ID NO 38
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 38
catggcataa agcagttact aca                                             23

<210> SEQ ID NO 39
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 39
ccagtccaat ggatcagatg                                                 20

<210> SEQ ID NO 40
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 40
cacccagttg accctatctt c                                               21

<210> SEQ ID NO 41
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 41
```

-continued caacgttcac gtagcagctc                                           20

<210> SEQ ID NO 42
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 42
ggcttattga gttcgcctac a                                         21

<210> SEQ ID NO 43
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 43
ggtacccgat catgtcagag a                                         21

<210> SEQ ID NO 44
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 44
tactcagccg ctttctttgc                                           20

<210> SEQ ID NO 45
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 45
ctgttgtggt tgtgccaaag                                           20

<210> SEQ ID NO 46
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 46
tcgattcaaa ccatccaaca                                           20

<210> SEQ ID NO 47
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 47
gggcctgtac ccatttgag                                            19

<210> SEQ ID NO 48
<211> LENGTH: 20
<212> TYPE: DNA

```
<213> ORGANISM: Artificial sequence
<220> FEATURE:
<223> OTHER INFORMATION: synthetic polynucleotide

<400> SEQUENCE: 48
catcacctca ctgcatggac                                                    20

<210> SEQ ID NO 49
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 49
ggcaggatct cctgtcatct                                                    20

<210> SEQ ID NO 50
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 50
cggaccgcta tcaggacata                                                    20

<210> SEQ ID NO 51
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 51
gatcggccat tgaacaagat                                                    20

<210> SEQ ID NO 52
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 52
tctcctgaac ggctggatac                                                    20

<210> SEQ ID NO 53
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 53
gggtacccat gtccttgttg                                                    20

<210> SEQ ID NO 54
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 54
ccgttttcgg aagttgacag                                                    20
```

<210> SEQ ID NO 55
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 55
accagcgtgt ccaggaag                                                 18

<210> SEQ ID NO 56
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 56
gctgctgcac gaggaagt                                                 18

<210> SEQ ID NO 57
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 57
aaggaacaca gctcccacac                                               20

<210> SEQ ID NO 58
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 58
gaggatttgt tccgcatcag                                               20

<210> SEQ ID NO 59
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 59
ttttcagttt gagaacagcc ttt                                           23

<210> SEQ ID NO 60
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 60
cttgtggaag ccacaggaat                                               20

<210> SEQ ID NO 61
<211> LENGTH: 20
<212> TYPE: DNA
<213> ORGANISM: Artificial sequence
<220> FEATURE:

<223> OTHER INFORMATION: synthetic polynucleotide

<400> SEQUENCE: 61
tgtcccttgc tgtcctaaca				20

<210> SEQ ID NO 62
<211> LENGTH: 18
<212> TYPE: DNA
<213> ORGANISM: Artificial sequence
<220> FEATURE:
<223> OTHER INFORMATION: synthetic polynucleotide

<400> SEQUENCE: 62 cagggtctc ggtgacag				18

<210> SEQ ID NO 63
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 63
agtacgtgct cgctcgatg				19

<210> SEQ ID NO 64
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 64
gagcggcgat accgtaaag				19

<210> SEQ ID NO 65
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 65
catcagagca gccgattgt				19

<210> SEQ ID NO 66
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 66
gcagcgttac ctctatcgta				20

<210> SEQ ID NO 67
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 67
gctaattcag aatcactttg				20

<210> SEQ ID NO 68
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 68
gactgagtat aaacttgtgg                                           20

<210> SEQ ID NO 69
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 69
tcccctcttg gtgcctgtgt g                                         21

<210> SEQ ID NO 70
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 70
aagcccttcc tgctaatctc ggag                                      24

<210> SEQ ID NO 71
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 71
gcacggatgg catcttggac c                                         21

<210> SEQ ID NO 72
<211> LENGTH: 44
<212> TYPE: DNA
<213> ORGANISM: Artificial sequence
<220> FEATURE:
<223> OTHER INFORMATION: synthetic polynucleotide

<400> SEQUENCE: 72
gccgccatgg cagttctttt gtatccattt gtctctttat ctgc                44

<210> SEQ ID NO 73
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 73
gccgctcgag ctcttgtgtg tatgaagaca gtgacactg                      39

<210> SEQ ID NO 74
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 74
tgagtgttaa aatattgata aagtttttg                                29

<210> SEQ ID NO 75
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 75
cctaggtgtg taaaactcta agatattcc                                29

<210> SEQ ID NO 76
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 76
cttgtaaagg acggcagcc                                           19

<210> SEQ ID NO 77
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 77
cgtacgcaga ctgtagagca gc                                       22

<210> SEQ ID NO 78
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 78
cacacctagg tgagtgttaa aatattg                                  27

<210> SEQ ID NO 79
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 79
gtagctcact agtggtcgcc                                          20

<210> SEQ ID NO 80
<211> LENGTH: 91
<212> TYPE: DNA
<213> ORGANISM: Artificial sequence
<220> FEATURE:
<223> OTHER INFORMATION: synthetic polynucleotide

<400> SEQUENCE: 80
aatgatacgg cgaccaccga gatctacact ctttccctac acgacgctct tccgatctct    60
gctgaaaatg actgagtata aactagtagt c                                  91

```
<210> SEQ ID NO 81
<211> LENGTH: 86
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (25)..(30)
<223> OTHER INFORMATION: n is a, c, g, or t

<400> SEQUENCE: 81
caagcagaag acggcatacg agatnnnnnn gtgactggag ttcagacgtg tgctcttccg     60
atcctgccgt cctttacaag cgtacg                                         86

<210> SEQ ID NO 82
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 82
gacgtaaacg gccacaagtt                                                20

<210> SEQ ID NO 83
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 83
gaacttcagg gtcagcttgc                                                20

<210> SEQ ID NO 84
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 84
cgagggcgat gccacctacg                                                20

<210> SEQ ID NO 85
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 85
tttgttgccc tttattgcag                                                20

<210> SEQ ID NO 86
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 86
cccttgcggt attctttgtt                                                20

<210> SEQ ID NO 87
```

```
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 87
tgcagttgtt ggctccaaca c                                              21

<210> SEQ ID NO 88
<211> LENGTH: 33
<212> TYPE: DNA
<213> ORGANISM: Artificial sequence
<220> FEATURE:
<223> OTHER INFORMATION: synthetic polynucleotide

<400> SEQUENCE: 88
ctgctgaaaa tgactgagta taaactagta gtc                                 33

<210> SEQ ID NO 89
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 89
agcagttggc ctttaattgg tt                                             22

<210> SEQ ID NO 90
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 90
aatgatacgg cgaccaccga gatctacac                                      29

<210> SEQ ID NO 91
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 91
gctgaaaatg actgagtata aactagtagt c                                   31

<210> SEQ ID NO 92
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 92
ttagcagttg gcctttaatt gg                                             22

<210> SEQ ID NO 93
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 93
```
gcacggatgg catcttggac c                                           21

<210> SEQ ID NO 94
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 94 tccctcttg gtgcctgtgt g                                            21

<210> SEQ ID NO 95
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 95
ggctggctgc cgtcctttac                                             20

<210> SEQ ID NO 96
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 96
caagctcatg cgggtgtgtc                                             20

<210> SEQ ID NO 97
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 97
tgaccctacg atagaggtaa cg                                          22

<210> SEQ ID NO 98
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 98
ctcatccaca aagtgattct ga                                          22

<210> SEQ ID NO 99
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 99
tgaccctacg atagaggtaa cg                                          22

<210> SEQ ID NO 100
<211> LENGTH: 29
<212> TYPE: DNA

```
<213> ORGANISM: Artificial sequence
<220> FEATURE:
<223> OTHER INFORMATION: synthetic polynucleotide

<400> SEQUENCE: 100
tgagtgttaa aatattgata aagtttttg                                29

<210> SEQ ID NO 101
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 101
tccgaattca gtgactacag atg                                      23

<210> SEQ ID NO 102
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 102
tgagtgttaa aatattgata aagtttttg                                29

<210> SEQ ID NO 103
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 103
tcccctcttg gtgcctgtgt g                                        21

<210> SEQ ID NO 104
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 104
ggctggctgc cgtcctttac                                          20

<210> SEQ ID NO 105
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 105
cgggaagtcg gcgcttacga tc                                       22

<210> SEQ ID NO 106
<211> LENGTH: 17
<212> TYPE: DNA
<213> ORGANISM: Artificial sequence
<220> FEATURE:
<223> OTHER INFORMATION: synthetic polynucleotide

<400> SEQUENCE: 106
atgactgagt ataaact                                             17
```

<210> SEQ ID NO 107
<211> LENGTH: 16
<212> TYPE: DNA
<213> ORGANISM: Artificial sequence
<220> FEATURE:
<223> OTHER INFORMATION: synthetic polynucleotide

<400> SEQUENCE: 107
ctcatccaca aagtga                                                    16

<210> SEQ ID NO 108
<211> LENGTH: 19
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (8)..(12)
<223> OTHER INFORMATION: n is a, c, g, or t
<220> FEATURE:
<221> NAME/KEY: misc_feature
<222> LOCATION: (15)..(19)
<223> OTHER INFORMATION: n is a, c, g, or t

<400> SEQUENCE: 108
nnnnnttnnn nnaannnnn                                                 19

<210> SEQ ID NO 109
<211> LENGTH: 31
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (12)..(16)
<223> OTHER INFORMATION: n is a, c, g, or t
<220> FEATURE:
<221> NAME/KEY: misc_feature
<222> LOCATION: (19)..(23)
<223> OTHER INFORMATION: n is a, c, g, or t
<220> FEATURE:
<221> NAME/KEY: misc_feature
<222> LOCATION: (26)..(30)
<223> OTHER INFORMATION: n is a, c, g, or t

<400> SEQUENCE: 109
attctgccta annnnnttnn nnnaannnnn a                                   31

<210> SEQ ID NO 110
<211> LENGTH: 38
<212> TYPE: DNA
<213> ORGANISM: Artificial sequence
<220> FEATURE:
<223> OTHER INFORMATION: synthetic polynucleotide

<400> SEQUENCE: 110
cggattctgc ctaaacaagt tgggataagc cacatgcc                            38

<210> SEQ ID NO 111
<211> LENGTH: 38
<212> TYPE: DNA
<213> ORGANISM: Artificial sequence
<220> FEATURE:

<223> OTHER INFORMATION: synthetic polynucleotide

<400> SEQUENCE: 111
cggattctgc ctaagctaat tgacgaaagg cctatgcc                                38

<210> SEQ ID NO 112
<211> LENGTH: 38
<212> TYPE: DNA
<213> ORGANISM: Artificial sequence
<220> FEATURE:
<223> OTHER INFORMATION: synthetic polynucleotide

<400> SEQUENCE: 112
cggattctgc ctaaattcct tggcgcaatt acaatgcc                                38

<210> SEQ ID NO 113
<211> LENGTH: 21
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t

<400> SEQUENCE: 113
aannnnnttn nnnnaannnn n                                                  21

<210> SEQ ID NO 114
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 114
ttgagcgtag tttcactccg                                                    20

<210> SEQ ID NO 115
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 115
tatgggttag tcccaccata                                                    20

<210> SEQ ID NO 116
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 116
gctaagatgt gacttaagcc                                                    20

```
<210> SEQ ID NO 117
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 117
gcgctgcgtc gtgcaccggg                                                    20

<210> SEQ ID NO 118
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 118
cctgcacgtg atgaacgggg                                                    20

<210> SEQ ID NO 119
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 119
gtggtgggcc gcagtcacaa                                                    20

<210> SEQ ID NO 120
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 120
aggagctcct gacactcgga                                                    20

<210> SEQ ID NO 121
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 121
tcttaccagg attccatcca                                                    20

<210> SEQ ID NO 122
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 122
gtatttcctg aacagatccg                                                    20

<210> SEQ ID NO 123
<211> LENGTH: 20
<212> TYPE: DNA
<213> ORGANISM: Artificial sequence
<220> FEATURE:
<223> OTHER INFORMATION: synthetic polynucleotide
```

```
<400> SEQUENCE: 123
tctctaatcc atcttcccag                                               20

<210> SEQ ID NO 124
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 124
tgactgctcc gagaagaaca                                               20

<210> SEQ ID NO 125
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 125
ggtggcgtta gactctgccg                                               20

<210> SEQ ID NO 126
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 126
tcatggctga tgcaatgcgg                                               20

<210> SEQ ID NO 127
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 127
gatattgctg aagagcttgg                                               20

<210> SEQ ID NO 128
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 128
gaatagcctc tccacccaag                                               20

<210> SEQ ID NO 129
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 129
gcgaggtatt cggctccgcg                                               20

<210> SEQ ID NO 130
<211> LENGTH: 20
```

```
<212> TYPE: DNA
<213> ORGANISM: Artificial sequence
<220> FEATURE:
<223> OTHER INFORMATION: synthetic polynucleotide

<400> SEQUENCE: 130
atgttgcagt tcggctcgat                                               20

<210> SEQ ID NO 131
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 131
tgatggcgtt ggcaagtcag cgcttacaat c                                  31

<210> SEQ ID NO 132
<211> LENGTH: 46
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 132
agtagtcgtt ggagctggtg gcgtnggnaa rtcngcnctn acnath                  46

<210> SEQ ID NO 133
<211> LENGTH: 48
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
```

```
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 133
ctagtagtcg ttggagctgg tggcgtnggn aartcngcnc tnacnath              48

<210> SEQ ID NO 134
<211> LENGTH: 49
<212> TYPE: DNA
<213> ORGANISM: Artificial sequence
<220> FEATURE:
<223> OTHER INFORMATION: synthetic polynucleotide

<400> SEQUENCE: 134
tagtagtcgt tggagctgat ggcgttggaa aatctgctct gacgatcca             49

<210> SEQ ID NO 135
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 135
gatggcgtgg gcaagtcggc gctgacaata                                  30

<210> SEQ ID NO 136
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 136
gttggcgtcg ggaaatctgc tctcacaatt                                  30

<210> SEQ ID NO 137
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 137
cgtggcgttg gaaaatcggc ctcacaata                                   29

<210> SEQ ID NO 138
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 138
ggtcgcgtcg ggaagtcggc cctaacgatc                                  30

<210> SEQ ID NO 139
<211> LENGTH: 30
<212> TYPE: DNA
<213> ORGANISM: Artificial sequence
```

```
<220> FEATURE:
<223> OTHER INFORMATION: synthetic polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 139
nntnncgtng gnaartcngc nctnacnath                                30

<210> SEQ ID NO 140
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 140
ggtggcgtag gcaagagcgc cttgacgata                                30

<210> SEQ ID NO 141
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 141
atgactgagt ataaacttgt ggtggttgga gctggtggc                      39

<210> SEQ ID NO 142
<211> LENGTH: 39
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
```

<400> SEQUENCE: 142
atgactgagt ataaactagt agtcgttgga gctnntnnc        39

<210> SEQ ID NO 143
<211> LENGTH: 38
<212> TYPE: DNA
<213> ORGANISM: Artificial sequence
<220> FEATURE:
<223> OTHER INFORMATION: synthetic polynucleotide

<400> SEQUENCE: 143
atgactgagt ataaacttgg gtggttggag ctggtggc         38

<210> SEQ ID NO 144
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 144
atgactgagt ataaacttgg tggttggagc tggtggc          37

<210> SEQ ID NO 145
<211> LENGTH: 36
<212> TYPE: DNA
<213> ORGANISM: Artificial sequence
<220> FEATURE:
<223> OTHER INFORMATION: synthetic polynucleotide

<400> SEQUENCE: 145
atgactgagt ataaactggt ggttggagct ggtggc           36

<210> SEQ ID NO 146
<211> LENGTH: 34
<212> TYPE: DNA
<213> ORGANISM: Artificial sequence
<220> FEATURE:
<223> OTHER INFORMATION: synthetic polynucleotide

<400> SEQUENCE: 146
atgactgagt ataatggtgg ttggagctgg tggc             34

<210> SEQ ID NO 147
<211> LENGTH: 34
<212> TYPE: DNA
<213> ORGANISM: Artificial sequence
<220> FEATURE:
<223> OTHER INFORMATION: synthetic polynucleotide

<400> SEQUENCE: 147
ctggtcgcgt tggaaagtcc gccctaacca taca             34

<210> SEQ ID NO 148
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 148
gttggcgtcg ggaagtcggc gcttacgatc                  30

COMPOSITIONS AND METHODS FOR MULTIPLEXED QUANTITATIVE ANALYSIS OF CELL LINEAGES

CROSS-REFERENCE

This application claims the benefit of U.S. Provisional Patent Application No. 62/481,067 filed Apr. 3, 2017, which application is incorporated herein by reference in its entirety.

STATEMENT REGARDING FEDERALLY SPONSORED RESEARCH

This invention was made with Government support under contracts CA124435, CA194910, CA207133 and GM118165 awarded by the National Institutes of Health. The Government has certain rights in the invention.

INTRODUCTION

Genome sequencing has catalogued the somatic alterations in human cancers at the genome-wide level and identified many potentially important genes (e.g., putative tumor suppressor genes, putative oncogenes, genes that could lead to treatment resistance or sensitivity). However, the identification of genomic alterations does not necessarily indicate their functional importance in cancer, and the impact of gene inactivation or alteration, alone or in combination with other genetic alterations (either somatic or germline) or microenvironmental differences, remains difficult to glean from cancer genome sequencing data alone.

The molecular and cellular impacts of genetic alterations on neoplastic growth have been directly investigated using knockdown, knockout, and overexpression studies in cell lines as well as genetically engineered mouse model systems. Over the past several decades the analysis of gene function in cancer cell lines in culture has provided insights into many aspects of cancer. However, the near-optimal growth of cancer cell lines in culture, widespread pre-existing genetic and epigenetic changes, and the lack of the autochthonous microenvironment limit the ability of these systems to provide insight into how different genes constrain or drive in vivo phenotypes (e.g. cancer growth, metastasis, therapy responses). In contrast, genetically engineered mouse models of human cancer facilitate the introduction of defined genetic alterations into normal adult cells which results in the initiation and growth of tumors within their natural in vivo setting. This is of particular importance as many pathways are influenced by properties of the in vivo tumor microenvironment.

While in vivo systems such as CRISPR/Cas based genetic targeting have increased the scale of in vitro and in vivo functional analyses, in vivo systems have continued to rely on relatively crude measurements of tumor growth, limiting their application to the analysis of genes with the most dramatic effects. The lack of rigorously quantitative systems to analyze gene function in vivo has precluded a broad understanding of pathways that drive or constrain tumor growth, or impact any of the other important aspects of carcinogenesis (e.g., tumor suppressor pathways).

There is a need for compositions and methods that facilitate precise quantification of clonal population size (e.g., the size of each tumor, the number of neoplastic cells in each tumor or subclone, and the like) in an individual with a plurality of clonal cell populations (e.g., a plurality of distinguishable cell lineages—being either distinct, identifiable tumors, or distinct identifiable subclones within a tumor). The compositions and methods of this disclosure address this need, and provide the ability to uncover whether different individual genes (e.g., tumor suppressors, oncogenes) or genetic alterations (e.g. insertions, deletions, point mutations), or combinations of genes and/or genetic alterations, have different overall effects on cell population growth (e.g., tumor growth), as well as other phenotypes of importance (e.g., tumor evolution, progression, metastatic proclivity). The compositions and methods of this disclosure also provide the ability to test the effect of potential therapeutics, e.g., radiation, chemotherapy, fasting, compounds such as drugs, biologics, etc., on the growth of multiple different clonal cell populations (e.g., multiple tumors of similar genotype but with different initiation events, multiple tumors that have different genotypes, and the like) within the same tissue (e.g., within the same individual), which would drastically reduce error introduced by sample-to-sample variability (e.g., animal-to-animal variability). These methods also facilitate development and testing of rational drug combinations.

SUMMARY

Compositions and methods are provided for measuring population size for a plurality of clonal cell populations in the same tissue (e.g., in the same individual) or in different tissues. As an example, in some cases a subject method is a method of measuring tumor size for a plurality of clonally independent tumor cell populations (e.g., different tumors) in the same tissue (e.g., in the same individual).

As an illustrative example, as described below in the working examples, the inventors combined cell barcoding (e.g., tumor barcoding) and high-throughput sequencing (referred to in the working examples as "Tuba-seq") with genetically engineered mouse models of human cancer to quantify tumor growth with unprecedented resolution. Precise quantification of individual tumor sizes allowed them to uncover the impact of inactivating different tumor suppressor genes (e.g., known tumor suppressor genes). Further, the inventors integrated these methods with multiplexed CRISPR/Cas9-mediated genome editing, which allowed parallel inactivation and functional quantification of a panel of putative tumor suppressor genes—and led to the identification of functional lung tumor suppressors. The method is a rapid, multiplexed, and highly quantitative platform to study the impact of genetic alterations on cancer growth in vivo.

Also as described in the working examples below, the inventors used multiplexed somatic homology directed repair (HDR) with barcoded HDR donor templates to produce genetically diverse barcoded tumors (e.g., tumors that have genetically diverse point mutations in a defined gene) within individual mice, and employed quantitative tumor analysis (using high-throughput sequencing) to rapidly and quantitatively interrogate the function of multiple precise mutations (e.g., defined point mutations) simultaneously in the same animal.

In some embodiments, a subject method includes a step of contacting a tissue (e.g., muscle, lung, bronchus, pancreas, breast, liver, bile duct, gallbladder, kidney, spleen, blood, gut, brain, bone, bladder, prostate, ovary, eye, nose, tongue, mouth, pharynx, larynx, thyroid, fat, esophagus, stomach, small intestine, colon, rectum, adrenal gland, soft tissue, smooth muscle, vasculature, cartilage, lymphatics, prostate, heart, skin, retina, and the reproductive and genital systems, e.g., testicle, reproductive tissue, etc.) with a plurality of cell markers that are heritable and distinguishable from one another, to generate a plurality of distinguishable lineages of heritably marked cells within the contacted tissue. In some embodiments, the cell markers used to contact the tissue are barcoded nucleic acids (e.g., RNA molecules; or circular or linear DNA molecules such as plasmids, natural or synthesized single- or double-stranded nucleic acid fragments, and minicircles). In some embodiments (e.g., in cases where the cell markers are barcoded nucleic acids), the cell markers can be delivered to the tissue via viral vectors (e.g., lentiviral vectors, adenoviral vectors, adeno-associated viral (AAV) vectors, and retroviral vectors). In some cases, the tissue to be contacted already includes neoplastic cells prior to contact with cell markers. In some cases, the cell markers can induce neoplastic cell formation and/or tumor formation. In some cases, components linked to the cell markers can induce neoplastic cell formation and/or tumor formation. In some cases, the cell markers are barcoded nucleic acids that can induce neoplastic cell formation and/or tumor formation (e.g., homology directed repair (HDR) DNA donor templates; nucleic acids encoding a genome editing protein(s); nucleic acids encoding oncogenes; nucleic acids encoding a protein(s), e.g., wild type and/or mutant protein(s) [e.g., wild type or mutant cDNA that encodes a protein that is detrimental to tumors, e.g., in some way other than growth/proliferation]; CRISPR/Cas guide RNAs; short hairpin RNAs (shRNAs); nucleic acids encoding targeting components for other genome editing systems; etc.).

Subject methods can also include (after sufficient time has passed for at least a portion of the heritably marked cells to undergo at least one round of division) a step of detecting and measuring quantities of at least two of the plurality of cell markers present in the contacted tissue—thereby generating a set of measured values, which represent the identity and quantity of cell markers that remain in the contacted tissue, e.g., heritably associated with the marked cells. In some cases (e.g., when the cell markers are barcoded nucleic acids) the detecting and measuring can be performed via a method that includes high-throughput sequencing and quantification of the number of sequence reads for each detected barcode.

In some cases, the generated set of measured values is used as input to calculate (e.g., using a computer) the number of heritably marked cells present in the contacted tissue (e.g., for at least 2, at least 3, at least 4, at least 5, at least 100, at least 1,000, at least 10,000, or at least 100,000 of the detected distinguishable lineages of heritably marked cells)(e.g., in some cases in a range of from 10 to 1,000,000; from 10 to 100,000; from 10 to 10,000; or from 10 to 1,000; of the detected distinguishable lineages of heritably marked cells). The calculated number of heritably marked cells can be absolute (e.g., an actual number of cells determined to be present), or can be relative (e.g., a population size for a first lineage of heritably marked cells can be determined relative to a population size for a second lineage of heritably marked cells without necessarily determining the actual number of cells present in either lineage).

In some embodiments, a subject method includes a step of administering a test compound (e.g., a drug) to the tissue (e.g., via administration to an individual, via contacting a synthetic ex vivo tissue such as an organoid, and the like), e.g., after introducing the cell markers, e.g., after a step of inducing neoplastic cells (or subclones) via contacting tissue with the plurality of cell markers. In some such cases, the step of administering the test compound is followed by a step of measuring population size (e.g., tumor size, number of neoplastic cells in each tumor) for a plurality of marked cell lineages/cell populations. Because multiple cell populations can be measured (e.g., multiple tumor sizes can be measured) for distinct and distinguishable marked cell lineages within the same tissue (e.g. within the same animal), the risk of error due to sample-to-sample variation (e.g., animal-to-animal variation) of drug response can be greatly reduced, if not eliminated.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 19. Comparison of systems to assess tumor suppressor gene function in lung adenocarcinoma mouse models. The method of tumor suppressor gene inactivation (Cre/LoxP-mediated deletion of a floxed allele versus CRISPR/Cas9-mediated genome editing), the ability to quantify tumor number and size through genetic barcoding of individual tumors, and the ability to inactivate multiple genes in a pooled format is indicated. Particularly relevant advantages and disadvantages of each system are shown, as well as example references. All highlighted studies are in lung cancer except Maresch et al. who used pooled sgRNA transfection to study pancreatic cancer. The reality of using floxed alleles to assess tumor suppressor gene function in lung adenocarcinoma models is best exemplified by the fact that over the past 15 years only six of the tumor suppressor genes that we queried have been investigated using floxed alleles in combination with $Kras^{LSL-G12D}$. The lack of quantitative methods also severely hampers the identification of genes with only moderate tumor suppressive effects due to known and unknown technical and biological variables (e.g. reproducibility of tumor initiation, gender, age, and strain of mice). Data generated by deleting genes with floxed alleles is also limited by the difficulty in comparing between different experimental setups used in different laboratories (e.g. different viral titer, time after initiation, method of quantification, mouse strain). Thus the relative effect of different tumor suppressor genes is difficult to glean from the literature. Finally, the quantification of individual tumor cell number by tumor barcoding provides not only unprecedented precision but also uncovers gene-specific effects on tumor size distributions that likely reflect distinct functional mechanisms of tumor suppression.

R26$^{LSL-Tomato}$;H11$^{LSL-Cas9}$ (PT;H11$^{LSL-Cas9}$), and R26$^{LSL-Tomato}$;H11$^{LSL-Cas9}$ (T;H11$^{LSL-Cas9}$) mice by intratracheal administration of AAV-Kras$^{HDR}$/sgKras/Cre. b. Light images that correspond to the fluorescence images in FIG. 2a. Higher magnification histology images document adenocarcinoma histology and greater nuclear atypia in the p53-deficient tumors. Upper scale bars=5 mm. Lower scale bars=50 µm. c. Additional examples of AAV-Kras$^{HDR}$/sgKras/Cre-induced lung tumors in LT;H11$^{LSL-Cas9}$, PT;H11$^{LSL-Cas9}$, and T;H11$^{LSL-Cas9}$ mice. Scale bars=5 mm. Note that, due to the high transduction efficiency, most lung cells express Tomato, but the tumors are much brighter because of the large number and density of cells in each tumor. d. Total lung weight in mice of each genotype with tumors initiated with AAV-Kras$^{HDR}$/sgKras/Cre. Each dot represents one mouse. e. Number of surface lung tumors identified under a fluorescence dissecting scope in mice of each genotype infected (transduced) with AAV-Kras$^{HDR}$/sgKras/Cre diluted 1:10. Each dot represents one mouse. f. Histology of a lymphatic micrometastasis that formed in a PT;H11$^{LSL-Cas9}$ mouse with AAV-Kras$^{HDR}$/sgKras/Cre-initiated lung tumors. Scale bar=50 µm. g. Number of mice of each genotype that had disseminated tumors cells in the pleural cavity (DTCs>10) and lymph node metastases. The numbers represent the number of mice with DTCs or metastases/total number of mice analyzed.

Figure 30:
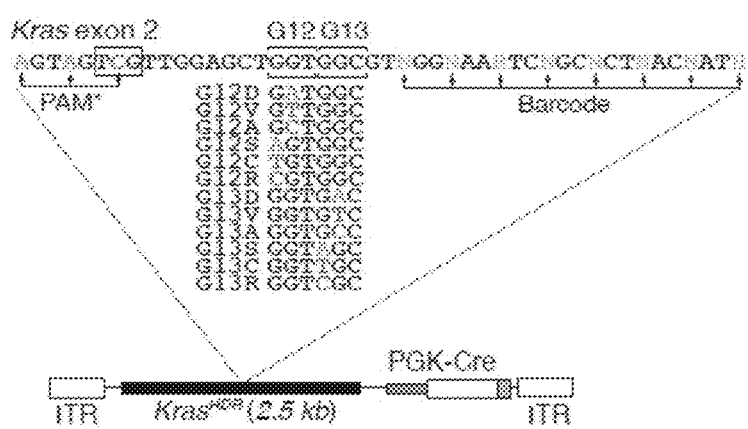

FIG. 30. Nuclease-free AAV-mediated HDR does not occur at a high enough rate to initiate large numbers of lung tumors. a. Schematic of control AAV vector library that contains a 2.5 kb Kras HDR template with the 12 single-nucleotide, non-synonymous mutations and barcode, but without the sgRNA targeting Kras. (The sequence of Kras exon 2 in (a) is set forth in SEQ ID NO: 132.) b. Representation of each Kras codon 12 and 13 allele in the AAV-Kras$^{HDR}$/Cre plasmid pool. Percentages are the average of triplicate sequencing. c. Titer of the AAV vector libraries (vg=vector genomes). Importantly, the control AAV-Kras$^{HDR}$/Cre viral preparation is higher titer than AAV-Kras$^{HDR}$/sgKras/Cre. d. Quantification of the number of LT, PT, and T mice that developed tumors after administration of 60 µL of undiluted or 1:10 diluted AAV-Kras$^{HDR}$/Cre pool.

Figure 31:
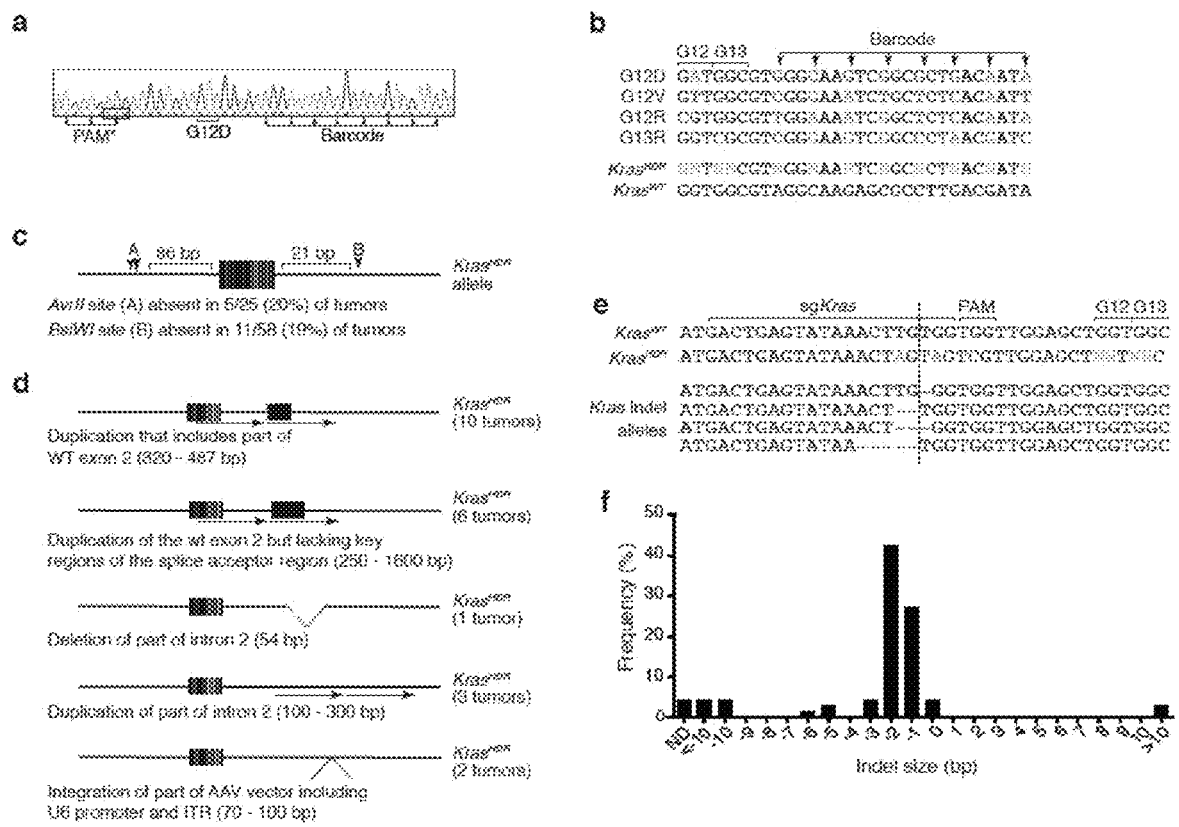

FIG. 31. Analysis of individual tumors identifies oncogenic Kras alleles and uncovers indels in the non-HDR Kras allele. a. Example sequencing trace of a Kras$^{HDR}$ allele with PAM* mutations, a G12D mutation, and a barcode. (The sequence of (a) is set forth in SEQ ID NO: 134) b. Sequences of four representative oncogenic Kras alleles detected in individual lung tumors by Sanger sequencing. (The sequence of G12D is set forth in SEQ ID NO: 135. The sequence of G12V is set forth in SEQ ID NO: 136. The sequence of G12R is set forth in SEQ ID NO: 137. The sequence of G13R is set forth in SEQ IDS NO: 138.) Each primary tumor analyzed had a unique variant-barcode pair, as expected given ~2.4×10$^4$ possible barcodes per variant. The altered bases in the AAV-Kras$^{HDR}$ template sequence and the wild type Kras sequence at this locus are shown for reference. (The sequence of Kras' is set forth in SEQ ID NO: 139. The sequence of Kras' is set forth in SEQ ID NO: 140.) c. HDR events generally occurred outside of the two engineered restriction sites. However, some tumors had Kras alleles consistent with recombination between exon 2 and one of the restriction sites, suggesting recombination very close to the Cas9/sgKras-induced double-strand DNA break. d. Diagram of oncogenic Kras alleles in individual tumors that did not undergo perfect HDR. Both perfect and imperfect HDR events are found in each mouse genotype (perfect HDR in 14/30 tumors in LT;H11$^{LSL-Cas9}$ mice and 3/7 tumors in PT;H11$^{LSL-Cas9}$ mice). Imperfect HDR events included alleles likely integrating into the Kras locus through homologous recombination of the 5' end of the AAV-Kras$^{HDR}$ template upstream of exon 2 and ligation of the 3' end of the AAV-Kras$^{HDR}$ template to the exon 2 region immediately downstream of the Cas9/sgKras-induced double-strand DNA break. This imperfect HDR resulted in insertions or deletions in the intronic sequence downstream of Kras exon 2. Insertions and deletions were variable in length (sizes approximated by Sanger sequencing or gel electrophoresis) and sometimes included part or all of the wild type exon 2, or in rare cases, segments of the AAV-Kras$^{HDR}$/sgKras/Cre vector. None of these partial HDR events were predicted to alter splicing from the mutant exon 2 to exon 3, consistent with the requirement for expression of the oncogenic Kras allele for tumor formation. e,f. The oncogenic Kras allele in large individual tumors from treated PT;H11$^{LSL-Cas9}$ and LT;H11$^{LSL-Cas9}$ mice was almost always accompanied by inactivation of the other Kras allele through Cas9-mediated indel formation in exon 2. Sanger sequencing identified indels adjacent to the PAM sequence in 47/48 (98%) of individual tumors. Example indels (e) and a summary of all indels (The sequence of Kras$^{WT}$ is set forth in SEQ ID NO: 141. The sequence of Kras$^{HDR}$ is set forth in SEQ ID NO: 142. The sequences of the Kras Indel alleles from top to bottom are set forth in SEQ ID NO: 143-146.) (f) are shown. ND indicates that a wild type allele could not be detected, which is consistent with either loss of heterozygosity, a very large indel, or a large deletion that encompassed one of the primer binding sites.

Figure 32:
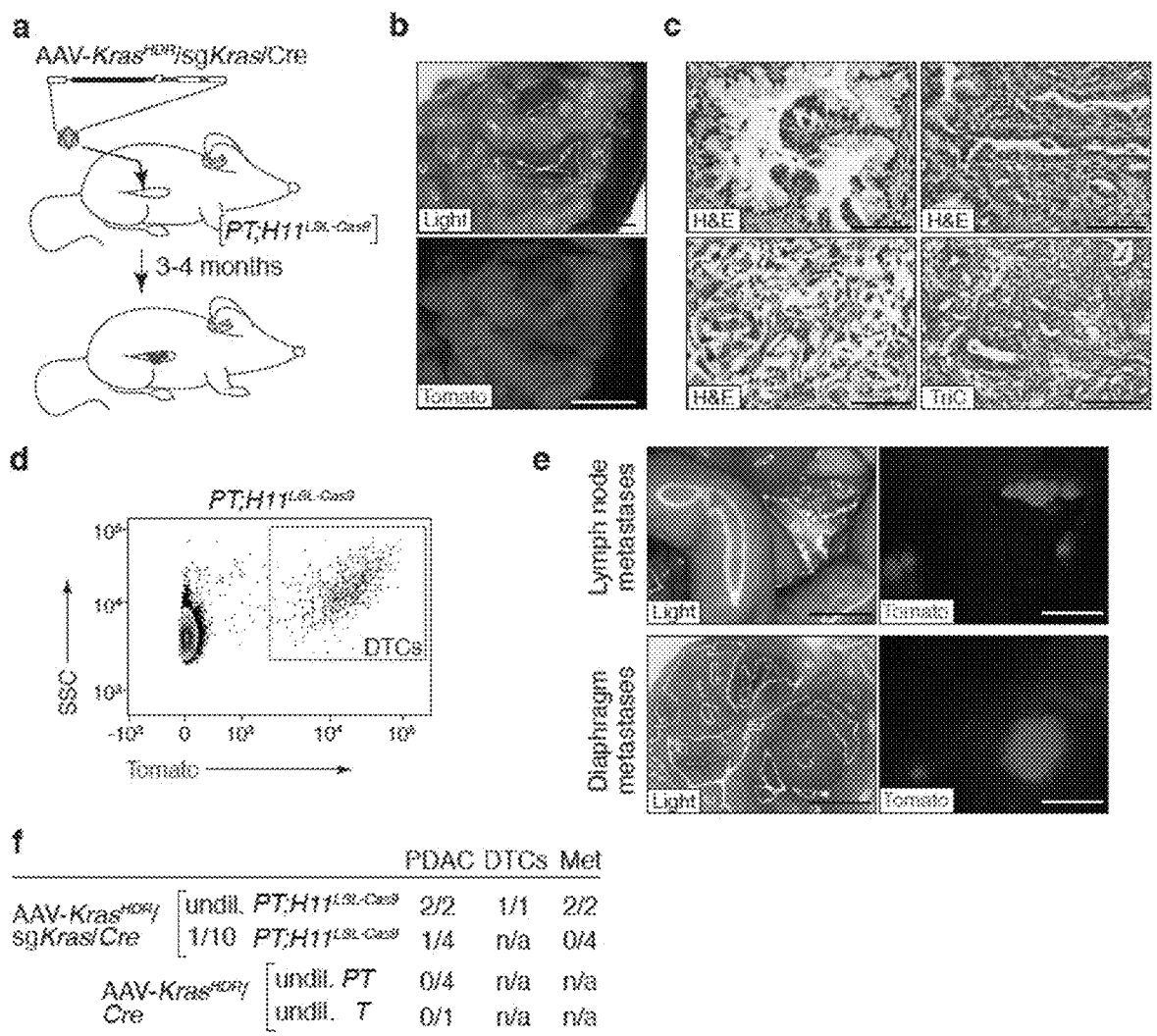

FIG. 32. HDR-mediated introduction of oncogenic mutations into the endogenous Kras locus in pancreatic cells leads to the formation of pancreatic ductal adenocarcinoma. a. Schematic of retrograde pancreatic ductal injection of AAV-Kras$^{HDR}$/sgKras/Cre into PT;H11$^{LSL-Cas9}$ mice to induce pancreatic cancer. b. Representative light and fluorescence images of pancreatic tumors that developed in PT;H11$^{LSL-Cas9}$ mice transduced with AAV-Kras$^{HDR}$/sgKras/Cre. Scale bars=5 mm. c. Histology images of different stages of pancreatic tumor progression including a pre-cancerous PanIN lesion (upper left), a well-differentiated tumor region (top right), and poorly differentiated PDAC (bottom left). Bottom right shows the development of a collagen-rich stromal environment (stained with Trichrome) within PDAC. Scale bars=75 µm. d. Representative FACS plots showing Tomato$^{positive}$ disseminated tumor cells (DTCs) in the peritoneal cavity of a PT;H11$^{LSL-Cas9}$ mouse with AAV-Kras$^{HDR}$/sgKras/Cre-initiated PDAC. Plot shows FSC/SSC-gated viable cancer cells (DAPI/CD45/CD31/F4-80/Ter119$^{negative}$). e. HDR-induced PDACs can progress to gain metastatic ability, seeding metastases in lymph nodes and on the diaphragm. Light and fluorescence dissecting scope images are shown. Scale bars=3 mm. f. Incidence of PDAC, DTCs in the peritoneal cavity, and metastases in the indicated genotypes of mice (shown as the number of mice with cancer, DTCs, or metastases out of the total number of mice analyzed) 3-13 months post-infection (transduction) with the indicated AAV vector libraries.

Figure 33:
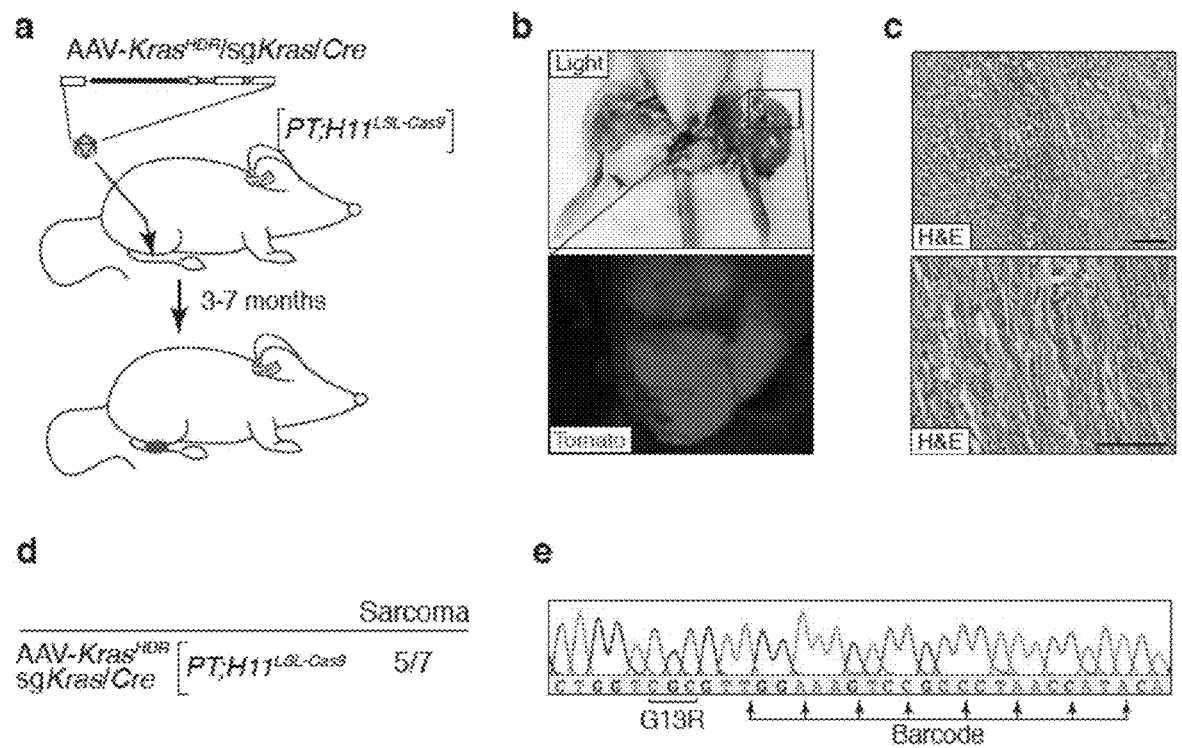

FIG. 33. HDR-mediated induction of oncogenic Kras in skeletal muscle induces sarcomas. a. Schematic of intramuscular injection of AAV-Kras$^{HDR}$/sgKras/Cre into the gastrocnemii of pT;H11$^{LSL-Cas9}$ mice to induce sarcomas. b. Representative whole mount light (top panel) and fluorescence dissecting scope (bottom panel) images of mouse gastrocnemii following injection with AAV-Kras$^{HDR}$/sgKras/Cre. Right gastrocnemius has sarcoma, while the left does not, despite efficient transduction as evidenced by widespread Tomatopositive tissue (data not shown). Scale bars=5 mm. c. Images of histological H&E sections confirming the presence of sarcoma with stereotypical histology and also invasion into the surrounding muscle. Scale bars=75 μm. d. Incidence of sarcomas in pT;H11$^{LSL-Cas9}$ mice 3-7 months after intramuscular injection of AAV-Kras$^{HDR}$/sgKras/Cre. Incidence represents the number of mice that developed sarcomas out of the total number of mice injected. One of the 7 treated mice has not yet been analyzed but did not have an obvious sarcoma six months post-infection (transduction). e. Sequencing of the Kras$^{HDR}$ locus in a sarcoma reveals a mutant Kras allele and barcode. (The sequence of (e) is set forth in SEQ ID NO: 147.)

FIG. 34. Samples and preparation for Illumina® sequencing of bulk lung tissue to quantify the size and number of lung tumors with each mutant Kras allele. a. Bulk lung tissue samples from mice intratracheally administered with AAV-Kras$^{HDR}$/sgKras/Cre for Illumina® sequencing of barcoded Kras$^{HDR}$ alleles. Sample name, mouse genotype, and dilution of AAV-Kras$^{HDR}$/sgKras/Cre are indicated. The weight, tumor number, number of dissected tumors, as well as the amount of DNA amplified and the number of PCR reactions pooled for Illumina® sequencing for each sample are shown. Repeat samples are technical replicates. ND=No data. b. Simplified pipeline for the normalization of sequencing reads from bulk lung samples using reads from a benchmark control of known cell number to enable estimation of cell number in each tumor and allow data from separate mice to be combined. (The sequence of (b) is set forth in SEQ ID NO: 148.)

Figure 35:
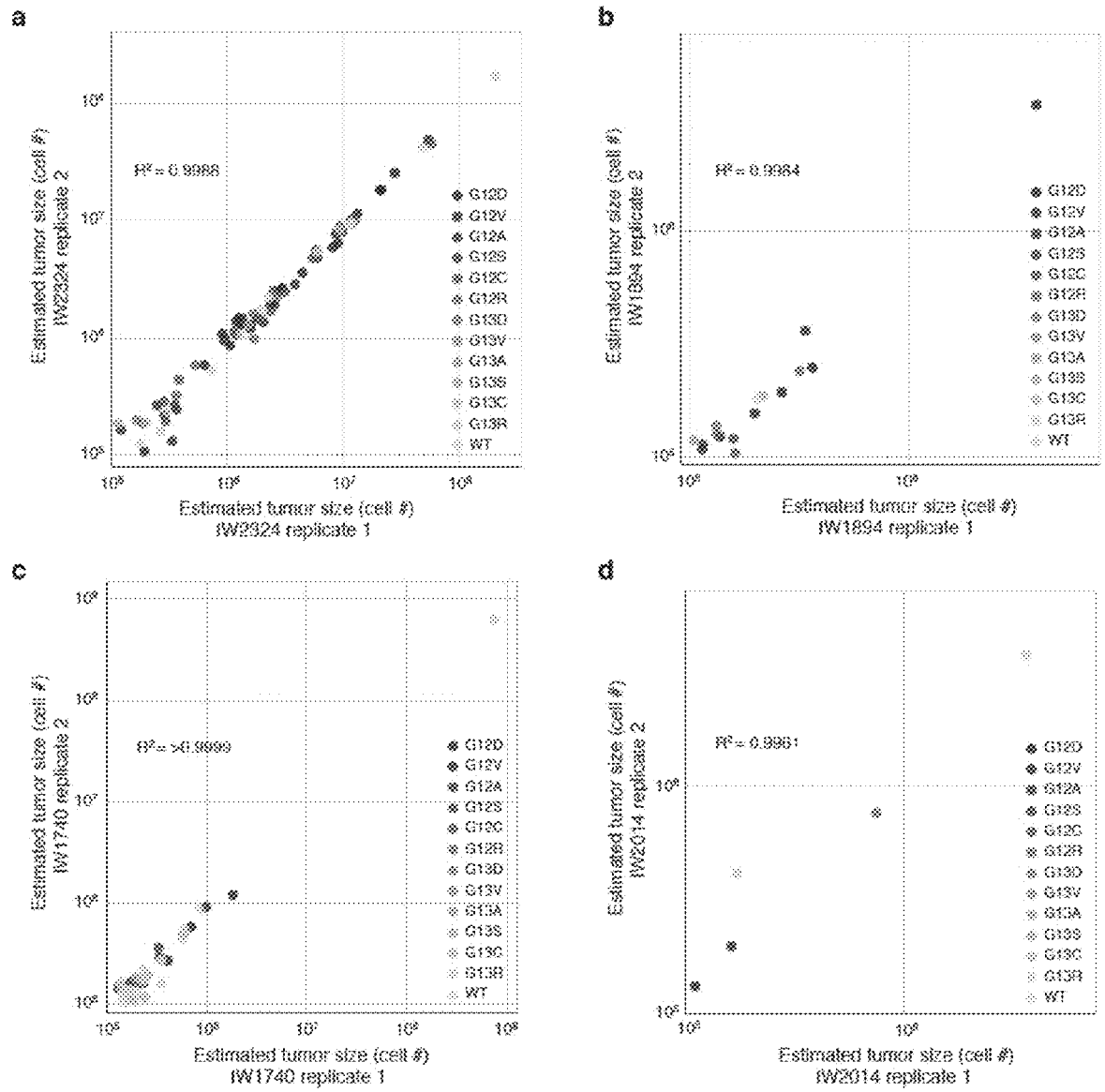

FIG. 35. Reproducibility of barcode sequencing-based parallel analysis of tumor genotype, size, and number from bulk tissue. a-d. Regression plot of individual tumors with the indicated Kras$^{HDR}$ allele and a unique barcode detected by high-throughput sequencing across technical replicates (i.e. independent DNA extraction from bulk tissue lysate and PCR reactions). Replicates in a and b were PCR amplified using primers with different multiplexing tags, but were run on the same sequencing lane. Replicates in c and d were PCR amplified using the same primers, but were run on different sequencing lanes. Mice with above average tumor burden (a,c) and below average tumor burden (b,d), as estimated measured by bulk lung weight, were analyzed to confirm the technical and computational reproducibility of this pipeline across samples of variable tumor number.

Figure 36:
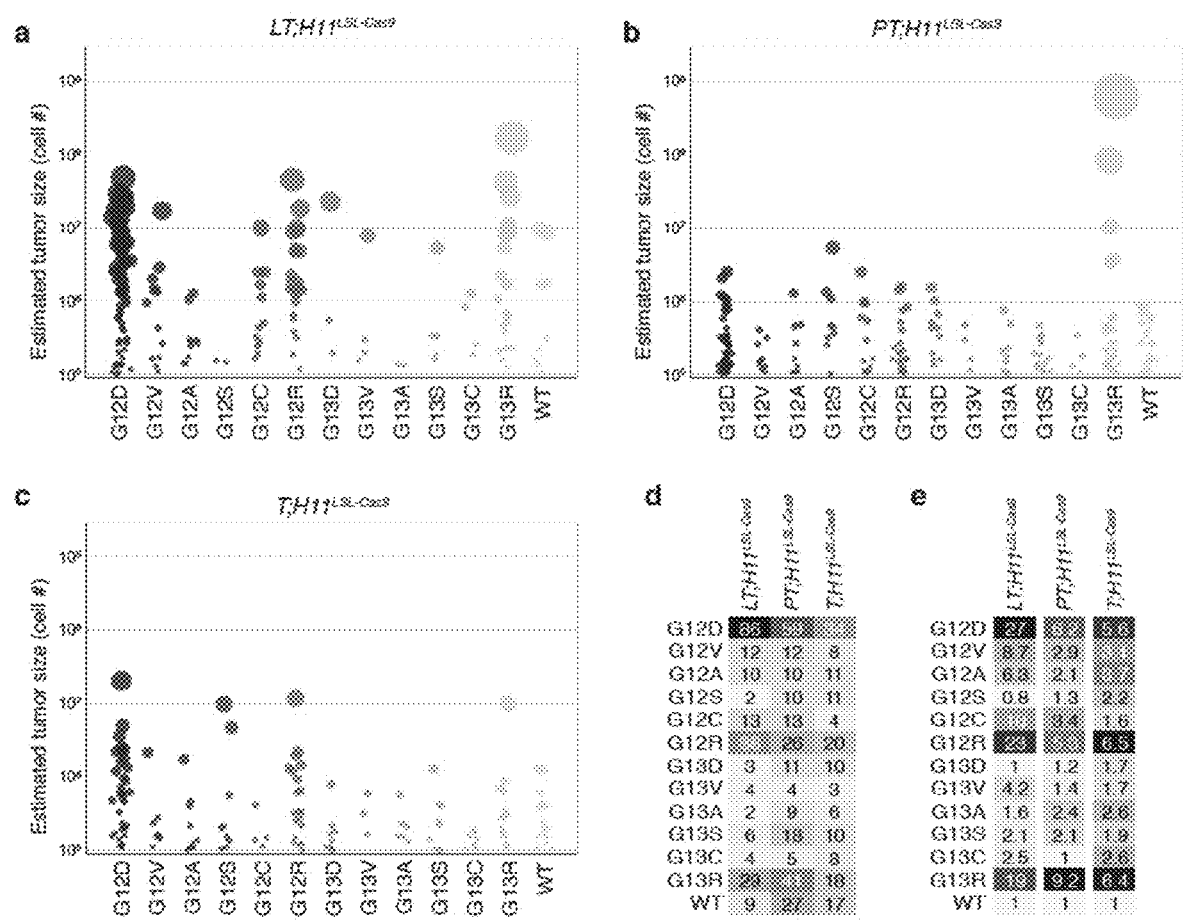

FIG. 36. High-throughput barcode sequencing of tumors from bulk lung tissue uncovers diverse numbers and sizes of tumors. a-c. Tumor size distributions of all Kras variants across all LT;H11$^{LSL-Cas9}$ (N=6) (a), PT;H11$^{LSL-Cas9}$ (N=7) (b), or T;H11$^{LSL-Cas9}$ (N=3) (c) mice. Each dot represents a tumor with a unique Kras variant-barcode pair. The size of each dot is proportional to the size of the tumor it represents, which is estimated by normalizing tumor read counts to the normalization control reads counts. Lesions harboring WT Kras$^{HDR}$ alleles are thought to be hitchhikers in tumors with oncogenic Kras$^{HDR}$ alleles (see Methods). d,e. Tables of raw (d) and normalized (e) number of tumors harboring each Kras variant across each genotype (including tumors with each variant that were identified by individual tumor dissection and analysis). In e, the number of tumors harboring each Kras variant is normalized to the initial representation of each variant in the AAV plasmid library and to the number of lesions harboring a WT allele within the same genotype. Note that the color intensity scale of the heatmaps in e is unique to each genotype for ease of comparison.

Figure 37:
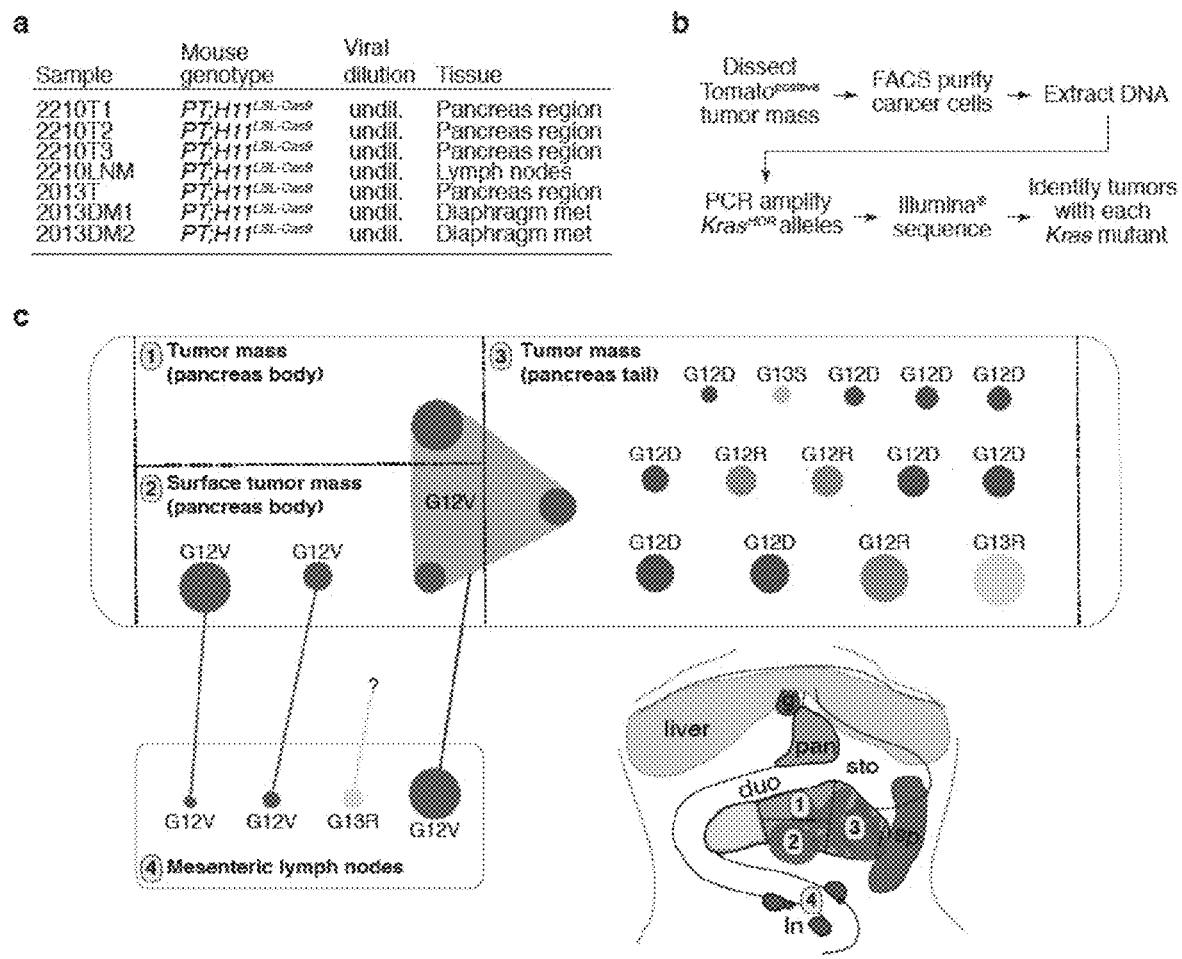

FIG. 37. High-throughput sequencing of pancreatic tumor masses and metastases identifies oncogenic Kras mutants. a. Bulk pancreas tissue and metastasis samples from mice administered with AAV-Kras$^{HDR}$/sgKras/Cre by retrograde pancreatic ductal injection for Illumina sequencing of barcoded Kras$^{HDR}$ alleles. Sample name, mouse genotype, viral dilution, and tissue are indicated. The Kras$^{HDR}$ alleles present in distinct regions of the primary tumor masses as well as metastases were analyzed by Illumina® sequencing after FACS isolating FSC/SSC-gated viable cancer cells (DAPI/CD45/CD31/F4-80/Ter119$^{negative}$) from these samples. b. Analysis pipeline to identify Kras$^{HDR}$ alleles in AAV-Kras$^{HDR}$/sgKras/Cre-initiated tumor masses within the pancreata of PT;H11$^{LSL-Cas9}$ mice. c. Multi-region sequencing of a large pancreatic tumor mass in a single AAV-Kras$^{HDR}$/sgKras/Cre-treated PT;H11$^{LSL-Cas9}$ mouse uncovered a diverse spectrum of mutant Kras alleles and linked primary tumors with their metastatic offspring. Each dot represents a tumor with the indicated Kras variant and a barcode unique to the indicated sample (labeled 1-4). Dots connected across different primary tumor samples (labeled 1-3) shared the same Kras variant-barcode pair, and are thus presumably regions of the same primary tumor that were present in multiple samples. A colored line link primary tumors and lymph node metastases harboring the same Kras variant-barcode pair, indicating a clonal relationship. The size of each dot is scaled according to the size of the tumor it represents (diameter of the dot=relative size$^{1/2}$). Since the size of pancreatic tumors is not normalized to a control, tumor sizes can only be compared to other tumors within the same sample. Thus, the largest tumors within each sample have been scaled to the same standard size. g=gallbladder, sto=stomach, duo=duodenum, pan=pancreas, sp=spleen, ln=mesenteric lymph nodes.

Figure 4:
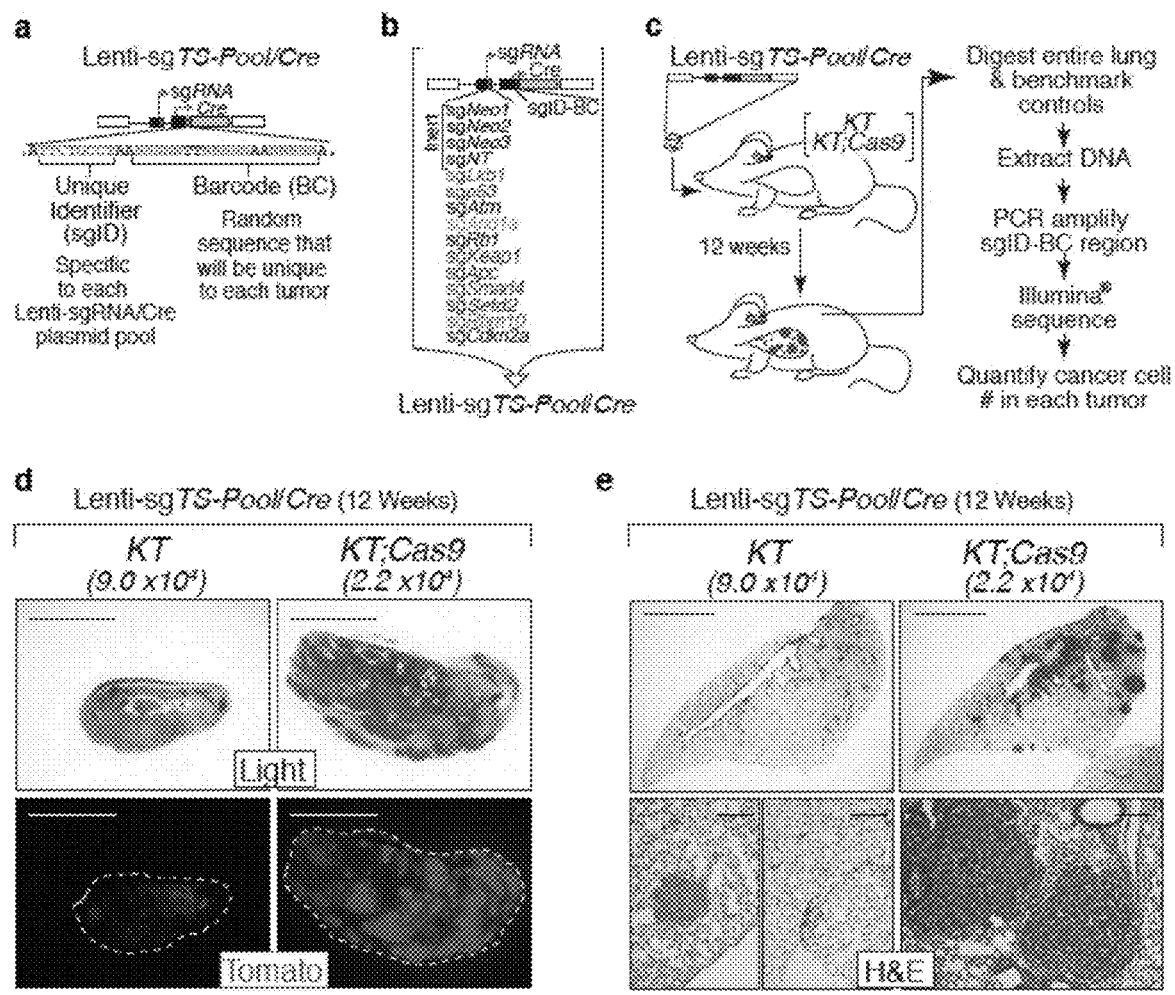
FIG. 4. Rapid quantification of tumor suppressor phenotypes using Tuba-seq and multiplexed CRISPR/Cas9 mediated gene inactivation. a, Schematic of the Lenti-sgTS-Pool/Cre vector that contain a two-component barcode with an 8-nucleotide "sgID" sequence linked to each sgRNA as well as a random 15 nucleotide random barcode (BC). (The two-component barcode sequence is set forth in SEQ ID NO: 109.) b, Lenti-sgTS-Pool/Cre contains four vectors with inert sgRNAs and eleven vectors targeting known and candidate tumor suppressor genes. Each sgRNA vector contains a unique sgID and a random barcode. NT=Non-Targeting. c, Schematic of multiplexed CRISPR/Cas9-mediated tumor suppressor inactivation coupled with Tuba-seq to assess the function of each targeted gene on lung tumor growth in vivo. Tumors were initiated with Lenti-sgTS-Pool/Cre virus in KT and KT;H11$^{LSL-Cas9}$ (KT;Cas9) mice. d, Bright field (top) and fluorescence dissecting scope images (bottom) of lung lobes from KT and KT;Cas9 mice 12 weeks after tumor initiation with Lenti-sgTS-Pool/Cre. Lung lobes are outlined with white dashed lines in the fluorescence images. Viral titer is indicated. Scale bars=5 mm. e, Histology confirms that KT mice have hyperplasias and small tumors, while KT;Cas9 mice have much larger tumors. Viral titer is indicated. Top scale bars=3 mm. Bottom scales bars=500 μm.
Figure 38:
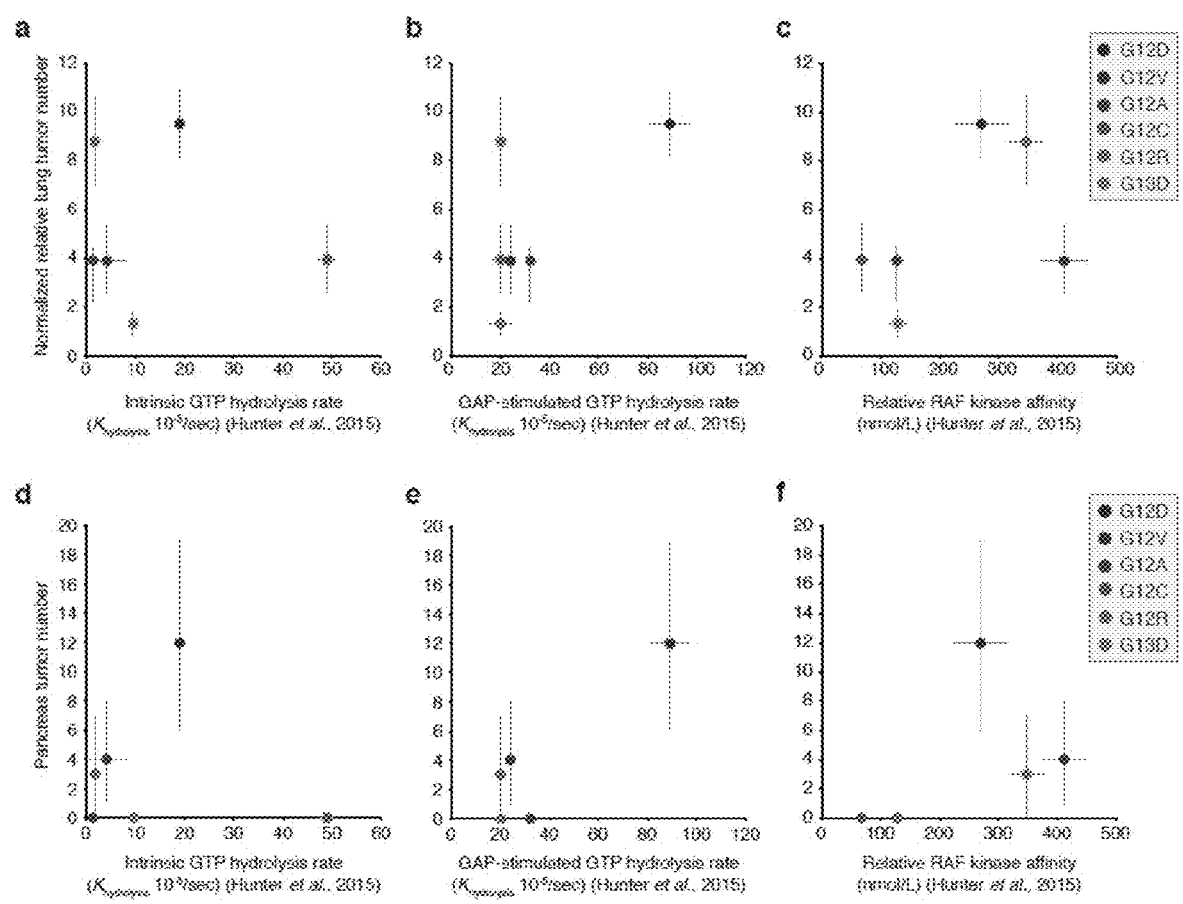

FIG. 38. Relationship between the in vivo oncogenicities and biochemical behaviors of Kras mutants. a-c. Relative number of lung tumors in mice transduced with AAV-Kras$^{HDR}$/sgKras/Cre (see FIG. 4b) as a function of the indicated biochemical property reported in Hunter et al., 2015. Relative lung tumor number is normalized to the initial representation of each Kras variant in the AAV-Kras$^{HDR}$/sgKras/Cre plasmid pool. Vertical bars represent the 95% confidence interval for the normalized relative lung tumor number. Horizontal bars represent the standard error of the mean of three replicate experiments as described in Hunter et al., 2015. P120GAP was used to determine GAP-stimulated GTP hydrolysis rates (Hunter et al., 2015). d-f. Number of pancreatic tumors in mice transduced with AAV-Kras$^{HDR}$/sgKras/Cre (see FIG. 4f) as a function of the indicated biochemical property reported in Hunter et al., 2015. Vertical bars represent the 95% confidence interval for pancreas tumor number. Horizontal bars represent the standard error of the mean of three replicate experiments as described in Hunter et al., 2015. P120GAP was used to determine GAP-stimulated GTP hydrolysis rates (Hunter et al., 2015).

Figure 39:
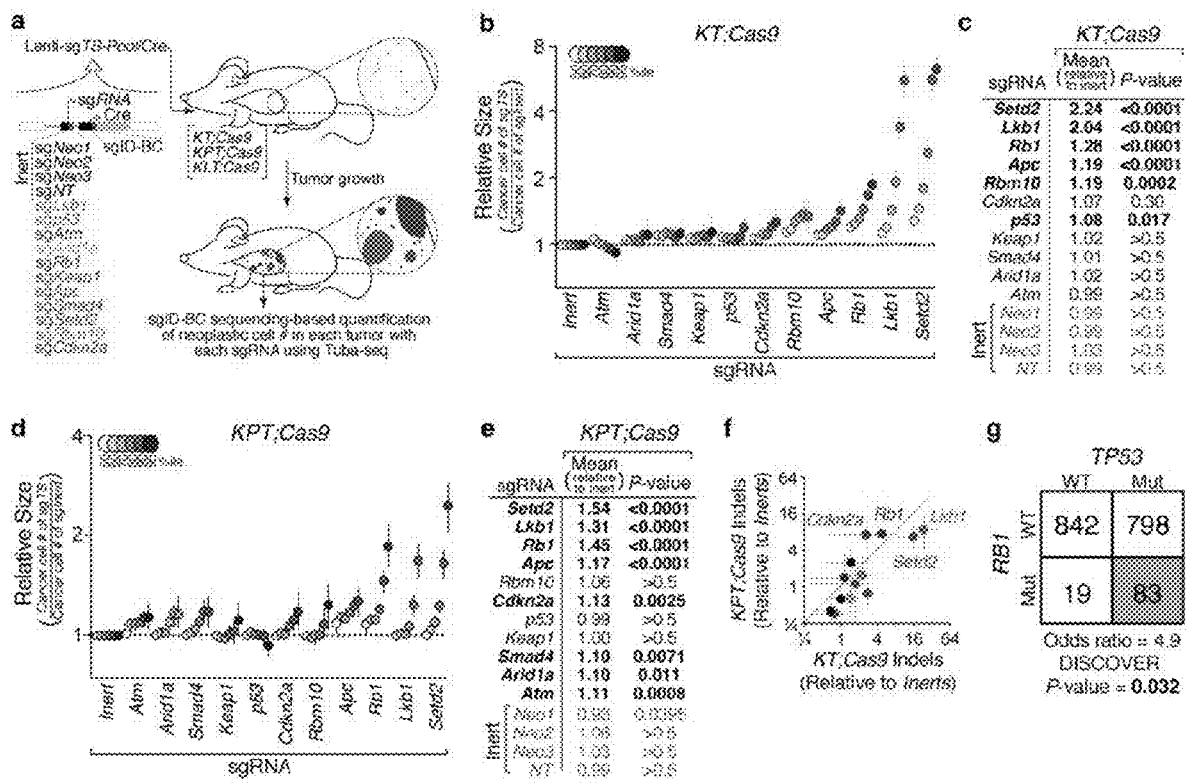

FIG. 39. Investigating combined genetic alterations: p53 deficiency alters the growth effects of tumor suppression in KrasG12D-driven lung tumors in vivo. a. Tuba-seq approach to study combinatorial tumor suppressor inactivation in vivo. Tumors were initiated with Lenti-sgTS-Pool/Cre (containing four inert sgRNA vectors and eleven vectors targeting known and candidate tumor suppressor genes) in three different genetically-engineered mouse backgrounds: Kras$^{LSL-G12D/+}$; Rosa26$^{LSL-tdTomato}$;H11$^{LSL-Cas9}$ (KT;Cas9), KT;p53$^{flox/flox}$;Cas9 (KPT;Cas9), and KT;Lkb1$^{flox/flox}$;Cas9 (KLT;Cas9). Each sgRNA vector contains a unique sgID and a random barcode, which was used to quantify individual tumor sizes via deep sequencing. b. Analysis of the relative tumor sizes in KT;Cas9 mice 15 weeks after tumor initiation. Relative size of tumors at the indicated percentiles is merged data from 10 mice, normalized to the average size of sgInert tumors. Error bars throughout this study denote 95% confidence intervals determined by bootstrap sampling. Percentiles that are significantly different from sgInert are in color. c. Estimates of mean tumor size, assuming a log normal tumor size distribution, identified sgRNAs that significantly increased growth in KT;Cas9 mice. Bonferroni-corrected, bootstrapped P-values are shown. sgRNAs with P-values <0.05 are bold. d,e. Same as b,c, except for merged data from 12 KPT;Cas9 mice. f. Abundance of indels at targeted loci relative to median of genome-targeting inert sgRNAs Neo1-3. Coloring according to a. g. Functional mutations in TP53 and RB1 in human lung adenocarcinomas from TCGA and GENIE datasets (N=1792). RB1 and TP53 alterations co-occur.

Figure 40:
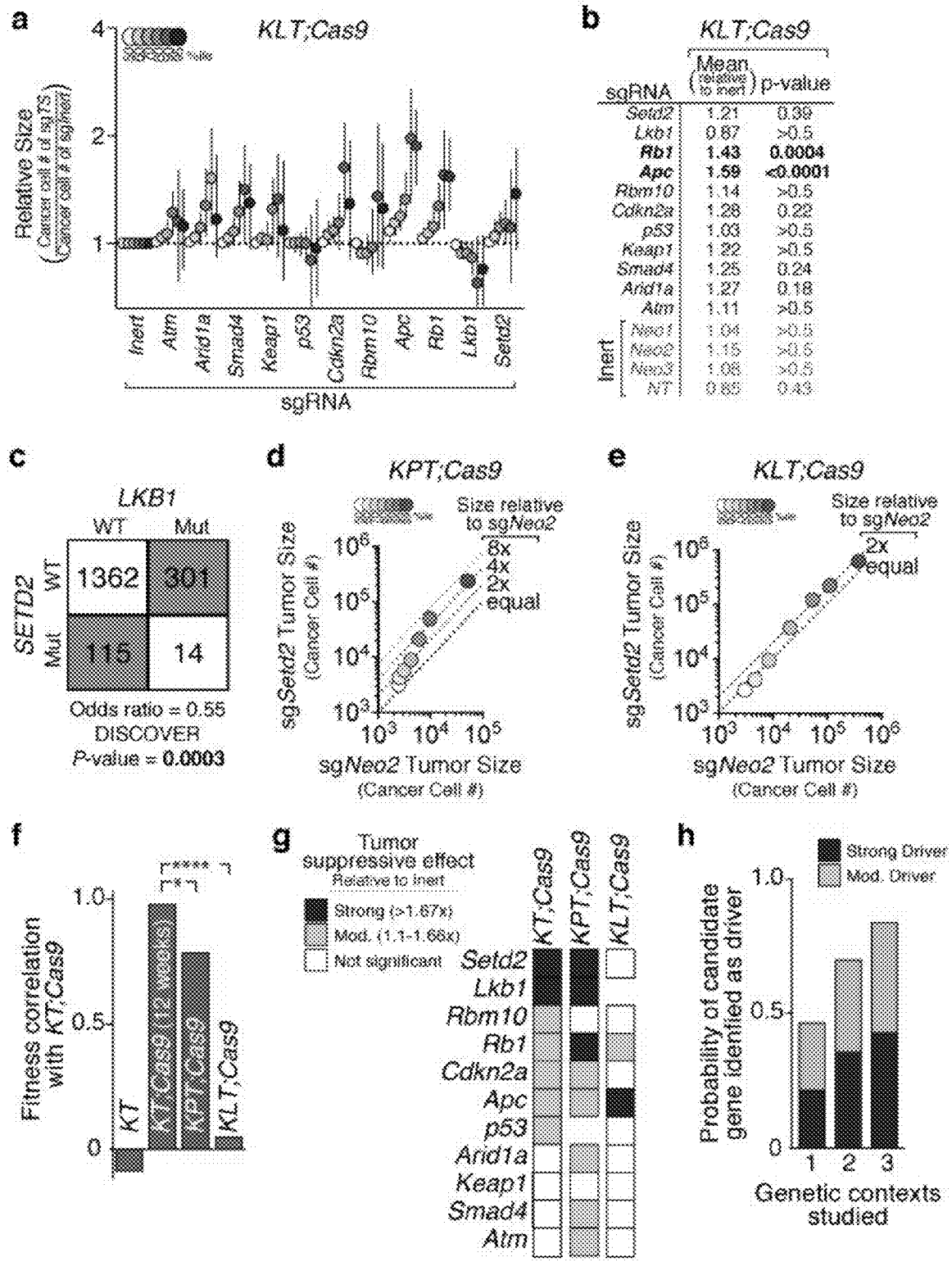

FIG. 40. Investigating combined genetic alterations: Attenuated effects of tumor suppressor inactivation in Lkb1-deficient tumors further highlights a rugged fitness landscape. a. Tumor sizes at the indicated percentiles for each sgRNA relative to the average of sgInert-containing tumors at the same percentiles. Merged data from 13 KT;Lkb1$^{flox/flox}$;Cas9 (KLT;Cas9) mice 15 weeks after tumor initiation with Lenti-sgTS-Pool/Cre is shown. Percentiles that are significantly different from sgInert are in color. b. Estimates of mean tumor size, assuming a log normal tumor size distribution, identified sgRNAs that significantly increase growth in KLT;Cas9 mice. Bonferroni-corrected, bootstrapped P-values are shown. sgRNAs with P-values <0.05 are bold. c. Mutual exclusivity of LKB1 (STK11) and SETD2 mutations in human lung adenocarcinomas from TOGA and GENIE datasets (N=1792). d. Tumor sizes in KPT;Cas9 mice with Lenti-sgSetd2/Cre-initiated tumors (N=7) versus KPT;Cas9 mice with Lenti-sgNeo2/Cre initiated tumors (N=3). Lenti-sgSetd2/Cre-initiated tumors have an LN mean that is 2.4 times higher than Lenti-sgNeo2/Cre-initiated tumors and a 95$^{th}$ percentile tumors size that is 4.6 times higher. e. Tumor sizes in KLT;Cas9 mice with Lenti-sgSetd2/Cre-initiated tumors (N=7) versus KLT;Cas9 mice with Lenti-sgNeo2/Cre initiated tumors (N=5). The relative LN Mean and relative 95$^{th}$ percentile are 2.2 and 2.8, which are both significantly less than in FIG. 2d (P<0.04, and P<0.0001 respectively). f. Pearson correlations of fitness effect of tumor suppressors (determined by LN mean) across genetic backgrounds. sgp53 and sgLkb1 growth rates are excluded in KPT;Cas9 and KLT;Cas9 mice. *P<0.05, ****P<0.0001. g. Differential effect of each tumor suppressor gene within the context of oncogenic Kras-driven lung tumors, as well as with coincident p53- or Lkb1-deficiency. 95$^{th}$ percentiles that significantly deviate from sgInert tumors are shown in blue. h. Likelihood of identifying candidate tumor suppressors as a driver (as defined in g) versus the number of genetic backgrounds studied. All genetic contexts were averaged.

FIG. 41. The current state of genetically-engineered mouse models of lung cancer for the analysis of the putative tumor suppressor alterations in this study and the frequency of these genomic alterations in human lung adenocarcinoma. a. Summary of data from published studies in which the putative tumor suppressor genes studied here were inactivated in the context of oncogenic Kras-driven lung cancer models, with or without inactivation of p53 or Lkb1. b. The percent of tumors with potentially inactivating alterations (frameshift or non-synonymous mutations, or genomic loss) in each tumor suppressor gene for all tumors (All) as well as for tumors with potentially inactivating alterations in TP53 (TP53$^{mut}$) or LKB1 (LKB1$^{mut}$). The percent of tumors with each type of alteration is indicated. Data is shown for two clinical cancer genomics studies: The Cancer Genome Atlas (TOGA, 2014), and the Genomics Evidence Neoplasia Information Exchange (GENIE, 2017) database.

Figure 42:
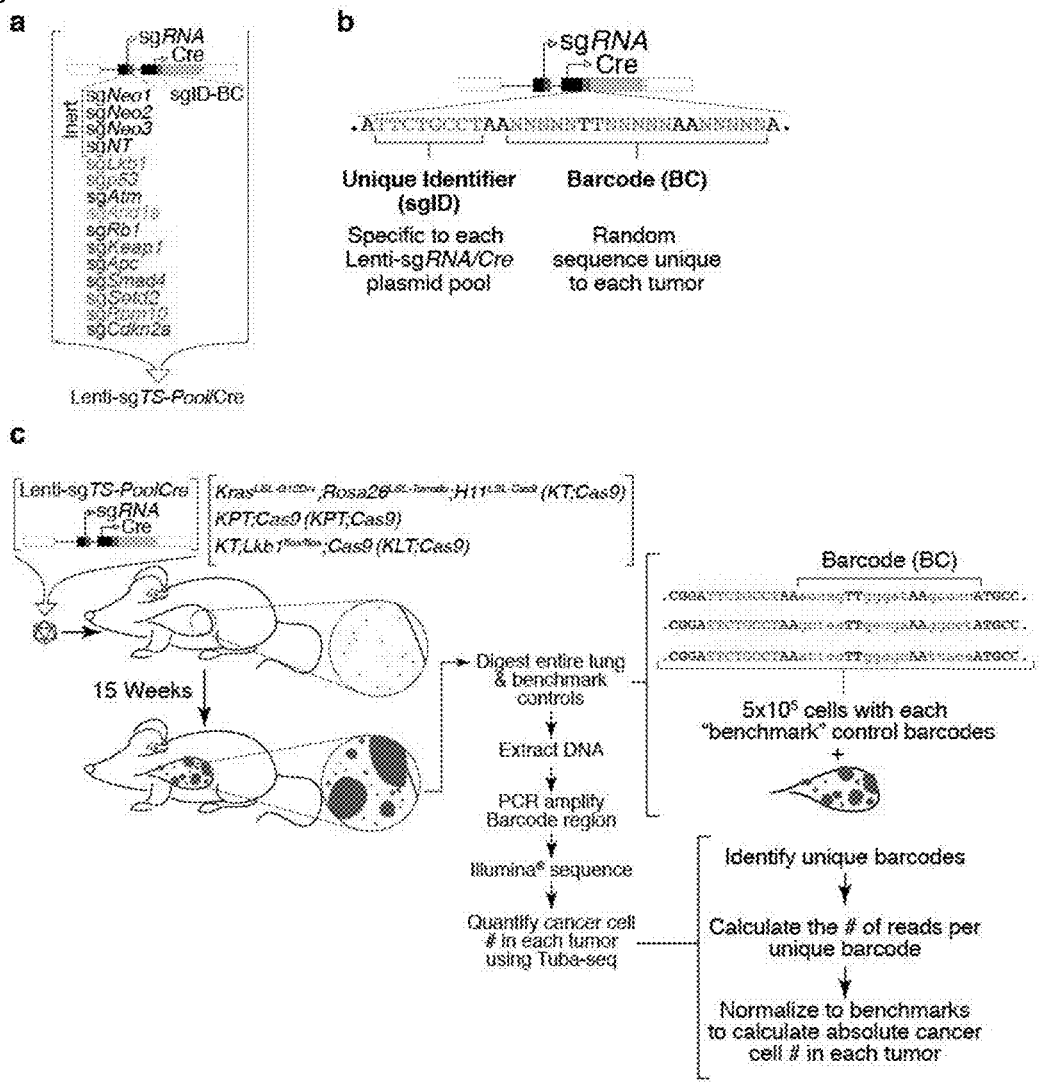

FIG. 42. Description of multiplexed lentiviral vectors, tumor initiation, and Tuba-seq pipeline to quantify tumor size distributions in vivo. a. Lenti-sgTS-Pool/Cre contains four vectors with inert sgRNAs and eleven vectors with tumor suppressor gene targeting sgRNAs. Each sgRNA vector contains a unique sgID and a random barcode. NT=Non-Targeting. b. Schematic of the sgID-barcode region of the vectors in Lenti-sgTS-Pool/Cre. Lenti-sgTS-Pool/Cre contains vectors with fifteen different 8-nucleotide unique identifiers (sgIDs) which link a given sgID-barcode read to a specific sgRNA. These vectors also contains a 15-nucleotide random barcode element. This double barcode system allows identification of individual tumors, as well as the sgRNA in the vector that initiates each tumor. (The sequence of the sgID-barcode region is set forth in SEQ ID NO: 109.) c. Transduction of lung epithelial cells with the barcoded Lenti-sgTS-Pool/Cre pool initiates lung tumors in genetically engineered mouse models with (1) a Cre-regulated oncogenic KrasG12D (Kras$^{LSL-G12D/+}$) allele, (2) a Cre reporter allele (Rosa26$^{LSL-Tomato}$), (3)) a Cre-regulated Cas9 allele (H11$^{LSL-Cas9}$), as well as (4) homozygous floxed alleles of either p53 or Lkb1. Lentiviral vectors stably integrate into the genome of the transduced cell. Tumors were initiated in KT;Cas9, KPT;Cas9, and KLT;Cas9 mice to generate 31 different genotypes of lung tumors. Mice were analyzed after 15 weeks of tumor growth. Genomic DNA was extracted from whole lungs, after the addition of barcoded "bench-mark" cell lines, the sgID-barcode region was PCR amplified, deep-sequenced, and analyzed to determine the relative expansion of each uniquely barcoded tumor using the Tuba-seq pipeline. (The sequences of the sgID-barcode regions in (c) from top to bottom are set forth in SEQ ID NOs:110-112.)

Figure 43:
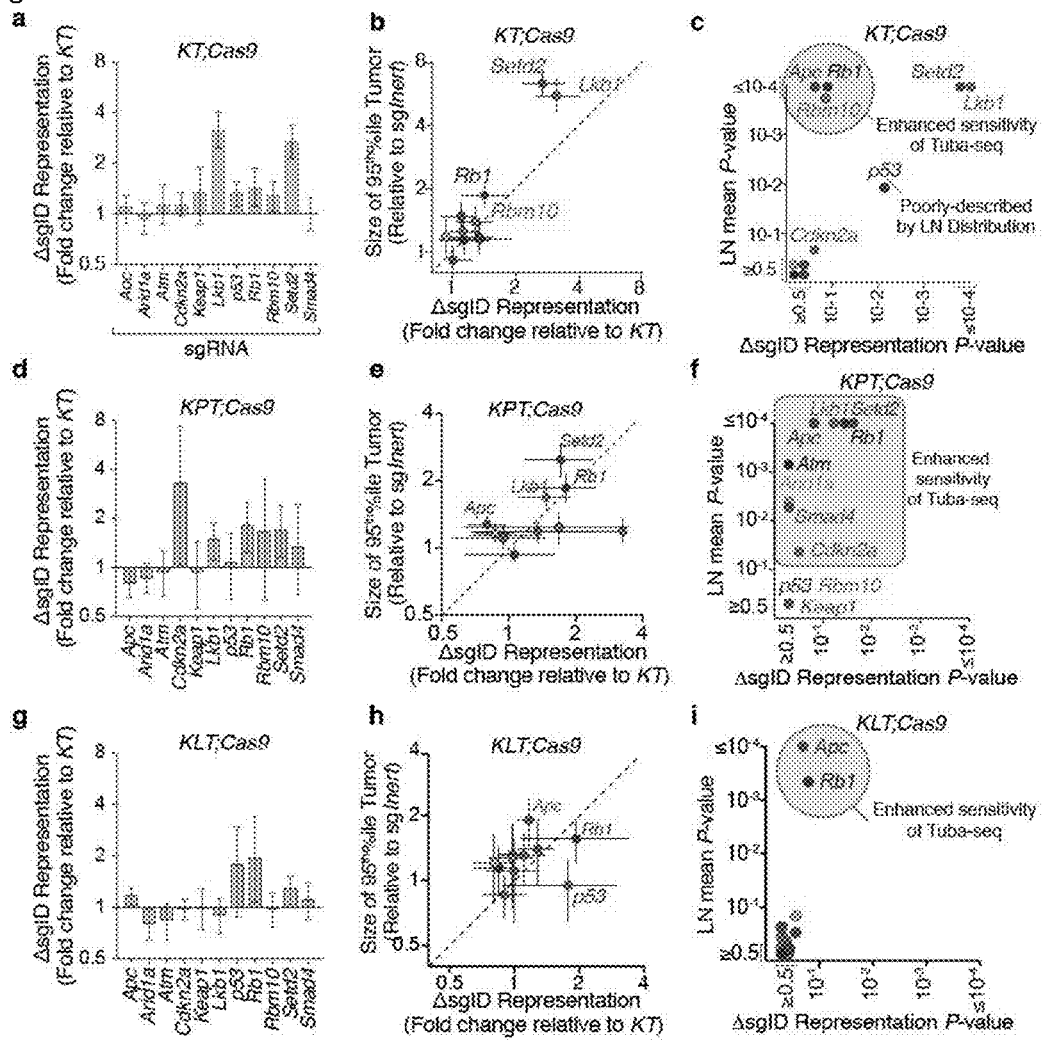

FIG. 43. Tumor suppression in Kras$^{G12D}$-driven lung adenocarcinoma in vivo. a. Fold change in sgID representation (ΔsgID representation) in KT;Cas9 mice relative to KT mice, which lack Cas9 and therefore should not expand relative to sgInert. Several sgRNAs (sgIDs) increase in representation, reflecting the increased growth of tumors with inactivation of the targeted tumor suppressor genes. Means and 95% confidence intervals are shown. b,c. The ability to detect tumor suppressive effects is improved by analyzing individually-barcoded tumors compared to bulk sgRNA representation (ΔsgID representation). (b) Analysis of the relative size of the 95$^{th}$ percentile tumor with each sgRNA identifies somewhat similar estimates of relative tumor size as bulk ΔsgID representation, which exhibits wider confidence intervals. (c) P-value of the Log-Normal mean (LN mean) measure of relative tumor size versus P-value ΔsgID representation. Because individual tumor sizes are measured and then properly normalized to eliminate exogenous sources of noise, both the 95$^{th}$ percentile and LN Mean metrics identify functional tumor suppressors with greater confidence and precision. p53 loss is an exception, as its growth effects are poorly described by a Log-Normal distribution. All P-values are two-sided and obtained via 2×10$^6$ Bootstrapping permutation tests and a Bonferroni-correction for the number of investigated tumor suppressors. d-f. Same as in a-c, except for growth effects in KPT;Cas9 mice. Fold change is relative to KT mice, while 95$^{th}$ percentile and LN Mean size estimates are relative to KPT;Cas9 internal sgInert controls. g-i. Same as in a-c, except for growth effects in KLT;Cas9 mice. No tumor suppressors would have been identified without Tuba-seq.

Figure 44:
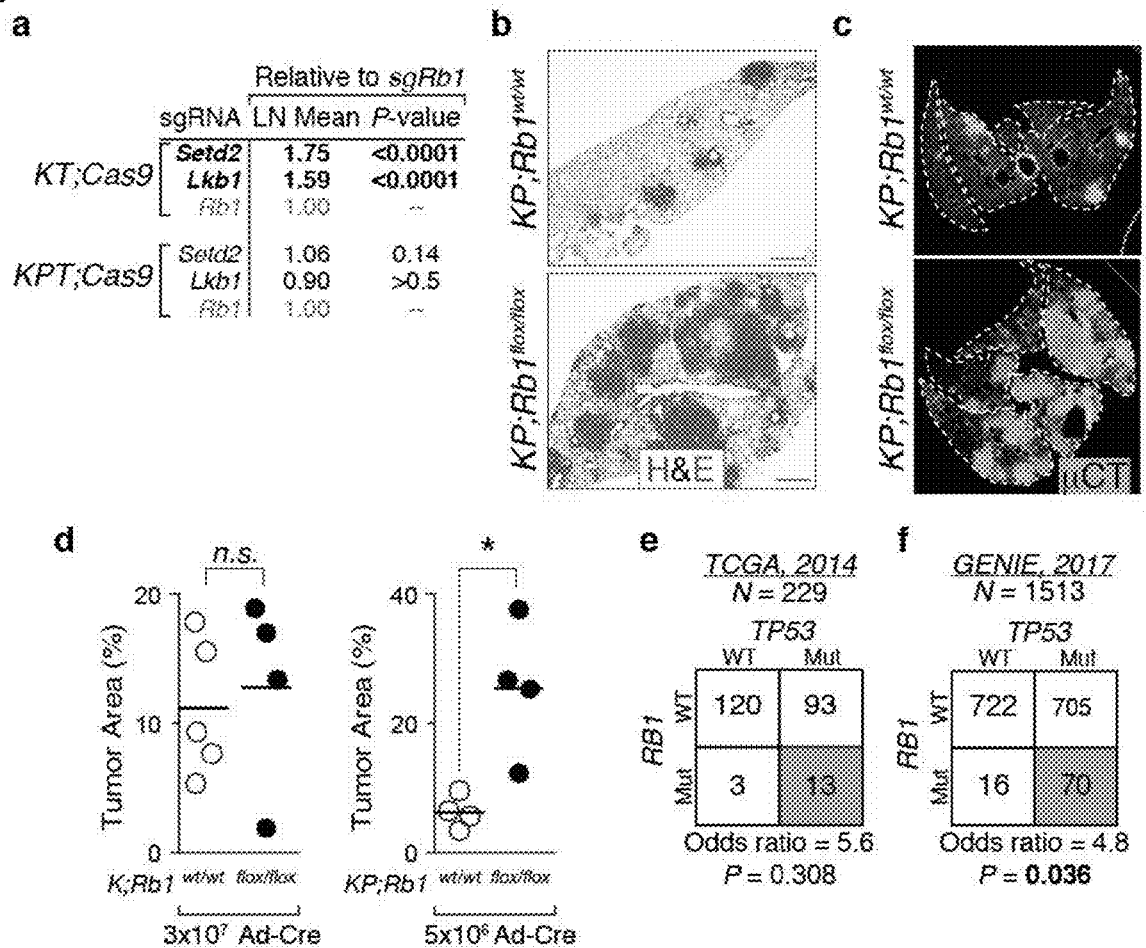

FIG. 44. Rb and p53 tumor suppressor cooperativity in lung adenocarcinoma identified by Tuba-seq, confirmed in a mouse model using Cre/lox regulated alleles, and supported by the co-occurrence of RB1 and TP53 mutations in human lung adenocarcinoma. a. Relative LN Mean size of sgSetd2, sgLkb1 and sgRb1 tumors. Rb1 inactivation increase tumor size less that Setd2 or Lkb1 inactivation in the p53-proficient KT;Cas9 background. Conversely, Rb1 inactivation increases tumor size to a similar extent as Setd2 or Lkb1 inactivation in the p53-deficient KPT;Cas9 background. P-values test null hypothesis of similar LN Mean to sgRb1. $P<0.05$ in bold. b. H&E staining of representative lung lobes from KP and KP;Rb1$^{flox/flox}$ mice with tumors initiated with Adeno-CMV/Cre. Mice were analyzed 12 weeks after tumor initiation. Scale bars=500 μm. c. Representative ex vivo μCT images of the lungs from KP and KP;Rb1$^{flox/flox}$ mice are shown. Lung lobes are outlined with a dashed white line. d. Quantification of percent tumor area in K;Rb1$^{wt/wt}$, K;Rb1$^{flox/flox}$, KP;Rb1$^{wt/wt}$, and KP;Rb1$^{flow/flox}$ mice. Histological quantification confirms that Rb1-deletion increases tumor burden more dramatically in p53-deficient tumors. * p-value <0.05, n.s.=not significant. Titer of Ad-Cre is indicated. e,f. Co-occurence of RB1 and TP53 mutations in two human lung adenocarcinoma genomics datasets: (e) TCGA 2014 dataset, and (f) the GENIE consortium 2017. P-values were calculated using the DISCOVER statistical independence test for somatic alterations.

Figure 45:
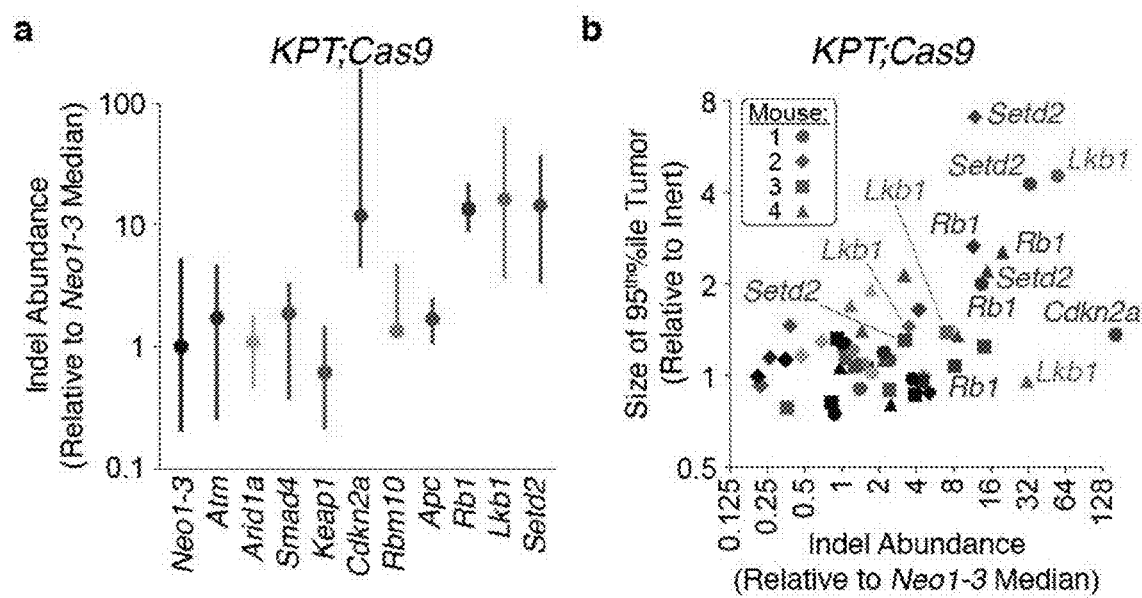

FIG. 45. Deep sequencing of targeted genomic loci confirms creation of indels at all targeted loci and shows selective expansion of cancer cells with indels in the strongest tumor suppressor genes. a. Indel abundance in each region targeted by sgRNAs, as determined by deep sequencing of total lung DNA from the targeted regions of four KPT;Cas9 mice. Indel abundance is normalized to the median abundance of sgNeo1, sgNeo2, and sgNeo3. Error bars denote range of abundances observed, while dots denote median. Indels were obseverved in all targeted regions. sgp53 is not shown, as its target site is deleted by Cre-mediated recombination of the p53$^{floxed}$ alleles. b. Indel abundance as described in (a) versus the 95th percentile tumor size determined by Tuba-seq (as described in FIG. 1d). Each dot represents a single sgRNA in an individual mouse and each mouse is represented by a unique shape. Indel abundance correlated with Tuba-seq size profiles (as expected), however indel abundance does not measure individual tumor sizes and exhibits greater statistical noise. The largest single tumor in this entire analysis, as determined by Tuba-seq, was an sgCdkn2a tumor that similarly appeared as an outlier in the indel analysis—further corroborating faithful analysis of genetic events by Tuba-seq.

Figure 46:
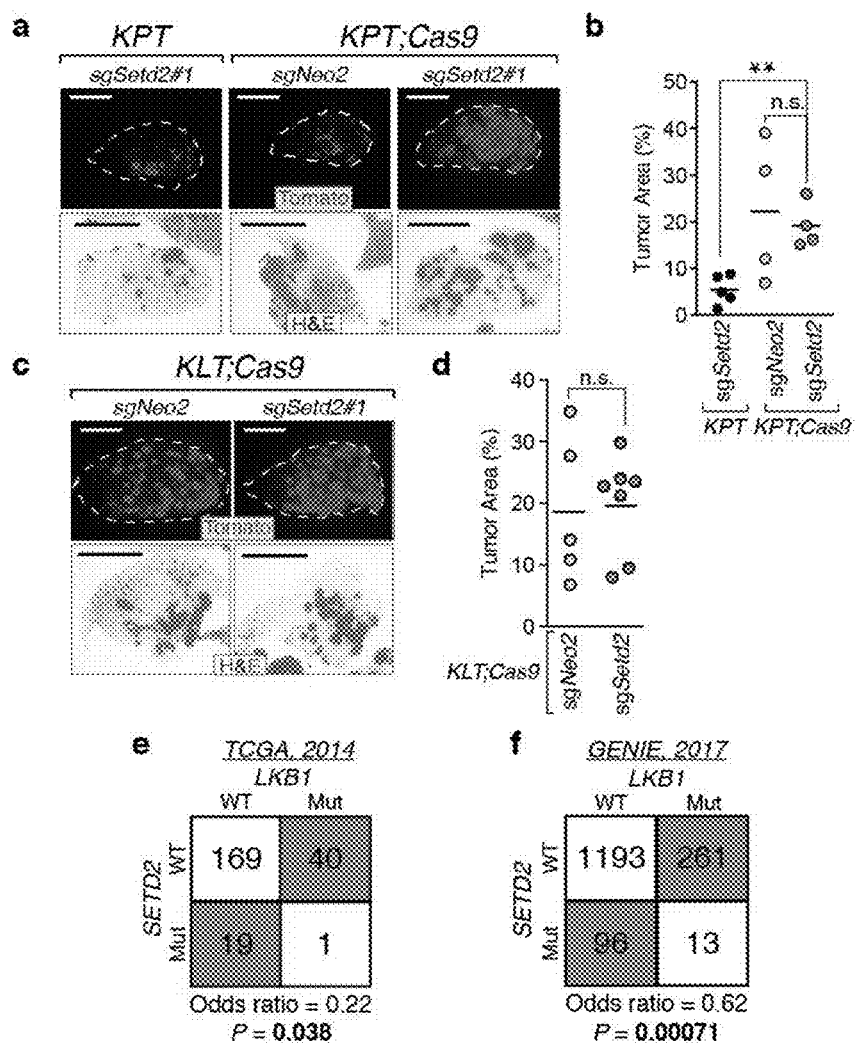

FIG. 46. Validation of the redundancy between Setd2 and Lkb1 in mouse models and in human lung adenocarcinomas. a. Fluorescence dissecting scope images (top) and H&E stained section (bottom) of lung lobes from KPT and KPT; Cas9 mice with Lenti-sgSetd2#1/Cre or Lenti-sgNeo2/Cre initiated tumors. Mice were analyzed after 9 weeks of tumor growth. Lung lobes are outlined with a white dashed line in fluorescence dissecting scope images. Top scale bars=5 mm. Bottom scale bars=4 mm. b. Quantification of percent tumor area in KPT;Cas9 mice with Lenti-sgSetd2#1/Cre or Lenti-sgNeo2/Cre initiated tumors, and KPT mice with Lenti-sgSetd2#1/Cre initiated tumors. Each dot represents a mouse and horizontal bars are the mean. There is an increase in tumor area between KPT;Cas9 and KPT mice with tumors initiated with the same virus, but no difference between KPT;Cas9 mice tumors initiated with Lenti-sgSetd2#1/Cre and those initiated with Lenti-sgNeo2/Cre, presumably due to high mouse-to-mouse variability. Because these lentiviral vectors were barcoded, we performed Tuba-seq analysis of these mice to quantify the size of induced tumors. sgSetd2 increased tumor sizes in KPT;Cas9 relative to sgNeo2. ** $P<0.01$, n.s. is not significant. c,d. Same as a,b except for KLT;Cas9 mice with Lenti-sgSetd2#1/Cre or Lenti-sgNeo2/Cre initiated tumors. Mice were analyzed after 9 weeks of tumor growth. Top scale bars=5 mm. Bottom scale bars=4 mm. e,f. The co-occurrence of SETD2 and LKB1 (HGNC name STK11) in two human lung adenocarcinoma genomics datasets: (e) TOGA 2014 dataset[14] (N=229 patients), and (f) the GENIE Consortium (N=1563 patients). Two-sided P-values were calculated using the DISCOVER statistical independence test.

FIG. 47. Correspondence of Tuba-seq fitness measurements to human genomic patterns. a. Relative fitness measurements and human co-occurrence rates of the nineteen pairwise interactions that we investigated. LN Mean Ratio is the ratio of relative LN Mean (sgTS/sgInert) within the background of interest divided by the mean relative LN mean of all three backgrounds. Background rate can be either an unweighted average of the three backgrounds (raw), or weighted by each background's rate of occurrence in human lung adenocarcinoma (weighted). *OR="Odds Ratio" of the co-occurrence rate of a gene pair within the human data. One sided P-values of human co-occurrence rates (>0.5 suggest mutual exclusivity) were determined using the DISCOVER test. Combined P-values generated using Stouffer's Method (Methods). $P<0.025$ and $P>0.975$ are in bold. Fitness measurements and co-occurrence rates generally correspond (Spearman's r=0.50, P-value=0.03 for weighted LN Mean Ratio; r=0.4 for unweighted). b. Graphical summary of fitness measurements and co-occurrence rates from a. Human Genetics Cooperativity was defined by a Combined Odds Ratio >1 and Redundant <1. Cooperativity for Tuba-seq data denotes a LN Mean Ratio >1 and Redundant <1. c. Number of statistically-significant genetic interactions suggested from a pan-cancer analysis of twenty-one tumor types. Tumor types abbreviations are borrowed from TCGA. Lung adenocarcinoma (LUAD) is black and is predicted to contain a quantity of genetic interactions that is similar to the median, suggesting that the ruggedness of the fitness landscape studied here may be representative of cancer evolution in general.

Figure 48:
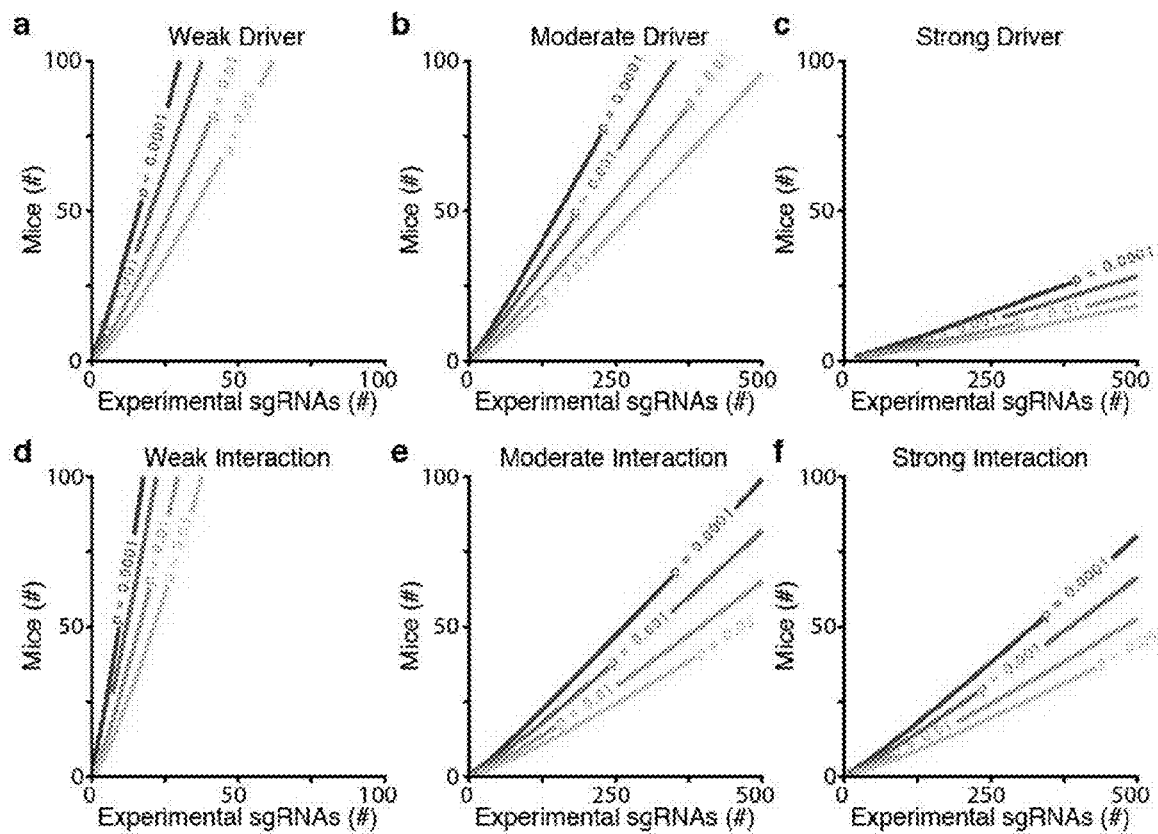

FIG. 48. Power analysis of larger genetic surveys. By assuming log normal tumor size distributions, the statistical power of Tuba-seq to detect driver growth effects and non-additive driver interactions in larger genetic surveys can be projected. Future experiments could utilize larger mouse cohorts and larger pools of sgRNAs targeting putative tumor suppressors. In all hypothetical experiments, the Lenti-sgTS-Pool/Cre titers and fraction of the pool with inert sgRNAs (for normalization) were kept consistent with our original experiments. a. P-value contours for the confidence in detecting a weak driver (parameterized by the sgCdkn2a distribution in KT;Cas9 mice). Any experimental setups above a contour detects weak drivers with a confidence greater than or equal to the P-value of the contour. b,c. Same as in a, except for moderate and strong drivers respectively (parameterized by sgRb1 and sgLkb1 in KT;Cas9 mice). sgRNA pool size is extended to 500 targets (instead of 100 targets in a pool) because larger screens are possible when investigating genes with these effect strengths. d-f. Same as in a-c, except for driver interactions. Driver interactions (LN Mean Ratio) are defined as a ratio of driver growth rates (sgTS/sgInert in background #1)/(sgTS/sgInert in background #2) that were statistically different from the null hypothesis of one. (d) A weak driver interaction parameterized by Rbm10-p53 (7% effect size). (e) A moderate driver interaction parameterized by Rb1-p53 (13% effect size). (f) A strong driver interaction parameterized by Setd2-Lkb1 (68% effect size).

DETAILED DESCRIPTION

Before the present methods and compositions are described, it is to be understood that this invention is not limited to a particular method or composition described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells (e.g., a population of such cells) and reference to "the protein" includes reference to one or more proteins and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and Compositions

As summarized above, compositions and methods are provided for measuring population size for a plurality of clonal cell populations in the same individual. As an example, in some cases a subject method is a method of measuring tumor size (e.g., the number of neoplastic cells within a tumor) for a plurality of clonally independent tumor cell populations (e.g., different tumors) of the same individual. In some cases a subject method includes: (a) contacting a tissue of an individual with a plurality of cell markers that are heritable and distinguishable from one another, to generate a plurality of distinguishable lineages of heritably marked cells within the contacted tissue; (b) after sufficient time has passed for at least a portion of the heritably marked cells to undergo at least one round of division, detecting and measuring quantities of at least two of the plurality of cell markers present in the contacted tissue, thereby generating a set of measured values; and (c) calculating, using the set of measured values as input, a number of heritably marked cells present in the contacted tissue for at least two of said distinguishable lineages of heritably marked cells.

Contacting a Tissue

In some embodiments, a subject method includes a step of contacting a tissue (e.g., a tissue of an individual) (e.g., muscle, lung, bronchus, pancreas, breast, liver, bile duct, gallbladder, kidney, spleen, blood, gut, brain, bone, bladder, prostate, ovary, eye, nose, tongue, mouth, pharynx, larynx, thyroid, fat, esophagus, stomach, small intestine, colon, rectum, adrenal gland, soft tissue, smooth muscle, vasculature, cartilage, lymphatics, prostate, heart, skin, retina, and reproductive and genital systems, e.g., testicle, reproductive tissue, and the like) with a plurality of cell markers that are heritable and distinguishable from one another, to generate a plurality of distinguishable lineages of heritably marked cells within the contacted tissue. In some cases, the tissue is an engineered tissue grown outside of an animal (e.g., an organoid, cells in culture, etc.). In some cases, the tissue is part of a living animal, and therefore the tissue can be considered a tissue of an individual and said contacting can be performed by administering (e.g., via injection) the cell markers to the individual.

Any convenient route of administration can be used (e.g., intratracheal, intranasal, retrograde pancreatic ductal, intramuscular, intravenous, intraperitoneal, intravesicular, intraarticular, topically, subcutaneous, orally, intratumoral, and the like). In some cases, administration is via injection (e.g., injection of a library, such as a viral library, directly into the target tissue). In some cases, the transfer of markers into cells is via electroporation (e.g., nucleofection), transfection (e.g., using calcium phosphate, cationic polymers, cationic lipids etc), hydrodynamic delivery, sonoporation, biolistic particle delivery, or magnetofection. Any convenient delivery vector can be used (e.g., viral particles, viral-like particles, naked nucleic acids, plasmids, oligonucleotides, exosomes, lipoplexes, gesicles, polymersomes, polyplexes, dendrimers, nanoparticles, biolistic particles, ribonucleoprotein complexes, dendrimers, cell-penetrating peptides, etc.).

The tissue can be any tissue type from any desired animal. For example, in some embodiments the contacted tissue is an invertebrate tissue (e.g., an ectdysozoan, lophotrocozoan, porifera, cnidarian, ctenophoran, arthropod, annelid, mollusca, flatworm, rotifera, arthropod, insect, or worm tissue). In some embodiments the contacted tissue is a vertebrate tissue (e.g., an avian, fish, amphibian, reptilian, or mammalian tissue). Suitable tissues also include but are not limited to tissue from: rodents (e.g., rat tissue, mouse tissue), ungulates, farm animals, pigs, horses, cows, sheep, non-human primates, and humans. The target tissue can include, but is not limited to: muscle, lung, bronchus, pancreas, breast, liver, bile duct, gallbladder, kidney, spleen, blood, gut, brain, bone, bladder, prostate, ovary, eye, nose, tongue, mouth, pharynx, larynx, thyroid, fat, esophagus, stomach, small intestine, colon, rectum, adrenal gland, soft tissue, smooth muscle, vasculature, cartilage, lymphatics, prostate, heart, skin, retina, and reproductive and genital systems, e.g., testicle, reproductive tissue, and the like.

In some cases the tissue is contacted for the purpose of inducing cells to become neoplastic, e.g., in some cases the tissue is contacted for the purpose of initiating multiple independent tumors to form. For example, in some cases the introduced cell markers (and/or components linked with the cell markers) cause neoplastic transformation (lead to neoplastic cell formation) and the outcome of multiple different neoplastic initiating events can be compared to one another because each event was uniquely marked with an identifiable heritable cell marker. In some such cases, the cell markers initiate the same genetic change such that the induced tumors begin due to the same type (or even identical) genetic perturbation, but the outcome of each initiating event can be tracked because each individual cell marker is distinguishable from the others. The purpose of such a method may be, for example, to track multiple independent cell lineages in the same tissue (and/or same animal) in order to generate a population size (e.g., tumor size, number of neoplastic cells in each tumor) distribution profile for a given genotype of interest. Alternatively, in some cases different genetic perturbations are used (e.g., the cell makers can cause two or more different genetic perturbations, components linked to the cell makers can cause two or more different genetic perturbations) and the outcomes from different genotypes in the same tissue (e.g., in some cases in the same animal) can be compared (e.g., different tumors with different genetic underpinnings that are present in the same tissue, e.g., multiple different tumors in the lung, muscle, kidney, and the like).

In some embodiments the tissue already contains neoplastic cells (e.g., tumors) prior to the contact with the cell markers. In some cases, a tumor is contacted with the cell markers (e.g., the cell markers can be injected into the tumor, injected into the bloodstream to contact the tumor[s], administered to another organ or tissue to contact the tumor[s], etc.). As an example, in some cases, the cell markers are used as a way to mark independent neoplastic cells such as different cells within a neoplasm or tumor, and each marked cell can then be treated as a separate lineage—one can track the number of cells produced for each tracked lineage by counting the number of cells with each marker present (cells with each marker present) after one or more rounds of cell division. In some case, the method includes genetically modifying the cells into which the cell markers are introduced. For example, a tissue may already have one or more tumors prior to performing a subject method, and the purpose of introducing the cell markers is to test the effect of introducing additional genetic modifications to the tumor cells (i.e., changes in addition to those already present in the neoplastic cells). As such, each distinguishable cell marker can be associated with a different genetic change (e.g., by pairing nucleic acids encoding guide RNAs that target particular genetic targets with a unique identifier such as a DNA barcodes so that each guide RNA, and therefore each genetic modification, is associated with a unique identifier such as a DNA barcode). In such a case, the marked lineage represents sets of cells that are genetically different (e.g., has a mutation at a particular genetic locus) from one another.

Alternatively, in some cases each of the tumors is genetically the same and the cell markers track lineages that are not necessarily genetically different from one another. This allows the performer of the method to track multiple independent cell lineages in the same animal and to generate a population size (e.g. tumor size, number of neoplastic cells in tumors) distribution profile for a given genotype of interest.

Cell Markers

A plurality of cell markers (i.e., introduced (heterologous, artificial) cell markers—where the markers are not those that pre-exist in the cells—e.g., the introduced markers are not simply pre-existing clonal somatic mutations in a tumor) is two or more (e.g., 3 or more, 5 or more, 10 or more, or 15 or more, 50 or more, 100 or more, 200 or more, 500 or more, 1000 or more, 10,000 or more, 100,000 or more, 1,000,000 or more, 1,000,000,000 or more, etc.) cell markers. Likewise, a plurality of marked cell lineages is two or more (e.g., 3 or more, 5 or more, 10 or more, or 15 or more, 100 or more, 1,000 or more, 10,000 or more, 100,000 or more, etc.) marked cell lineages. Any convenient heritable cell markers (that are distinguishable from one another) can be used and a number of heritable cell markers will be known to one of ordinary skill in the art. In some cases, the cell markers (i.e., introduced (heterologous, artificial) that are heritable and distinguishable from one another) are barcoded nucleic acids. In some cases, the barcoded nucleic acids can be integrated into the genomes of the target cells or in some cases the barcoded nucleic acids can be maintained episomally. Barcoded nucleic acids include nucleotide sequences that provide a unique identifier for each cell lineage that will be detected and quantified/measured. In some case, the plurality of cell markers that are heritable and distinguishable from one another is a library of barcoded nucleic acids, where the exact sequence of the barcode has some random element. For example, in some cases the barcode can be described with a series of Ns (e.g., positions in the nucleic acid sequence for which each nucleotide is not defined but is one of all possible or a defined subset of canonical or non-canonical nucleotides). A subject barcoded nucleic acid can include any convenient number of Ns.

In some cases, a subject barcoded nucleic acid (a plurality/library) includes 5 or more (e.g., 6 or more, 7 or more, 8 or more, 10 or more, 12 or more, or 15 or more) randomized positions, e.g., 5 or more (e.g., 6 or more, 7 or more, 8 or more, 10 or more, 12 or more, or 15 or more) positions at which the nucleotide is not predetermined. In some cases the formula for a library (plurality) of barcoded nucleic acids includes a stretch of nucleotides at least 10 base pairs (bp) long (e.g., at least 12 bp, 15 bp, 17 bp, or 20 bp long) in which 5 or more positions (e.g., 6 or more, 7 or more, 8 or more, 10 or more, 12 or more, or 15 or more positions) are not defined (i.e., positions at which the base identity differs among members of the library). In some cases the formula for a library (plurality) of barcoded nucleic acids includes a stretch of nucleotides in which from 5 to 40 positions (e.g., 5 to 30, 5 to 25, 5 to 20, 5 to 18, 5 to 15, 5 to 10, 8 to 40, 8 to 30, 8 to 25, 8 to 20, 8 to 18, 8 to 15, 8 to 10, 10 to 40, 10 to 30, 10 to 25, 10 to 20, 10 to 18, 10 to 15, 12 to 40, 12 to 30, 12 to 25, 12 to 20, 12 to 18, or 12 to 15 positions) are not defined (i.e., positions at which the base identity differs among members of the library). In some cases the formula for a library (plurality) of barcoded nucleic acids includes a stretch of nucleotides in which from 5 to 1000 positions (e.g., 5 to 800, 5 to 600, 5 to 500, 5 to 250, 5 to 150, 5 to 100, 5 to 50, 5 to 30, 5 to 25, 5 to 20, 5 to 18, 5 to 15, 5 to 10, 8 to 1000, 8 to 800, 8 to 600, 8 to 500, 8 to 250, 8 to 150, 8 to 100, 8 to 50, 8 to 40, 8 to 30, 8 to 25, 8 to 20, 8 to 18, 8 to 15, 8 to 10, 10 to 1000, 10 to 800, 10 to 600, 10 to 500, 10 to 250, 10 to 150, 10 to 100, 10 to 50, 10 to 40, 10 to 30, 10 to 25, 10 to 20, 10 to 18, 10 to 15, 12 to 1000, 12 to 800, 12 to 600, 12 to 500, 12 to 250, 12 to 150, 12 to 100, 12 to 50, 12 to 40, 12 to 30, 12 to 25, 12 to 20, 12 to 18, or 12 to 15 positions) are not defined (i.e., positions at which the base identity differs among members of the library).

The barcoded nucleic acids can be linear (e.g., viral) or circular (e.g., plasmid) DNA molecules. The barcoded nucleic acids can be single-stranded or double-stranded DNA molecules. Non-limiting examples include plasmids, synthesized nucleic acid fragments, synthesized oligonucleotides, minicircles, and viral DNA. Barcoded nucleic acids can be RNA molecules, DNA (DNA molecules), RNA/DNA hybrids, or nucleic acid/protein complexes.

In some cases, cell markers may include a plurality of biomarkers (e.g., antibodies, fluorescent proteins, cell surface proteins) that are heritable and distinguishable from each other, alone or in combination with a plurality of other biomarkers of the same or different type, that are distinguishable from each other as well as distinguishable from the plurality of other biomarkers when used in combination. In such as case, the biomarkers may be present in a predefined or randomized manner, inside or outside individual cells and/or cell lineages, and can be quantified and/or measured using methods that will be commonly known by one of ordinary skill in the art (e.g. high-throughput/next-generation DNA sequencing, microscopy, flow-cytometry, mass spectrometers, etc).

Cell markers can be delivered to cells using any convenient method. In some cases, the cell markers (e.g., barcoded nucleic acids) are delivered to the tissue via viral vector. Any convenient viral vector can be used and examples include but are not limited to: lentiviral vectors, adenoviral vectors, adeno-associated viral (AAV) vectors, bocavirus vectors, foamy virus vectors, and retroviral vectors.

In one example from the working examples below (see FIG. 4a), the plurality of cell markers was delivered to the target tissue via lentiviral vectors. A library of lentiviral particles was used in which each viral particle included one barcoded nucleic acid that included a two-component barcode, where the first component was unique to each encoded guide RNA and the second component was unique to each molecule so that in turn it would be unique to each cell lineage that was to be detected and quantified/measured. The formula for the sequence of the barcode's second component was NNNNNTTNNNNNAANNNNN (SEQ ID NO: 108). Thus, in a stretch of 19 base pairs, 15 of them were not defined (e.g., randomized). Each barcoded nucleic acid of the library: (i) encoded a CRISPR/Cas guide RNA; (ii) included a first barcode—a unique identifier 8-nucleotide barcode that was linked to the guide RNA such that each different guide RNA sequence was linked to its own unique 8-nucleotide barcode; (iii) included a second barcode—the random 19 nucleotide barcode above with 15 undefined positions [for tracking cell lineage]; and (iv) encoded a gene editing protein (CRE), the expression of which would lead to Cas9 expression in the target tissue. Thus, in this case, multiple different members of the plurality of barcoded nucleic acids included the same first barcode, where each first barcode had a 'corresponding' guide RNA. However, the second barcode was unique to each member of the library such that each cell lineage that will be detected and quantified/measured would have a unique identifier. Thus, while some members shared a first barcode sequence because they shared a common guide RNA, each member of the library had a unique second barcode that could be used to track each integration (i.e., each lineage).

In some cases, a plurality of cell markers that are heritable and distinguishable are associated with one or more (e.g., 1 or more, 2 or more, 3 or more, 5 or more, 7 or more, 9 or more, 11 or more, 13 or more, 15 or more, or 20 or more) pluralities of cell markers that are heritable and distinguishable from one another as well as distinguishable from the cell markers of the other pluralities of cell markers they are associated with. For example, one barcoded nucleic acid may include a four-component barcode, where the first component is unique to a candidate therapy (e.g. candidate anti-cancer compound), the second component is unique to each individual (e.g. a mouse who may or may not receive the candidate therapy), the third component is unique to an encoded guide RNA, and the fourth component is unique to each molecule, so that in turn, the barcoded nucleic acid would be unique to each cell lineage that was to be detected and quantified/measured. Thus, in this example, the number of cells in each cell lineage can be quantified/measured and each cell lineage can also be directly linked by its four-component nucleic acid barcode to the specific genetic perturbation induced by the guide RNA in that cell lineage, the specific candidate therapy encountered by that cell lineage, and the specific individual (e.g., mouse) within which the cell lineage resided.

In some cases, the barcode is incorporated into a DNA donor template for homology directed repair (HDR) or, e.g., any other mechanism that incorporates a defined nucleic acid sequence into a desired position in the genome. For example, the HDR repair template may be used to introduce the same coding change (e.g. same coding allele), or even a subset of desired changes, into the genome of the cells it contacts, but each integration event can be independently tagged because the library of HDR templates has been randomized at particular positions. In one example from the working examples below (see, e.g., FIG. 23a), the plurality of cell markers (a library of AAV particles in which each AAV particle included one HDR template) was delivered to the target tissue by AAV particles. The HDR template in each AAV included one of the 12 possible non-synonymous, single-nucleotide point mutations in Kras codons 12 and 13 or the wild type Kras sequence as well as a random 8-nucleotide barcode in the wobble positions of the adjacent codons to uniquely tag each cell that undergoes HDR. The barcode was (N)GG(N)AA(R)TC(N)GC(N)CT(N)AC(N)AT(H) (SEQ ID NO: 1), and thus was a stretch of 22 base pairs in which 8 positions were not defined.

In some cases, the cell markers may contact the tissue in response to external perturbation (e.g., candidate anti-cancer therapy). In such a case, the administration of the external perturbagen may occur stochastically, with tunable probabilities, or as a result of a combinatorial matching of signals (e.g., a predefined physiological state of the cell, the level of expression of a specific gene, set of genes, or sets of genes, the level of activity of a specific pathway or pathways, and/or other signals internal or external to the cell or cell lineage [e.g., the identity of the tissue, levels of blood supply, immune state of the whole individual, physical location of the cell, etc]). For example, a cell marker (e.g. barcoded DNA) may contact the tissue upon expression of both a guide RNA, under the control of an enhancer specific to particular type of epithelial cell, and Cas9, in response to a compound being administered to the individual within which the tissue exists.

In some cases, the cell markers may contact a healthy or diseased cell population or tissue in vivo in an individual living organism, or in vitro in a cell population in culture or an organoid culture. In some cases, cell markers may contact a neoplastic cell lineage that is increasing or decreasing in number or static. In some cases, cell markers may contact the tissue in response to administration of a drug or other physiological or environmental perturbation, stochastically with tunable probabilities, or via a counting mechanism that induced the cell marker to contact the tissue after a certain number of cell divisions, exactly or stochastically, with tunable mean and variance and other moments, or as a result of a combinatorial matching of signals.

Genetic Modification (Alteration) of Target Cells

As noted above, in some embodiments, the method includes genetically modifying the cells into which the cell markers are introduced. In some such cases, the introduced cell markers are the agents of the genetic modification. For example, in some cases the cell markers are barcoded nucleic acids that induce genetic modification (e.g., genomic modification) and in some such cases are barcoded nucleic acids that induce neoplastic cell formation. For example, expression of an RNA (e.g., guide RNA) and/or protein (e.g., Cre, a CRISPR/Cas RNA-guided protein, etc.) from the barcoded nucleic acids can lead to one or more genomic alterations, and in some cases the genomic alterations result in transformation of the target cell into a neoplastic cell (e.g., which in some cases can result in tumor formation).

However, whether a cell marker (e.g., barcoded nucleic acid) introduces a genomic modification can be independent of whether it can induce neoplastic cell formation. For example, in some cases a barcoded nucleic acid can encode an oncogene (a gene that when expressed as a protein can lead to neoplastic cell formation). In some such cases, the barcoded nucleic acid does not induce a genomic change in the target cell but does induce neoplastic cell formation due to expression of the oncogene. In some cases, an oncogene encodes a wild type protein that can cause a cell to become neoplastic when the protein is overexpressed. In some cases an oncogene encodes a mutated protein (e.g., mutated form of KRAS) that can cause a cell to become neoplastic when the protein is expressed. In some cases a cell marker (e.g., barcoded nucleic acid) introduces a genomic modification in the target cell but the modification only induces neoplastic formation (e.g., tumor/cancer formation) in combination with one or more additional genomic modifications that may occur before, during, or a period time after the introduction of the cell marker and associated genomic modification.

On the other hand, in some cases a cell marker (e.g., barcoded nucleic acid) introduces a genomic modification in the target cell but the modification does not induce neoplastic formation (e.g., tumor/cancer formation). For example in some cases a barcoded nucleic acid integrates into the genome of a target cell in an inert way.

In some cases a barcoded nucleic acid encodes a protein (e.g., wild type or mutant protein) where the protein is not necessarily related to cancer, e.g., the protein(s) can be involved in any biological process of interest and its expression may not have an effect on cell proliferation and/or neoplastic cell formation (e.g., may not be an oncogene or a tumor suppressor). In some such cases the nucleic acid integrates into the genome of target cells and in other cases the nucleic acid does not integrate into the genome (e.g., can be maintained episomally). In some cases a barcoded nucleic acid encodes wild type or mutant protein, e.g., a cDNA, that encodes a protein that is detrimental to tumors, e.g., in some way other than growth/proliferation control.

In some embodiments a subject cell marker (e.g., barcoded nucleic acid) both introduces a genomic modification in the target cell and also induces neoplastic cell formation (e.g., tumor/cancer formation). For example, in some cases a barcoded nucleic acid can cause editing at a target locus to modify a tumor suppressor, alter the expression of an oncogene, edit a gene (e.g., Kras) to become a neoplastic-inducing allele, etc.

As noted above, expression of an RNA (e.g., guide RNA) and/or protein (e.g., Cre, a CRISPR/Cas RNA-guided protein, etc.) from a barcoded nucleic acid can lead to one or more genomic alterations, and in some cases the genomic alterations result in transformation of the target cell into a neoplastic cell (e.g., which in some cases can result in tumor formation). In some embodiments, genomic alteration of the target cells can be temporally separated from the initiation of neoplastic character (e.g., from tumor initiation). As an example, a vector(s) could be engineered to allow temporal control of a CRISPR/Cas guide RNA and/or temporal control of CRISPR/Cas nucleic acid-guided protein activity (e.g., Cas9 activity).

In some cases, a protein that introduces genetic (e.g., genomic) modification is expressed in the target cells. The protein can be introduced into a target cell as protein or as a nucleic acid (RNA or DNA) encoding the protein. The protein may also already be encoded by a nucleic acid in the cell (e.g., encoded by genomic DNA in the cell) and the method includes inducing the expression of the protein. In some cases a protein that introduces a genetic modification in target cells of a target tissue is a genome editing protein/endonuclease (some of which are 'programmable' and some of which are not). Examples include but are not limited to: programmable gene editing proteins (e.g., transcription activator-like (TAL) effectors (TALEs), TALE nucleases (TAL-ENs), zinc-finger proteins (ZFPs), zinc-finger nucleases (ZFNs), DNA-guided polypeptides such as *Natronobacterium gregoryi* Argonaute (NgAgo), CRISPR/Cas RNA-guided proteins such as Cas9, CasX, CasY, Cpf1, and the like) (see, e.g., Shmakov et al., Nat Rev Microbiol. 2017 March; 15(3):169-182; and Burstein et al., Nature. 2017 Feb. 9; 542(7640):237-241); transposons (e.g., a Class I or Class II transposon—e.g., piggybac, sleeping beauty, Tc1/mariner, Tol2, PIF/harbinger, hAT, mutator, merlin, transib, helitron, maverick, frog prince, minos, Himar1 and the like); meganucleases (e.g., I-SceI, I-CeuI, I-CreI, I-DmoI, I-ChuI, I-DirI, I-FlmuI, I-FlmuII, I-AniI, I-SceIV, I-CsmI, I-PanI, I-PanII, I-PanMI, I-SceII, I-PpoI, I-SceIII, I-LtrI, I-GpiI, I-GZeI, I-OnuI, I-HjeMI, I-MsoI, I-TevI, I-TevII, I-TevIII, PI-MleI, PI-MtuI, PI-PspI, PI-Tli I, PI-Tli II, PI-SceV, and the like); megaTALs (see, e.g., Boissel et al., Nucleic Acids Res. 2014 February; 42(4): 2591-2601); phage-derived integrases; a Cre protein; a Flp protein; and the like. In some cases the genome editing nuclease (e.g., a CRISPR/Cas RNA-guided protein) has one or more mutations that remove nuclease activity (is a nuclease dead protein) and the protein is fused to a transcriptional activator or repressor polypeptide (e.g., CRISPRa/CRISPRi). In some cases the genome editing nuclease (e.g., a CRISPR/Cas RNA-guided protein) has one or more mutations that remove nuclease activity (is a nuclease dead protein) or partially remove nuclease activity (is a nickase protein), may have one or more additional mutations that modulate protein function or activity, and the protein is fused to a deaminase domain (e.g., ADAR, APOBEC1, etc.), which itself may have one or more additional mutations that modulate protein function or activity, or fused to the deaminase domain and one or more additional proteins or peptides (e.g., the bacteriophage Gam protein, uracil glycosylase inhibitor, etc.), which may also have one or more additional mutations that modulate protein function or activity (e.g., RNA base editors, DNA base editors).

In some cases, an editing protein such as Cre or Flp can be introduced into the target tissue for the purpose of inducing expression of another protein (e.g., a CRISPR/Cas RNA-guided protein such as Cas9) from the genome, e.g., an animals can contain a lox-stop-lox allele of Cas9 and an introduced Cre protein (e.g., encoded by a barcoded nucleic acid) results in removal of the 'stop' and thus results in expression of the Cas9 protein.

In some embodiments, the barcoded nucleic acids can induce neoplastic cell formation and include one or more of: homology directed repair (HDR) DNA donor templates, nucleic acids encoding oncogenes (including wild type and/or mutant alleles of proteins), nucleic acids encoding CRISPR/Cas guide RNAs, nucleic acids encoding short hairpin RNAs (shRNAs), and nucleic acids encoding a genome editing protein (e.g., see above).

In some cases when the barcoded nucleic acids are HDR DNA donor templates, they can introduce mutations into the genome of target cells. In some such cases, a genome editing nuclease is present in the cell (either introduced or induces as part of the subject method or already expressed in the targeted cells) that will cleave the targeted DNA such that the donor templates are used to insert the barcoded sequence. In some cases, a library (plurality) of HDR DNA donor templates includes members that have unique sequence identifiers (barcodes) for each molecule, but the molecules result in the same functional perturbation (e.g., they may all result in expression of the same protein, e.g., in some cases with a mutated amino acid sequence, but they may differ in the wobble positions of the codons then encode the protein such that the resulting multiple cell lineages are distinguishable from one another despite expressing the same mutated protein). In some cases, a library (plurality) of HDR DNA donor templates includes members that have unique sequence identifiers (barcodes) for each molecule, and the molecules result in the different functional perturbations (e.g., can target different genetic loci, can target the same loci but introduce different alleles, etc.).

In some cases the barcoded nucleic acids are CRISPR/Cas guide RNAs or are DNA molecules that encode CRISPR/Cas guide RNAs. A library of such molecules can include molecules that target different loci and/or molecules that target the same locus. In some cases the barcoded nucleic acids encode an oncogene, which for purposes of this disclosure includes wild type proteins that can cause neoplastic cell formation when overexpressed as well as mutated proteins (e.g., KRAS—see working examples below) that can cause neoplastic cell formation. A library of such molecules can include molecules that express the same oncogene or a library of molecules that express different oncogenes. In some cases the barcoded nucleic acids include short hairpin RNAs (shRNAs) and/or DNA molecule(s) that encode shRNAs (e.g., which can be targeted to any desired gene, e.g., tumor suppressors). A library of such molecules can include molecules that express the same shRNAs or a library of molecules that express different shRNAs. In some cases the barcoded nucleic acids include RNAs and/or DNAs that encode one or more genome editing proteins/endonucleases (see above for examples, e.g., CRISPR/Cas RNA-guided proteins such as Cas9, Cpf1, CasX or CasY; Cre recombinase; Flp recombinase; ZFNs; TALENs; and the like). A library of such molecules can include molecules that express the same genome editing proteins/endonucleases or a library of molecules that express different genome editing proteins/endonucleases.

In some embodiments, the cell markers are distinguishably labeled particles (e.g., beads, nanoparticles, and the like). For example, in some cases the particles can be labeled with distinguishable mass tags (which can be analyzed via mass spectrometry), with distinguishable fluorescent proteins, with distinguishable radio tags, and the like.

Detecting/Measuring/Calculating

Subject methods can also include, e.g., after sufficient time has passed for at least a portion of the heritably marked cells to undergo at least one round of division, a step of detecting and measuring quantities of at least two of the plurality of cell markers present in the contacted tissue.

In some cases, the period time that elapsed between steps (a) and (b) [between contacting a tissue with a plurality of cell makers and detecting/measuring the cell markers present in the tissue] is a period of time sufficient for at least a portion (e.g., at least two of the distinguishably marked cells) of the heritably marked cells to undergo at least one round of division (e.g., at least 2 rounds, 4 rounds, 6 rounds, 8 rounds, 10 rounds, or 15 rounds of cell division). In some cases, the period time that elapsed between steps (a) and (b) [between contacting a tissue with a plurality of cell makers and detecting/measuring the cell markers present in the tissue] is 2 or more hours (e.g., 4 or more, 6 or more, 8 or more, 10 or more, 12 or more, 15 or more, 18 or more, 24 or more, or 36 or more hours). In some cases, the period time that elapsed between steps (a) and (b) [between contacting a tissue with a plurality of cell makers and detecting/measuring the cell markers present in the tissue] is 1 or more days (e.g., 2 or more, 3 or more, 4 or more, 5 or more, 7 or more, 10 or more, or 15 or more, 20 or more, or 24 or more days). In some cases, the period time that elapsed between steps (a) and (b) [between contacting a tissue with a plurality of cell makers and detecting/measuring the cell markers present in the tissue] is 1 or more week (e.g., 2 or more, 3 or more, 4 or more, 5 or more, 7 or more, or 10 or more weeks). In some cases, the period time that elapsed between steps (a) and (b) [between contacting a tissue with a plurality of cell makers and detecting/measuring the cell markers present in the tissue] is in a range of from 2 hours to 60 weeks (e.g., from 2 hours to 40 weeks, 2 hours to 30 weeks, 2 hours to 20 weeks, 2 hours to 15 weeks, 10 hours to 60 weeks, 10 hours to 40 weeks, 10 hours to 30 weeks, 10 hours to 20 weeks, 10 hours to 15 weeks, 18 hours to 60 weeks, 18 hours to 40 weeks, 18 hours to 30 weeks, 18 hours to 20 weeks, 18 hours to 15 weeks, 1 day to 60 weeks, 1 day to 40 weeks, 1 day to 30 weeks, 1 day to 20 weeks, 1 day to 15 weeks, 3 days to 60 weeks, 3 days to 40 weeks, 3 days to 30 weeks, 3 days to 20 weeks, 3 days to 15 weeks, 1 week to 60 weeks, 1 week to 40 weeks, 1 week to 30 weeks, 1 week to 20 weeks, or 1 week to 15 weeks). In some cases, the period time that elapsed between steps (a) and (b) [between contacting a tissue with a plurality of cell makers and detecting/measuring the cell markers present in the tissue] is in a range of from 2 hours to 300 weeks (e.g., from 2 hours to 250 weeks, 2 hours to 200 weeks, 2 hours to 150 weeks, 2 hours to 100 weeks, 2 hours to 60 weeks, 2 hours to 40 weeks, 2 hours to 30 weeks, 2 hours to 20 weeks, 2 hours to 15 weeks, 10 hours to 300 weeks, 10 hours to 250 weeks, 10 hours to 200 weeks, 10 hours to 150 weeks, 10 hours to 100 weeks, 10 hours to 60 weeks, 10 hours to 40 weeks, 10 hours to 30 weeks, 10 hours to 20 weeks, 10 hours to 15 weeks, 18 hours to 300 weeks, 18 hours to 250 weeks, 18 hours to 200 weeks, 18 hours to 150 weeks, 18 hours to 100 weeks, 18 hours to 60 weeks, 18 hours to 40 weeks, 18 hours to 30 weeks, 18 hours to 20 weeks, 18 hours to 15 weeks, 1 day to 300 weeks, 1 day to 250 weeks, 1 day to 200 weeks, 1 day to 150 weeks, 1 day to 100 weeks, 1 day to 60 weeks, 1 day to 40 weeks, 1 day to 30 weeks, 1 day to 20 weeks, 1 day to 15 weeks, 3 days to 300 weeks, 3 days to 250 weeks, 3 days to 200 weeks, 3 days to 150 weeks, 3 days to 100 weeks, 3 days to 60 weeks, 3 days to 40 weeks, 3 days to 30 weeks, 3 days to 20 weeks, 3 days to 15 weeks, 1 week to 300 weeks, 1 week to 250 weeks, 1 week to 200 weeks, 1 week to 150 weeks, 1 week to 100 weeks, 1 week to 60 weeks, 1 week to 40 weeks, 1 week to 30 weeks, 1 week to 20 weeks, or 1 week to 15 weeks).

The amount (level) of signal detected for each distinguishable cell marker (e.g., barcoded nucleic acid) can be used to determine the number of cells present in the contacted tissue (the tissue into which the heritable cell markers were introduced). Any convenient method can be used to detect/measure the cell markers, and one of ordinary skill in the art will understand that the type of cell markers used will drive what method should be used for measuring. For example, if mass tags are used, then mass spectrometry may be the method of choice for measuring. If barcoded nucleic acids are used as the cell markers, then sequencing (e.g., high-throughput/next generation sequencing) may be the method of choice for measuring. In some cases, high-throughput sequencing is used and the number of sequence reads for each detected barcode can be used to determine the number of cells that contained that particular barcode. In some case the metric of importance is not the number of cells in each lineage but rather the number of clonal lineages that exceed a certain number of cells.

In some cases, sequencing (e.g., high-throughput/next generation sequencing) is performed on PCR products, where the PCR products are from PCR reactions that amplified the barcode region from the cell markers within the cells (in some cases from the genomic region in which barcoded nucleic acids integrated) (see, e.g., FIG. 1a).

In some cases, the quantification of the number of neoplastic cells in tumors, as well as additional phenotyping and analysis, is conducted from pooled samples, samples sorted via single, multiple, or combinatorially arranged biomarkers (e.g., fluorescent proteins, cell-surface proteins, and antibodies), or via dissection of individual tumors from the tissue, organ, cell culture, or other possible means of cell propagation.

In some cases, 'benchmarks' can be used to aid in calculating a cell number. For example, in some cases controls can be 'spiked' into the sample. For example, spiked (spike in) controls can be used to determine the number of sequence reads per cell (e.g., number of cells per sequence read). For example, in some cases a spiked (spike in) control can also be used to correlate the amount of measured DNA with the number of cells from which the DNA was derived. For example, a known number of cells can be used to prepare DNA, and the DNA can be processed in parallel with DNA extracted from cells of the contacted tissue (tissue contacted with heritable cell markers according to the methods of the disclosure). Such a spiked (spike in) control (a 'benchmark') can include its own unique barcode. The results from the spiked controls can be used to derive/calculate the number of cells represented by the number of sequence reads detected in the sequencing reaction (i.e., spiked (spike in) controls can be used to provide a coefficient for converting amount of measured value, e.g., number of sequence reads, into a cell number, e.g., an absolute cell number). Such a process can be referred to as 'normalizing', e.g., sequencing results provide a number of reads for each unique barcode that is detected, and this value can then be compared to one or more 'benchmarks' in order calculate an absolute number of cells that had included the detected unique barcodes (see, e.g., FIG. 1a).

In some cases because multiple clonal cell populations are detectable by contacting a subject tissue with the heritable cell markers, and in some cases each distinguishable cell population has a similar genotype, the subject methods can be used to provide a distribution of population size (e.g., a distribution of tumor size) for a particular phenotype. For example, if the initial contacting causes a similar genomic alteration in all contacted cells (e.g., if all cells receive a guide RNA targeting the same locus, if all cells receive a nucleic acid encoding the same oncogene allele, and the like), but each cell population (e.g., tumor) is independent, the resulting cell population sizes can provide a clonal cell population size distribution for that particular genotype. For example, the goal of performing a subject method may be to search for genetic changes that alter tumor behavior in particular ways (e.g., change the size distribution without change the number of tumors per se). For example, the working examples below (e.g., see working example 1) include a demonstration that animals with tumors having p53-deficiency generated a tumor size distribution that was power-law distributed for the largest tumors (consistent with a Markov process where very large tumors are generated by additional, rarely acquired driver mutations). Conversely, animals with tumors having Lkb1 inactivation increased the size of a majority of lesions suggesting an ordinary exponential growth process (e.g., see FIGS. 10, 13, 16, and 20).

Size distribution measurements can be used in a number of different ways. For example, one can determine the baseline size distribution of cell population size (e.g., tumor size) for a given genotype by performing the methods described herein, and compare it to the size distribution that is measured when similarly treated animals are also treated with a test compound (e.g., candidate anti-cancer therapy). The change in size distribution can be used as a measure of whether the test compound was effective. As an illustrative example, the inventors determined a baseline measurement for tumor size distribution for mice with tumors that had p53-deficiency, and found that p53-deficiency tended to lead to some tumors that were much larger compared to other tumors. Thus, the size distribution of the p53-deficient tumors was not a standard distribution but instead included outlier tumors. Using the methods described herein, it is possible to screen for potential therapeutics (e.g., small molecules, large molecules, radiation, chemo, fasting, antibodies, immune cell therapies, enzymes, viruses, biologics, compounds, and the like) that change the tumor size distribution, but do not necessarily cure animals of tumors. For example, a therapy (e.g., a compound) can be found that, although it does not eradicate all p53-deficient tumors, it instead inhibits the outlier large tumors from forming. Such a change may not be detected using standard methods because the tested compound would not necessarily reduce overall tumor number (tumor burden) or even average tumor size (and such a compound might be discarded using other methods as a compound that has no effect on inhibiting tumor growth)—but such a therapy (e.g., compound) may be very useful in clinical settings to treat patients with p53-deficient tumors because it would be effective against the most advanced tumors (e.g., the biggest, more dangerous tumors)(e.g., reduce the risk of outlier tumors).

Thus, in some cases, subject methods can be used for screening candidate therapies (e.g., small molecules, large molecules, radiation, chemotherapy, fasting, antibodies, immune cell therapies, enzymes, viruses, biologics, compounds, and the like) for their effect on population size (e.g., the growth/proliferation of tumors). For example, a subject method can be performed in the presence of a test therapy, e.g., compound (e.g., drug)(e.g., the method can include a step of contacting the tissue, e.g., via administration to an individual, with the test compound), and the effect of the drug can be measured, e.g., via comparison to parallel experiments in which no drug (e.g., control vehicle) was added. In cases where the lineage marked cell populations are genetically the same (or similar) such a method can test whether the compound has an effect on size distribution of the cell populations. In cases where the differentially marked cells have different genotypes (e.g., different genes have been mutated and/or are being expressed in the different cell lineages), the therapy (e.g., compound) can be tested against multiple different genotypes at the same time, e.g., in the same animal in cases where the tissue is in a living animal in vivo. In some cases, such experiments and/or therapy (e.g., compound) screens can be performed on tissues grown in culture (e.g., 2D cultured tissue, 3D cultured tissue, organoid cultures). In some cases, such methods can be performed in non-human animals such as rodents (e.g., mice, rats), pigs, guinea pigs, non-human primates, and the like.

Any perturbagen (e.g., small molecules, large molecules [e.g. antibodies or decoy receptors], radiotherapies, chemotherapies, inducers of inflammation, hormones, nanoparticles, immune cell therapies, enzymes, viruses, environmental interventions (e.g. intermittent fasting, acute exercise, diet control), and the like) can be assessed for its effect on population size for a plurality of marked cell populations. Genetic perturbations can also be induced in all clonal lineages to assess their impact. In the case where all lineages are of the same initial genotype, then the response of individual clonal lineages (e.g. tumors) can be determined. In the case where the clonal lineages have been induced to have different defined alterations, then the impact of the inducible genetic perturbations on clonal lineages with different alterations can be determined. Systems to generate inducible genetic alteration include but are not limited to the use of the Flp/FRT or Cre/loxP systems (in cell lineages that have not been initiated with Flp or Cre-regulated alleles) or tetracycline regulatable systems (e.g. tTA or rtTA with TRE-cDNA(s) and/or TRE-shRNA(s) and/or TRE-sgRNA(s)). Regulatable CRISPR/Cas9 genome editing and secondary transduction of neoplastic cells could generated genomic alterations in a temporal manner.

In some cases, the effect of and response to (e.g. pharmacological, chemical, metabolic, pharmacokinetic, immunogenic, toxicologic, behavioral, etc.) an external perturbagen (e.g. candidate anti-cancer therapy) by an individual with a plurality of marked cell populations will be assessed before, during, and/or after the measuring of cell markers.

In some embodiments, a subject method includes, after generating heritably marked cells (e.g., heritably marked tumors), transplanting one or more of the marked cell populations (e.g., all or part of a tumor or tumors) into a recipient (e.g., a secondary recipient) or a plurality of recipients, e.g., to seed tumors in the recipient(s). In some cases, such a step can be considered akin to 'replica plating,' where one can screen a large number animals against a test compound, where each animal is seeded from cells from the same starting tumor. Thus, in some cases, the method includes a step in which a test compound is administered to the recipient(s) of the transplant (e.g., the method can include detecting and measuring quantities of at least two of the plurality of cell markers present in the secondary recipient), e.g., to assess growth of the transplanted cells (and some cases this can be done in the presence and/or absence of a test compound). Thus, a subject method can be used as part of serial transplantation studies, where the initially generated heritably marked cells (e.g., heritably marked tumors) are transplanted into one or more recipients, and the number of heritably marked cells present in the contacted tissue can be calculated for at least two of the distinguishable lineages of heritably marked cells. In some of the above cases (e.g., serial transplant) a test compound can be administered to the serial transplant recipient and the results can be compared to controls (e.g., animals that received a transplant but not the test compound, animals that received test compound but not transplant, and the like).

In some embodiments, one or more heritably marked cells are re-marked (e.g., re-barcoded). In other words, in some cases, a population of cells (e.g., a tumor) that has already been heritably marked is contacted with a second plurality of cell markers that are heritable and distinguishable from one another as well as distinguishable from the cell markers of the first plurality of cell markers. In this way, the user can investigate, e.g., the variability present within marked cell populations (e.g., tumors). In some embodiment the heritable marker itself changes over time to record the phylogeny of the cells with a clonal lineage (e.g. evolving nucleotide barcodes).

The heritable lineage marker can also be encoded within an expressed gene (either endogenous or engineered) which facilitates the cell lineage to be determined through analysis of mRNA or cDNA from the marked cells. In some cases, cell markers are converted into a different type of cell markers (e.g. barcoded DNA expressed by a marked cell as barcoded RNA or protein). In such a case, one of ordinary skill in the art will understand that the method used for measuring the cell marker will be determined by the type of cell marker desired to be measured, at the time of measurement. For example, if barcoded DNA is used as the cell marker and the barcoded DNA is expressed as barcoded RNA, then RNA sequencing (e.g., whole transcriptome sequencing, single cell RNA sequencing, etc.) may be the method used for measuring if RNA barcodes are the type of cell marker that are desired to be measured, or DNA sequencing (e.g., whole genome sequencing, whole exome sequencing, targeted DNA sequencing, etc.) may be the method used for measuring if DNA barcodes are the type of cell marker that are desired to be measured. In such a case, the choice of cell marker to measure may be driven by the desired phenotype of the cells to investigate and directly link to cell markers (e.g. barcoded RNA cell markers may be measured using single cell RNA sequencing so the RNA expression pattern can be directly linked to the cell marker). In some cases, cell lineage markers can be measured using single cell analysis methods (e.g. single cell RNA-seq, flow cytometry, mass cytometry (CyTOF), MERFISH, single cell proteomics) such that individual cells from each lineage can be related to individual cells from each other lineage. In such a case, the phenotypes of the cells within each lineage are investigated. In such a case, these analyses can also used to assess the phenotypic response of cells of different lineages to external perturbations (e.g., drug treatment).

When detecting and measuring a heritable cell marker (e.g., a barcoded nucleic acid), in some cases the measurement is derived from a whole tissue. As such, a tissue sample can be a portion taken from a tissue, or can be the entire tissue (e.g., a whole lung, kidney, spleen, blood, pancreas, etc.). As such, cell markers (e.g., nucleic acids) can be extracted from a tissue sample so as to represent the remaining tissue or can be extracted from an entire tissue.

In some cases, a biological sample is a blood sample. In some cases the biological sample is a blood sample but the contacted tissue was not the blood. For example, in some cases a heritably marked cell can secrete a compound (e.g. a unique secreted marker such as a protein or nucleic acid) into the blood and the amount of the compound present in the blood can be used to calculate the number of cells present that secret that particular compound. For example, heritably marked cells can in some cases secret a fluorescent protein into the blood, and the fluorescent protein can be detected and measured, and used to calculate the cell population size for cells secreting that particular compound. In some cases, these secreted heritable markers are detected in unperturbed individuals or after administration of an external perturbagen (e.g. drug).

In some cases, a biological sample is a bodily fluid (e.g., blood, blood plasma, blood serum, urine, saliva, fluid from the peritoneal cavity, fluid from the pleural cavity, cerebrospinal fluid, etc.). In some cases the biological sample is a bodily fluid but the contacted tissue was not the bodily fluid. For example, in some cases a heritably marked cell can release an analyte (e.g. a unique marker such as a protein, nucleic acid, or metabolite) into the urine and the amount of the compound present in the urine can be used to calculate the number of cells or number of cell lineages that released that particular compound, either in alone or in response to an external perturbagen (e.g. candidate anti-cancer therapy).

In some cases, the measuring of cell markers in a biological sample is performed in parallel with the analysis of cells, cellular components (e.g. cell-free DNA, RNA, proteins, metabolites, etc.), or any other analytes (e.g. DNA, RNA, proteins, metabolites, hormones, dissolved oxygen, dissolved carbon dioxide, vitamin D, glucose, insulin, temperature, pH, sodium, potassium, chloride, calcium, cholesterol, red blood cells, hematocrit, hemoglobin, etc.) that may be directly or indirectly associated with the cell markers and that may be present in the same biological sample or in a separate biological sample.

In some cases, as noted above, the detecting and measuring is performed on a biological sample collected from an individual (e.g., a blood sample). In some cases, the detecting and measuring is performed on a tissue sample of the contacted tissue, which can in some cases be a portion of the contacted tissue or can be the whole tissue.

When detecting and measuring, biomarkers (other than the introduced heritable cell markers) can be taken in to account. For example, a subject method can include a step of detecting and/or measuring a biomarker of the heritably marked cells, and categorizing the heritably marked cells based on the results of the biomarker measurements. Such a biomarker can indicate any of number of cellular features, e.g., proliferation status (e.g., detection of Ki-67 protein, BrdU incorporation, etc.), cell type (e.g., using biomarkers of various cell types), developmental cell lineage, stemness (e.g., whether a cell is a stem cell and/or what type of stem cell), cell death (e.g. Annexin V staining, cleaved caspase 3, TUNEL, etc), and cellular signaling state (e.g., detecting phosphorylation state of signaling proteins, e.g., using phospho-specific antibodies).

In some cases understanding the genotype specificity of a certain therapy or perturbation can be used to inform (by similarity to other therapies or perturbations) the mechanism of action of that therapy or perturbation. By uncovering the genotype specificity the methods disclosed herein can be used to make and test prediction of combination therapies for defined genotypes. Panels of therapies can be tested to establish their genotype specifity.

Kits and Systems

Also provided are kits and systems, e.g., for practicing any of the above methods. The contents of the subject kits and/or systems may vary greatly. A kit and/or system can include, for example, one or more of: (i) a library of heritable cell markers that are distinguishable from one another (e.g., barcoded nucleic acids); (ii) directions for performing a subject method; (iii) software for calculating the number of cells from values generated from the detecting and measuring steps of the subject methods; (iv) a computer system configured.

In addition to the above components, the subject kits can further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, flash drive, etc., on which the information has been recorded. Yet another means that may be present is a website address which may be used via the internet to access the information at a removed site. Any convenient means may be present in the kits.

Utilities

Examples of various applications of the subject matter of this disclosure include, but are not limited to the following:

Quantifying the Effect of More Complex Genotypes:

The inventors have already generated and validated lentiviral vectors that express pairs of CRISPR/Cas single guide RNAs (sgRNAs), facilitating deletion of two target genes in each tumor. Generation of Lentiviral-Cre vectors with sgRNAs targeting pairwise combinations of tumor suppressors will uncover co-operative and antagonistic interactions between tumor suppressors in a highly-parallel manner.

Multiplexed In Vivo Genome Editing to Enable Combination Therapy Screening.

Due to the adaptive ability of many systems, combination therapies are emerging as an effective way to treat many diseases. The sheer number of potential therapeutic combinations quickly creates a difficult situation where every combination could never be tested in patients or even pre-clinical animal models. However, this un-assayable matrix of drug combinations could contain a combination that would work for patients. Combining drug treatments with CRISPR/Cas-mediated deletion of genes coding for additional drug targets could allow multiplexed modeling of therapeutic combinations. Interrogation of the effects of >100 pairwise drug treatments can be performed in parallel using the compositions and methods described in this disclosure. For example, investigating these permutations in the context of three lung cancer genotypes in mouse models of human lung cancer, would generate a semi-high-throughput system to interrogate the effects of pairwise drug targeting in vivo.

Extension to Other Cancer Types:

The methods described herein can be used to uncover pharmacogenomic susceptibilities of cell growth/proliferation (e.g., in the context of neoplasms, e.g., lung adenocarcinoma) and the methods can be applied to any convenient cancer type and/or any convenient situation in which population size of distinguishable lineages is of interest. For example, the approaches outlined in this disclosure could be adapted to any cancer that can be induced in genetically-engineered models (e.g., sarcoma, bladder cancer, prostate cancer, ovarian cancer, pancreas cancer, hematopoietic, etc.), e.g., using viral vectors.

With the wide diversity of tumor genotypes within human lung adenocarcinoma and the growing number of potential therapies, the multiplexed quantitative platform described in this disclosure can become a mainstay of translational cancer biology. The approaches described herein will allow translational studies to effectively match the correct therapies to the correct patients and will have a direct impact on patient care in the clinic. It can also help with carrying out clinical trials with a subpopulation of patients that have tumors that are the likeliest to respond to treatment—thus improving success rate of drug development and also rescuing drugs that had failed in a less targeted clinical trial.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-57 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of measuring population size for a plurality of clonal cell populations in the same tissue, the method comprising:

(a) contacting a biological tissue with a plurality of cell markers that are heritable and distinguishable from one another, to generate a plurality of distinguishable lineages of heritably marked cells within the contacted tissue;

(b) after sufficient time has passed for at least a portion of the heritably marked cells to undergo at least one round of division, detecting and measuring quantities of at least two of the plurality of cell markers present in the contacted tissue, thereby generating a set of measured values; and (c) calculating, using the set of measured values as input, a number of heritably marked cells present in the contacted tissue for at least two of said distinguishable lineages of heritably marked cells.

2. The method of 1, wherein the heritably marked cells within the contacted tissue are neoplastic cells.

3. The method of 1 or 2, wherein said tissue comprises neoplastic cells and/or tumors prior to step (a).

4. The method of any one of 1 to 3, wherein said detecting and measuring of step (b) is performed on a biological sample collected from the tissue.

5. The method of any one of 1 to 3, wherein said detecting and measuring of step (b) is performed on a tissue sample of the contacted tissue.

6. The method of any one of 1 to 5, wherein each cell marker of the plurality of cell markers corresponds to a known cell genotype for a lineage of heritably marked cells.

7. The method of any one of 1 to 6, wherein said contacting comprises genetically altering cells of the tissue to generate the heritably marked cells.

8. The method of any one of 1 to 7, wherein said method is a method of measuring tumor size for a plurality of tumors of the same tissue.

9. The method of any one of 1 to 8, wherein the step of contacting the tissue comprises inducing neoplastic cells.

10. The method of any one of 1 to 9, wherein the cell markers are agents that induce or modify neoplastic cell formation and/or tumor formation.

11. The method of any one of 1 to 10, wherein said detecting and measuring is performed after sufficient time has passed for tumors to form in the contacted tissue as a result of said contacting.

12. The method of any one of 1 to 11, wherein the plurality of cell markers comprises barcoded nucleic acids.

13. The method of 12, wherein said detecting and measuring comprises high-throughput sequencing and quantification of the number of sequence reads for each detected barcode.

14. The method of any one of 1 to 13, wherein the plurality of cell markers comprises barcoded nucleic acids that induce neoplastic cell formation.

15. The method of any one of 12 to 14, wherein the barcoded nucleic acids induce neoplastic cell formation and include one or more of: homology directed repair (HDR) DNA donor templates, nucleic acids encoding one or more oncogenes, nucleic acids encoding one or more wildtype proteins, nucleic acids encoding one or more mutant proteins, nucleic acids encoding one or more CRISPR/Cas guide RNAs, nucleic acids encoding one or more short hairpin RNAs (shRNAs), and nucleic acids encoding one or more genome editing proteins.

16. The method of 15, wherein the genome editing protein is selected from: a CRISPR/Cas RNA-guided protein, a CRISPR/Cas RNA-guided protein fused to a transcriptional activator or repressor polypeptide, a Cas9 protein, a Cas9 protein fused to a transcriptional activator or repressor polypeptide, a zinc finger nuclease (ZFN), a TALEN, a phage-derived integrase, a Cre protein, a Flp protein, and a meganuclease protein.

17. The method of any one of 12 to 16, wherein the barcoded nucleic acids are linear or circular DNA molecules.

18. The method of any one of 12 to 16, wherein the barcoded nucleic acids are selected from: plasmids, synthesized nucleic acid fragments, and minicircles.

19. The method of any one of 12 to 16, wherein the barcoded nucleic acids are RNA molecules.

20. The method of any one of 12 to 16, wherein the barcoded nucleic acids are RNA/DNA hybrids or nucleic acid/protein complexes.

21. The method of any one of 1 to 19, wherein the tissue is an invertebrate tissue.

22. The method of any one of 1 to 19, wherein the tissue is a vertebrate tissue.

23. The method of any one of 1 to 19, wherein the tissue is a mammalian or a fish tissue.

24. The method of any one of 1 to 19, wherein the tissue is a rat tissue, a mouse tissue, a pig tissue, a non-human primate tissue, or a human tissue.

25. The method of any one of 1 to 24, wherein the tissue is part of a living animal.

26. The method of any one of 1 to 24, wherein the tissue is an engineered tissue grown outside of an animal.

27. The method of any one of 1 to 26, wherein the tissue is selected from: muscle, lung, bronchus, pancreas, breast, liver, bile duct, gallbladder, kidney, spleen, blood, gut, brain, bone, bladder, prostate, ovary, eye, nose, tongue, mouth, pharynx, larynx, thyroid, fat, esophagus, stomach, small intestine, colon, rectum, adrenal gland, soft tissue, smooth muscle, vasculature, cartilage, lymphatics, prostate, heart, skin, retina, reproductive system, and genital system.

28. The method of any one of 1 to 27, wherein after sufficient time has passed for at least a portion of the heritably marked cells to undergo at least one round of division, the method further comprises: (i) detecting and/or measuring a biomarker of the heritably marked cells, and (ii) categorizing the heritably marked cells based on the results of said detecting and/or measuring of the biomarker.

29. The method of 28, wherein the biomarker of one or more of: cell proliferation status, cell type, developmental cell lineage, cell death, and cellular signaling state.

30. The method of any one of 1 to 29, wherein the cell markers are delivered to the tissue via viral vector.

31. The method of 30, wherein the viral vector is selected from: a lentiviral vector, an adenoviral vector, an adeno-associated viral (AAV) vector, and a retroviral vector.

32. A method of measuring tumor size for a plurality of clonally independent tumors of the same tissue, the method comprising:
    (a) contacting a tissue with a plurality of barcoded nucleic acid cell markers, thereby generating a plurality of distinguishable lineages of heritably marked neoplastic cells within the contacted tissue;
    (b) after sufficient time has passed for at least a portion of the heritably marked neoplastic cells to undergo at least one round of division, performing high-throughput nucleic acid sequencing to detect and measure quantities of at least two of the of barcoded nucleic acid cell markers present in the contacted tissue, thereby generating a set of measured values; and
    (c) calculating, using the set of measured values as input, a number of heritably marked neoplastic cells present in the contacted tissue for at least two of said distinguishable lineages of heritably marked neoplastic cells.

33. The method of 32, wherein said tissue comprises neoplastic cells and/or tumors prior to step (a).

34. The method of 32 or 33, wherein the high-throughput nucleic acid sequencing of step (b) is performed on a biological sample collected from the tissue.

35. The method of 32 or 33, wherein the high-throughput nucleic acid sequencing of step (b) is performed on a tissue sample of the contacted tissue.

36. The method of any one of 32 to 35, wherein each barcoded nucleic acid cell marker of the plurality of barcoded nucleic acid cell markers corresponds to a known cell genotype for a lineage of heritably marked neoplastic cells.

37. The method of any one of 32 to 36, wherein said contacting comprises genetically altering cells of the tissue to generate the heritably marked neoplastic cells.

38. The method of any one of 32 to 37, wherein the barcoded nucleic acids induce neoplastic cell formation.

39. The method of any one of 32 to 37, wherein the barcoded nucleic acids induce neoplastic cell formation and include one or more of: homology directed repair (HDR) DNA donor templates, nucleic acids encoding one or more oncogenes, nucleic acids encoding one or more wildtype proteins, nucleic acids encoding one or more mutant proteins, nucleic acids encoding CRISPR/Cas guide RNAs, nucleic acids encoding short hairpin RNAs (shRNAs), and nucleic acids encoding a genome editing protein.

40. The method of 39, wherein the genome editing protein is selected from: a CRISPR/Cas RNA-guided protein, a CRISPR/Cas RNA-guided protein fused to a transcriptional activator or repressor polypeptide, a Cas9 protein, a Cas9 protein fused to a transcriptional activator or repressor polypeptide, a zinc finger nuclease (ZFN), a TALEN, a phage-derived integrase, a Cre protein, a Flp protein, and a meganuclease protein.

41. The method of any one of 32 to 40, wherein the barcoded nucleic acids are linear or circular DNA molecules.

42. The method of any one of 32 to 40, wherein the barcoded nucleic acids are selected from: plasmids, synthesized nucleic acid fragments, and minicircles.

43. The method of any one of 32 to 42, wherein the barcoded nucleic acids are RNA/DNA hybrids or nucleic acid/protein complexes.

44. The method of any one of 32 to 43, wherein the tissue is an invertebrate tissue.

45. The method of any one of 32 to 43, wherein the tissue is a vertebrate tissue.

46. The method of any one of 32 to 43, wherein the tissue is a mammalian or a fish tissue.

47. The method of any one of 32 to 43, wherein the tissue is a rat tissue, a mouse tissue, a pig tissue, a non-human primate tissue, or a human tissue.

48. The method of any one of 32 to 47, wherein the tissue is part of a living animal.

49. The method of any one of 32 to 47, wherein the tissue is an engineered tissue grown outside of an animal.

50. The method of any one of 32 to 49, wherein the tissue is selected from: muscle, lung, bronchus, pancreas, breast, liver, bile duct, gallbladder, kidney, spleen, blood, gut, brain, bone, bladder, prostate, ovary, eye, nose, tongue, mouth, pharynx, larynx, thyroid, fat, esophagus, stomach, small intestine, colon, rectum, adrenal gland, soft tissue, smooth muscle, vasculature, cartilage, lymphatics, prostate, heart, skin, retina, and reproductive system, and genital system.

51. The method of any one of 32 to 50, wherein after sufficient time has passed for at least a portion of the heritably marked neoplastic cells to undergo at least one round of division, the method further comprises: (i) detecting and/or measuring a biomarker of the heritably marked neoplastic cells, and (ii) categorizing the heritably marked neoplastic cells based on the results of said detecting and/or measuring of the biomarker.

52. The method of 51, wherein the biomarker of one or more of: cell proliferation status, cell type, developmental cell lineage, cell death, and cellular signaling state.

53. The method of any one of 32 to 52, wherein the cell marker is delivered to the tissue via viral vector.

54. The method of 53, wherein the viral vector is selected from: a lentiviral vector, an adenoviral vector, an adeno-associated viral (AAV) vector, a bocavirus vector, a foamy virus vector, and a retroviral vector.

55. The method of any one of 1-54, wherein the method includes contacting the tissue with a test compound (e.g., test drug) and determining whether the test compound had an effect on cell population size and/or distribution of cell population sizes.

56. The method of any one of 1-55, wherein, after generating the heritably marked cells, the method includes transplanting one or more of the heritably marked cells (e.g., transplanting one or more tumors) into one or more recipients (e.g., a secondary recipient, e.g., to seed tumors in the secondary recipient).

57. The method of 56, where a test compound is administered to the one or more recipients and the method comprises detecting and measuring quantities of at least two of the plurality of cell markers present in the recipient(s) (e.g., to assess growth of the transplanted cells in response to the presence of the test compound).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Tuba-Seq: A Quantitative and Multiplexed Approach to Uncover the Fitness Landscape of Tumor Suppression In Vivo Cancer growth and progression are multi-stage, stochastic evolutionary processes. While cancer genome sequencing has been instrumental in identifying the genomic alterations that occur in human tumors, the consequences of these alterations on tumor growth within native tissues remains largely unexplored. Genetically engineered mouse models of human cancer enable the study of tumor growth in vivo, but the lack of methods to quantify the resulting tumor sizes in a precise and scalable manner has limited our ability to understand the magnitude and the mode of action of individual tumor suppressor genes. Here, we present a method that integrates tumor barcoding with ultra-deep barcode sequencing (Tuba-seq) to interrogate tumor suppressor function in mouse models of human cancer. Tuba-seq uncovers different distributions of tumor sizes in three archetypal genotypes of lung tumors. By combining Tuba-seq with multiplexed CRISPR/Cas9-mediated genome editing, we further quantified the effects of eleven of the most frequently inactivated tumor-suppressive pathways in human lung adenocarcinoma. This approach identifies the methyltransferase Setd2 and the splicing factor Rbm10 as novel suppressors of lung adenocarcinoma growth. With unprecedented resolution, parallelization, and precision Tuba-seq enables a broad quantification of the fitness landscape of tumor suppressor gene function.

Results

Tumor Barcoding with Ultra-Deep Barcode Sequencing (Tuba-Seq) Enables the Precise and Parallel Quantification of Tumor Sizes.

Oncogenic KRAS is a key driver of human lung adenocarcinoma, and early stage lung tumors can be modeled using LoxP-Stop-LoxP $Kras^{G12D}$ knock-in mice ($Kras^{LSL-G12D/+}$) in which expression of Cre in lung epithelial cells leads to the expression of oncogenic $Kras^{G12D}$. LKB1 and P53 are frequently mutated tumor suppressors in oncogenic KRAS-driven human lung adenocarcinomas and Lkb1- and p53-deficiency increase tumor burden in mouse models of oncogenic $Kras^{G12D}$-driven lung tumors (FIG. 7a). Viral-Cre-induced mouse models of lung cancer enable the simultaneous initiation of a large number of tumors and individual tumors can be stably tagged by lentiviral-mediated DNA barcoding. Therefore, we sought to determine whether high-throughput sequencing of the lentiviral barcode region from bulk tumor-bearing lungs could quantify the number of cancer cells within each uniquely barcoded tumor (FIG. 7b).

To interrogate the growth of oncogenic $Kras^{G12D}$-driven lung tumors as well as the impact of Lkb1 and p53 loss on tumor growth, we initiated lung tumors in $Kras^{LSL-G12D/+}$; $Rosa26^{LSL-Tomato}$ (KT), KT;Lkb1$^{flox/flox}$ (KLT), and KT;p53$^{flox/flox}$ (KPT) mice with a library of Lentiviral-Cre vectors containing greater than $10^6$ unique DNA barcodes (Lenti-mBC/Cre; FIG. 1a and FIG. 7b). Eleven weeks after tumor initiation, KT mice developed widespread hyperplasias and some small tumor masses (FIG. 1b and FIG. 7c). Interestingly, while KLT mice had large tumors of relatively uniform size, KPT mice had a very diverse range of tumor sizes (FIG. 1b).

Figure 1:
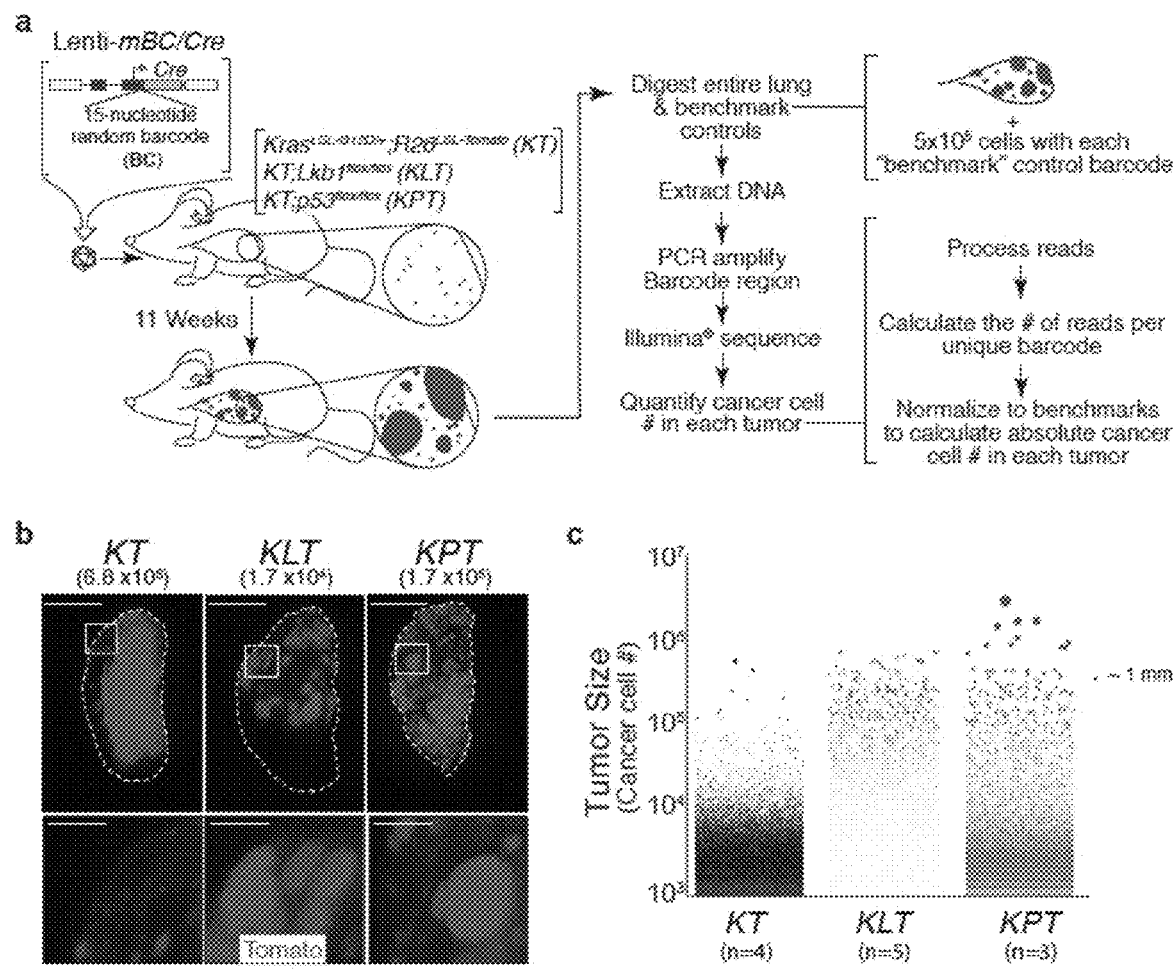
FIG. 1. Tuba-seq combines tumor barcoding with high-throughput sequencing to allow parallel quantification of tumor sizes. a, Schematic of Tuba-seq pipeline to assess lung tumor size distributions. Tumors were initiated in KrasLSL-G12D/+;Rosa26LSL-Tomato (KT), KT;Lkb1flox/flox (KLT), and KT;p53flox/flox (KPT) mice with Lenti-mBC/Cre, a virus containing a random 15-nucleotide DNA barcode (BC). Tumor sizes were calculated via bulk barcode sequencing of the DNA from the tumor bearing lungs. b, Fluorescence dissecting scope images of lung lobes from KT, KLT, and KPT mice with Lenti-mBC/Cre initiated tumors. Lung lobes are outlined with white dashed lines. The titer of Lenti-mBC/Cre is indicated. Different titers were used in different genetic background to generate approximately equal total tumor burden despite differences in overall tumor growth. Scale bars in upper panels=5 mm. Scale bars in lower panels=1 mm. c, Tumor size distributions in KT, KLT, and KPT mice (number of mice per group is indicated). Each dot represents a tumor. The area of each dot is proportional to the number of cancer cells in each tumor. A dot corresponding to the approximate number of cancer cells in a spherical tumor with a 1 mm diameter is shown to the right of the data for reference.
Figure 2:
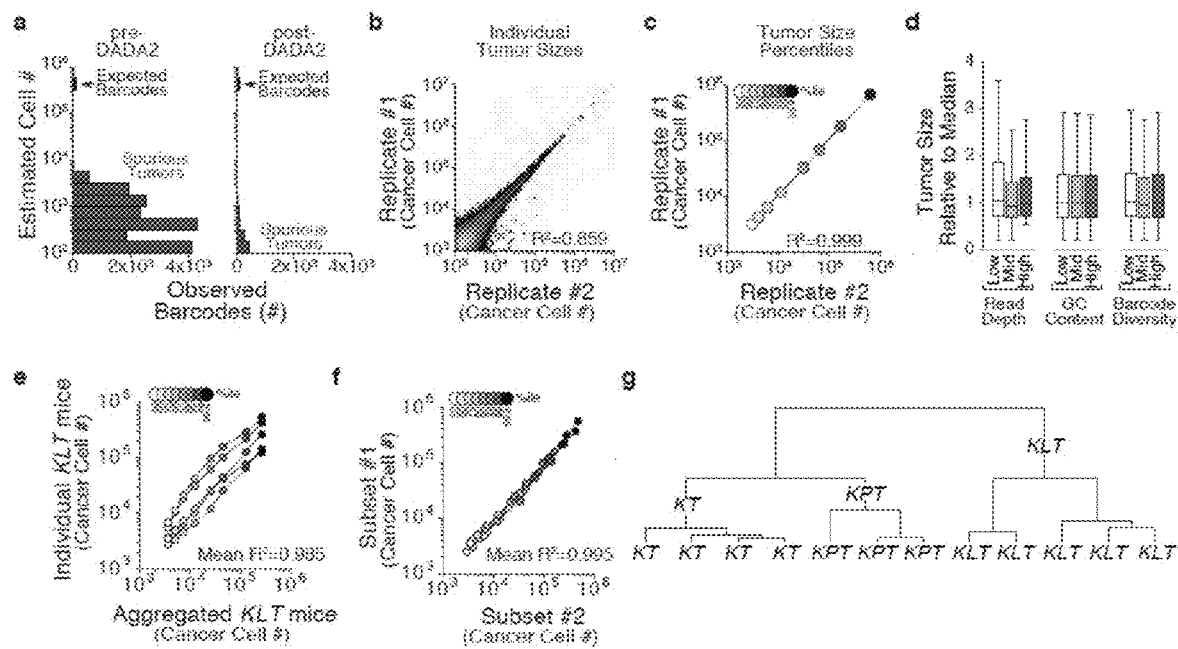
FIG. 2. Tuba-seq is a robust and reproducible method to quantify tumor sizes. a, DADA2, a denoising algorithm designed for deep sequencing of amplicon data, eliminates recurrent read errors that can appear as spurious tumors. Cell lines with known barcodes were added to each lung sample from each mouse ($5\times10^5$ cells each). Recurrent read errors that derive from these known barcodes appear as spurious tumors at ~5,000 cells. DADA2 identifies and greatly reduces these recurrent read (sequencing) errors. b,c, Technical replicate sequencing libraries prepared from an individual bulk lung sample demonstrate high correspondence between individual lesion sizes (b) and size profiles (c) (tumors at the 50 to 99.9th percentiles are shown). d, Our analysis pipeline is robust to variation in read depth, GC content of the DNA barcodes, and diversity of the barcode library. Tumors were partitioned into thirds corresponding to high, moderate, and low levels of each technical parameter: the sequencing depth, GC content of tumor barcodes, and estimated number of unique barcodes (see Methods). Whiskers capped at 1.5 IQR. e, Reproducibility of size distributions across five KLT mice. Mice have overall similar size profiles despite small mouse-to-mouse differences in tumor sizes. Sizes of the tumors at the indicated percentiles in individual mice are connected by a line. f, Reproducibility of size profiles improves when tumors within the same mouse are compared, suggesting significant mouse-to-mouse variability in tumor sizes. Tumors in each mouse were partitioned into two groups and the profiles of these groups were compared. Sizes of the tumors at the indicated percentiles in an individual mouse are connected by a line. g, Unsupervised hierarchical clustering of the KT, KPT, and KLT mice based on the total least-squares distance between tumors sizes at defined percentiles (clustered by Ward's Variance Minimization Algorithm). Mice cluster by genotype suggesting that Tuba-seq identifies reproducible differences in the size spectrum of each genotype.
Figure 8:
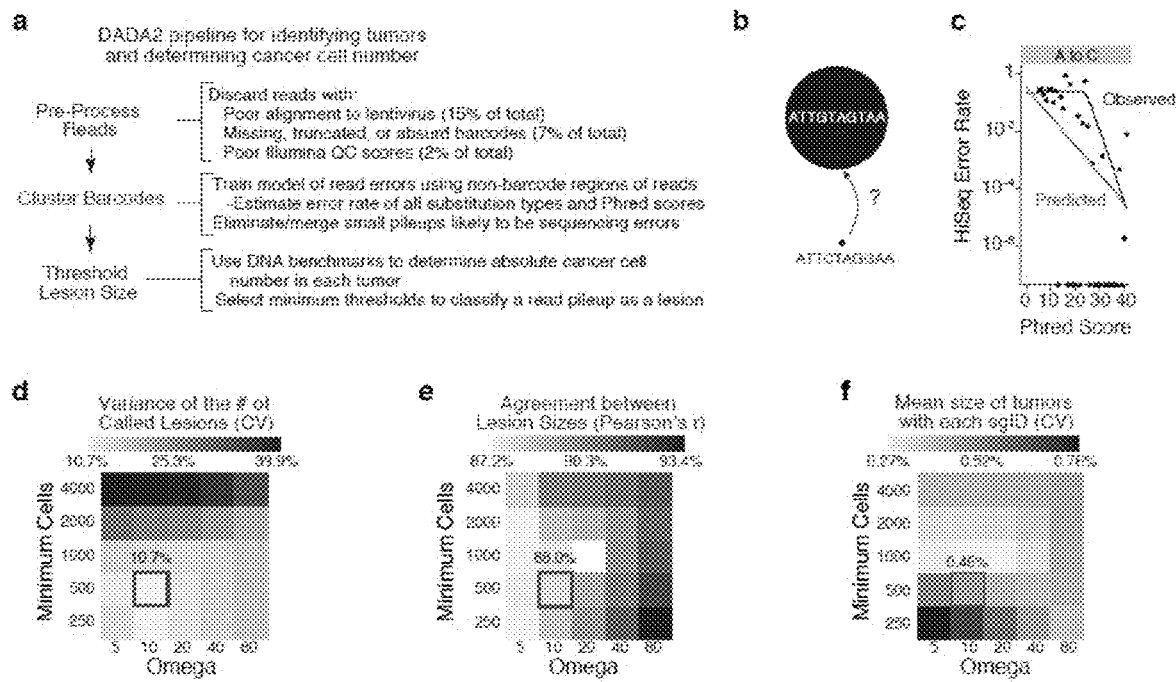
FIG. 8. Tuba-seq pipeline to quantify tumor sizes in vivo. a, Illumina® sequencing of the DNA barcode region of the integrated lentiviral vectors enables precise measurement of lesion sizes. First, reads with poor Phred quality scores or unexpected sequences were discarded. Next, reads were piled-up into groups with unique barcodes. Recurrent Illumina® sequencing errors were delineated from small lesions using DADA2, a model of Illumina® sequencing errors initially designed to identify full read-length deep-sequencing amplicons. Small barcode pileups deemed to be recurrent sequencing errors from the amplified barcode region of large tumors were combined with these larger pileups by this clustering algorithm. Read pileups were translated into absolute cell number using the benchmark controls. Lastly, a minimum cutoff to call lesions was established using both sequencing information and absolute cell number to maximize reproducibility of the pipeline. b,c, A unique read pileup may not correspond to a unique lesion but rather arise from recurrent sequencing errors of the barcode from a very large tumor (e.g., much larger tumor). DADA2 was used to merge small read pileups with larger lesions of sufficient size and sequence similarity. The algorithm calculates the sequencing error rates from the non-degenerate regions of our deep sequenced region (i.e. the region of the lentiviral vectors that flank the barcode) (b). The likelihood of every transition and transversion (A to C shown) was calculated for every Illumina® Phred score to generate an error model specific for each run (The sequence of (b) is set forth in SEQ ID NO: 110.) (c). The advertised Phred error rates (red) are generally lower than observed (black; LOESS regression used for regularization). These error models (trained to each Illumina® machine) were then used to determine if smaller read pileups should be bundled into larger pileups with strong sequence similarity (suggesting that the smaller pileup is a recurrent read error) or left as a separate lesion. d-f, We sequenced our first experimental samples (KT, KLT, and KPT from FIG. 1) on three different Illumina® machines to vet and parameterize DADA2. A sound lesion calling protocol was expected to show (d) strong similarity in the number of called lesions, (e) good correlation between barcode sizes, and (f) similar mean sizes of each sgID pool across the 3 runs. The three runs naturally varied in sequencing depth (40.1×10$^6$, 22.2×10$^6$, and 34.9×10$^6$ reads after pre-processing) and naturally varied in their expected error rate per base (0.85%, 0.95%, and 0.25%)—offering useful technical perturbations to vet concordance of the method. We found that truncating lesion sizes at 500 cells and truncating the DADA2 clustering probability (omega) at 10-10 (red square) offered a profile of lesion sizes at very small scales, while still minimizing variability in our test metrics.

To quantify the cancer cell number in every lesion using ultra-deep sequencing, we PCR-amplified the integrated lentiviral barcode region from ~1/10$^{th}$ of bulk lung DNA isolated from each mouse and sequenced this to an average depth of greater than $10^7$ reads per mouse (FIG. 1a, Methods). We observed over one-thousand-fold variation in tumor sizes within mice (FIG. 1c). Barcode reads from small lesions could represent unique tumors or be generated from recurrent sequencing errors of similar barcodes from larger tumors. To minimize the occurrence of these spurious tumors, we aggregated reads expected to be derived from the same tumor barcode using an algorithm that generates a statistical model of sequencing errors (DADA2: FIG. 2 and FIG. 8). The DADA2 aggregation rate and minimum tumor size were also selected to maximize reproducibility of our tumor-calling pipeline (FIG. 8d-f). These approaches greatly limit, but likely do not entirely eliminate, the effect of recurrent sequencing errors on tumor quantification (FIG. 2a).

Figure 9:
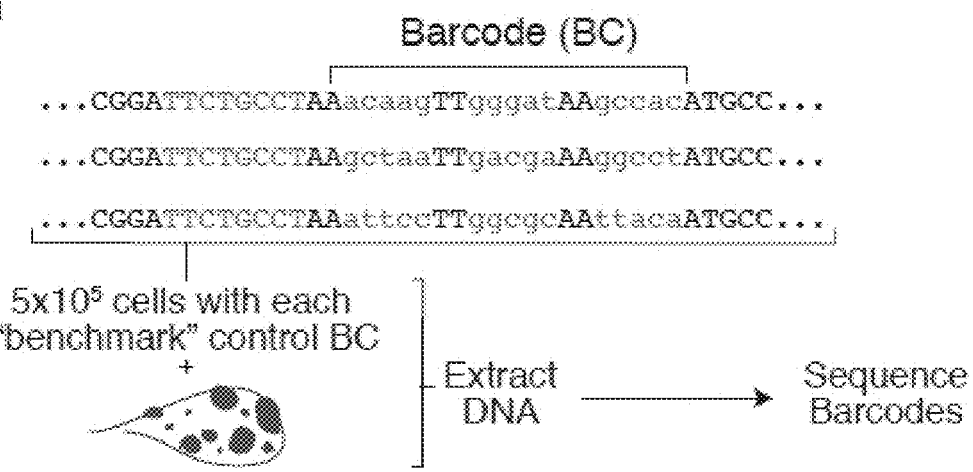
FIG. 9. Benchmark controls allow calculation of the number of cancer cells in each tumor within each lung sample. a, Schematic of the protocol using three benchmark control cell lines with known barcodes. 5×10$^5$ cells of each cell line was added to each lung sample. DNA was then extracted from the lung plus all three benchmark controls, and the barcodes were PCR amplified and deep sequenced. We then calculated the number of cancer cells in each tumor within that lung sample by dividing the % reads associated with the benchmarks by the % reads observed from each tumor (unique barcode) and multiplying by 5×10$^5$ to obtain cancer cell number. (The sequences of (a) from top to bottom are set forth in SEQ ID NOs: 110-112.) b, Example of two lungs with very different tumor burdens. These benchmark cell lines can be used determine the number of cancer cells within individual tumors regardless of overall tumor burden. It should also be noted, that the surrounding "normal lung" tissue has no impact on this calculation as this tissue has no lentiviral integration and thus will contribute no reads. The generation of a titration of benchmark controls (e.g., of 5×10$^5$, 5×10$^4$, 5×10$^3$, 5×10$^2$, or 50 cells) facilitates the resolution of Tuba-seq to be extended to smaller clonal expansions).
Figure 10:
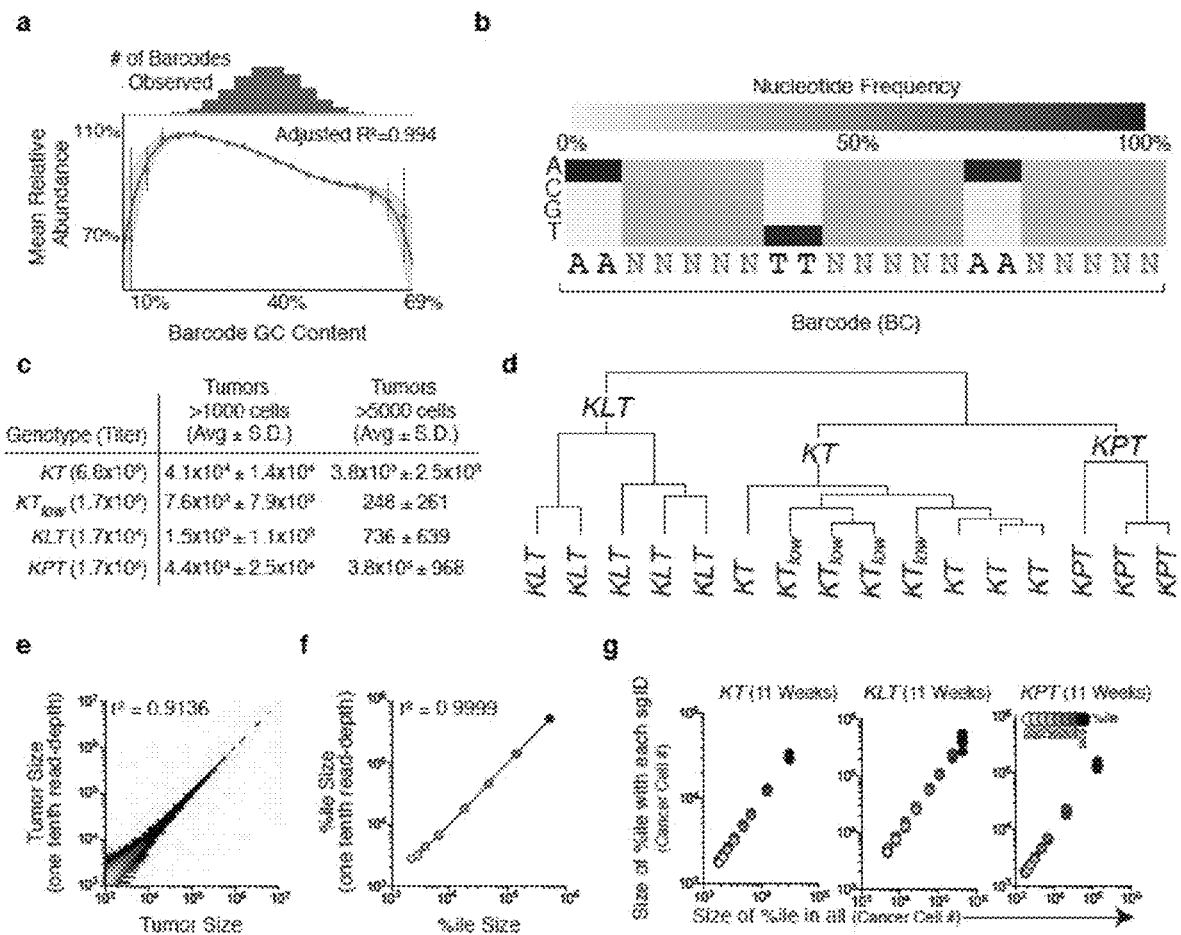
FIG. 10. The DADA2-based tumor calling pipeline is robust and reproducible. a, Tumor sizes exhibited a subtle GC-bias. Residual tumor size variability was minimized by log-transformation of sizes and normalization of each tumor by the mean size of each sgRNA in every mouse. Barcodes with intermediate GC-content appear to be PCR-amplified most efficiently. A 4th-order polynomial fit to the residual bias corrected lesion sizes most effectively. This correction was calculated and applied to all subsequent analyses, which adjusted each lesion size by an average of 5%, and reduced the standard deviation of lesions sizes of each sgID in each mouse by only 2.9% relative to the mean—suggesting that, while measurable, variability introduced by GC-bias was minimal. b, The random barcodes exhibited a high-degree of randomness across the intended nucleotides. (The sequence of (b) is set forth in SEQ ID NO: 113.) c, Number of lesions called per mouse using Tuba-seq. Numbers of tumors above two different cell number cutoffs (1000 and 500) are shown as the average number of tumors per mouse±the standard deviation. KT mice were exposed to a high titer (6.8×10$^5$) (used in the main text) and a lower titer (1.7×10$^{-5}$; KT$^{low}$). There was no statistically significant difference in the number of tumors observed per capsid at either cell cutoff suggesting that barcode diversity is still not limited above half a million tumors and that small tumors are not caused by tumor crowding. d, Unsupervised hierarchical clustering of the KT, KT$^{low}$, KPT, and KLT mice based on the total least-squares distance between tumors sizes at defined percentiles (linkage determined by Ward's Incremental algorithm.) Mice of the same genotype, but different viral titers, cluster together, suggesting that size profile differences are determined primarily by tumor genetics (genootype), not differences in viral titer. e, f, Lesion sizes are not dramatically affected by differences in read depth. The barcode region from the tumor-bearing lungs of an individual mouse was sequenced at very high depth and then randomly down-sampled to typical read depth. (e) The tumor size distributions of the full (x-axis) and downsampled (y-axis) data sets were very similar, indicating our analysis parameters are unbiased by, and fairly robust to, read depth. (f) The percentiles calculations are also reproducible upon down-sampling. g, KT, KLT, and KPT mice with Lenti-mBC/Cre initiated tumors (from FIG. 1) have tumors with six unique Lenti-sgID-BC/Cre viruses (each harboring a unique sgID and naturally varying barcode diversity). This allowed us to quantify the variation in DADA2-called tumor sizes with six replicates within each mouse. Tumor size distributions are reproducibly called when using all tumors from each mouse and when using each subset of tumors with a given sgID. The size of the tumor at the indicated percentiles are plotted for KT (left), KLT (middle), and KPT (right). Each dot represents the value of a percentile calculated using tumors within a single sgID. Percentiles are represented in greyscale. The six replicate percentile values of tumor size with differing sgIDs are difficult to distinguish since their strong correlation means that markers for each sgID are highly overlapping.

Quantification of the absolute number of cancer cells in each tumor would allow the aggregation of data from individual mice of the same genotype and the comparison of tumor sizes across genotypes. To enable the conversion of read count to cancer cell number, we added cells with known barcodes to each lung sample at a defined number prior to tissue homogenization and DNA extraction (FIG. 1a and FIG. 9). Thus, by normalizing tumor read counts to "benchmark" read counts we could calculate the absolute number of cancer cells in each tumor in each mouse (FIG. 1a and FIG. 9).

Tuba-seq is highly reproducible between technical replicates and is insensitive to many technical variables that could bias tumor size distributions including sequencing errors, variation in the intrinsic error rate of individual Illumina® sequencing machines, barcode GC content, barcode diversity, tumor number within mice, and read depth (FIG. 2b-d, FIG. 10). While moderate measurement error exists at small sizes, this does not bias the overall size distributions. Tumor size distributions were also highly reproducible between mice of the same genotype ($R^2>0.98$; FIG. 2e,f, FIG. 10g). In fact, unsupervised hierarchical clustering of size distributions clearly separated mice according to their genotype, even when tumors were induced with different titers of Lenti-mBC/Cre (FIG. 2g and FIG. 10d). Our method did, however, detect variation in the spectrum of tumor sizes between mice of the same genotypes. This variation is much greater than the random noise observed between two fractions of tumors within the same mouse suggesting that Tuba-seq is significantly more precise than the intrinsic variability in tumor burden between mice (FIG. 2e,g). Thus, Tuba-seq rapidly and precisely quantified the number of cancer cells within thousands of lung lesions in KT, KLT, and KPT mice (FIG. 1c, FIG. 10c).

Analysis of Tumor Sizes Uncovers Two Modes of Tumor Suppression

Figure 3:
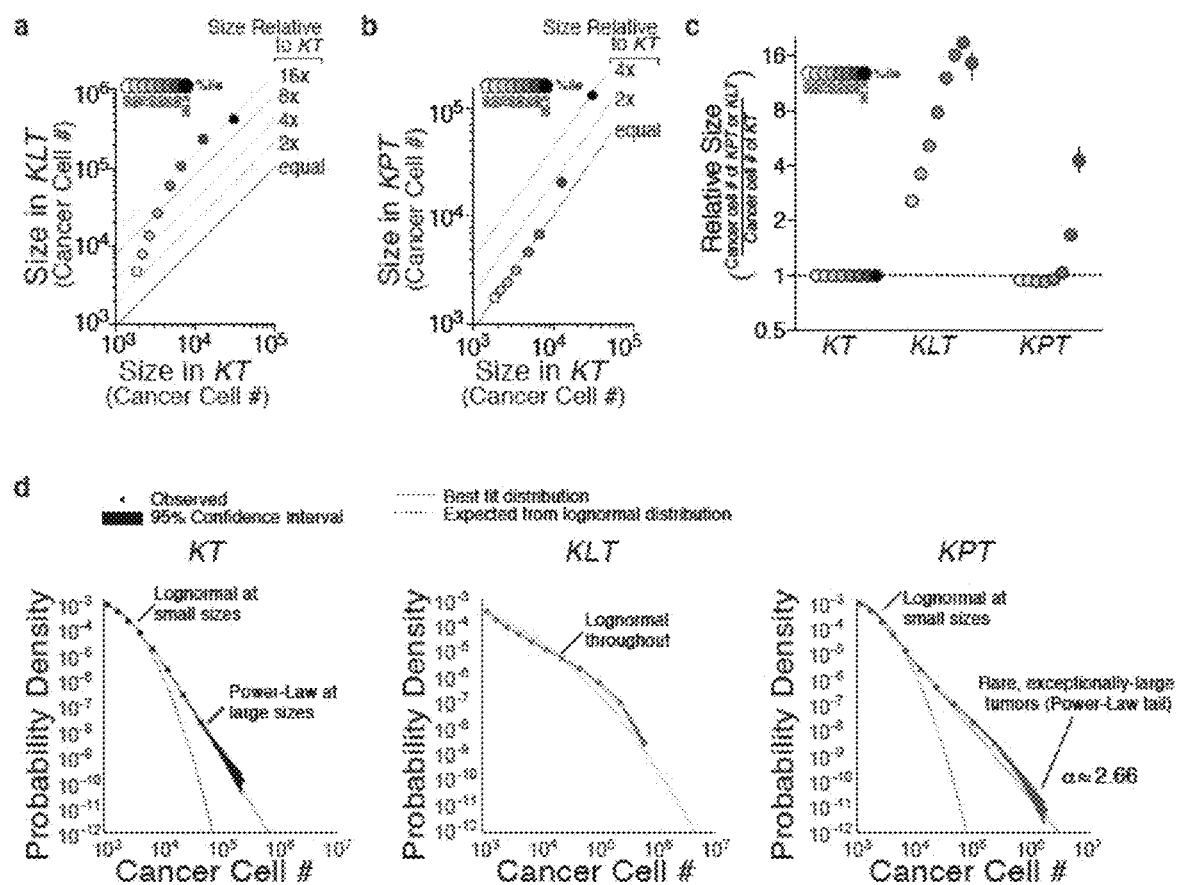
FIG. 3. Massively parallel quantification of tumor sizes enables probability distribution fitting across multiple genotypes. a, b, Tumor size at the indicated percentile in KLT (n=5) mice (a) and KPT (n=3) mice (b) versus tumor size at the indicated percentile in KT mice (n=7). Each percentile was calculated using all tumors from all mice of each genotype 11 weeks after tumor initiation with Lenti-mBC/Cre. c, Tumor sizes at the indicated percentiles for each genotype relative to KT tumors at the same percentiles. Error bars are 95% confidence intervals obtained via bootstrapping. Percentiles that are significantly different from the corresponding KT percentiles are in color. d, As anticipated for exponential tumor growth with normally distributed growth rates, tumor size distributions were most closely fit by a log normal distribution. Tumors in KLT mice are best described by a log normal distribution throughout their entire size spectrum (middle). The tumor size distributions in KT mice (left) and KPT mice (right) were better explained by combining a log normal distribution at smaller scales with a power-law distribution at larger scales. These differences are fundamentally important in considering how individual genes (or combinations of genes) lead to increased tumors growth. Power-law relationships decline linearly on log-log axes, consistent with rare, yet very large tumors within the top ~1% of tumors in KT mice and ~10% of tumors in KPT mice. Note: only tumors in KPT mice ever exceed one million cells after 11 weeks, consistent with p53-deficiency enabling the generation of the largest tumors in our study.

To assess the effect of either p53- or Lkb1-deficiency on tumor growth, we calculated the number of cancer cells in the tumors at different percentiles within the distribution. Interestingly, while tumors in KLT mice were consistently larger than KT tumors, deletion of p53 did not alter the number of cancer cells in the vast majority of tumors (FIG. 3a-c). Instead, a small fraction of p53-deficient tumors grew to exceptional sizes, and were among the largest in any of the mice (FIG. 1c).

To better understand the difference in tumor growth imparted by p53- and Lkb1-deficiency, we defined the mathematical distributions that best fit the tumor size distributions in KT, KLT, and KPT mice. Lkb1-deficient tumors were lognormally distributed across the full range of the distribution (FIG. 3d). A log normal distribution is expected from simple exponential tumor growth with normally distributed rates. To estimate average tumor size without allowing very large tumors to greatly shift this metric, we also calculated the maximum likelihood estimator of the mean number of cancer cells given a log normal distribution of tumor sizes (LN mean). By this measure KLT tumors had, on average, 7-fold more cancer cells than KT tumors, consistent with the role of Lkb1 in restraining proliferation (FIG. 3a,c). Despite greater tumor burden and visibly larger tumors in KPT mice, p53-deficiency did not increase our estimate of mean lesion size. Instead, p53-deficient tumors were power-law distributed at large sizes and the elevated total tumor burden was driven by rare, exceptionally large tumors (FIG. 3d). This suggests that p53-deficient tumors acquire additional rare, yet profoundly tumorigenic events that drive subsequent rapid growth.

Figure 11:
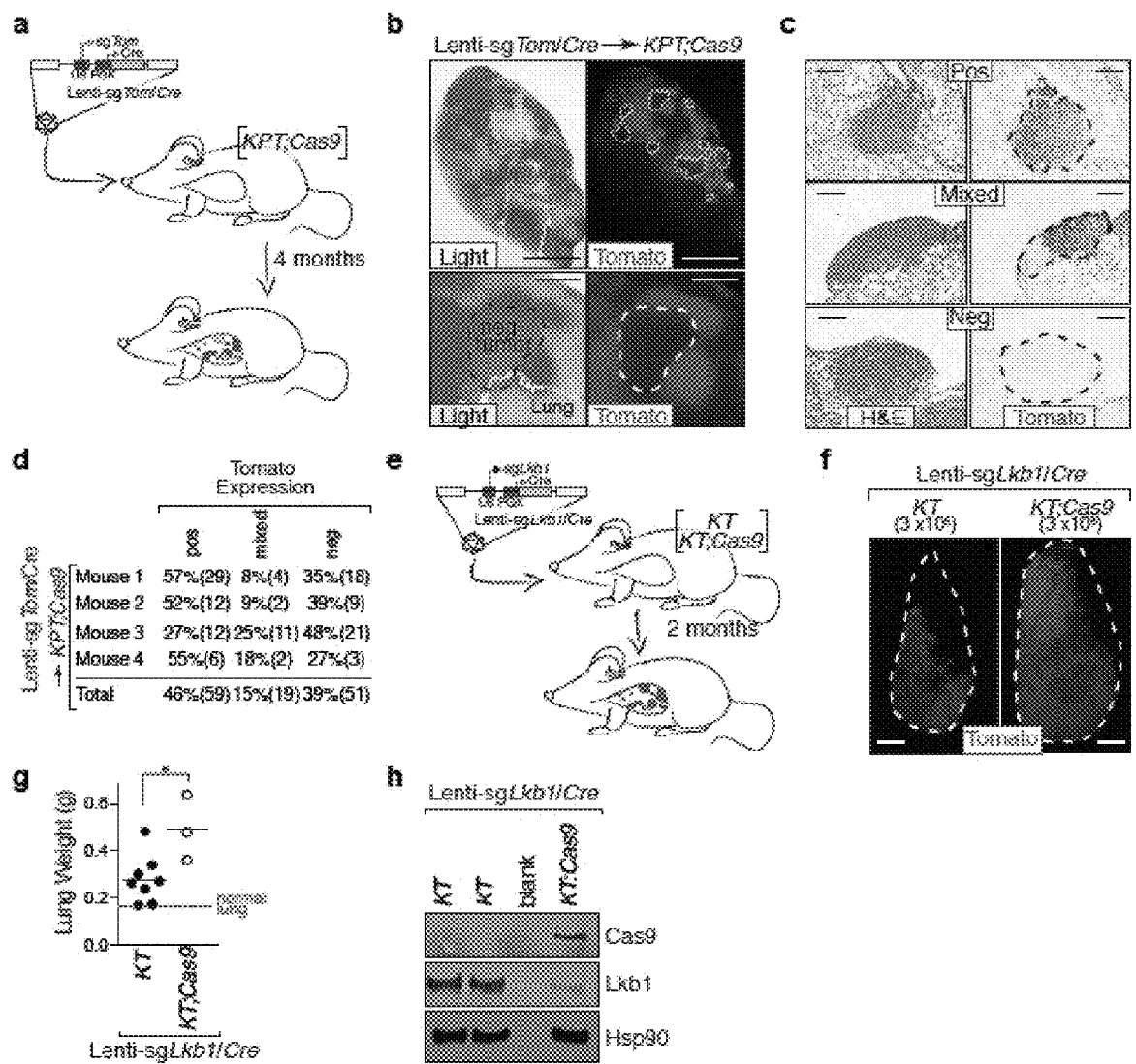
FIG. 11. Efficient genome editing in lung tumors initiated with Lentiviral-sgRNA/Cre vectors in mice with the $H11^{LSL-Cas9}$ allele. a, Schematic of the experiment to test somatic genome editing in the lung cancer model using a Lenti-sg Tomato/Cre (Lenti-sgTom/Cre) viral vector and the $H11^{LSL-Cas9}$ allele. All mice were homozygous for the $R26^{LSL-Tomato}$ allele to determine the frequency of homozygous deletion. b, Fluorescence dissecting scope images of a lung lobe from a KPT;Cas9 mouse with Lenti-sgTomato/Cre-initiated tumors. Tomato-negative tumors are outlined with dashed lines. Top scale bars=5 mm; bottom scale bars=1 mm. c, Immunohistochemistry for Tomato protein uncovered Tomato-positive (Pos), Tomato-mixed (Mixed), and Tomato-negative (Neg) tumors. Tumors are outlined with dashed lines. Scale bars=200 μm. d, Quantification of Tomato expression in four KPT;Cas9 mice with Lenti-sg Tom/Cre initiated tumors indicates that approximately half of the tumors have CRISPR/Cas9-mediated homozygous inactivation of the targeted gene in at least a fraction of the cancer cells. Percent of Tomato positive, mixed, and negative tumors is shown with the number of tumors in each group indicated in brackets. e, Schematic of the experiment to test somatic genome editing in the lung using Lenti-sgLkb1/Cre virus and the $H11^{LSL-Cas9}$ allele. f, Fluorescence dissecting scope images of lung lobes of KT and KT;Cas9 mice infected (transduced) with Lenti-sgLkb1/Cre show increased tumor burden in the KT;Cas9 mouse. Lung lobes are outlined with white dashed lines. Scale bars=2 mm. g, Tumor burden, represented by lung weight, is increased in Lenti-sgLkb1/Cre- infected (transduced) KT;Cas9 mice relative to KT mice, consistent with successful deletion of the tumor suppressor Lkb1. Normal lung weight is indicated by the dotted red line. * p-value <0.02. Each dot is a mouse and the bar represents the mean. h, Western blot showing that Lenti-sgLkb1/Cre initiated tumors in KT;Cas9 mice express Cas9 and lack Lkb1 protein. Hsp90 shows loading.
Figure 12:
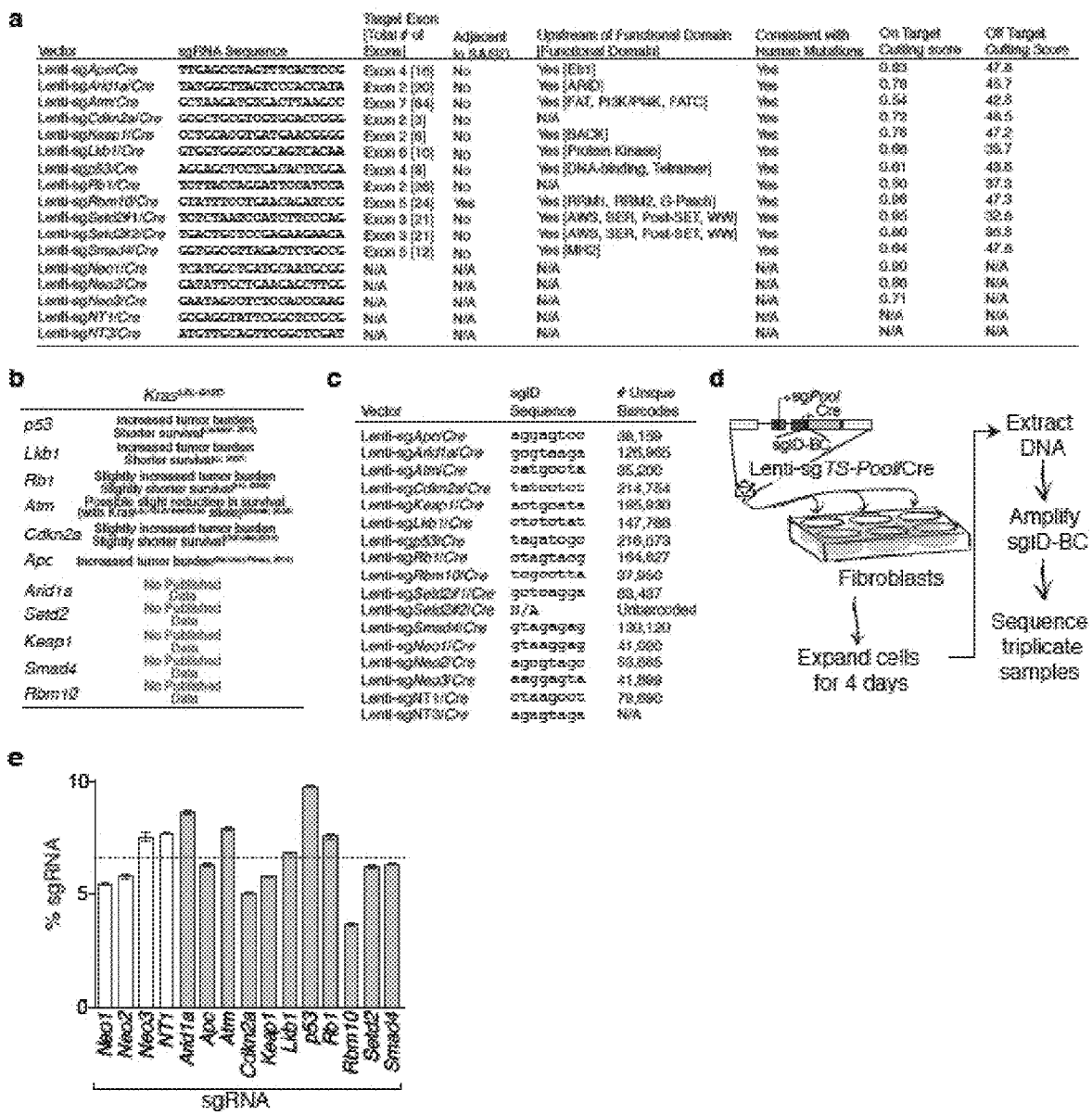
FIG. 12. Selection and characterization of sgRNAs targeting eleven known and candidate tumor suppressor genes. a, sgRNAs were selected based on their location within each gene, their proximity to splice acceptor/splice donor (SA/SD) regions, whether they were upstream of (or within) annotated functional domains, whether they were upstream of (or adjacent to) documented human mutations, as well as their predicted ontarget cutting efficiency score (the maximum score is 1.0; higher score=greater activity) and off target cutting score (the maximum score is 100.0; higher score=greater specificity) (Doench et al., Nature Biotechnology, 2014; Hsu et al., 2013). (The SEQ ID NOs of the sgRNA sequences are set forth as follows: Lenti-sgApc/Cre: (SEQ ID NO: 114); Lenti-sgArid1a/Cre: (SEQ ID NO: 115); Lenti-sgAtm/Cre: (SEQ ID NO: 116); Lenti-sgCdkn2a/Cre: (SEQ ID NO: 117); Lenti-sgKeap1/Cre: (SEQ ID NO: 118); Lenti-sgLkb1/Cre: (SEQ ID NO: 119); Lenti-sgp53/Cre: (SEQ ID NO: 120); Lenti-sgRb1/Cre: (SEQ ID NO: 121); Lenti-sgRbm10/Cre: (SEQ ID NO: 122); Lenti-sgSetd2#1/Cre: (SEQ ID NO: 123); Lenti-sgSetd2#2/Cre: (SEQ ID NO: 124); Lenti-sgSmad4/Cre: (SEQ ID NO: 125); Lenti-sgNeo1/Cre: (SEQ ID NO: 126); Lenti-sgNeo2/Cre: (SEQ ID NO: 127); Lenti-sgNeo3/Cre: (SEQ ID NO: 128); Lenti-sgNT1/Cre: (SEQ ID NO: 129); Lenti-sgNT3/Cre: (SEQ ID NO: 130).) b, Summary of data from published studies in which these tumor suppressor genes were inactivated in the context of $Kras^{G12D}$-driven lung cancer models c, Each vector has a unique sgID and was diversified with random barcodes. The sgID for each of the vectors and the estimated number of barcodes associated with each sgRNA is indicated. d, Schematic of the experiment to assess the initial representation of each sgRNA within Lenti-sgTS-Pool/Cre. e, The percent of each sgRNA within Lenti-sgTS-Pool/Cre, as determined by sequencing of samples from three replicate infections. Mean+/−SD is shown. The percent of each vector in the pool deviated only slightly from the expected representation of each vector (red dashed line).

Generation of a Library of Barcoded Lentiviral Vectors for Multiplexed CRISPR/Cas9-Mediated Inactivation of Tumor Suppressor Genes Human lung adenocarcinomas have diverse genomic alterations but there is a paucity of quantitative data describing their impact on tumor growth (FIGS. 7a and 12b). To simultaneously quantify the tumor-suppressive function of many known and candidate tumor suppressor genes in parallel, we combined Tuba-seq and conventional Cre-based mouse models with multiplexed CRISPR/Cas9-mediated in vivo genome editing (FIG. 4a-c). Assessing different tumor genotypes in a single mouse should also maximize the resolution of Tuba-seq, by eliminating the effect of mouse-to-mouse variability. We first confirmed efficient Cas9-mediated gene inactivation in lung tumors in mice with an $H11^{LSL-Cas9}$ allele by initiating tumors with Lentiviral-sgRNA/Cre vectors targeting either the tdTomato reporter or Lkb1 (FIG. 11). Homozygous inactivation of tdTomato was achieved in around 40% of tumors and Cas9-mediated Lkb1 inactivation increased tumor burden (FIG. 11). These data demonstrate our ability genetically alter tumors in Kras-driven lung cancer models using these methods.

Figure 13:
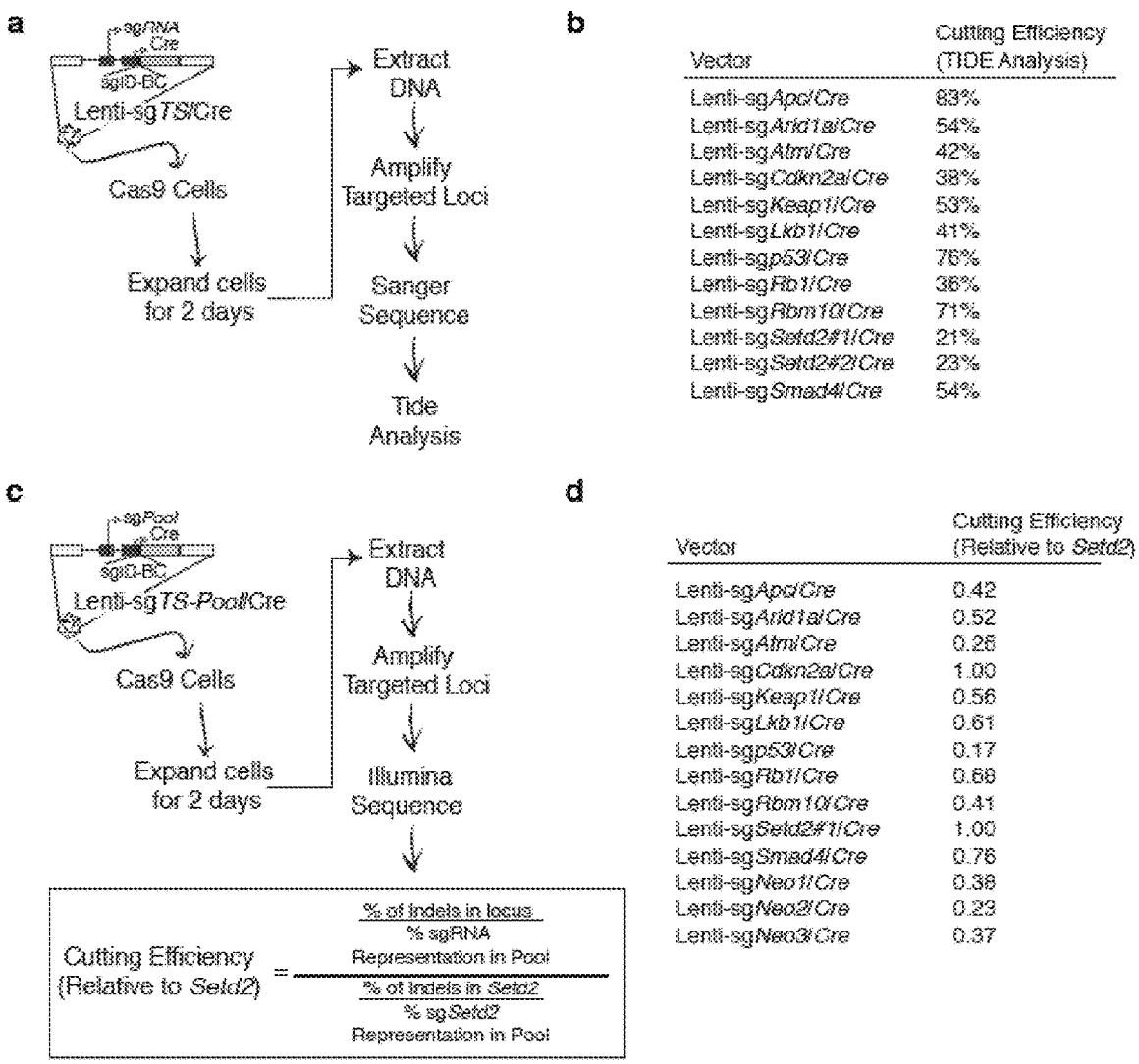
FIG. 13. In vitro sgRNA cutting efficiency. a, Schematic of the experiment to assess the in vitro cutting efficiency of each sgRNA by infecting Cas9 cells with lentivirus carrying each individual sgRNA. We tested three individual sgRNAs for each targeted loci and we report the cutting efficiency of the best sgRNA. b, Cutting efficiency of the best sgRNA for each targeted tumor suppressor. Cutting efficiency was assessed by Sanger sequencing and TIDE analysis software (Brinkman et al., Nucl. Acids Res., 2014). c, Schematic of the experiment to assess the in vitro cutting efficiency of each sgRNA by infecting Cas9 cells with Lenti-sgTS-Pool/Cre. Cells were harvested 48 hours after infection (transduction), genomic DNA was extracted, the 14 targeted regions were PCR amplified, and the products were sequenced. By calculating the % of indels at each region, and normalizing to both the representation in the pool and Setd2 indel %, a relative cutting efficiency was determined for each sgRNA within the pool. d, Relative cutting efficiency of each sgRNA including the inert Neo-targeting controls.

We selected eleven known and putative lung adenocarcinoma tumor suppressor genes, which represent diverse pathways, including genes that are broadly involved in chromatin remodeling (Setd2 and Arid1a), splicing (Rbm10), DNA damage response (Atm and p53), cell cycle control (Rb1 and Cdkn2a), nutrient and oxidative stress sensing (Lkb1 and Keap1), environmental stress responses (p53), as well as TGF-β and Wnt signaling (Smad4 and Apc, respectively) (FIG. 4b and FIG. 7a). We identified efficient sgRNAs that generated indels early in the transcripts, upstream of known functional domains, and upstream of most mutations present in human tumors (FIG. 12a). To allow accurate quantification of the number of cancer cells in each tumor using Tuba-seq, we diversified each tumor suppressor-targeting Lenti-sgRNA/Cre vector and four Lenti-sgInert/Cre negative control vectors with a two-component barcode. This barcode consisted of a unique 8-nucleotide "sgID" specific to each sgRNA and a random 15-nucleotide barcode (BC) to uniquely tag each tumor (sgID-BC; FIG. 4a,b and FIG. 12c-e). In vitro cutting efficiency was determined for each of the sgRNAs individually and within the pool (FIG. 13).

Parallel Quantification of Tumor Suppressor Function In Vivo

Figure 14:
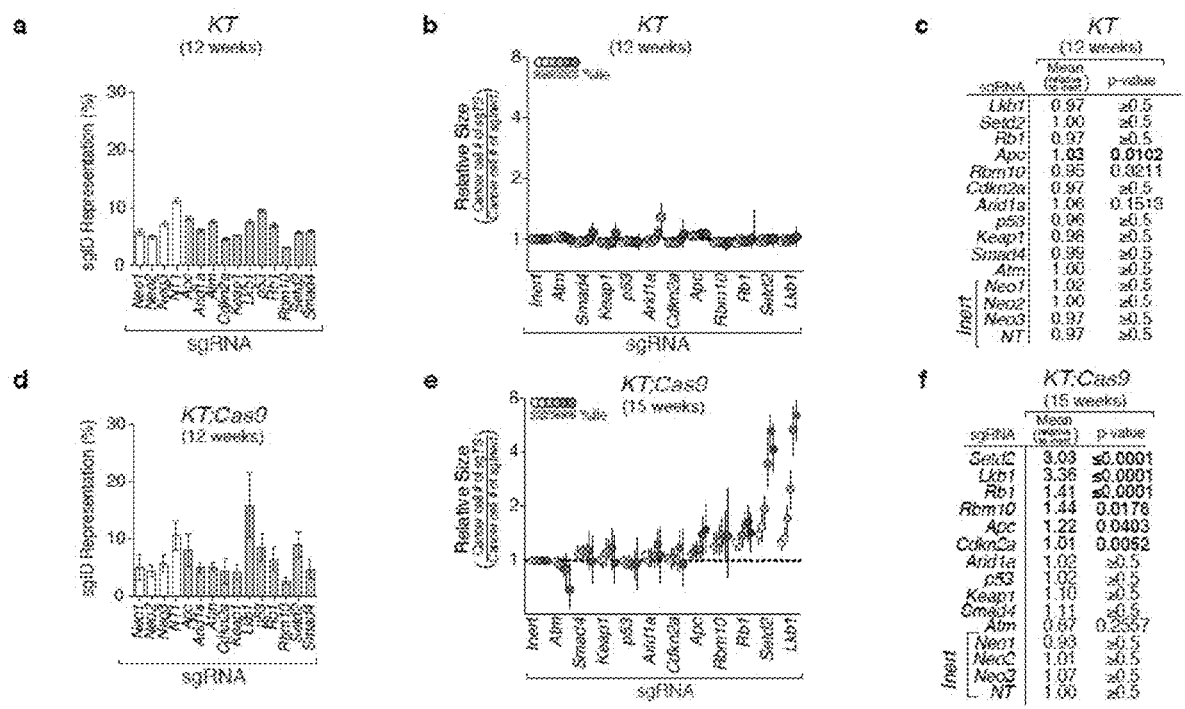
FIG. 14. Identification and validation of tumor suppressors at multiple time points using Tuba-seq. a, Percent representation of each Lenti-sgRNA/Cre vector in KT mice 12 weeks after tumor initiation (calculated as 100 times the number of reads with each sgID/all sgID reads). As there is no Cas9-mediated gene inactivation in KTmice, the percent of each sgID in these mice represents the percent of viral vectors with each sgRNA in the Lenti-sgTS-Pool/Cre pool. b, Analysis of the relative tumor sizes in KT mice (which lack Cas9) 12 weeks after tumor initiation with Lenti-sgTS-Pool/Cre identified essentially uniform tumor size distributions. Relative tumor size at the indicated percentiles represents merged data from 10 mice, normalized to the average of sgInert tumors. 95% confidence intervals are shown. Percentiles that are significantly different from sgInert are in color. c, Estimates of mean tumor size, assuming a log normal tumor size distribution, showed expected minor variability in KTmice. Bonferroni-corrected, bootstrapped p-values are shown. p-values <0.05 and their corresponding means are bold. d, Percent representation of each Lenti-sgRNA/Cre vector in KT;Cas9 mice 12 weeks after tumor initiation (calculated as 100 times the number of reads with each sgID/all sgID reads). e, Tumor sizes at the indicated percentiles for each sgRNA relative to the average of sgInert-containing tumors at the same percentiles. Merged data from 3 KT;Cas9 mice 15 weeks after tumor initiation with Lenti-sgTS-Pool/Cre is shown. Dotted line represents no change from Inert. Error bars represent 95% confidence intervals. Percentiles in which the confidence intervals do not overlap the dotted line are in color. f, Estimates of mean tumor size, assuming lognormality, identified sgRNAs with significant growth advantage in KT;Cas9 mice. Bonferroni-corrected, bootstrapped p-values are shown. p-values <0.05 and their corresponding mean estimates are in bold.

To quantify the effect of inactivating each gene on lung tumor growth in a multiplexed manner, we initiated tumors in KT and KT;H11$^{LSL-Cas9}$ (KT;Cas9) mice with a pool of the eleven barcoded Lenti-sgRNA/Cre vectors and four barcoded Lenti-sgInert/Cre vectors (Lenti-sgTS-Pool/Cre; FIG. 4b,c). Despite receiving a lower dose of virus compared to KT mice, KT;Cas9 mice had an increase in the number and size of macroscopic tumors relative to KT mice 12 weeks after tumor initiation (FIG. 4d,e). To determine the number of cancer cells in each tumor with each sgRNA, we amplified the sgID-BC region from bulk tumor-bearing lung DNA, deep sequenced the product, and applied our Tuba-seq analysis pipeline. We calculated the entire distribution of growth effects for each tumor suppressor relative to the distribution of inert sgRNAs within each mouse. For each sgRNA, the number of cancer cells in the tumors at different percentiles within the distribution were divided by the sizes of the corresponding percentiles in the inert distribution (FIG. 5a). This relative and within-mouse comparison maximized the precision of Tuba-seq (Methods). We also determined the relative log normal (LN) mean size of tumors containing each of the eleven tumor-suppressor-targeting sgRNAs to identify tumor suppressors that generally repress cancer growth (FIG. 5b). These analyses confirmed the known tumor-suppressive function of Lkb1, Rb1, Cdkn2a, and Apc in Kras$^{G12D}$-driven lung tumor growth (FIG. 5a,b and FIG. 12b). Tumors initiated with Lenti-sgTS-Pool/Cre in KT mice (which lack the H11$^{LSL-Cas9}$ allele) had only minor differences in the size distributions of tumors with each sgRNA (FIG. 14a-c).

To assess the reproducibility of this method, we analyzed an additional cohort of KT;Cas9 mice 15 weeks after tumor initiation with Lenti-sgTS-Pool/Cre. We confirmed the tumor-suppressive effect of all tumor suppressors identified at 12 weeks post-tumor initiation (FIG. 5c and FIG. 14e-f). Our ability to detect tumor suppressors using multiplexed Lentiviral-sgRNA/Cre delivery and tumor barcode sequencing was reproducible as assessed by both the LN mean size and the relative number of cancer cells in the 95$^{th}$ percentile tumor (FIG. 5c and FIG. 14e,f). The growth effects at the 95$^{th}$ percentile tumors were exceedingly well correlated ($R^2$=0.953) and the p-values associated with LN mean were similar between the two time points despite the use of only 3 mice at the 15 week time-point (FIG. 5c).

Figure 5:
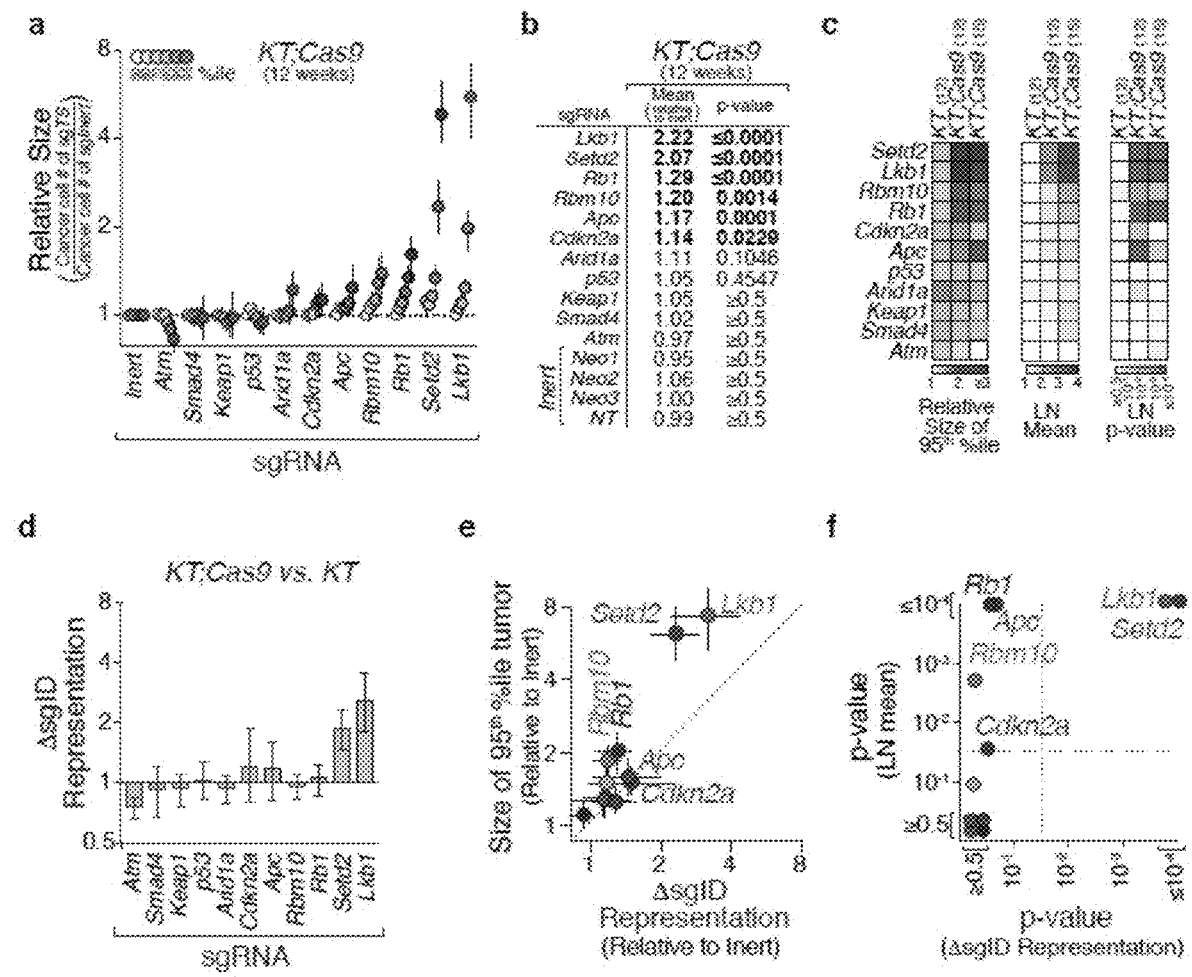
FIG. 5. Tuba-seq uncovers known and novel tumor suppressors with unprecedented resolution. a, Analysis of the relative tumor sizes in KT;Cas9 mice 12 weeks after tumor initiation with Lenti-sgTS-Pool/Cre identified six tumor growth suppressing genes. Relative size of tumors at the indicated percentiles represents merged data from 8 mice, normalized to the average size of sgInert tumors. 95% confidence intervals are shown. Percentiles that are significantly greater than sgInert are in color. b, Estimates of mean tumor size, assuming a log normal tumor size distribution, identified sgRNAs that significantly increase growth in KT;Cas9 mice. Bonferroni-corrected, bootstrapped p-values are shown. p-values <0.05 and their corresponding means are bold. c, Relative size of the 95th percentile tumors (left), log normal (LN) mean (middle), and log normal (LN) p-value (right) for tumors with each sgRNA in KT and KT;Cas9 mice 12 weeks after tumor initiation, and KT;Cas9 mice 15 weeks after tumor initiation. d, Fold change in overall sgID representation in KT;Cas9 mice relative to KT mice (ΔsgID Representation) identified several sgRNAs that increase in representation, consistent with increased growth of tumors with inactivation of the targeted tumor suppressor genes. ΔsgID Representation is the fold change in percent of reads with each sgID in KT;Cas9 mice versus KT mice, normalized such that ΔsgID Representation for sgInert=1. Means and 95% confidence intervals are shown. e,f, The ability to detect tumor suppressive effects is drastically improved by incorporating individual tumor sizes from barcode sequencing compared to only incorporating sgRNA representation. All current approaches rely on sgRNA representation, which is far inferior to Tuba-seq. The relative size of the 95$^{th}$ percentile tumor and the log normal statistical significance determined by Tuba-seq identified more genes as tumor suppressors than the average fold change in ΔsgID representation and their associated p-values (e and f). Error bars in (e) are 95% confidence intervals. Dotted lines in (f) indicate the 0.05 significance threshold. Dot color corresponds to the sgRNA color in FIG. 4b.
Figure 6:
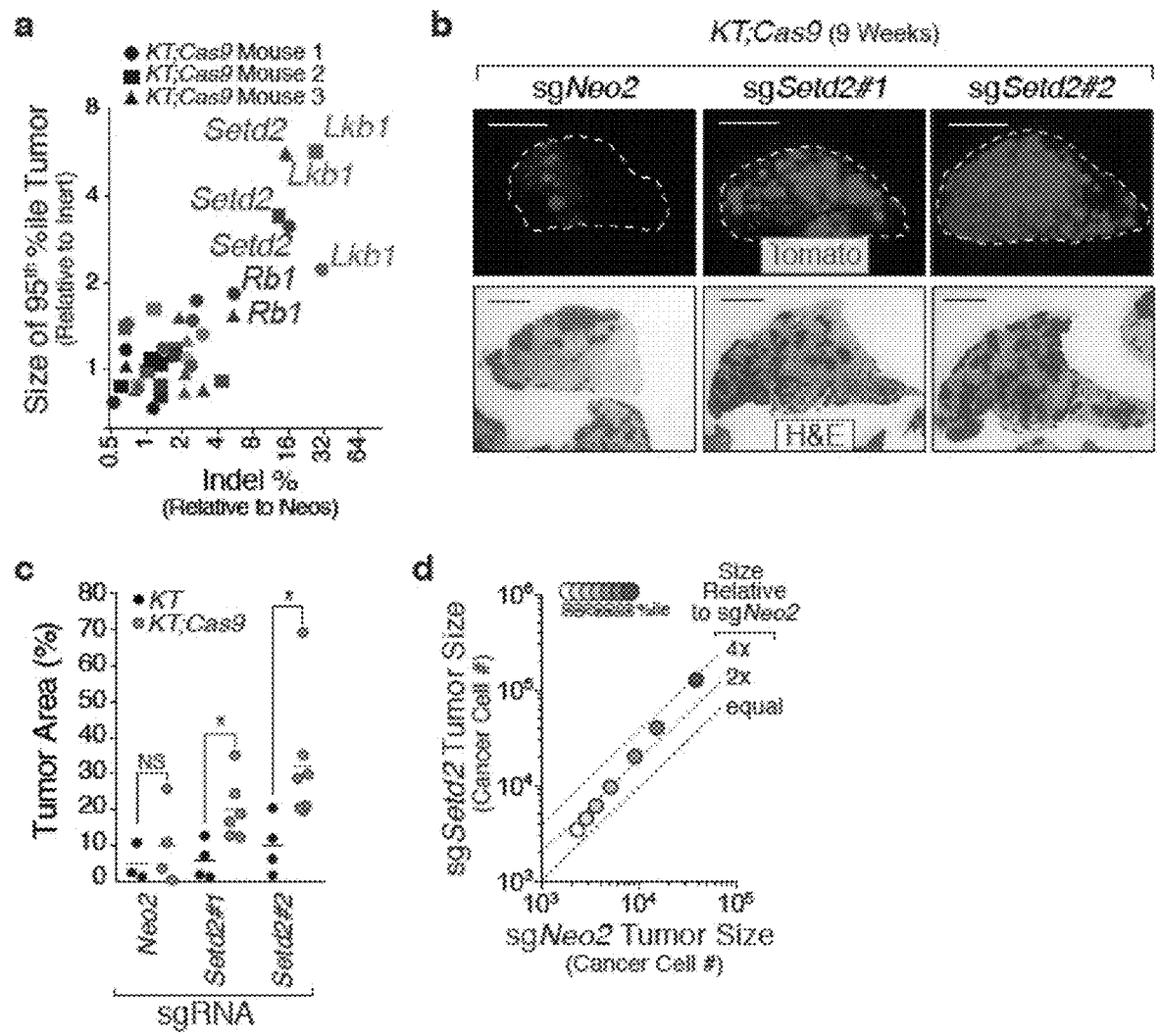
FIG. 6. Independent methods identify Setd2 as a potent suppressor of lung tumor growth. a, The percent of reads containing indels at the targeted locus was normalized to the average percent of reads containing indels in 3 independent Neomycin loci. This value is plotted versus the size of the 95$^{th}$ percentile tumor for each sgRNA for three individual mice. We demonstrate a high frequency of indels in Setd2, Lkb1, and Rb1 consistent with selection for on-target sgRNA cutting. Each dot represents an sgRNA from a single mouse. sgNeo dots are in black and all other dots are colored according to FIG. 4b. b, Fluorescence dissecting scope images and H&E of lung lobes from KT;Cas9 mice infected (transduced) with Lenti-sgSetd2#1/Cre, Lenti-sgSetd2#2/Cre, or Lenti-sgNeo2/Cre analyzed 9 weeks after tumor initiation. Lung lobes are outlined with white dashed lines in the fluorescence dissecting scope images. Upper scale bars=5 mm. Lower scale bars=2 mm. c, Quantification of percent tumor area by histology shows a significant increase in tumor burden in KT;Cas9 mice infected (transduced) with Lenti-sgSetd2#1/Cre or Lenti-sgSetd2#2/Cre compared to KT mice infected (transduced) with the same virus. Each dot represents a mouse and the bars are the mean. * p-value <0.05. NS=not significant. d, Tumor size at the indicated percentile from KT;Cas9 mice with Lenti-sgSetd2#1/Cre initiated tumors versus Lenti-sgNeo2/Cre initiated tumors (N=4 mice/group). Percentiles were calculated using all tumors from all mice in each group FIG. 7. Frequency of genomic alterations in human lung adenocarcinoma and description of tumor initiation and barcoding. a, The percent of tumors with potentially inactivating alterations (frameshift or non-synonymous mutations, or genomic loss) in each tumor suppressor gene is shown for all tumors (All) as well as in tumors with oncogenic KRAS mutations (KRAS$^{mut}$). The number and percent of tumors with oncogenic mutations in KRAS in each dataset is indicated. b, Inhalation of barcoded lentiviral-Cre vectors initiate lung tumors in genetically engineered mouse models. Importantly, the lentiviral vectors stably integrate into the genomes of the transduced cells. The relative expansion of each uniquely barcoded cell can be determined by high-throughput sequencing-based methods. c, Hemotoxilin and Eosin (H&E) staining of lung tissue sections from Kras$^{LSL-G12D/+}$;R26$^{LSL-Tomato}$ (KT) mice infected (transduced) with 1.7×10$^4$ Lenti-Cre virus. These mice develop small expansions of neoplastic cells as well as larger adenomas. Scale bars=50 μm.
Figure 15:
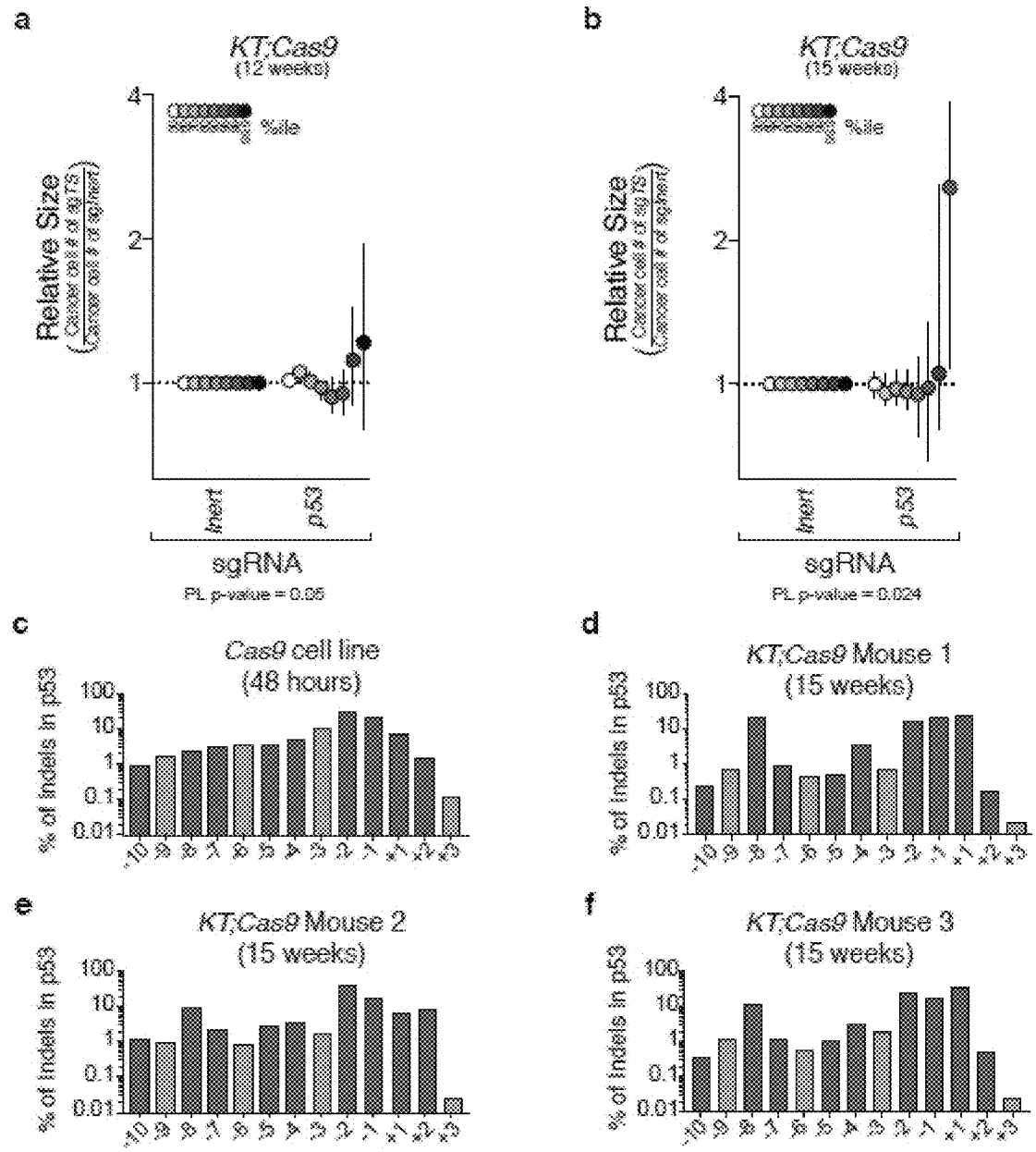
FIG. 15. Identification of p53-mediated tumor suppression in KT;Cas9 mice with Lenti-sgTS/Cre initiated tumors at two independent time points. a,b, Analysis of the relative tumor sizes in KT;Cas9 mice 12 weeks (a) and 15 weeks (b) after tumor initiation with Lenti-sgTS-Pool/Cre identify p53 as a tumor suppressor using power-law statistics at both time points. Relative tumor size at the indicated percentiles is merged data from 8 and 3 mice, respectively, normalized to the average of sgInert tumors. 95% confidence intervals are shown. Percentiles that are significantly larger from sgInert are in color. Power-law p-values are indicated. Note that in this experimental setting only the very largest sgp53 initiated tumors are greater in size than the sgInert tumors. This is likely partially explained by the relatively poor cutting efficiency of sgp53 (FIG. 13d). c-f, Percent of each size indel at the p53 locus (from ten nucleotide deletions (−10) to three nucleotide insertions (+3)) were calculated by dividing the number of reads with indels of a given size by the total number of reads with indels. Inframe indels are shown in grey. We assessed the spectrum of indels at the p53 locus generated in vitro, in a Cas9 expressing cell line infected (transduced) with Lenti-sgTS-Pool/Cre 48 hours after infection (transduction). (c) There is no preference for out of frame mutations. We then analyzed three individual KT;Cas9 mice with Lenti-sgTS-Pool/Cre initiated tumors after 15 weeks of disease progression (d-f). There were fewer in-frame indels (−9, −6, −3 and +3) consistent with selection for out-of-frame loss-of-function alterations in tumors that expand, consistent with the tumor suppressive function of p53. These types of analyses, while consistent with the Tuba-seq findings, are imprecise relative to the Tuba-seq platform.

Identification of p53-Mediated Tumor Suppression and Recapitulation of Tumor Size Distributions within the Tumor Suppressor Pool Consistent with the distribution of tumor sizes in KPT mice, neither LN mean nor the analysis of tumors up to the 95$^{th}$ percentile uncovered an effect of targeting p53 in KT;Cas9 mice with Lenti-sgTSPool/Cre initiated tumors (FIG. 5). As anticipated, Lenti-sgp53/Cre-initiated tumors exhibited a power-law distribution at larger sizes and sgp53 was enriched within the largest tumors in KT;Cas9 mice with Lenti-sgTSPool/Cre induced tumors (FIG. 15a,b). This is consistent with p53 inactivation enabling a small fraction of tumors to grow to large sizes. The effect of targeting p53 was greater at the later 15-week time point consistent with the progressive accumulation of additional alterations and the known effect of p53 in limiting tumor progression (FIG. 15a, FIG. 15b).

Importantly, in KT;Cas9 mice with Lenti-sgTSPool/Cre initiated tumors Lkb1-deficient tumors exhibited a log normal distribution of tumor sizes consistent with the data from KLT mice (FIG. 16a). Thus, both p53-deficient and Lkb1-deficient tumors generated through CRISPR/Cas9-mediated genome editing have similar size distributions to those initiated using traditional floxed alleles. This suggests that even in a pooled setting, quantification of individual tumor sizes can uncover distinct and characteristic distributions of tumor sizes upon tumor suppressor inactivation.

Identification of Setd2 and Rbm10 as Suppressors of Lung Tumor Growth In Vivo

Figure 16:
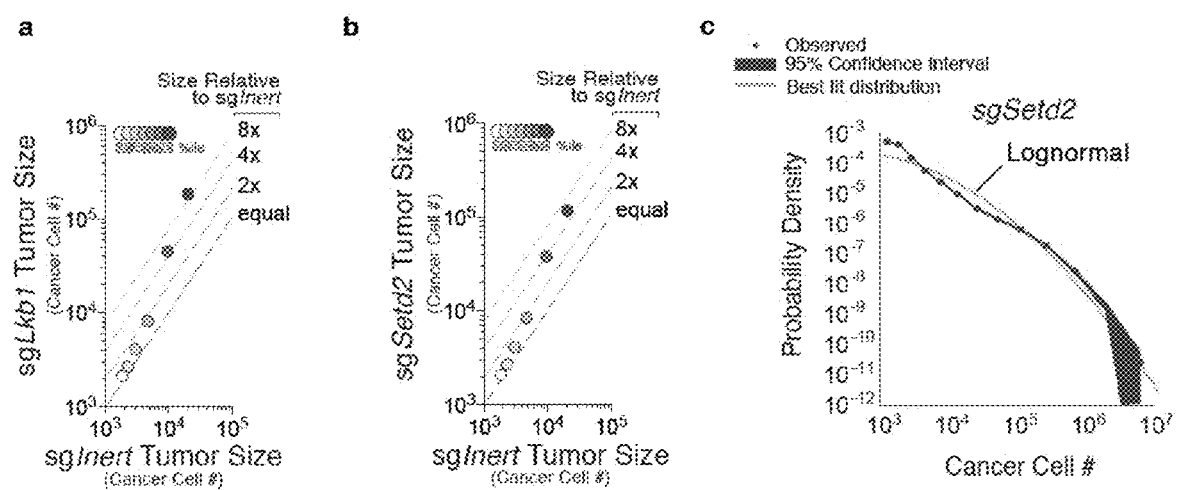
FIG. 16. Analysis of tumor size distributions demonstrates that Lkb1 and Setd2 deficiencies are log normal. a,b, Size of tumors at the indicated percentile (% ile) with sgLkb1 (a) or sgSetd2 (b) versus sgInert-initiated tumor size at the same percentile. Each percentile was calculated using all tumors with each sgRNA from all KT;Cas9 mice with Lenti-sgTS-Pool/Cre initiated tumors analyzed 12 weeks after tumor initiation (N=8 mice). The size relative to sgInert-initiated tumors is indicated with dashed lines. c, Probability density plot for tumors initiated with Lenti-sgSetd2/Cre in KT;Cas9 mice with Lenti-sgTS-Pool/Cre initiated tumors shows lognormally distributed tumor sizes very similar to those seen in KLT mice. This indicates that Setd2 deficiency drives tumor growth without providing a significant increase in the generation of, or tolerance to, additional advantageous alterations.

Interestingly, in addition to appropriately uncovering several tumor suppressors with known effects on lung tumors growth in vivo, Tuba-seq also identified the methyltransferase Setd2 and the splicing factor Rbm10 as major suppressors of lung tumor growth. Setd2 is the sole histone H3K36me3 methyltransferase and may also affect genome stability through methylation of microtubules. Despite being frequently mutated in several major cancer types, including lung adenocarcinoma, very little is known about its role as a tumor suppressor in vivo. Setd2 inactivation dramatically increased tumor size, with many sgSetd2-containing tumors having greater than five-fold more cancer cells than control tumors (FIG. 5a,b and FIG. 16b). Interestingly, tumors initiated with Lenti-sgSetd2/Cre exhibited a log normal distribution of tumor sizes (FIG. 16c). In fact, only Lkb1-inactivation generated a similar fitness advantage, underscoring the potential importance of SETD2 mutations in driving rampant tumor growth in lung adenocarcinoma patients (FIG. 16).

Splicing factors have also emerged as potential tumor suppressors in many cancer types. Although components of the spliceosome are mutated in 10-15% of human lung adenocarcinomas, very little is known about their functional contribution to tumor suppression. Rbm10 inactivation significantly increased the number of cancer cells in the top 50 percent of lung tumors and increased the LN mean size (FIG. 5a,b). These data suggest that the absence of Setd2-mediated lysine methylation and aberrant pre-mRNA splicing each have profound pro-tumorigenic effects in lung adenocarcinoma.

Tuba-Seq is a Precise and Sensitive Method to Quantify Tumor Suppression In Vivo Quantifying the number of cancer cells in many tumors harboring distinct genetic alterations within the same mouse allowed for the identification and elimination of multiple sources of biological and technical variation (Methods). By initiating many lesions per mouse, barcoding every lesion, pooling multiple sgRNAs into each mouse, and including inert sgRNAs with the pool we could identify and correct for many sources of variability in tumor growth. Without these key features, our analysis would have been confounded by variability in the number of initiated tumors (CV=27%), mean tumor sizes between mice of the same genotype (CV=38%), as well as a subtle correlation between the mean effect size of inactivating different tumor suppressor genes within individual mice (CV=11%).

By calculating the size of each tumor, rather than using bulk measurements such as the representation of the sgRNA within all tumors, we more precisely and sensitively ascertained the growth effect of inactivating different tumor suppressors. Interestingly, two thirds of our identified tumor suppressors (Apc, Rb1, Rbm10, and Cdkn2a) were only identified when we considered the number of cancer cells in each barcoded tumor, but not when we only considered the fold change in sgID representation (FIG. 5d). In fact, effect size, statistical significance, and ability to detect tumor suppressors with small effect were all improved using the Tuba-seq pipeline compared to simply analyzing the change in sgID representation (FIG. 5e,f). Thus, Tuba-seq provides the level of resolution required to accurately capture the growth-suppressing effects of functional tumor suppressor genes.

Confirmation of On-Target CRISPR/Cas9-Mediated Genome Editing

As an orthogonal approach to investigate the selection for tumor suppressor inactivation and to confirm on-target sgRNA-mediated genome editing, we PCR-amplified and deep-sequenced each sgRNA-targeted region from bulk lung DNA from three Lenti-sgTS-Pool/Cre infected (transdcued) KT;Cas9 mice. A relatively high fraction of Setd2, Lkb1, and Rb1 alleles had inactivating indels at the targeted sites consistent with on-target sgRNA activity and the expansion of tumors with inactivation of these genes (FIG. 6a and FIGS. 15c-f and 17a,b).

Figure 17:
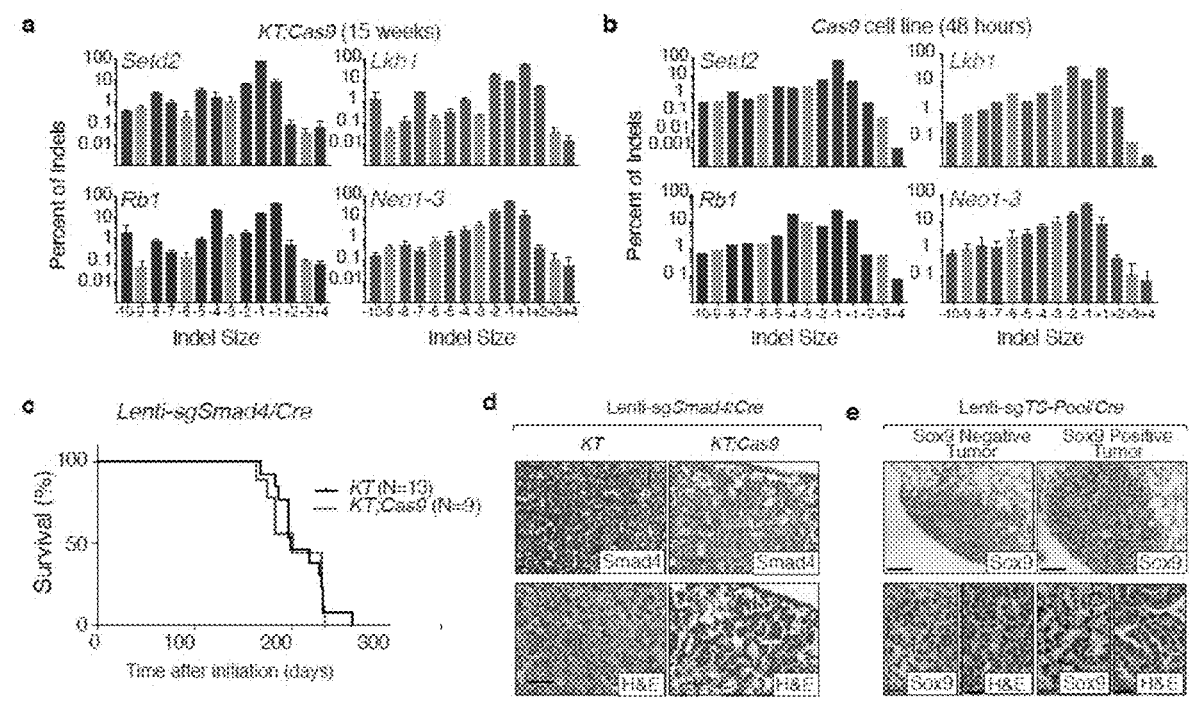
FIG. 17. Confirmation of on-target sgRNA effects. a,b, Percent of each indel (from ten nucleotide deletions (−10) to four nucleotide insertions (+4)) were calculated by dividing the number of reads with indels of a given size by the total number of reads with indels within each top tumor suppression gene. (a) Average percentage and standard deviation of three KT;Cas9 mice with Lenti-sgTS-Pool/Cre-initiated tumors are shown for Setd2, Lkb1, Rb1, and the average of the three targeted sites in Neo (Neo1-3). Inframe mutations are shown in grey. Average and standard deviations for Neo1-3 was calculated by averaging all three mice and all three Neo target sites as a single group. In general, there were fewer inframe indels (−9, −6, −3 and +3) consistent with selection for out-of-frame loss-of-function alterations in these genes in tumors that expand. (b) We also assessed the spectrum of indels generated in vitro, in a Cas9-expressing cell line infected (transduced) with Lenti-sgTS-Pool/Cre 48 hours after infection (transduction). We detected no preference for inframe mutations in any of these genomic locations, suggesting that the bias in the KT;Cas9 mice is most likely due to advantageous expansion of tumors with out-of-frame indels (i.e., null allele). c, Kaplan-Meier survival curve of KT and KT;Cas9 mice with Lenti-sgSmad4/Cre-induced tumors. CRISPR/Cas9-mediated inactivation of Smad4 in the presence of oncogenic $Kras^{G12D}$ does not reduce survival, suggesting limited, if any, increase in tumor growth from Smad4 inactivation. d, The majority of tumors in Lenti-sgSmad4/Cre infected (transduced) KT;Cas9 mice had lost Smad4 protein expression compared to KT mice infected (transduced) with the same virus, consistent with indel creation at the Smad4 locus. Scale bars=50 μm. e, Several tumors in Lenti-sgTS-Pool/Cre− infected (transduced) KT;Cas9 mice had a distinct papillary histology, uniformly large nuclei, and were Sox9 positive, consistent with the published phenotype of Apc-deficient, Kras-driven lung tumors (Sanchez-Rivera et al., Nature, 2014). Representative Sox9-negative and Sox9-positive tumors are shown. Scale bars=100 μm (top) and 25 μm (bottom).

Amplification and sequencing of the targeted regions of these genes from bulk lung DNA from Lenti-sgTS-Pool/Cre infected (transdcued) KT;Cas9 mice also confirmed that all targeted genes contained indels (FIG. 6a). Although all of the genes included in our pool are recurrently mutated in human lung adenocarcinoma and frequently mutated in tumors with oncogenic KRAS (FIG. 7a), Arid1a, Smad4, Keap1, and Atm were not identified by any metrics as tumor suppressors (FIGS. 5 and 6a, and FIG. 14d-f). The lack of tumor-suppressive function of Atm is consistent with results using an Atm$^{floxed}$ allele, and we confirmed the lack of tumor-suppressive function of Smad4 on oncogenic Kras$^{G12D}$-driven lung tumor growth in vivo in KT;Cas9 mice infected (transdcued) with Lenti-sgSmad4/Cre (FIG. 17c,d). For these genes, changes in gene expression or environmental state, additional time, or coincident oncogene and/or tumor suppressor alterations may be required for inactivation of these pathways to confer a growth advantage in lung cancer cells.

Figure 18:
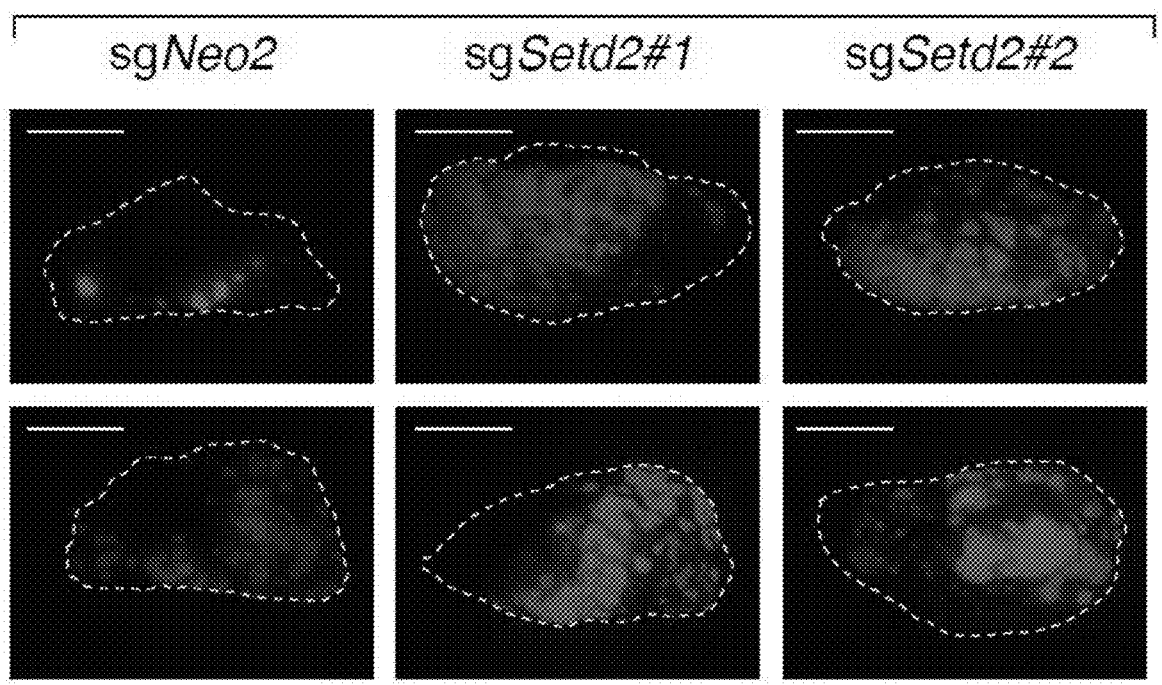
FIG. 18. Additional images showing increased tumor burden in mice with CRISPR/Cas9-mediated inactivation of Setd2 using each of two independent sgRNAs. Additional representative fluorescence dissecting scope images of lung lobes from KT;Cas9 mice with tumors initiated with Lenti-sgNeo2/Cre (left), Lenti-sgSetd2#1/Cre (middle), or Lenti-sgSetd2#2/Cre (right) analyzed 9 weeks after tumor initiation. Lung lobes are outlined with white dashed lines. Scale bars=5 mm.

To further validate the tumor-suppressive effect of Setd2 and to assess the histology of Setd2-deficient tumors, we induced tumors in KT and KT;Cas9 mice with lentiviral vectors containing an inert sgRNA (sgNeo2) or either of two distinct sgRNAs targeting Setd2. KT;Cas9 mice with tumors initiated with either of the Lenti-sgSetd2/Cre vectors developed large adenomas and adenocarcinoma and had significantly greater overall tumor burden than KT mice with tumors initiated with the same virus (FIG. 6b,c). While histological analysis of these mice uncovered large mouse-to-mouse variability, the analysis of individual tumor sizes by Tuba-seq confirmed a nearly four-fold increase in the number of cancer cells in Setd2-deficient tumors relative to control tumors (FIG. 6c,d and FIG. 18). Importantly, the validation of Setd2 tumor suppression by conventional methods required many more mice than our initial screen of eleven putative tumor suppressors emphasizing the benefit of multiplexing sgRNAs to increase throughput and decrease costs.

Discussion

Figure 19:
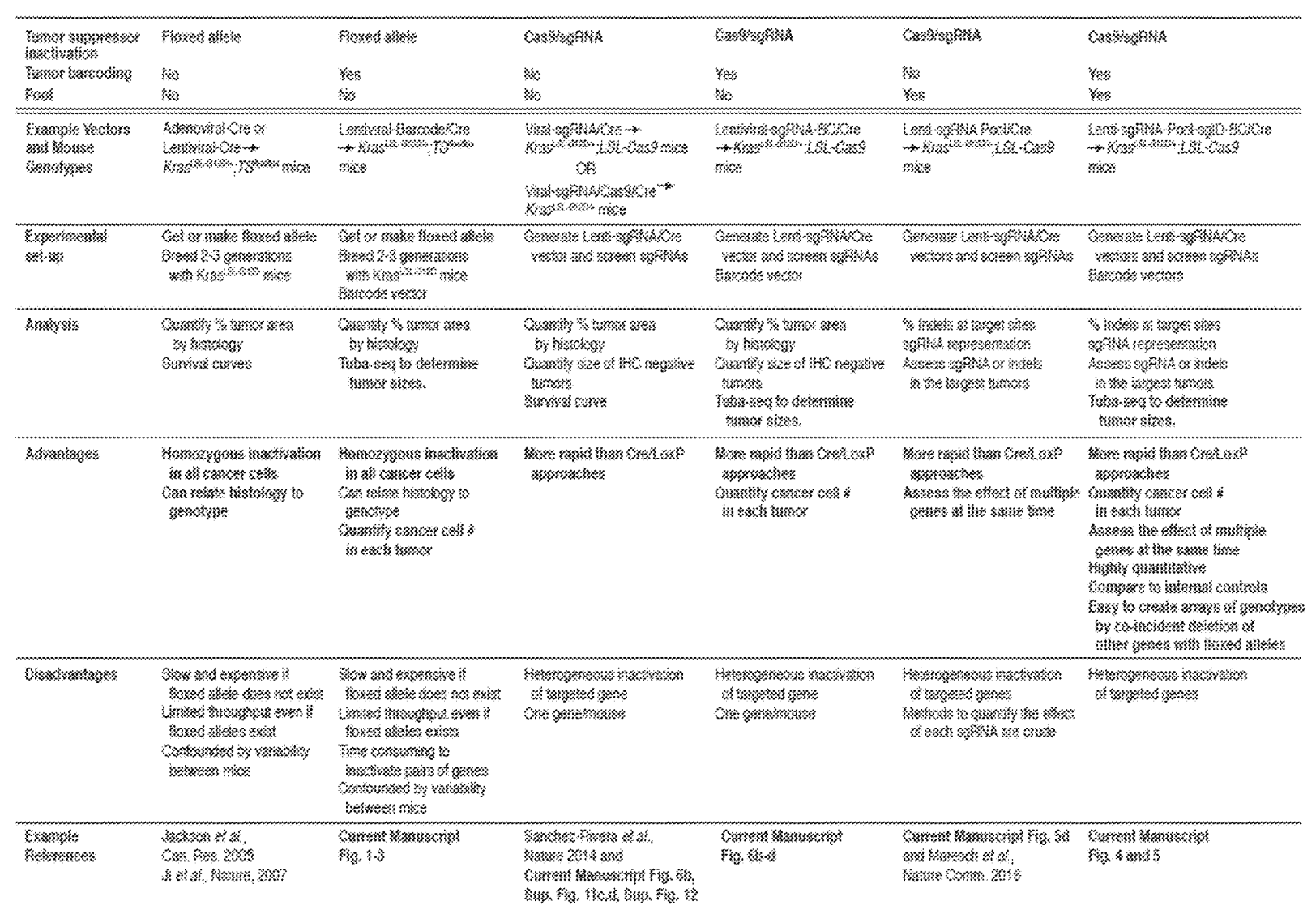

While many putative tumor suppressors have been identified from cancer genome sequencing, limited strategies exist to test their function (e.g., in vivo) in a rapid, systematic, and quantitative manner (FIG. 19). By combining DNA barcoding, high-throughput sequencing, and CRISPR/Cas9-mediated genome editing, Tuba-seq not only increases the throughput of these analyses, but also enables exceptionally precise and detailed quantification of tumor growth in vivo.

Interestingly, tumors initiated at the same time, within the same mouse, with the same genomic alterations grew to vastly different sizes after only 12 weeks of growth. Thus, additional spontaneous alterations, differences in the state of the initial transformed cell, or the local microenvironment may impact how rapidly a tumor grows and whether it has the capacity for continued expansion. Tuba-seq was also uniquely able to uncover genotype-specific distributions of tumor sizes that revealed properties of gene function. p53-deficiency generated a tumor size distribution that is power-law distributed for the largest tumors, consistent with a Markov process where very large tumors are generated by additional, rarely acquired driver mutations. Conversely, Lkb1 inactivation increased the size of a majority of lesions suggesting an ordinary exponential growth process. Thus, tumor suppressors can have different modes of tumor suppression, identified via Tuba-seq, that may portend their molecular function. Interestingly, Setd2 has recently been suggested to methylate tubulin, and Setd2-deficiency can lead to various forms of genomic instability including micronuclei and lagging chromosomes due to alterations in microtubules. Genome instability would be expected to generate rare, advantageous alterations and tumors growth that is highly-stochastic and power-law distributed. However, the size distribution of Setd2-deficient lung tumors in our studies was strictly log normal, therefore we speculate that the main impact of Setd2 loss is the induction of gene expression programs that generally dysregulate growth (FIG. 6d and FIG. 16b,c).

The scale of our analyses, which evaluated thousands of individual tumors, dramatically improved our ability to identify functional tumor suppressor genes. Estimating tumor growth via bulk measurements would have identified only a third of the tumor suppressors that we uncovered as advantageous to tumor growth (FIG. 5d-f). Unlike conventional floxed alleles, CRISPR/Cas9-mediated genome editing in the lung generated homozygous null alleles in approximately half of all tumors (FIG. 11d). Thus, while the lack of uniform homozygous deletion of targeted genes would reduce the tumor suppressive signal from bulk measurements, by barcoding and analyzing each tumor, Tuba-seq effectively overcomes this technological limitation.

By analyzing a large number of tumor suppressors, our data suggest that early neoplastic cells reside in an evolutionarily nascent state where many tumor suppressor alterations were adaptive and conferred a growth advantage. In contrast, CRISPR/Cas9 screens in cancer cell lines have found that additional tumor suppressor alterations provide little advantage and can even be detrimental. This finding is consistent with cancer cell lines residing in a much more mature evolutionary state, approaching optimal growth fitness due to their origin from advanced-stage disease as well as selection for optimal proliferative ability in culture. Furthermore, the intimate link between tumor suppression and many aspects of the in vivo environment underscores the importance of analyzing the effects of tumor suppressor loss in tumors in vivo (or for example in the context of a tissue such as an organoid culture or 3D cultured tissue).

Interestingly, the frequency of tumor suppressor alterations in human cancer did not directly correspond to the magnitude of their tumor suppressor function. For example, SETD2 and RBM10 are mutated in similar percentages of human lung adenocarcinomas, but Setd2-deficiency conferred a much greater growth benefit than Rbm10-deficiency (FIG. 5a,b). This highlights the growing need for methods that allow rapid and quantitative analyses of gene function in vivo to determine the functional importance of low-frequency putative tumor suppressors that may be profoundly important for individual patients.

There is a very limited understanding of the clinical importance of tumor suppressor alterations, and this remains a major unmet need, but strong drivers of tumor growth may represent more attractive clinical targets than weak drivers. Tuba-seq permits investigation of more complex combinations of tumor suppressor gene loss, as well as the analysis of other aspects of tumor growth and progression. Tuba-seq is also adaptable to study other cancer types and should allow the investigation of genes that normally promote, rather than inhibit, tumor growth. Finally, this method allows the investigation of genotype-specific therapeutic responses which could ultimately lead to more precise and personalized patient treatment.

Statistical Properties of Lesions in this Study

Figure 20:
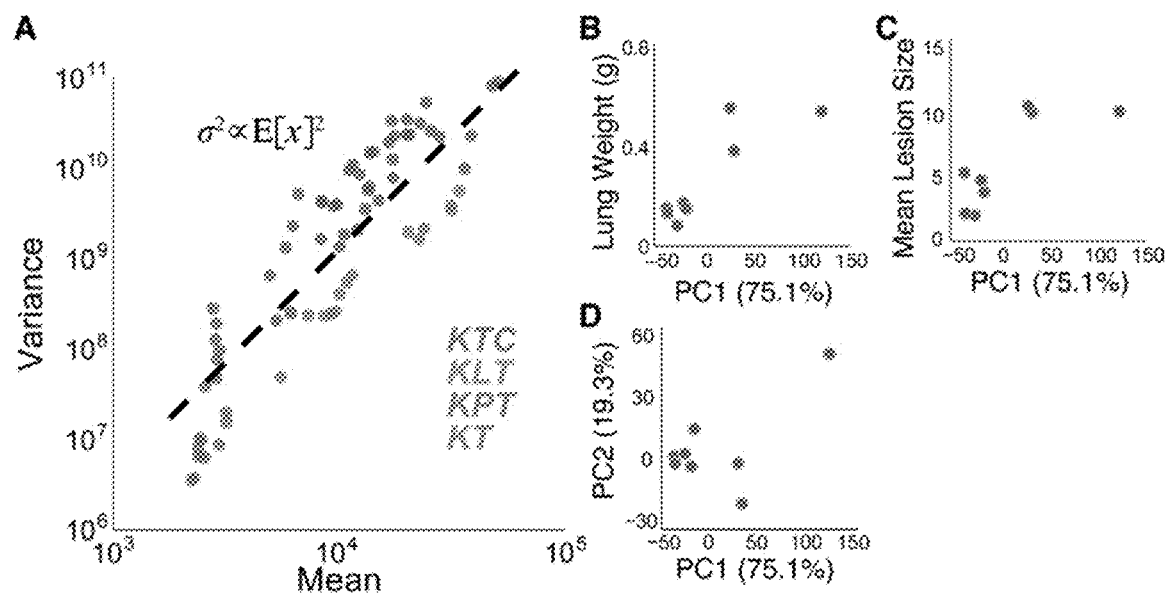
FIG. 20. Statistical properties of tumor size distributions and the covariance of sgRNA tumor sizes across mice. a. The mean and variance of each sgID distribution in every mouse with Lenti-sgPool/Cre initiated tumors. Mouse genotypes are colored as indicated. In general, variance increased with the square of the mean for all genotypes, suggesting that a log-transformation of lesion size should stabilize variance and avoid heteroskedasticity. Some distributions exhibit a variance that increased by more than the square of the mean. b-d. Mouse-to-mouse variability in response to genetic alterations was interrogated in KT;Cas9 mice sacrificed at 12 weeks. The covariance of the LN MLE mean of each sgRNA in each mouse was investigated. Genotype means sizes positively correlated with each other across mice (e.g. a mouse with larger sgLkb1 tumors also harbored larger sgSetd2 tumors.) PCA decomposition of the correlation matrix amongst all 12 sgRNAs (sgInerts consolidated) uncovered a substantial level of mouse-to-mouse variability explicable by a single Principle Component (PC1) vector. Each dot represents a single mouse projected onto PC1, which explains 75% of observed variability between mice in sgRNA mean sizes. (b) PC1 correlates with overall lung weight and (c) mean lesion size, indicating that mice with larger tumors are more susceptible to tumor growth driven by strong drivers (PC1 correlated with sgSetd2 and sgLkb1 size, data not shown.) (d) The mice do not appear to form distinct clusters when projected onto the first two Principle Components. Replicate mice were almost always siblings housed in the same cages. We minimized extrinsic sources of noise using a Mixture of Principal Components model (see Methods.)
Figure 21:
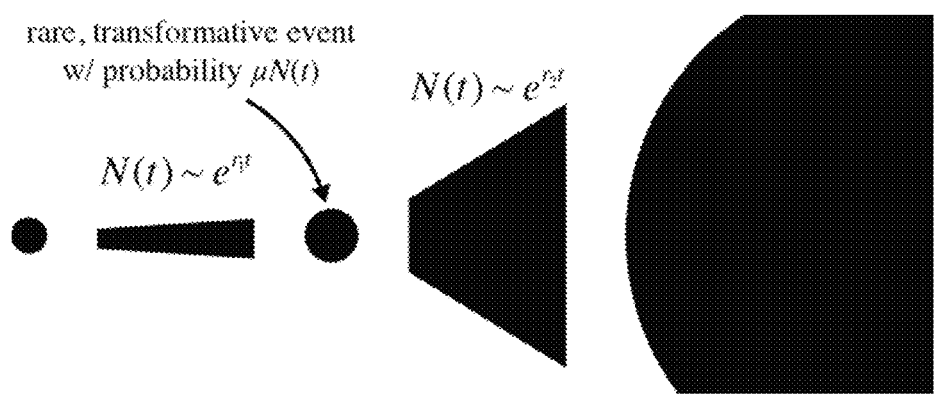
FIG. 21. Mathematical models of tumor progression.
Figure 22:
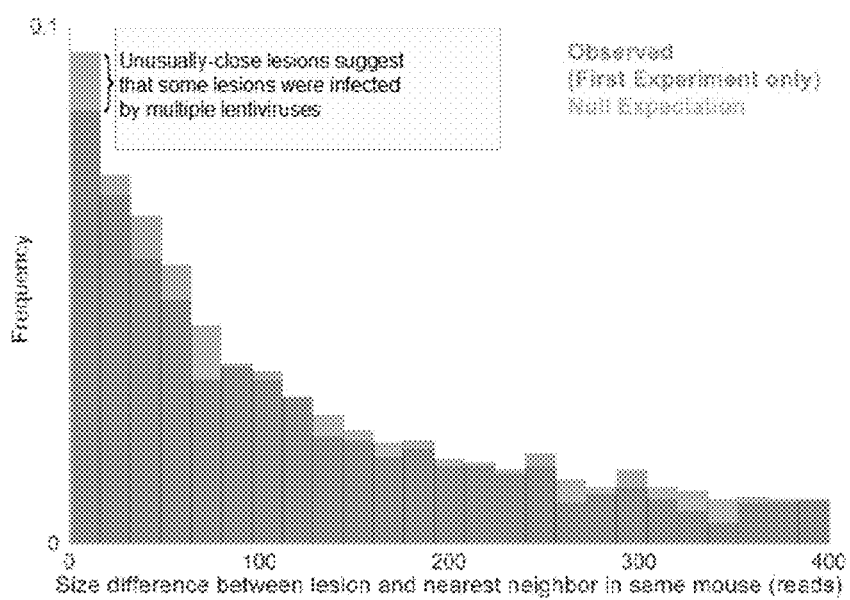
FIG. 22. Frequency of lentiviral infections (transductions) compared to size difference between each lesion and its nearest neighbor in the same mouse.

The distributions of tumor sizes were generally log normal with inclinations towards a $2^{nd}$-order power law when looking within a Mouse-sgRNA pair (FIG. 20). Each tumor in our study was assigned a log-transformed size $t_{mrb}$ defined by the mouse m that harbored it, the cognate sgRNA r identified by its first barcode, and a unique barcode sequence (consensus of the DADA2 cluster) b. Our approach was designed to interrogate and address a variety of sources of error: we found that (i) the number of instigated tumors within replicate mice, (often littermates) infected (transducued) with the same lentiviral titer via the same intubation procedure, varied greatly, (ii) the mean tumor size varied within replicate mice, (iii) certain mice were more amenable to growth of tumors with sgRNAs targeting specific tumor suppressors, and (iv) the size of tumors with the same sgRNA within the same mouse varied dramatically.

|  | CV | Interrogated by | Minimized using |
|---|---|---|---|
| Source of Variance |  |  |  |
| Efficiency of Infection (transduction) | 27% | Random Barcodes | DADA2 clustering |
| Mouse | 38% | Inert sgRNAs | Normalization to Inert Mean |
| Mouse-Tumor Suppressor Interactions | 11% | Multiplexed sgRNAs | PCA Mixture Model |
| Stochastic Progression | 511% | Multiple Infections | Lognormal MLE of Mean |
| Variable of Interest |  |  |  |
| Tumor Suppressor | 31% |  | n.a. |

Overall, the effect of a tumor suppressor inactivation on tumor burden is small compared to these other sources. Prior viral-Cre-based genetically engineered mouse models address the main source of variability by initiating hundreds to thousands of tumors per mouse. We observe stochasticity in the size of tumors instigated within the same mouse with the same genetic constructs even in this setting. The number of cancer cells in individual tumors in these experiments is never measured accurately; instead, total tumor area is most often measured, which is a conflation of mean tumor size and the number of instigated tumors. Thus, this approach is flawed because (i) the sampled mean size is not the best estimator of mean size, (ii) the number of instigated tumors is never directly measured (a quantity that varies with a Coefficient of Variation (CV) of 27%), (iii) variability in the mouse background is ignored, and (iv) the methods used to assess tumor area also introduce variability. For these reasons, the magnitude of effect of even the most powerful tumor suppressor in a $Kras^{G12D/+}$ background (Setd2) is smaller than the variance between replicate mice (FIG. 6c).

The variability in the number of lesions instigated by viral-Cre vectors within individual mice also affects estimates of a tumor suppressor's effect. By uniquely barcoding each tumor and then precisely calling tumors using our computational approach detailed in the Methods, we minimize this source of variability. Variance in the number of called lesions in our pipeline exhibited a CV of 10.7% across repeated sequencing runs, whereas the variance in called lesions between replicate mice exhibited a CV of 27%. Therefore, our estimates of tumor number, based on unique DNA barcodes, are significantly more precise than presuming the number of tumors is constant between replicate mice (which likely have different numbers of epithelial cells infected (transdcued) by lentiviral vectors due to technical variability with the infection (transduction)). Below, we interrogate, mitigate, and discuss the remaining sources of variability listed in the above Table.

sgRNA-Agnostic Mouse-to-Mouse Variability

Our multiplexed approach interrogates growth effects attributable to (i) the CRISPR/Cas9-target tumor suppressor gene, (ii) the individual mice, and (iii) their interactions. This is only possible because we included many sgRNAs within each mouse and measured many lesions with the same sgRNA in the same mouse. We observed a statistically significant difference between ostensibly replicate mice in the mean, log-transformed, bias-corrected expectation size of each sgRNA ($\eta_{mr}=E_{mr}[t_{mrb}]$). These differences could be succinctly summarized and then subtracted from $t_{mrb}$ to better resolve the strength of each tumor suppressor.

Mice exhibited both sgRNA-agnostic growth perturbations $\eta_m=E_r[\eta_{mr}]$ (i.e. there was a spectrum of tumor-susceptible and tumor-resistive mice) and sgRNA-dependent covariance within the mice $\eta_{mr}$ (e.g. mice that harbored unusually large Lkb1-deficient tumors also harbored unusually large Setd2-deficient tumors). About 40% of the mouse-to-mouse variability was eliminated by correctly normalizing $\eta_m$, while the variability in $\eta_{mr}$ not ascribable to sgRNA-agnostic factors was estimated to be only 10.7%. We could only eliminate a fifth of this $\eta_{mr}$ variability (detailed below). Therefore, most of the variability in tumor susceptibility appears to be sgRNA-agnostic, however subtle gene-mouse covariance is still consequential when estimating average tumor growth advantages to precisions <10%.

Replicate mice, i.e. those with the same genetic-engineered elements analysed at the same time-point after tumor initiation, were often littermates and cage-mates, but descend from a mixed 129/BL6 backgrounds. While these mice likely have a far more homogenous genotype and environment than real-world patients, relevant differences between individual mice still emerged. It is important to note that while these trends can be identified in our data due to our unprecedented resolution, the variation is small and should have an even greater effect on experiments that compare different mice constructs (for example conventional approaches that compare tumor growth in mice with and without a floxed allele of a gene of interest, or our own results from mice with tumors initiated with Lenti-sgSetd2/Cre versus Lenti-sgNeo/Cre (see FIG. 6)).

Because each mouse contained several inert sgRNAs (whose means did not differ appreciably from each other within a mouse) we were able to subtract the sgRNA-agnostic mice effects simply by normalizing sizes relative to the aggregated inert sgRNA mean: $\mu_{mr}=E_{mr}[t_{mrb}]-E_{m,inerts}[t_{mrb}]$. In our nonparametric approach, we simply divide by the median inert sgRNA, which tends to be almost identical the LN MLE mean.

sgRNA-Specific Mouse-to-Mouse Variability

The availability of multiple active sgRNAs in a single mouse allowed us to interrogate sgRNA-specific mouse effects. Overall, the $\mu_{mr}$ matrix was highly positively correlated between active sgRNAs in KT;Cas9 mice. We decomposed these correlations using Principle Component Analysis (PCA). The first Principle Component (PC1) explained 75% of the variance in $\mu_{mr}$ across replicate KT;Cas9 mice. We tested several hypotheses for this covariance:

1. Mice that harbored larger tumors on average might also harbor larger tumor variance in log-scale. If so, then sgLkb1 to sgInert tumor size ratio would co-vary with the sgSetd2 to sgInert tumors size ratio.
2. Mouse gender drives these diverging growth patterns.
3. Cas9 endonuclease cutting efficiency varied between mice that are $H11^{LSL-Cas9/+}$ versus mice that are $H11^{LSL-Cas9/LSL-Cas9}$.
4. An unknown genetic or environmental factor within the mouse perturbs the strength of a subset of drivers.

We investigated these first two hypotheses by comparing PC1 to mean tumor size and by comparing KT;$H11^{LSL-Cas9/+}$ to KT;$H11^{LSL-Cas9/LSL-Cas9}$ mice in our KT;Cas9 12-week cohort. PC1 correlated well with both mean tumor size (as calculated via our pipeline) and lung weight (FIG. 20b-d). Lung weight (in grams) was determined at the time of lung sample collection and is likely influenced by tumor number and mean tumor size. The correlation of lung weight with PC1, like mean tumor size, ensures that these observed trends are not a pipeline artefact. Mouse gender also co-varied with PC1 (Point-Biserial Correlation r=0.75, data not shown) and is consistent with our first hypothesis, as male mice exhibit both larger tumors and a larger size discrepancy between strong drivers and inerts.

$H11^{LSL-Cas9}$ allele status (heterozygous or homozygous) was not statistically-significantly correlated with PC1 (r=0.34, data not shown) in 12-week KT;Cas9 mice. Therefore, we do not believe that being heterozygous or homozygous for the $H11^{LSL-Cas9}$ allele contributes substantially the efficacy of gene inactivation.

Finally, the hypothesis of a latent genetic or environmental factor is too open-ended to be tested here. However, our methodology permits studies of these factors moving forward.

Thus, we conclude that tumor permissivity and mouse gender are mostly responsible for these sgRNA-specific differences between replicate mice, and that Cas9 endonuclease heterozygosity does not seem to appreciably affect tumor growth, and results from our analysis pipeline concur with other mouse measurements.

A Mixture of Probabilistic Principle Components model was used to eliminate $\eta_{mr}$ from $\mu_{mr}$. This model defines the log-likelihood of a mouse arising from the same distribution as the others in its cohort of replicates. In essence, this model identifies mice with anomalous sgRNA profiles. However, rather than categorize mice as either 'outlier' or 'acceptable' mice, we simply weighted each mouse based its likelihood of outlying. Statistically, an 'outlier' is defined as a point that appears to be drawn from a different distribution than its cohort. Indeed, we found that similar outlier mice were identified using Mahalanobis distance—a common metric for identifying outliers in multidimensional data. However, the Mahalanobis distance metric requires some threshold for classifying outliers that would be ad hoc in our application. Weighting mice using our Mixture of Probabilistic Principle Components Model, reduced the variability of $E_r[\mu_{mr}]$ for KT;Cas9 mice by 2.1%. Although this is only a mild improvement, we included this correction in our final report of the mean growth advantage conferred by an sgRNA because we felt that this value should account for every source of variability identified. The final reported mean growth effect of each sgRNA in a cohort of replicate mice was an arithmetic mean of $\mu_{mr}$ across all mice weighted by the likelihood of each mouse m in our mixture model P(m; $\mu_{mr}$), i.e.

$$\frac{\sum_m P(m; \mu_{mr})\mu_{mr}}{\sum_m P(m; \mu_{mr})}.$$

Our Parametric and Nonparametric Approaches, and Statistical Tests

Comprehensively measuring the size spectrums of tumor growth and then identifying all the exogenous factors behind this spectrum presents a conundrum: growth advantages could be summarized with a highly-processed measure of tumor size that accounted for every known, quantified concern, or growth advantages could be summarized more explicitly in a manner that makes fewer assumptions. We chose both extremes. The qualitative conclusions do not differ much in either case; however, we present both approaches because the agreement is encouraging and because the different approaches may appeal to readers with different sensibilities.

Our approach based on Maximum Likelihood estimation is detailed in the section above. Summarily, it attempts to account for our understanding of the log normal shape of size distributions, and mouse-to-mouse variability in (i) the number of instigated tumors, (ii) overall tumor permissivity, and (iii) sgRNA-specific variability. It leverages the multidimensionality of our size measurements and corrects for every known exogenous factor that we found. Below, we discuss the limitations of assuming log-normality and extend the parametric approach to tumor suppressor distributions exhibiting power-law tails.

Our nonparametric approach presents percentiles of $t^{(nonparametric)}_{mrb}$ (defined above) to assay for increased tumor growth at various locations in the size distributions. It makes no assumption of the shape of the tumor distributions and does not model mouse-to-mouse variability. Although by correcting for the median size of inerts and the number of tumors residing in each mouse, a majority of the mouse-to-mouse variability is eliminated. For this reason, after the first experiment, percentiles were always reported relative to their corresponding inert percentile. Autocorrelation between different percentile tiers for the sgRNA is expected and observed; the different percentile tiers are not statistically-independent values and we deploy no statistical test that assumes their independence.

The nonparametric approach generally finds that the 90 to $99^{th}$ percentiles of distributions of active sgRNAs are maximally deviant from the inerts. Our finding that distributions are at least log-normally skewed is consistent with this phenomenon. Furthermore, active sgRNAs can introduce inframe insertions and deletions that should mimic the inert distribution, so we expected the smallest tumors in an active sgRNA distribution—with in-frame mutations or no mutations—to mimic inert sizes. Lastly, the haploinsufficiency of a single null allele is generally unknown, but if haploinsufficiency is partially dominant or non-existent then size distributions would be most deviant at higher (90 to $99^{th}$) percentiles.

Therefore, we used the $95^{th}$ percentile as a crude summary of the growth benefit of a driver, as it approximately balanced our concerns of the null-mutation rate, zygosity, statistical resolution (which declines at higher percentiles), and our understanding of the size distributions in general. Our data suggest that loss of a tumor suppressor does not necessarily lead to a growth advantage across all individual tumors (for examples p53-versus Lkb1-deficiency in FIGS. 1 and 2). Indeed, the $95^{th}$ percentile measure fails to detect p53 in our experiment for reasons that are in line with the expected consequence of p53 loss and fat-tailed distributions. Nonetheless, simplifications can be useful and the $95^{th}$ percentile of sizes summarizes differences in growth well.

All confidence intervals and p-values were obtained via bootstrapping of $t_{mrb}$. After bootstrap sampling, all subsequent steps in our analysis pipelines were recalculated for every bootstrap (normalizations to inerts, PCA, etc.). Bootstrapping samples were equal in size to the original $t_{mrb}$ for each experiment (e.g. the tumors in KT;Cas9 mice analyzed 12-weeks after tumor initiation) and were sampled with replacement. 200,000 samples were drawn for every 95% confidence interval reported and 2,000,000 samples were drawn for every p-value reported. Confidence intervals of ratios reflect uncertainty in both the active sgRNA distribution and the inert sgRNA distribution. Therefore, when the confidence interval of an sgRNA ratio does not subsume 1, the null hypothesis that this summary statistic of the sgRNA matches the inert sgRNA can be rejected with p<0.05 (assuming no correction for Multiple Hypotheses).

All p-values report the two-sided hypothesis that an sgRNA summary statistic differs from the inert sgRNA summary statistic and were Bonferroni-corrected for our multiple hypotheses that any one of the 11 active sgRNAs could incur a growth advantage or disadvantage. While active sgRNAs were always compared to the entire sgRNA distribution (four different inert sgRNAs), the inert sgRNAs were compared only to the distribution of the other three inerts. p-values were not reported beyond 0.0001, as this is the resolution limit of bootstrapping when limited to 2,000, 000 samples.

Comprehensive Parametric Description of Size Distributions

Lesion sizes were approximately lognormally distributed with excessive quantities of very large lesions in some genotypes. We fit a wide variety of 2-3 parameter probability distributions to the observed distribution of lesion sizes for each genotype and time: (Log)-Normal, (Log)-Gamma, (Log)-Logistic, Exponential, Beta, Generalized-Extreme Value (including Gumbel), and Power-Law (including Pareto). All lesion size distributions were best fit with either a Log normal, Log-gamma, or Log-Logistic distribution, although no single distribution outperformed all others. A Kolmogorov-Smirnov test often rejected the best-fitting single distribution—i.e. only a least-improper fit could be found in many cases. This shortcoming, underscores the enormous quantities of tumor sizes that we were able to measure for the first time and the complexities of tumor progression. Therefore, we investigated multi-family parametric fits.

A combination of Log normal and Power-Law scaling, for some distributions, best described our data. Although Log-Gamma and Log-Logistic fits were sometimes superior to Log normal fits, these alternative distributions merely have faster-growing higher moments, which is suggestive of Power-Law behaviour. Moreover, the Maximum Likelihood Estimators of Log-Gamma and Log-Logistic distribution parameters must be solved numerically without guarantee of convergence.

Care was taken to identify Power-Law distributions impartially. Potential Power-Law fits were parameterized using maximum likelihood and adjudicated using marginal likelihood:

1. The Maximum Likelihood Log normal fit $$\text{Max}_{\mu_r, \sigma_r} \left[ \sum_{m,b} \mathcal{LN}(t_{mrb}; \mu_r, \sigma_r) \right]$$

for each sgRNA distribution for the entire support of positive real numbers was identified. Here, $\mathcal{LN}$ denotes the probability density of a log normal distribution.

2. The Maximum Likelihood Power-Law fit for tumors over the domain $[x^{(min)}_r, \infty)$ was identified:

$$\text{Max}_{x^{(min)}_r, \alpha_r} \left[ \sum_{m,b} \begin{matrix} \mathcal{LN}(t_{mrb}; \mu_r, \sigma_r) \\ \mathcal{PL}(t_{mrb}; x^{(min)}_r, \alpha_r) \end{matrix} \text{ if } \begin{matrix} t_{mrb} < x^{(min)}_r \\ t_{mrb} \geq x^{(min)}_r \end{matrix} \right]$$

Here $\mathcal{PL}$ denotes the probability density of a Power-Law or Pareto Distribution with exponent $\alpha_r$ and the log normal fit from step 1 is used. Note that a Power-Law is undefined when $x^{(min)} = 0$ and so it is customary to test power-laws over a limited support with a freely-floating minimum.

3. The multi-fit model was adjudicated using Marginal Likelihood: the likelihood of the observed data corrected for the model's degrees of freedom using Bayesian-Information Criterion (BIC).

This approach is recommended by Alstot et al and their accompanying software package was used for this analysis. Details of the maximum likelihood fits are provided in FIG. 3. Reported p-values are a transformation of the Marginal Likelihoods of a joint log normal and power-law fit, such that p=1/(1+Exp[Marginal Likelihood]). These values test the null hypothesis that the data is log normal-distributed throughout its entire support.

We also test the hypothesis that sizes are distributed according to an Exponentially-Truncated Power Law. This comparison is a common counter-hypothesis to an ordinary Power Law and would imply that scale-free behavior exists only over a finite interval[3]. We do not see good evidence for Exponentially-truncated Power Law behaviour (data not shown). For this reason, we believe that the data support scale-free models of tumor progression in the genotypes discussed below.

We observe strong, recurring evidence that p53-deficient tumors are power-law distributed at large scales. Power-law dynamics were observed in all incarnations of the $Kras^{G12D/+}/p53\Delta$ genotype (KPT tumors, and both KT;Cas9sgp53 tumor time-points). The marginal likelihoods for all of these Power-Law distribution fits were good or excellent. This agreement strongly supports the hypothesis that the $Kras^{G12D/+}/p53\Delta$ genotype is power-law distributed in tumor size.

In general, the ML exponent of power-law fits was approximately two ($\alpha \sim 2$). Power-law dynamics have been hypothesized to explain cancer incidence rates, however tumor size distributions have not been well studied because measurements to test this hypothesis were previously prohibitively time-consuming and costly, so we explored a simple evolutionary model that yields a power-law distribution of sizes in the next section. Our deep interrogation of lesion sizes proved useful in not only precisely identifying driver growth advantages, but also in uncovering aspects of their underlying mode of action.

Additional Rarely-Acquired Driver Mutations Predict a Power Law Distribution of Tumor Sizes p53-deficient tumors exhibit a Power-Law distribution of sizes in their rightmost tail (FIG. 3d). Power law distributions generally do not arise from a single-step Markov process and, instead, arise from compound random processes, e.g. random walks or accretion processes[6]. The simplest, and we believe most-likely, explanation for this observed power law distribution is a combination of exponential processes, namely the rare acquisition of a second driver event in exponentially-expanding, p53-deficient tumors.

Suppose that tumor size N(t) initially grows exponentially over time t with rate $r_1$, such that $N(t)=e^{r_1 t}$. Let $N(t=0)=1$, i.e. there is one tumorigenic cell at infection (transduction) time which is defined as t=0. Furthermore, we assume that at time t* a new clone with a new driver emerges in the tumor population and grows at a much faster rate $r_2$, such that this clone dominates the tumor population at the time of sacrifice $t^F$, i.e. $r_2(t^F-t^*) \gg r_1 t^F$. Note that $0 \leq t^* < t^F$. Lastly, suppose that this transformative clone emerges randomly in time with a probability that is proportional to the size of the tumor, i.e. $p(t^*) \sim \mu N(t)$. In this scenario, the size of tumors at time of analysis $N(t=t^F)=n$ is $$n = e^{r_2(t^F - t^*)}$$

$$n \propto e^{-r_2 t^*}$$

Based on the derivation reviewed in Newman, M. Power laws, Pareto distributions and Zipf's law. *Contemp. Phys.* 46, 323-351 (2005), entitled *Combinations of exponentials* (Section 4.1), we find:

$$p(n) = \frac{n^{-\left(1+\frac{r_1}{r_2}\right)}}{r_2}$$

Tumor sizes are power-law distributed with exponent $$1 + \frac{r_1}{r_2}.$$

This result implies either that the observed exponent must be less than 2 or that additional drivers must be acquired. The Maximum-Likelihood estimate of the exponent for KPT mice sacrificed at 11 weeks is slightly greater than two, while the exponent for sgp53 tumors in KT;Cas9 mice sacrificed at 15 weeks is slightly less than two (although both of these values subsume two in their 95% CI).

| Assumption | Description |
|---|---|
| $N(t) = e^{rt}$ | Exponential growth dynamics |
| $p(t^*) \sim \mu N(t)$ | 2nd driver arises w/probability proportional to population size |
| $r_2(t^F - t^*) \gg r_1 t^F$ | 2nd driver completes selective sweep by time of sacrifice |

All of the above assumptions made in other basic mathematical models of tumor progression[4]. Thus, we believe that a Markov Process is the best explanation of the observed Power-Law.

Lastly, we note that the transformative event at time t is unspecified. It could be a genetic alteration, an epigenetic change, a switch in cell signalling state, etc. We further note that there are other processes that may generate a Power-Law distribution.

Evidence of Tumors with Multiple Lentiviral Infections

Size measurements are precise enough to identify lesions putatively infected (transdcued) by multiple lentiviral vector. Our first experiment (KT, KLT, KPT mice) used larger viral titters (6,000 to 22,000 capsids), so we expected multiple infections to be more common. If two different viral vectors infected (transdcued) the same founding cell, then it would expand into a single tumor annotated as two lesions—by both lentiviral barcodes. Therefore, if we observed two barcoded tumors of the same size within an individual mouse, then we might expect that these arose from two lentiviral vectors initiating a single lesion. Thus, we investigated the size difference between each lesion and its nearest neighbor in the same mouse.

We observed that a small fraction of lesions were closer in size than expected, suggesting that some lesions may have arisen from cells that where initiated by infection (transduction) with more than one lentiviral vector. Our (null) expected distribution represents the size differences between an observed lesion size and their nearest neighbor in different (randomly-selected) mice. Although our data suggests that multiple infections occur in ~1% of tumors, we do not believe that that this rare occurrence substantially affects the other conclusions of our study because (i) multiple infections appear to be rare, and (ii) multiple infections should attenuate our estimates of a driver's growth benefit (as multiple-infections would confer a growth advantage to our baseline—the sgInert constructs). Nonetheless, this preliminary discovery once again illustrates our approaches ability to uncover new biology using old techniques.

Methods

Mice and Tumor Initiation $Kras^{LSL-G12D}$(K), $Lkb1^{flox}$(L), $p53^{flox}$(P), $R26^{LSL-Tomato}$ (T), and $H11^{LSL-Cas9}$(Cas9) mice have been described. Lung tumors were initiated by intratracheal infection (transduction) of mice as previously described using lentiviral-Cre vectors at the titers indicated. Tumor burden was assessed by fluorescence microscopy, lung weight, and histology as indicated. All experiments were performed in accordance with Stanford University Institutional Animal Care and Use Committee guidelines.

Generation of Barcoded Lenti-mBC/Cre and Lenti-sgPool/Cre Vector Pools

To enable quantification of the number of cancer cells in individual tumors in parallel using high-throughput sequencing, we diversified lentiviral-Cre vectors with a short barcode sequence that would be unique to each tumor by virtue of stable integration of the lentiviral vector into the initial infected (transdcued) lung epithelial cell. We generated tumors in a variety of mouse backgrounds with two different pools of barcoded lentiviral vectors. The first was a pool of ~10[6] uniquely barcoded variants of Lenti-PGK-Cre (Lenti-millionBC/Cre; Lenti-mBC/Cre, generated by pooling six barcoded Lenti-U6-sgRNA/PGK-Cre vectors) which we used to analyze the number of cancer cells in tumors induced in $Kras^{LSL-G12D/+};R26^{LSL-Tomato}$ (KT), $Kras^{LSL-G12D/+};p53^{flox/flox};R26^{LSL-Tomato}$(KPT), and $Kras^{LSL-G12D/+};Lkb1^{flox/flox};R26^{LSL-Tomato}$ (KLT) mice (FIG. 1). The second was a pool of 15 barcoded Lenti-U6-sgRNA/PGK-Cre vectors which we used to assess the tumor suppressive effect of candidate tumor suppressor genes in three different genetic backgrounds by infecting $KT;H11^{LSL-Cas9}$ (KT;Cas9) and KT mice. Our Lenti-sgInert/Cre vectors included three sgRNAs that target the NeoR gene within the $Rosa26^{LSL-Tomato}$ allele, which are actively cutting, but functionally inert, negative control sgRNAs.

Design, Generation, and Screening of sgRNAs

We generated lentiviral vectors carrying Cre as well as an sgRNA targeting each of 11 known and putative lung adenocarcinoma tumor suppressors: sgLkb1, sgP53, sgApc, sgAtm, sgArid1a, sgCdkn2a, sgKeap1, sgRb1, sgRbm10, sgSetd2, and sgSmad4. Vectors were also generated carrying inert guides: sgNeo1, sgNeo2, sgNeo3, sgNT1, and sgNT3. All possible 20-bp sgRNAs (using an NGG PAM) targeting each tumor suppressor gene of interest were identified and scored for predicted on-target cutting efficiency using an available sgRNA design/scoring algorithm[10]. For each tumor suppressor gene, we selected three unique sgRNAs predicted to be the most likely to produce null alleles; preference was given to sgRNAs with the highest predicted cutting efficiencies, as well as those targeting exons conserved in all known splice isoforms (ENSEMBL), closest to splice acceptor/splice donor sites, positioned earliest in the gene coding region, occurring upstream of annotated functional domains (InterPro; UniProt), and occurring upstream of known human lung adenocarcinoma mutation sites. Lenti-U6-sgRNA/Cre vectors containing each sgRNA were generated as previously described. Briefly, Q5 site-directed mutagenesis (NEB E0554S) was used to insert sgRNAs into the parental lentiviral vector containing the U6 promoter as well as PGK-Cre. The cutting efficiency of each sgRNA was determined by infecting LSL-YFP;Cas9 cells with each Lenti-sgRNA/Cre virus. Forty-eight hours after infection (transduction), flow cytometric quantification of YFP-positive cells was used to determine percent infection (transduction). DNA was then extracted from all cells and the targeted tumor suppressor gene locus was amplified by PCR.

PCR amplicons were Sanger sequenced and analyzed using TIDE analysis to quantify percent indel formation. Finally, the indel percent determined by TIDE was divided by the percent infection (transduction) of LSL-YFP;Cas9 cells, as determined by flow cytometry, to determine sgRNA cutting efficiency. The most efficient sgRNA targeting each tumor suppressor gene of interest was used for subsequent experiments. sgRNAs targeting Tomato and Lkb1 have been described previously, and we previously validated an sgRNA targeting p53 (unpublished data). Primers sequences used to amplify target indel regions for the top guides used in this study are below:

|  | F primer (5' → 3') | R primer (5' → 3') |
| --- | --- | --- |
| sgApc_1 | TGACTTTGCAGGGCAAGTTT (SEQ ID NO: 8) | CCCACTCCCCTGTTACCTTT (SEQ ID NO: 21) |
| sgArid1a_3 | CAGCAGTCCCCAACTCCATA (SEQ ID NO: 9) | GGAGCCATTTCTTGGGGTTA (SEQ ID NO: 22) |
| sgAtm_3 | GCCCCAAGTGAGAATCAGTG (SEQ ID NO: 10) | AGCTCTGGCTCCTTGTGGAT (SEQ ID NO: 23) |
| sgCdkn2a_2 | GGCTTCTTTCTTGGGTCCTG (SEQ ID NO: 11) | GGCTCATTTGGGTTGCTTCT (SEQ ID NO: 24) |
| sgKeap1_2 | CTGAGCCAGCAACTCTGTGA (SEQ ID NO: 12) | GGCCTATCCCACTTCTGAGC (SEQ ID NO: 25) |

-continued

| | F primer (5' → 3') | R primer (5' → 3') |
|---|---|---|
| sgRb1_3 | AACTGTGCTGGTGTGTGCAA (SEQ ID NO: 13) | ACACCACCACCACCATCATC (SEQ ID NO: 26) |
| sgRbm10_3 | CAAAGCTGGAAGCGAGACTG (SEQ ID NO: 14) | CTGGCTGGAGCTGTGAGAGT (SEQ ID NO: 27) |
| sgSetd2_1 | TCTGCAAGTTCAAGCGATGA (SEQ ID NO: 15) | TGGATTCAGGTGACCTAGATGG (SEQ ID NO: 28) |
| sgSetd2_2 | CCTCCAGCCGCTCCTCAT (SEQ ID NO: 16) | GAACGCCGAACCTAAGCAG (SEQ ID NO: 29) |
| sgSmad4_3 | GCCTTTCTGTGGAAATGGAA (SEQ ID NO: 17) | TTCCAGGCTGAGTGGTAAGG (SEQ ID NO: 30) |
| sgNeo_1 | TTGTCAAGACCGACCTGTCC (SEQ ID NO: 18) | CCACCATGATATTCGGCAAG (SEQ ID NO: 31) |
| sgNeo_2 | TCTGGACGAAGAGCATCAGG (SEQ ID NO: 19) | GCTCCAATCCTTCCATTCAA (SEQ ID NO: 32) |
| sgNeo_3 | CGCTGTTCTCCTCTTCCTCA (SEQ ID NO: 20) | TGGATACTTTCTCGGCAGGA (SEQ ID NO: 33) |

Barcode Diversification of Lenti-sgRNA/Cre

After identifying the best sgRNA targeting each tumor suppressor of interest, we diversified the corresponding Lenti-sgRNA/Cre vector with a known 8-nucleotide ID specific to each individual sgRNA (sgID; bold) and the 15-nucleotide random barcode (BC; underlined) (see FIG. 10a).

| | Primer (5' → 3') |
|---|---|
| Universal Reverse Primer | AGCTAGGGATCCGCCGCATAACCAGTG (SEQ ID NO: 34) |
| Barcoded Forward Primer | AGCTAGTCCGGNNNNNNNNAANNNNNTTNNNNNAANNNNNATGCCCAAGAAGAAGAGGAAGGTGTC (SEQ ID NO: 35) |

These primers were used to PCR amplify a region of the Lenti-PGK-Cre vector that included the 3' end of the PGK promoter and the 5' part of Cre. PCR was performed using PrimeSTAR® HS DNA Polymerase (premix) (Clontech, R040A) and PCR products were purified using the Qiagen® PCR Purification Kit (28106). The PCR insert was digested with BspEI and BamHI and ligated with the Lenti-sgRNA-Cre vectors cut with XmaI (which produces a BspEI compatible end) and BamHI.

To generate a large number of uniquely barcoded vectors, we ligated 300 ng of each XmaI, BamHI-digested Lenti-sgRNA-Cre vector with 180 ng of each BspEI, BamHI-digested PCR product using T4 Ligase (NEB, M0202L) and standard protocols (80 µl total reaction volume). Ligations were PCR purified using the Qiagen® PCR Purification Kit to remove residual salt. To obtain a pool of the greatest possible number of uniquely barcoded Lenti-sgRNA/Cre vectors, 1 µl of purified ligation was transformed into 20 µl of ElectroMAX DH10B cells (Thermo Fisher, 18290015). Cells were electroporated in 0.1 cm GenePulser/MicroPulser Cuvettes (Bio-Rad, 165-2089) in a BD MicroPulser™ Electroporator (Bio-Rad, 165-2100) at 1.9 kV. Cells were then rescued by adding 500 µl media and shaking at 200 rpm for 30 minutes at 37° C. For each ligation, bacteria were plated on seven LB-Amp plates (1 plate with 1 µl, 1 plate with 10 µl, and 5 plates with 100 µl). The following day, colonies were counted on the 1 µl or 10 µl plate to estimate the number of colonies on the 100 µl plates, and this was used as an initial estimation of number of unique barcodes associated with each ID.

10 ml of liquid LB-Amp was added to each plate of bacteria to pool the colonies. Colonies were scraped off of the plates into the liquid, and all plates from each transformation were combined into a flask. Flasks were shaken at 200 rpm for 30 minutes at 37° C. to mix. DNA was Midi-prepped using the Qiagen® HiSpeed MidiPrep Kit (12643). DNA concentrations were determined using a Qubit dsDNA HS Kit (Invitrogen, Q32851).

As a quality control measure, the sgID-BC region from each Lenti-sgRNA-sgID-BC/Cre plasmid pool was PCR amplified with GoTaq Green polymerase (Promega M7123) following manufacturer's instructions. These PCR products were Sanger sequenced (Stanford PAN facility) to confirm the expected sgID and the presence of a random BC. Since BspEI and XmaI have compatible overhangs but different recognition sites, the Lenti-sgRNA-sgID-BC/Cre vectors generated from successful ligation of the sgID/BC lack an XmaI site. Thus for pools that had a detectable amount of unbarcoded parental Lenti-sgRNA/Cre plasmid as determined by Sanger sequencing (>5%), we destroyed the parental unbarcoded vector by digesting the pool with XmaI (NEB, 100 µl reaction) using standard methods. These re-digested plasmid pools were re-purified using the Qiagen® PCR Purification Kit and concentration was redetermined by NanoDrop.

Generation of Lenti-mBC/Cre and Lenti-TS-Pool/Cre

To obtain a library with approximately $10^6$ associated barcodes to use in our initial experiments in mice that lacked the H11$^{LSL-Cas9}$ allele, we pooled six sgID-BC barcoded vectors to create Lenti-million Barcode/Cre (Lenti-mBC/Cre). We then pooled the barcoded Lenti-sgRNA-sgID-BC/Cre vectors (sgLkb1, sgp53, sgApc, sgAtm, sgArid1a, sgCdkn2a, sgKeap1, sgNeo1, sgNeo2, sgNeo3, sgNT1, sgRb1, sgRbm10, sgSetd2, and sgSmad4) to generate Lenti-sgTS-Pool/Cre. All plasmids were pooled at equal ratios as determined by Qubit concentration prior to lentivirus production.

Production, Purification, and Titering of Lentivirus

Lentiviral vectors were produced using polyethylenimine (PEI)-based transfection of 293T cells with the lentiviral vectors and delta8.2 and VSV-G packaging plasmids. Lenti-mBC/Cre, Lenti-sgTS-Pool/Cre, Lenti-sg Tomato/Cre, Lenti-sgLkb1, Lenti-sgSetd2#1/Cre, Lenti-sgSetd2#3/Cre, Lenti-sgNeo2/Cre, and Lenti-sgSmad4/Cre were generated for tumor initiation. Sodium butyrate (Sigma Aldrich, B5887) was added at a final concentration of 0.2 mM eight hours after transfection to increase production of viral particles. Virus-containing media was collected 36, 48, and 60 hours after transfection, concentrated by ultracentrifugation (25,000 rpm for 1.5-2 hours), resuspended overnight in PBS, and frozen at −80° C. Concentrated lentiviral particles were titered by infecting LSL-YFP cells (a gift from Dr. Alejandro Sweet-Cordero), determining the percent YFP-positive cells by flow cytometry, and comparing the infectious titer to a lentiviral preparation of known titer.

Generation of "Benchmark" Cell Lines

Three uniquely barcoded Lenti-Cre vectors with the sgID "TTCTGCCT" were used to generate benchmark cell lines that could be spiked into each bulk lung sample at a known cell number to enable the calculation of cancer cell number within each tumor. Plasmid DNA from individual bacterial colonies was isolated using the Qiagen® QIAprep Spin Miniprep Kit (27106). Clones were Sanger sequenced, lentivirus was produced as described above, and LSL-YFP cells were infected (transdcued) at a very low multiplicity of infection (transduction) such that approximately 3% of cells were YFP-positive after 48 hours. Infected (transdcued) cells were expanded and sorted using a BD Aria II™ (BD Biosciences). YFP-positive sorted cells were replated and expanded to obtain a large number of cells. After expansion, cells were re-analyzed for percent YFP-positive cells on a BD LSR II™ analyzer (BD Biosciences). Using this percentage, the number of total cells needed to contain $5 \times 10^5$ integrated barcoded lentiviral vectors was calculated for each of the three cell lines and cells were aliquoted and frozen based on this calculation.

Summary of all Mouse Infections

| Genotype | Virus Type | Viral Titer |
| --- | --- | --- |
| KT | Lenti-mBC/Cre | $6.8 \times 10^5$ |
| $KT_{low}$ | Lenti-mBC/Cre | $1.7 \times 10^5$ |
| KPT | Lenti-mBC/Cre | $1.7 \times 10^5$ |
| KLT | Lenti-mBC/Cre | $1.7 \times 10^4$ |
| KT | Lenti-TS-Pool/Cre | $9.0 \times 10^4$ |
| KT; Cas9 | Lenti-TS-Pool/Cre | $2.2 \times 10^4$ |
| KT; Cas9 | Lenti-sgNeo2/Cre | $9 \times 10^3$ |
| KT; Cas9 | Lenti-sgSetd2#1/Cre | $9 \times 10^3$ |
| KT; Cas9 | Lenti-sgSetd2#2/Cre | $9 \times 10^3$ |
| KT | Lenti-sgSmad4/Cre | $10^5$ |
| KT; Cas9 | Lenti-sgSmad4/Cre | $10^5$ |

Isolation of Genomic DNA from Mouse Lungs

For experiments in which barcode sequencing was used to quantify the number of cancer cells in each tumor the whole lungs from each mouse were homogenized using a Fisher TissueMeiser. $5 \times 10^5$ cells from each of the three individually barcoded benchmark cell lines were added at the time of homogenization. Tissue was homogenized in 20 ml lysis buffer (100 mM NaCl, 20 mM Tris, 10 mM EDTA, 0.5% SDS) with 200 μl of 20 mg/ml Proteinase K (Life Technologies, AM2544). Homogenized tissue was incubated at 55° C. overnight. To maintain accurate representation of all tumors, DNA was phenol-chloroform extracted and ethanol precipitated from $\sim 1/10^{th}$ of the total lung lysate using standard protocols. For lungs weighing less than 0.3 grams, DNA was extracted from $\sim 1/5^{th}$ of the total lung lysate, and for those weighing less than 0.2 grams, DNA was extracted from $\sim 3/10^{th}$ of the total lung lysate to increase DNA yield.

Preparation of sgID-BC Libraries for Sequencing

Libraries were prepared by amplifying the sgID-BC region from 32 μg of genomic DNA per mouse. The sgID-BC region of the integrated Lenti-sgRNA-BC/Cre vectors was PCR amplified using one of 24 primer pairs that contain TruSeq Illumina® adapters and a 5' multiplexing tag (TruSeq i7 index region indicated in bold):

|  | Primer (5' → 3') |
| --- | --- |
| Universal Forward Primer | AATGATACGGCGACCACCGAGATCTACACTCTTTCCCTA CACGACGCTCTTCCGATCTGCGCACGTCTGCCGCGCTG (SEQ ID NO: 36) |
| Reverse Primer | CAAGCAGAAGACGGCATACGAGATNNNNNNGTGACTGGA CTTCAGACGTGTGCTCTTCCGATCCAGGTTCTTGCGAAC CTCAT (SEQ ID NO: 37) |

We used a single-step PCR amplification of sgID-BC regions, which we found to be a highly reproducible and quantitative method to determine the number of cancer cells in each tumor. We performed eight 100 μl PCR reactions per mouse (4 μg DNA per reaction) using OneTaq 2× Master Mix with Standard buffer (NEB, M0482L) with the following PCR program:
1. 94 C 10 min
2. 94 C 30 sec
3. 55 C 30 sec
4. 68 C 30 sec
5. GO TO 2 (34×)
6. 68 C 7 min
7. 4 C infinity Pooled PCR products were isolated by gel electrophoresis and gel extracted using the Qiagen® MinElute Gel Extraction kit. The concentration of purified PCR products from individual mice was determined by Bioanalyzer (Agilent Technologies) and pooled at equal ratios. Samples were sequenced on an Illumina® HiSeq to generate 100 bp single-end reads (ELIM Biopharmaceuticals, Inc).

Identifying Distinct sgRNAs and Tumors Via Ultra-Deep Sequencing

The unique sgID-BC identifies tumors. These sgID-BCs were detected via next generation sequencing on the Illumina® HiSeq. The size of each tumor, with respect to cell number, was expected to roughly correspond to the abundance of each unique sgID-BC pair. Because tumor sizes varied by factors larger than the read sequencing error rate, distinguishing true tumors from recurrent read errors required careful analysis of the deep-sequencing data.

Tumors and their respective sgRNAs were identified in three steps: (i) abnormal and low quality reads were discarded from the ultra-deep sequencing runs, (ii) unique barcode pileups were bundled into groups that we predicted to arise from the same tumor, and (iii) cell number was estimated from these bundles in the manner that proved most reproducible.

Read Pre-Processing

Reads contained a two-component DNA barcode (an 8-nucleotide sgID and a 21-nucleotide barcode sequence that contains 15 random nucleotides) that began 49 nucleotides downstream of our forward primer and ended 22 nucleotides upstream of the end of our 100-bp single-end reads. We discarded unusual reads: those that lacked the flanking lentiviral sequences, those that contained unexpected barcodes, and those with high error rates. This was accomplished in three steps (FIG. 8a):
1. We examined the 12 lentiviral nucleotides immediately upstream and downstream of the sgID-BC. These 12 nucleotides were identified using pairs of adjacent 6-mer search strings, such that each 6-mer could tolerate one mismatch. Although we expected these 12 nucleotides to begin at position 37 within the read, we did not require this positioning or leverage this information. A nested 6-mer approach (with two opportunities to identify the lentiviral sequences flanking the sgID-BC) was used to minimize read discarding. This was particularly important in this first step because the non-barcoded regions of our reads were used to estimate sequencing error rates and, therefore, should not be biased against read errors. For ~7-8% of reads, this $2^{nd}$ 6-mer match salvaged the read, i.e. the 6-mers immediately flanking the sgID-BC were not as expected (despite our tolerance of one mismatch) yet the 6-mers immediately outside of these inner 6-mer sequences were recognizable and allowed us to salvage the read and identify the barcodes.
2. We then discarded reads in which the sgID-BC deviated in length by greater than two nucleotides in either direction. Because our first barcode was expected to contain one of the 15 sgIDs, we discarded reads that did not match one of these 15 sequences. One mismatch and one indel were permitted in the matching.
3. We then end-trimmed each read such that 18 bp flanked either end of the sgID-BC. We then filtered the trimmed reads according to quality score, retaining those that were predicted to contain no more than two sequencing errors. We also discarded reads with uncalled bases in the second (random) barcode and rectified uncalled bases elsewhere.

In these three stages, 14% of reads were discarded at stage one, ~7% at stage two, and <2% at stage three.

We then examined those reads that failed at each stage. By performing BLAST searches, we determined that those reads discarded at stage one often contained uninformative sequences corresponding to artifacts from either our preparation (Phi X bacteriophage genome and mouse genome) or other samples paired with us on the lane (common plasmid DNAs). In stage two, we found that reads with aberrant barcode lengths often contained large indels or had one or both of their sgID-BC completely missing. Lastly, very few reads were discarded in stage three due to the fact that internal regions of the reads exhibited higher quality scores than the corresponding termini. As a consequence of this trend, it is common practice to end-trim reads prior to discarding those reads predicted to contain greater than two sequencing errors.

Clustering of Unique Read Pileups Via DADA2 sgID-BC reads were aggregated into sets of identical sequences and counted. The counts of unique DNA barcode pairs do not directly correspond to unique tumors because large tumors are expected to generate recurrent sequencing errors (FIG. 8b). We therefore spent considerable effort developing a method to distinguish small tumors from recurrent sequencing errors arising from large tumors (consider, for example, that a tumor of 10 million cells will produce sequencing-error pileups that mimic a 10-100 thousand-cell tumor, if the Illumina® machine has a 0.1-1% error rate). DADA2 has been used previously to address this issue in barcoding experiments involving ultra-deep sequencing. However, because it was designed for ultra-deep sequencing of full-length Illumina amplicons, we had to tailor and calibrate it for our purposes.

In DADA2, the likelihood of barcode pileups resulting from a recurrent sequencing error of a larger pileup depends upon:
1. The abundance of the larger pileup,
2. The specific nucleotide differences between the smaller and larger pileups, and
3. The average quality scores of the smaller pileup at the variant positions.

Factors one and two are, at first, considered heuristically (to maximize computational speed) and then more precisely (when needed) via a Needleman-Wunsch algorithm. DADA2 splits a cluster into two when the probability that a smaller pileup was generated by sequencing errors is less than $\Omega$. Therefore, this value represents a threshold for splitting larger clusters. When this threshold is large, read pileups are split permissively (many called tumors, perhaps dividing large tumors), and when $\Omega$ is small, read pileups are split restrictively (few called tumors, perhaps aggregating distinct small tumors).

The likelihood of sequencing errors was inferred from our ultra-deep sequencing data. Phred quality scores provide a theoretical estimate of sequencing error rates, however these estimates tend to vary from Illumina® machine to Illumina® machine and do not account for the specifics of our protocol (including, for example, occasional errors introduced via PCR amplification, despite our use of high-fidelity polymerase). Ordinarily, DADA2 will estimate sequencing error rates simultaneously with the unique DNA clusters; however, our lentiviral constructs had non-degenerate regions outside of our sgID-BC region that could be used to estimate sequencing error rates directly. Moreover, estimating error rates and barcode clusters jointly was more computationally intensive, requiring greater than 20,000 CPU-hours for clustering our entire dataset and exploring the relevant clustering parameters.

A sequencing error model was trained to each Illumina® machine by:
1. Generating training pseudo-reads by concatenating the 18 nucleotides immediately upstream of our sgID-BC with the 18 nucleotides immediately downstream of the barcodes, then
2. Clustered these pseudo-reads using a single run of DADA2.
3. Using the error rates estimated from this training run to cluster the sgID-BC using a single run of DADA2.

We used a very low value of $\Omega=10^{-100}$ to estimate sequencing errors in the training run, as we expected only one cluster of lentiviral sgID-BC-flanking sequences. Altering this value did not affect our training run appreciably, but we nonetheless observed occasional very small derivative clusters from our lentiviral sequence even at this value. These derivative clusters are presumably rare DNA artifacts and never amounted to >2% of our processed reads. We felt that using a very stringent DADA2 run to estimate sequencing errors represented a superior approach (by virtue of the Goldilocks principle): a more permissive threshold might over-fit sequencing errors and underestimate sequencing error rates, while an approach where error rates were estimated directly from each read's deviance from expectation (akin to a DADA2 run where $\Omega=0$) would ignore the presence DNA artifacts in our data and, therefore, overestimate sequencing error rates.

We trained sequencing error rates on each Illumina® machine used in this study (seven in total). Training allowed the probability of every substitution type (A→C, A→T, etc) to be estimated. The error rates as a function of Phred quality score were determined using LOESS regression of the available data (FIG. 8c). In general, error rates were approximately two to three times higher than predicted by the Phred quality scores for transversions (and approximately consistent with expectations for transitions). This elevated error rate is typical and may reflect miscalibration of the machines and/or mutations introduced during PCR.

We then clustered the dual barcodes that passed our pre-processing filters using DADA2. Barcodes were given seven nucleotides of non-degenerate lentiviral flanking regions so that any indels within the barcodes could be identified (without adequate flanking sequences, DNA alignment algorithms sometimes miscall indels as multiple point mutations). During clustering, we also required (i) that clusters deviate from each other by at least two bases (i.e. MIN_HAMMING_DISTANCE=2), (ii) that new clusters only be formed when pileup size exceeded expectations under the error process by at least a factor of two (MIN_FOLD=2), and (iii) that the Needleman-Wunsch algorithm consider only alignments with at most four net insertions or deletions (BAND_SIZE=4, VECTORIZED_ALIGNMENT=FALSE). None of these choices affected the results appreciably, but they increased computational performance and offered additional verification that barcodes were aggregated into tumors of reasonable size.

Vetting and Calibration of Pipeline

We sequenced our first PCR-amplified, multiplexed DNA libraries (from KT, KLT, and KPT tumors) in triplicate to vet and design our tumor-calling approach.

Reproducibility was interrogated in three ways: (i) the correlation between estimated cell abundances for all barcodes and all mice, (ii) the variation in the number of lesions called for each sgID in each mouse in our first experiment, and (iii) the variation in mean size for each sgID—which should be constant in mice not expressing Cas9. Because the read depth of our triplicate run naturally varied ($40.1 \times 10^6$, $22.2 \times 10^6$, and $34.9 \times 10^6$ reads after pre-processing), these three runs were performed on distinct Illumina® machines with different sequencing error rates, and, because our initial lentiviral pool contained six different sgIDs with varying levels of barcode diversity, the technical variability in our vetting process well-approximated the technical variability of later experiments. In our tumor-size analysis pipeline, we found:

1. The mean abundance of our three "benchmark" DNA barcodes was more reproducible between replicate runs than the median abundance. Thus, this mean value of benchmark read abundance (corresponding to 500,000 cells) was used to convert read abundance into the absolute cell number of cancer cells in each tumor (FIG. 9).
2. Ignoring reads with ≥2 errors from the consensus barcode of a cluster improved reproducibility. Typically, ~80-90% of reads in a barcode cluster were exact matches to the consensus barcode, while ~5% of reads were single errors from this read, and ~5-15% of reads deviated at 2 errors. These reads with ≥2 errors were poorly correlated between replicate runs and hampered our ability to reproducibly estimate absolute cell number/tumor size. These reads, presumably, have neither enough evidence to be considered their own lesion, nor sufficient evidence to be counted towards the larger cluster. Therefore, these reads were excluded.
3. The cluster-splitting proclivity of DADA2 was thresholded at $\Omega = 10^{-10}$ and required that lesions contain ≥500 cells for FIGS. 1-3 and ≥1000 cells for FIGS. 4-6 to maximize reproducibility between replicate runs (FIG. 8d-f). Threshold parameters with high specificity (small $\Omega$, high minimum cell number) called lesion sizes more reproducibly, whereas threshold parameters with high sensitivity (large $\Omega$, low minimum cell number) called lesion quantities more reproducibly. Over-prioritizing only one facet of reproducibility would be imprudent. With two thresholds, considering different facets of measurement error, we better balanced these competing priorities.

With this pipeline, we interrogated the diversity of the barcode in our screen in several ways. First, we confirmed that nucleotides in this barcode were evenly distributed among A's, T's, C's, and G's (FIG. 10b). Second, we found no evidence for an excess of repeated string (e.g. sequences AAAAA). Third, we calculated the number of random barcodes paired to each sgID in our lentiviral pool. Due to the large number of uniquely barcoded variants of each vector that we generated through our barcode ligation approach, (see Barcode diversification of Lenti-sgRNA/Cre) most barcodes that exist in our lentiviral pool were never detected in any lesions in any of the experiments (because diversity is much higher that total lesion number). Nonetheless, we still inferred the amount of barcode diversity from the observed barcodes. To make this inference, we assumed that the probability of observing a barcode in i mice is Poisson distributed: $P(k=i; \lambda) = \lambda^k e^{-\lambda}/k!$, where $\lambda_r = L_r/D_r$, is a ratio of the number of called lesions $L_r$ for each sgID r in our entire dataset (a known quantity) divided by the total number of unique barcodes $D_r$ for each sgID. By noting that $\lambda_r/(1-e^{-\lambda_r}) = \mu_{non-zero}$, where $\mu_{non-zero} = \Sigma_{i=1}^{\infty} P(k=i; \lambda_r)$ is simply the mean number of occurrences of each barcode that occurred once or more, we could calculate $D_r$. Across our entire dataset, the average probability of the same barcode initiating two distinct tumors in the same mouse was 0.91%.

Good barcode diversity is also demonstrated by the six sgIDs in Lenti-mBC/Cre experiment. If barcode diversity was low and barcodes overlapped often within a mouse, then the mean sizes of the less diverse sgIDs would increase—as two distinct tumors with the same barcode would be bundled together. However, the mean sizes of each sgID vary by <1% within replicate mice, thus refuting this possibility. We also assessed our ability to call sgIDs accurately, despite sequencing errors, by processing deep-sequencing runs in two ways: by identifying each read's cognate sgID before clustering based on the raw read sequence or by identifying cognate sgIDs after clustering based on the consensus sequence of the cluster. Using either approach, 99.8% of reads paired to the same cognate sgID, thus providing assurance that sgIDs are accurately identified. We opted to employ the latter approach for our final analysis.

By thoroughly developing and vetting our tumor-calling pipeline, we salvaged an extra decade of size resolution. Our three DNA benchmarks (added to the lung samples at the very beginning of DNA preparation) (FIG. 9) offer a glimpse of this resolution. Sequencing errors of the DNA benchmarks are easily identified by the DNA benchmark's unique sgID and known secondary barcodes. While these sequencing errors are usually discarded, we can treat them as ordinary read pileups and observe the properties of potential sequencing errors. Without our calibrated analysis pipeline, the sequencing errors appear as lesions of $\sim 10^3$ cells; with our pipeline, these sequencing errors emerge as lesions of $\sim 10^2$ cells—below our minimum cell threshold (FIG. 2a).

More importantly, our pipeline is robust to technical perturbations. We more intensively profiled reproducibility with two additional technical perturbations in two specific mice from the first experiment. First, a KLT 11-week mouse (JB1349) was sequenced at great depth and then randomly down-sampled ten-fold to typical read depth (this down-sampling was more dramatic than any variability in read depth actually detected throughout our study). Lesion sizes were very highly correlated in this first perturbation (FIG. 2b). Additionally, a KT 11-week mouse (IW1301) was amplified in two PCR reactions with different multiplexing tags (FIG. 2c). PCR and multiplexing appears to hamper reproducibility more than read depth, although reproducibility is good overall. These mice also display two encouraging reproducibility trends: (i) larger lesions/tumors were most consistent between replicates, and (ii) the overall shape (histogram) of tumor lesion sizes were better correlated between the replicates than individual tumors (e.g. r=0.89 for each lesion in IW1301, whereas r=0.993 for the abundance of tumors within the 60 histogram bins of FIG. 8b). This second observation implies that our technical perturbations introduce unbiased noise. Also, all correlations compare logarithmic size; because larger tumors are better correlated, this transformation substantially reduces the Pearson correlation coefficient.

Minimizing the Influence of GC Amplification Bias on Tumor-Size Calling

We define each tumor in our study by a size $T_{mrb}$ corresponding to the mouse m that harbored it, the cognate sgRNA r identified by its first barcode, and a unique barcode sequence (consensus of the DADA2 cluster) b. Given the approximately log normal structure of our data (FIG. 3d and data not shown), we log-transformed and normalized sizes such that $T_{mrb}=Ln(T_{mrb}/E_{mr}[T_{mrb}])$. Here $E_{mr}[T_{mrb}]=\Sigma_b T_{mrb}/N_{mr}$ is the expected lesion size for a given mouse m and sgRNA r and we will use this notation for expectation values. This notation—where aggregated indices are dropped from subscripts—is used throughout. GC biases were subtle: the coefficient of variation (CV) of $E_{mr}[T_{mrb}]$ was 5.0%. This marginal distribution still exhibited a subtle dependence on the GC-content of the combined barcode sequence that was best described by a $4^{th}$-order least-squares polynomial fit $f_4$ (b) of $E_b[\tau_{mrb}]$ (adjusted $r^2=0.994$). The sgIDs were all designed with well-balanced GC-content, however the second barcode comprises random sequences. While the multinomial process of generating barcodes made intermediate levels of GC-content most common, some deviation of GC-content was observed. Maximal values of $f_4$ (b) arise at intermediate GC-content, suggesting that PCR biases amplification towards template DNA of intermediate melting temperature. We subtracted the effects of this GC-bias from log-transformed values: $t_{mrb}=Ln[T_{mrb}]-f_4$ (b). This correction alters tumor sizes by 5% on average.

Calculation of In Vitro Cutting Efficiency Using the Lenti-TS-Pool/Cre Virus

Cas9 expressing cell lines were infected (transdcued) with Lenti-TS-Pool/Cre virus and harvested after 48 hours. gDNA was extracted and targeted loci were amplified using the above primers.

Analysis of Indels at Target Sites

To confirm CRISPR/Cas9-induced indel formation in vivo, the targeted region of each gene of interest was PCR-amplified from genomic DNA extracted from bulk lung samples using GoTaq Green polymerase (Promega M7123) and primer pairs that yield short amplicons amenable to paired-end sequencing:

|        | F primer (5' → 3')              | R primer (5' → 3')              |
|--------|--------------------------------|--------------------------------|
| Apc    | CATGGCATAAAGCAGTTACTACA (SEQ ID NO: 38) | TCTCCTGAACGGCTGGATAC (SEQ ID NO: 52) |
| Arid1a | CCAGTCCAATGGATCAGATG (SEQ ID NO: 39) | GGGTACCCATGTCCTTGTTG (SEQ ID NO: 53) |
| Atm    | CACCCAGTTGACCCTATCTTC (SEQ ID NO: 40) | CCGTTTTCGGAAGTTGACAG (SEQ ID NO: 54) |
| Cdkn2a | CAACGTTCACGTAGCAGCTC (SEQ ID NO: 41) | ACCAGCGTGTCCAGGAAG (SEQ ID NO: 55) |
| Keap1  | GGCTTATTGAGTTCGCCTACA (SEQ ID NO: 42) | GCTGCTGCACGAGGAAGT (SEQ ID NO: 56) |
| Rb1    | GGTACCCGATCATGTCAGAGA (SEQ ID NO: 43) | AAGGAACACAGCTCCCACAC (SEQ ID NO: 57) |
| Rbm10  | TACTCAGCCGCTTTCTTTGC (SEQ ID NO: 44) | GAGGATTTGTTCCGCATCAG (SEQ ID NO: 58) |
| Setd2  | CTGTTGTGGTTGTGCCAAAG (SEQ ID NO: 45) | TTTTCAGTTTGAGAACAGCCTTT (SEQ ID NO: 59) |
| Smad4  | TCGATTCAAACCATCCAACA (SEQ ID NO: 46) | CTTGTGGAAGCCACAGGAAT (SEQ ID NO: 60) |
| Lkb1   | GGGCCTGTACCCATTTGAG (SEQ ID NO: 47) | TGTCCCTTGCTGTCCTAACA (SEQ ID NO: 61) |
| p53    | CATCACCTCACTGCATGGAC (SEQ ID NO: 48) | CAGGGGTCTCGGTGACAG (SEQ ID NO: 62) |
| Neo1   | GGCAGGATCTCCTGTCATCT (SEQ ID NO: 49) | AGTACGTGCTCGCTCGATG (SEQ ID NO: 63) |
| Neo2   | CGGACCGCTATCAGGACATA (SEQ ID NO: 50) | GAGCGGCGATACCGTAAAG (SEQ ID NO: 64) |
| Neo3   | GATCGGCCATTGAACAAGAT (SEQ ID NO: 51) | CATCAGAGCAGCCGATTGT (SEQ ID NO: 65) |

PCR products were either gel-extracted or purified directly using the Qiagen® MinElute kit. DNA concentration was determined using the Qubit HS assay, following manufacturer's instructions. All 14 purified PCR products were combined in equal proportions for each mouse. TruSeq Illumina® sequencing adapters were ligated on to the pooled PCR products with a single multiplexing tag per mouse using SPRIworks (Beckman Coulter, A88267) with standard protocols. Sequencing was performed on the Illumina HiSeq to generate single-end, 150-bp reads (Stanford Functional Genomics Facility).

Custom Python scripts were used to analyze the indel sequencing data. For each of the 14 targeted regions, an 8-mer was selected on either side of the targeted region to generate a 46 basepair region. Reads were required to contain both anchors and no sequencing errors were allowed. The length of each fragment between the two anchors was then determined and compared to the expected length. Indels were categorized according to the number of basepairs inserted or deleted.

The percent of indels for each individual locus in each individual mouse was calculated as follows:

$$\% \text{ Indels} = \frac{\text{Total Reads} - \textit{WildType} \text{ Reads}}{\text{Total Reads}}$$

Then the average % of indels in the three Neo loci was calculated and the % indels at every other targeted locus was normalized to this value to generate the % Indels relative to Neo that are plotted in FIG. 6a.

Calculation of In Vitro Cutting Efficiency Using the Lenti-TS-Pool/Cre Virus

Cas9 expressing cell lines were infected (transdcued) with Lenti-TS-Pool/Cre virus and harvested after 48 hours. gDNA was extracted and targeted loci were amplified using the above primers (see Analysis of indels at target sites). First, all primers were pooled and 15 rounds of PCR were performed using GoTaq Green polymerase (Promega M7123). These products were then used for subsequent amplification with individual primer pairs as described above. Sequencing libraries were prepared as described above.

Histology, Immunohistochemistry, and Tumor Analysis

Samples were fixed in 4% formalin and paraffin-embedded. Immunohistochemistry was performed on 4 μm sections with the ABC Vectastain kits (Vector Laboratories) with antibodies against Tomato (Rockland Immunochemicals, 600-401-379), Smad4 (AbCam, AB40759) and Sox9

(EMD Milipore, AB5535). Sections were developed with DAB and counterstained with haematoxylin. Haematoxylin and eosin staining was performed using standard methods.

Sections from lungs infected (transdcued) with Lenti-sgTomato/Cre, were stained for Tomato and tumors were scored as positive (>95% Tomato positive cancer cells), Negative (no Tomato-positive cancer cells), or mixed (all other tumors). Tumors were classified and counted from a single section through all lung lobes from 4 independent mice.

Quantification of Tumor Area and Barcode Sequencing of Tumors Induced with Lenti-sgSetd2 and Lenti-sgNeo Tumor-bearing lung lobes from mice infected (transdcued) with Lenti-sgSetd2#1/Cre, Lenti-sgSetd2#2/Cre or Lenti-sgNeo2/Cre virus were embedded in paraffin, sectioned, and stained with haematoxylin and eosin. Percent tumor area was determined using ImageJ.

The distribution of the number of cancer cells in individual tumors in KT;Cas9 mice infected (transdcued) with Lenti-sgSetd2#1/Cre and Lenti-sgNeo2/Cre was assessed by Illumina® sequencing of their respective lentiviral barcodes and subsequent analysis as described above.

Western Blotting for Lkb1 and Cas9

Microdissected Tomato-positive lung tumors from KT and KT;Cas9 mice with Lenti-sgLkb1/Cre initiated tumors were analyzed for Cas9 and Lkb1 protein expression. Samples were lysed in RIPA buffer and boiled with LDS loading dye. Denatured samples were run on a 4%-12% Bis-Tris gel (NuPage) and transferred onto a PVDF membrane. Membranes were immunoblotted using primary antibodies against Hsp90 (BD Transduction Laboratories, 610419), Lkb1 (Cell Signaling, 13031P), Cas9 (Novus Biologicals, NBP2-36440), and secondary HRP-conjugated anti-mouse (Santa Cruz Biotechnology, sc-2005) and anti-rabbit (Santa Cruz Biotechnology, sc-2004) antibodies.

Survival Analysis of Mice with Cas9 Mediated Inactivation of Smad4

To confirm lack of functional tumor suppression attributable to Smad4, KT and KT;Cas9 mice were infected (transdcued) intratracheally with $10^5$ Lenti-sgSmad4/Cre. Mice were sacrificed when they displayed visible signs of distress to assess survival.

Example 2: Multiplexed Quantitative Analysis of Oncogenic Variants In Vivo

Large-scale genomic analyses of human cancers have catalogued somatic point mutations thought to initiate tumor development and sustain cancer growth. However, determining the functional significance of specific alterations remains a major bottleneck in our understanding of the genetic determinants of cancer. Here, we present a platform that integrates multiplexed AAV/Cas9-mediated homology-directed repair (HDR) with DNA barcoding and high-throughput sequencing to simultaneously investigate multiple genomic alterations in de novo cancers in mice. Using this approach, we introduced a barcoded library of non-synonymous mutations into hotspot codons 12 and 13 of Kras in adult somatic cells to initiate tumors in the lung, pancreas, and muscle. High-throughput sequencing of barcoded $Kras^{HDR}$ alleles from bulk lung and pancreas uncovered surprising diversity in Kras variant oncogenicity. Rapid, cost-effective, and quantitative approaches to simultaneously investigate the function of precise genomic alterations in vivo will uncover novel biological and clinically actionable insights into carcinogenesis.

Results

To analyze the oncogenic function of diverse point mutations in vivo in a quantitative and relatively high-throughput manner, we developed a platform for somatic AAV/Cas9-mediated HDR that incorporates DNA barcoding and high-throughput sequencing in autochthonous mouse models of several cancer types (FIG. 23a-d). We designed, generated, and validated a library of AAV vectors to introduce all possible Kras codon 12 and 13 single-nucleotide non-synonymous point mutations into somatic mouse cells in a multiplexed manner (FIG. 23e-g and FIG. 27). Each AAV contained an sgRNA targeting the second exon of Kras, a ~2 kb Kras HDR template, and Cre-recombinase (AAV-$Kras^{HDR}$/sgKras/Cre; FIG. 23e and FIG. 27a-c).

Figure 23:
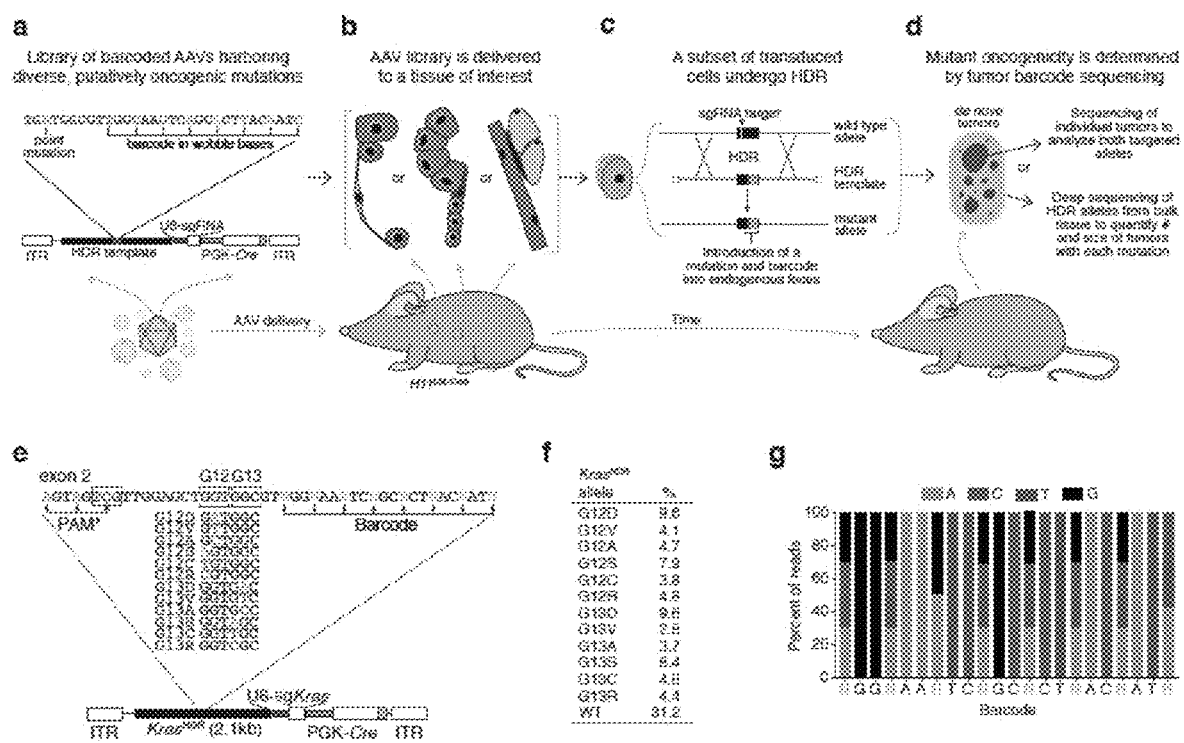
FIG. 23. A platform that integrates AAV/Cas9-mediated somatic HDR with tumor barcoding and sequencing to enable the rapid introduction and functional investigation of putative oncogenic point mutations in vivo. a-d. Schematic overview of the pipeline to quantitatively measure the in vivo oncogenicity of a panel of defined point mutations. A library of AAV vectors was generated such that each AAV contains 1) a template for homology directed repair (HDR) containing a putatively oncogenic point mutation and a random DNA barcode encoded in the adjacent wobble bases (The sequence of (a) is set forth in SEQ ID NO: 131.), 2) an sgRNA targeting the endogenous locus for HDR, and 3) Cre-recombinase to activate a conditional Cas9 allele ($H11^{LSL-Cas9}$) and other Cre-dependent alleles in genetically engineered mice (a). The AAV library is delivered to a tissue of interest (b). Following transduction, a subset of cells undergo AAV/Cas9-mediated HDR in which the locus of interest is cleaved by Cas9 at the sgRNA target site and repaired using the AAV HDR template. This results in the precise introduction of the desired point mutation and a unique DNA barcode into the targeted locus (c). Somatic cells engineered with a point mutation may develop into de novo tumors if the introduced mutation is sufficient to initiate tumorigenesis and drive tumor growth. d, Two independent approaches can be used to analyze tumors: 1) tumors can be sequenced individually to characterize both alleles of the targeted gene, or 2) barcoded mutant HDR alleles from entire bulk tumor-bearing tissues can be deep sequenced to quantify the number and size of tumors with each mutation. e. AAV vector pool for Cas9-mediated HDR into the endogenous Kras locus (AAV-$Kras^{HDR}$/sgKras/Cre). Each vector contains an HDR template with 1 of 12 non-synonymous Kras mutations at codons 12 and 13 (or wild type Kras), silent mutations within the PAM and sgRNA homology region (PAM*), and an 8-nucleotide random barcode within the wobble positions of the downstream codons for DNA barcoding of individual tumors. (The sequence of the template is set forth in SEQ ID NO: 132.) f. Representation of each Kras codon 12 and 13 allele in the AAV-$Kras^{HDR}$/sgKras/Cre plasmid library. g. Diversity of the barcode region in the AAV-$Kras^{HDR}$/sgKras/Cre plasmid library.

The $Kras^{HDR}$ template contained either wild type (WT) Kras or one of the 12 single-nucleotide non-synonymous mutations in codons 12 and 13 of Kras, as well as the genomic sequence flanking the second exon of Kras. Each $Kras^{HDR}$ template also contained silent mutations within the sgKras target sequence and associated protospacer adjacent motif (PAM*) to prevent Cas9-mediated cleavage of $Kras^{HDR}$ alleles. To enable the parallel quantification of individual tumors by high-throughput sequencing of DNA from bulk tissue, we diversified each $Kras^{HDR}$ template with a random eight-nucleotide barcode engineered into the wobble positions of the codons downstream of 12 and 13 (FIG. 23e and FIG. 27b,c).

Figure 28:
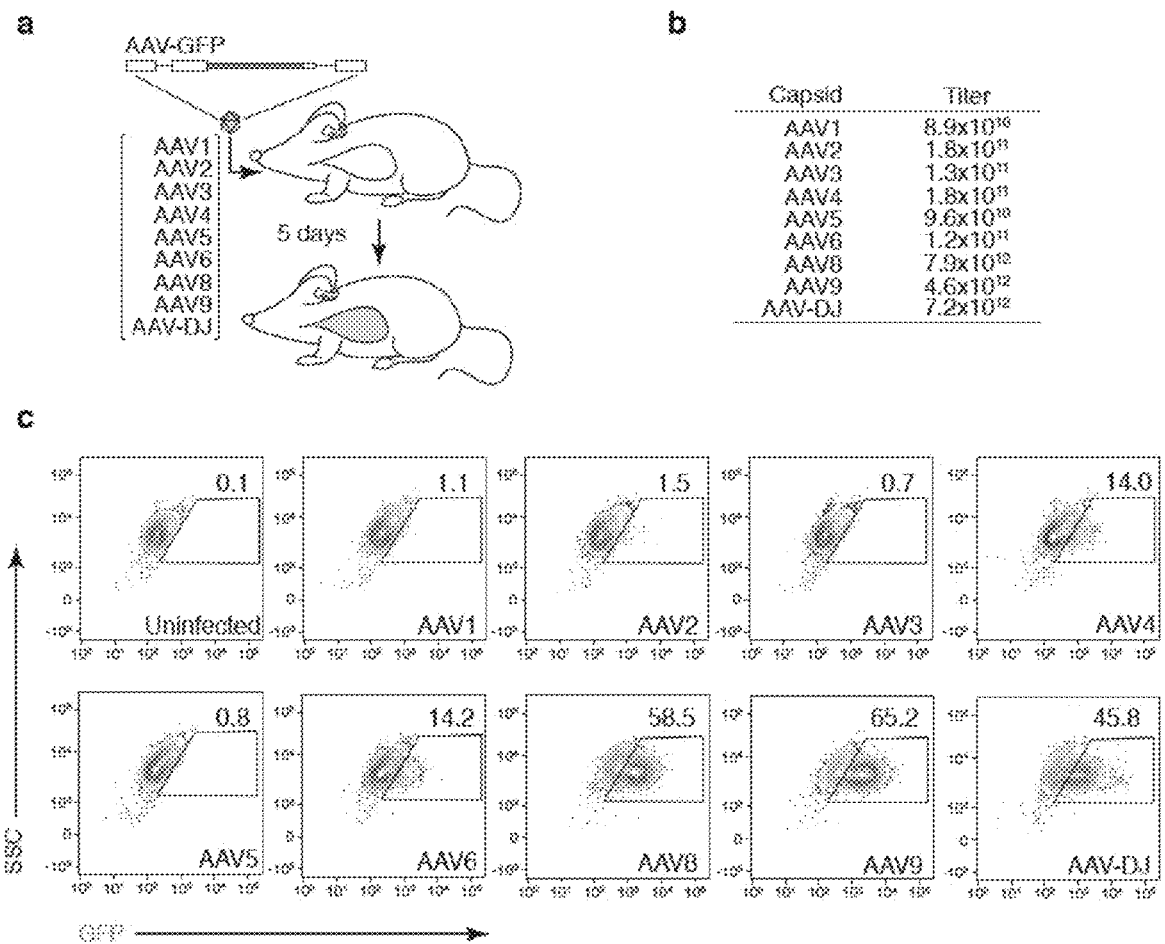
FIG. 28. Identification of an optimal AAV serotype for adult lung epithelial cell transduction. a. Outline of the experiment to screen 11 AAV serotypes for adult lung epithelial cell transduction. An AAV vector encoding GFP was packaged with different AAV capsid serotypes and administered intratracheally to wild-type recipient mice. 5 days post-treatment, the lungs were dissociated and the percent of GFP$^{positive}$ epithelial cells was determined by flow cytometry. b. Different AAV serotypes can be produced at different concentrations. Our goal was to identify the AAV serotypes capable of delivering DNA templates to lung epithelial cells, which is largely dictated by both the achievable viral titer and the per virion transduction efficiency. Thus, we did not normalize the titer of the AAV serotypes before infection (transduction), but rather determined the percent infection (transduction) following administrations of 60 µl of undiluted, purified virus. c. To assess the percent of lung epithelial cell transduced by the different AAV serotypes, we dissociated lungs of infection (transduction) mice into single cell suspensions and performed flow cytometry for GFP as well as for markers of hematopoietic cells (CD45, Ter119, and F4/80), endothelial cells (CD31), and epithelial cells (EpCAM). Plots show FSC/SSC-gated, viable (DAPI$^{negative}$), lung epithelial (CD45/Ter119/F4-80/CD31negative, EpCAM$^{positive}$) cells. The percent GFP$^{positive}$ epithelial cells in each sample is indicated above the gate. AAV8, AAV9, and AAVDJ were considerably better than all other serotypes (including AAV6 which failed to lead to efficient HDR in Platt et al., Cell, 2014), consistent with the high maximal titers of these serotypes. We chose to use AAV8 based on this data and the documented ability of AAV8 to efficiently transduce many other mouse cell types in vivo.

The AAV vectors also encoded Cre-recombinase. Cre-expression enabled tumor initiation in mice containing a Cre-regulated Cas9 allele ($H11^{LSL-Cas9}$), a fluorescent Cre-reporter allele ($R26^{LSL-Tomato}$), as well as floxed alleles of the well-known tumor suppressor genes p53 ($p53^{flox}$) or Lkb1 ($Lkb1^{flox}$). We packaged the AAV-$Kras^{HDR}$/sgKras/Cre library using an AAV8 capsid that enables high titer production, efficient transduction of mouse lung epithelial cells in vivo (FIG. 28), and transduction of a wide range of adult mouse tissues[35].

We initially transduced Cas9-expressing cells in culture with AAV-$Kras^{HDR}$/sgKras/Cre to determine whether AAV/Cas9-mediated HDR would be an unbiased method to engineer point mutations into the endogenous Kras locus (FIG. 27e). $Kras^{HDR}$-specific PCR amplification followed by high-throughput sequencing of transduced cells confirmed the generation of all point mutant Kras alleles (FIG. 27f,g). Furthermore, in vitro $Kras^{HDR}$ allele frequencies correlated with their representation in the AAV-$Kras^{HDR}$/sgKras/Cre plasmid library. This result confirms that HDR using our AAV vector is not discernably biased by any single-nucleotide Kras codon 12 or 13 point mutation in the $Kras^{HDR}$ template. Therefore, any differential expansion of tumors harboring specific Kras mutant alleles can be attributed to biochemical differences between Kras variants rather than differences in the efficiency of HDR using donor DNA templates with each Kras allele (FIG. 27h).

Figure 24:
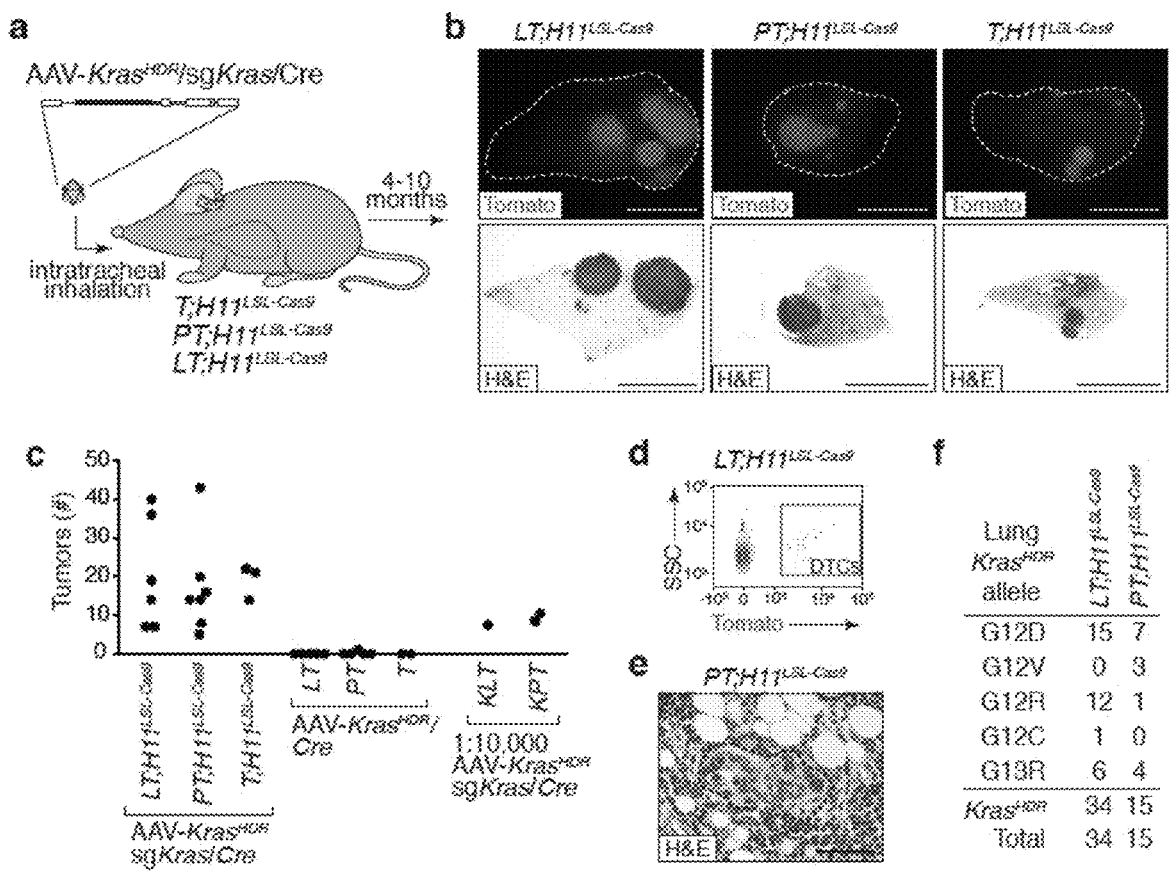
FIG. 24. AAV/Cas9-mediated somatic HDR initiates oncogenic Kras-driven lung tumors that can progress into a metastatic state. a. Schematic of the experiment to introduce point mutations and a DNA barcode into the endogenous Kras locus of lung epithelial cells in $Rosa26^{LSL-tdTomato}$; $H11^{LSL-Cas9}$ (T;$H11^{LSL-Cas9}$), $p53^{flox/flox}$;t;$H11^{LSL-Cas9}$ (PT; $H11^{LSL-Cas9}$), and $Lkb1^{flox/flox}$;T;$H11^{LSL-Cas9}$ (LT;$H11^{LSL-Cas9}$) mice by intratracheal administration of AAV-$Kras^{HDR}$/sgKras/Cre. b. Representative images of $Tomato^{positive}$ lung tumors and histology in AAV-$Kras^{HDR}$/sgKras/Cre-treated LT;$H11^{LSL-Cas9}$, PT;$H11^{LSL-Cas9}$, and T;$H11^{LSL-Cas9}$ mice. Scale bars=5 mm. c. Quantification of lung tumors in the indicated genotypes of mice infected (transduced) with the indicated AAV vectors (with and without sgKras). Each dot represents one mouse. $Kras^{LSL-G12D}$;LT(KLT) and $Kras^{LSL-G12D}$;PT(KPT) mice transduced with a 1:10,000 dilution of AAV-$Kras^{HDR}$/sgKras/Cre developed approximately half as many tumors as the PT;$H11^{LSL-Cas9}$ and LT;$H11^{LSL-Cas9}$ mice infected (transduced) with undiluted virus. Thus, assuming that all $Kras^{HDR}$ alleles in the AAV-$Kras^{HDR}$/sgKras/Cre library are oncogenic, this suggests that AAV/Cas9-mediated HDR occurs in approximately 0.02% of transduced cells. Alternatively, if only 20% of the mutant alleles in the AAV-$Kras^{HDR}$/sgKras/Cre library are assumed to drive tumor formation, then the rate of HDR is approximately 0.1%. d. Representative FACS plot showing $Tomato^{positive}$ disseminated tumor cells (DTCs) in the pleural cavity of an LT;$H11^{LSL-Cas9}$ mouse with AAV-$Kras^{HDR}$/sgKras/Cre-initiated lung tumors. e. Histology of a metastasis from an AAV-$Kras^{HDR}$/sgKras/Cre-initiated lung tumor in a PT;$H11^{LSL-Cas9}$ mouse. Scale bar=50 µm. f. Diverse HDR-generated oncogenic Kras alleles in individual lung tumors. Number of tumors with each allele is indicated. Alleles that were not identified in any lung tumors are not shown.
Figure 29:
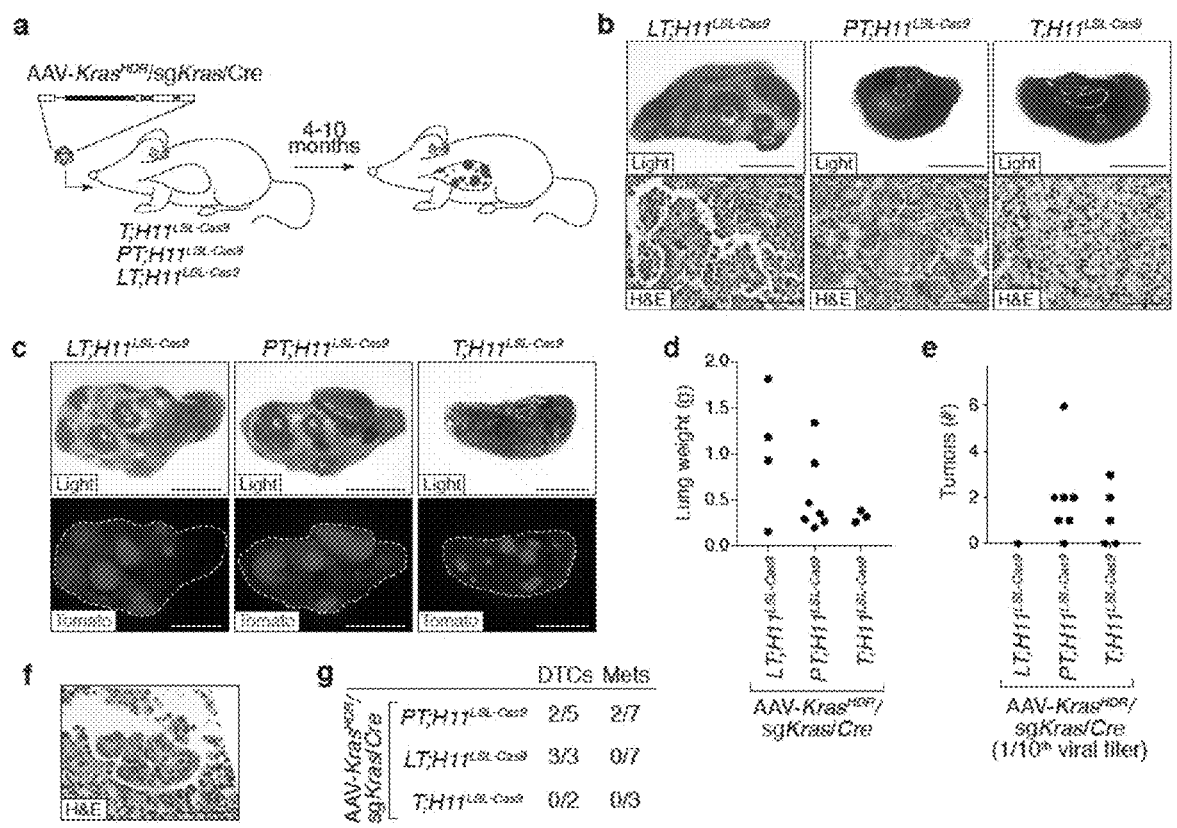
FIG. 29. AAV/Cas9-mediated in vivo HDR in lung epithelial cells initiates primary tumors that can progress to gain metastatic ability. a. Schematic of the experiment to introduce point mutations into the endogenous Kras locus and barcode lung epithelial cells in Lkb1$^{flox/flox}$; R26$^{LSL-Tomato}$;H11$^{LSL-Cas9}$ (LT;H11$^{LSL-Cas9}$), p53$^{flox/flox}$.

To determine whether HDR in somatic cells could initiate tumors, and to investigate whether Kras variants differ in their ability to drive tumorigenesis, we delivered AAV-$Kras^{HDR}$/sgKras/Cre library intratracheally to the lungs of mice with the $H11^{LSL-Cas9}$ allele (FIG. 24 and FIG. 29). Specifically, we transduced three different genotypes of mice to provide insight into whether concurrent inactivation of tumor suppressor genes modulates Kras variant oncogenicity: 1) $Rosa26^{LSL-Tomato}$; $H11^{LSL-Cas9}$ (T;$H11^{LSL-Cas9}$) mice, 2) $p53^{flox/flox}$;T;$H11^{LSL-Cas9}$ (PT;$H11^{LSL-Cas9}$) mice in which virally initiated tumors would lack p53, and 3) $Lkb1^{flox/flox}$;T;$H11^{LSL-Cas9}$ (LT;$H11^{LSL-Cas9}$) mice in which virally initiated tumors would lack Lkb1 (FIG. 24a and FIG. 29a).

LT;H11$^{LSL-Cas9}$ mice were the first to show signs of tumor development including tachypnea and weight loss approximately five months after AAV administration. This is consistent with the rapid growth of lung tumors in mice with a Cre-regulated Kras$^{G12D}$ allele and loss of Lkb1. LT;H11$^{LSL-Cas9}$ mice had very high tumor burdens, resulting from many primary lung tumors (FIG. 24b,c and FIG. 29b-d). Histological analysis of the lungs of these mice confirmed the presence of large adenomas and adenocarcinomas (FIG. 24b and FIG. 29b). PT;H11$^{LSL-Cas9}$ mice also developed numerous large primary lung tumors. Compared to the LT;H11$^{LSL-Cas9}$ tumors initiated in PT;H11$^{LSL-Cas9}$ mice had more pronounced nuclear atypia, a feature characteristic of p53-deficiency. Finally, T;H11$^{LSL-Cas9}$ mice developed smaller, less advanced lesions, even at later time points (FIG. 24b,c and FIG. 29b-d). Mice transduced with a 10-fold lower dose of AAV-Kras$^{HDR}$/sgKras/Cre developed proportionally fewer tumors (FIG. 29e).

Several LT;H11$^{LSL-Cas9}$ and PT;H11$^{LSL-Cas9}$ mice transduced with AAV-Kras$^{HDR}$/sgKras/Cre also developed invasive primary lung tumors, disseminated tumor cells (DTCs) in their pleural cavities, and lymph node metastases (FIG. 24d,e and FIG. 29f,g). Thus, AAV-Kras$^{HDR}$/sgKras/Cre-induced tumors can progress into malignant and metastatic lung cancer.

We estimated the efficiency of AAV/Cas9-mediated somatic HDR in the lung by infecting Kras$^{LSL-G12D}$;PT and Kras$^{LSL-G12D}$;LT mice with a 1:10,000 dilution of AAV-Kras$^{HDR}$/sgKras/Cre, such that oncogenic Kras$^{G12D}$ would be expressed in all virally transduced cells. These mice developed approximately half as many tumors as mice in which oncogenic Kras alleles were generated by AAV/Cas9-mediated somatic HDR. This result is consistent with an HDR frequency between 0.02% and 0.1%, enabling the robust initiation of multiple lung tumors in parallel in individual mice (FIG. 24c). Importantly, delivery of an analogous vector library without sgKras (AAV-Kras$^{HDR}$/Cre) to T, PT, and LT mice did not lead to efficient tumor initiation, suggesting that neither p53-nor Lkb1-deficiency, combined with high-level AAV vector transduction, is sufficient to drive lung tumorigenesis (FIG. 24c and FIG. 30).

To verify that tumors initiated using AAV-Kras$^{HDR}$/sgKras/Cre harbored mutant Kras$^{HDR}$ alleles, we analyzed the Kras locus in FACS-isolated Tomato$^{positive}$ cancer cells from large, individual lung tumors from LT;H11$^{LSL-Cas9}$ and PT;H11$^{LSL-Cas9}$ mice. PCR amplification using primers specific to the Kras$^{HDR}$ allele confirmed the presence of an oncogenic Kras allele with a unique barcode in each tumor (FIG. 24f and FIG. 31a,b). Interestingly, despite the absence of any detectable HDR bias and the relatively uniform representation of mutant alleles in the initial AAV library, only five of the thirteen Kras variants were identified in ~50 large lung tumors (FIG. 24f). This result is consistent with differential selection of Kras variants in lung tumorigenesis.

By analyzing individual tumors, we were able to carefully assess both the Kras$^{HDR}$ allele as well as the second Kras allele present in tumor cells (FIG. 31). Approximately half of the oncogenic Kras$^{HDR}$ alleles resulted from perfect HDR events, in which a Kras point mutation and a unique barcode were seamlessly recombined into the endogenous Kras locus. The remaining Kras$^{HDR}$ alleles were seamless from the 5' end through mutant exon 2, but contained small duplications, insertions, or deletions in intron 2 (FIG. 31d). Importantly, none of these alterations would be expected to disrupt splicing from mutant exon 2 into exon 3. Additionally, almost all tumors harbored Cas9-induced indels in the second Kras allele, which is consistent with frequent loss of the wild type KRAS allele in oncogenic KRAS-driven human tumors (FIG. 31e,f). While previous studies have documented enhanced Kras$^{G12D}$- and Kras$^{Q61L}$-driven lung tumor growth following inactivation of the wild type Kras allele in mice, our results suggest that many oncogenic Kras variants are likely suppressed by wild type Kras during lung tumor growth.

Figure 25:
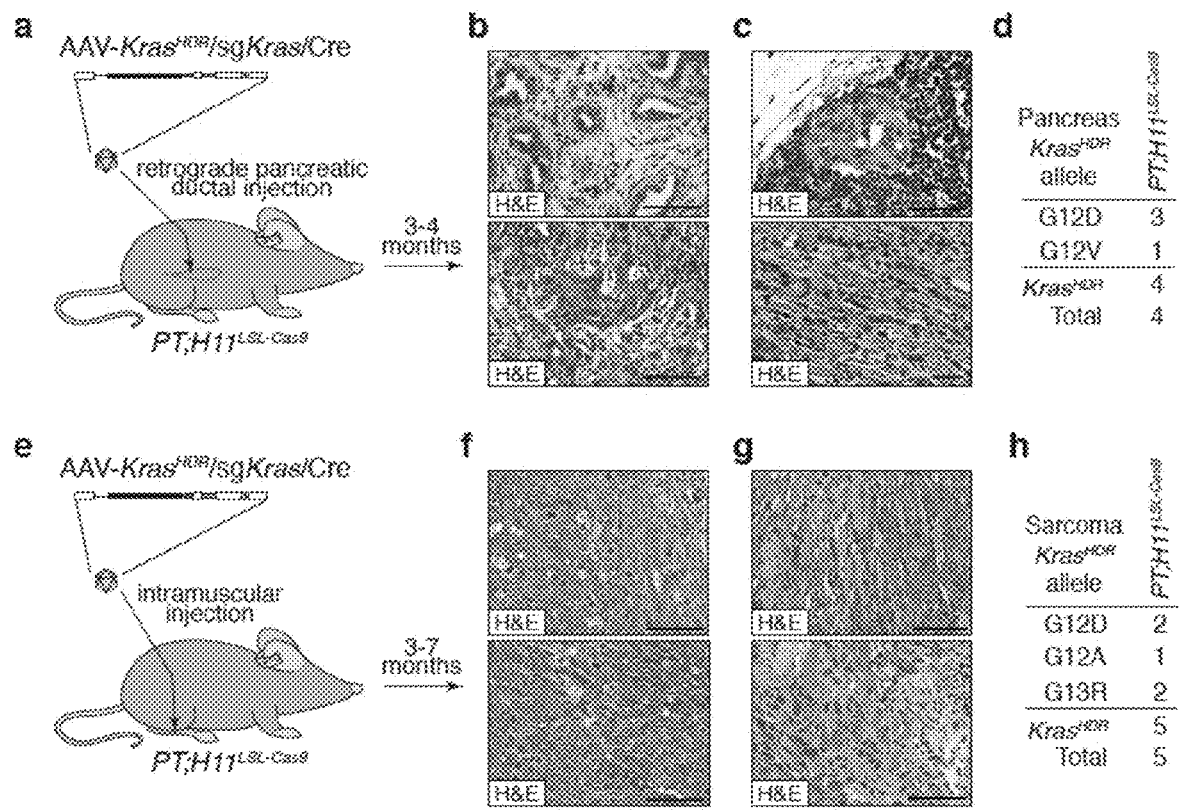
FIG. 25. Introduction of mutant Kras variants into somatic pancreas and muscle cells by AAV/Cas9-mediated HDR drives the formation of invasive cancers. a. Schematic of retrograde pancreatic ductal injection of AAV-$Kras^{HDR}$/sgKras/Cre into PT;$H11^{LSL-Cas9}$ mice to induce pancreatic cancer. b. Histology of pancreatic tumors initiated by retrograde pancreatic ductal injection of AAV-$Kras^{HDR}$/sgKras/Cre into PT;$H11^{LSL-Cas9}$ mice. Scale bars=75 µm. c. Histology of metastases in the lymph node (upper panel) and diaphragm (lower panel) in PT;$H11^{LSL-Cas9}$ mice with primary PDAC. Scale bars=50 µm. d. HDR-generated oncogenic Kras alleles in pancreatic tumor masses. Number of tumors with each allele is indicated. Alleles that were not identified in any pancreatic tumor masses are not shown. e. Schematic of intramuscular injection of AAV-$Kras^{HDR}$/sgKras/Cre into the gastrocnemii of PT;$H11^{LSL-Cas9}$ mice to induce sarcomas. f,g. Histology of stereotypical sarcoma (f) and invasive sarcoma (g) initiated by intramuscular injection of AAV-$Kras^{HDR}$/sgKras/Cre into the gastrocnemii of PT;$H11^{LSL-Cas9}$ mice. Scale bars=75 µm. h. HDR-generated oncogenic Kras alleles in sarcomas. Number of tumors with each allele is indicated. Alleles that were not identified in any sarcomas are not shown. These data document clonal marking of cell lineages across multiple tissues.

In addition to driving human lung cancer, oncogenic KRAS is nearly ubiquitous in human pancreatic ductal adenocarcinoma (PDAC). Expression of Kras$^{G12D}$ or Kras$^{G12V}$ and inactivation of p53 leads to the development of PDAC in mouse models. To determine whether AAV/Cas9-mediated somatic HDR could also induce cancer-initiating oncogenic point mutations in pancreatic epithelial cells, we transduced PT;H11$^{LSL-Cas9}$ mice with AAV-Kras$^{HDR}$/sgKras/Cre by retrograde pancreatic ductal injection (FIG. 25a and FIG. 32a). These mice developed precancerous pancreatic intra-epithelial neoplasias (PanINs) as well as PDAC (FIG. 25b and FIG. 32b,c,f). Several mice also developed invasive and metastatic PDAC, consistent with the aggressive nature of the human disease (FIG. 25c and FIG. 32d-f). Sequencing of Kras$^{HDR}$ alleles from several large pancreatic tumor masses uncovered oncogenic Kras alleles with unique barcodes (FIG. 24d). Interestingly, although just four samples were analyzed, only Kras$^{G12D}$ and Kras$^{G12V}$ were observed—the two most frequent KRAS mutations in human pancreatic cancer. Consistent with the requirement for oncogenic Kras to initiate PDAC, transduction of pancreatic cells in PT mice by retrograde pancreatic ductal injection of our negative control AAV-Kras$^{HDR}$/Cre vector did not induce any pancreatic tumors (FIG. 32f).

Human soft tissue sarcomas also frequently harbor mutations in the RAS pathway as well as in TP53. Sarcomas have been induced in genetically engineered mice through the expression of Kras$^{G12D}$ and inactivating p53. To determine whether AAV/Cas9-mediated somatic HDR could be used to introduce point mutations into Kras and drive sarcoma formation, we performed intramuscular injections of AAV-Kras$^{HDR}$/sgKras/Cre into the gastrocnemii of PT;H11$^{LSL-Cas9}$ mice (FIG. 25e and FIG. 33a). These mice developed rapidly growing and invasive sarcomas that harbored uniquely barcoded Kras$^{G12D}$, Kras$^{G12A}$, and Kras$^{G13R}$ alleles (FIG. 25f-h and FIG. 33). The successful application of this platform for modeling tumorigenesis—from initiation through malignant progression—in divergent tissues, highlights its broad applicability for multiplexed functional analyses of oncogenic driver mutations in a wide range of cancer types.

Figure 26:
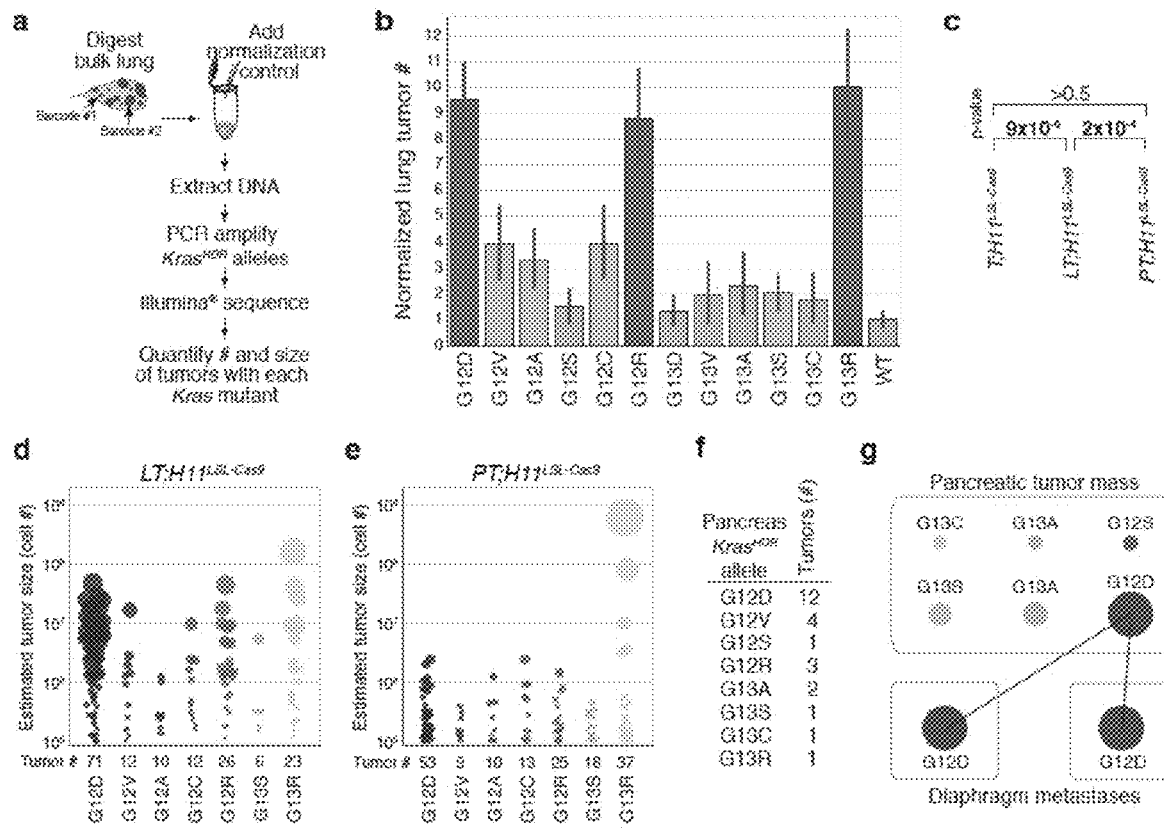
FIG. 26. Multiplexed, quantitative analysis of Kras mutant oncogenicity using AAV/Cas9-mediated somatic HDR and high-throughput sequencing of individually barcoded tumors. a. Pipeline to quantitatively measure individual tumor size and number from bulk lung samples by high-throughput sequencing of tumor barcodes. b. Number of lung tumors harboring each mutant Kras allele normalized to its initial representation (mutant representation in the AAV plasmid library/WT representation in the AAV plasmid library) and relative to WT (mutant tumor #/WT tumor #). Variants present in significantly more tumors than WT ($p<0.01$) are colored blue; darker blue indicates no significant difference from G12D ($p>0.05$), lighter blue indicates significantly less tumors with that variant than G12D ($p<0.01$). c. p-values from a two-sided multinomial chi-squared test of the number of lung tumors with each Kras variant across different genotypes. Significant p-values ($p<0.05$) are bold. d,e. Lung tumor size distributions for Kras variants identified as oncogenic in b across all LT;H11$^{LSL-Cas9}$ (d) or PT;H11$^{LSL-Cas9}$ (e) mice. Each dot represents one tumor with a unique Kras variant-barcode pair. The size of each dot is proportional to the size of the tumor it represents, which is estimated by normalizing tumor read counts to the normalization control reads counts. f. Diverse HDR-generated Kras alleles identified by tumor barcode sequencing of pancreatic tumor masses. Number of uniquely barcoded tumors with each allele is indicated. Alleles that were not identified in any pancreas tumor masses are not shown. g. High-throughput sequencing of the primary pancreatic tumor mass and metastases from a single AAV-Kras$^{HDR}$/sgKras/Cre-treated PT;H11$^{LSL-Cas9}$ mouse uncovered a diverse spectrum of mutant Kras alleles and enabled the establishment of clonal relationships between primary tumors and their metastatic offspring. Each dot represents one tumor with the indicated Kras variant and a unique barcode within the indicated sample. Dots that are linked by a colored line harbor the same barcode, suggesting that they are clonally related. The size of each dot is scaled according to the size of the tumor it represents (diameter of the dot=relative size$^{1/4}$). Since the size of pancreatic tumors is not normalized to a control, tumors sizes can only be compared within the same sample. Thus, the largest tumor in each sample is set to the same standard size.
Figure 27:
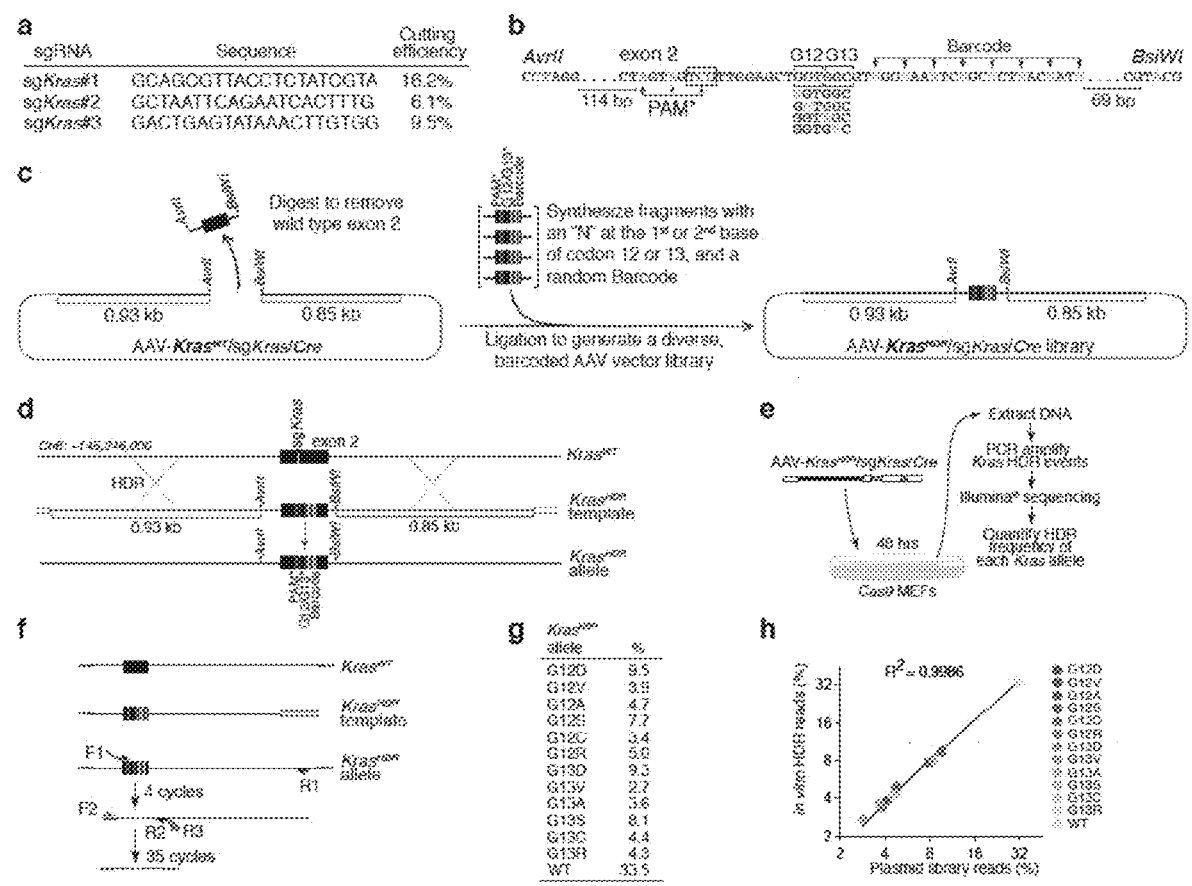
FIG. 27. Design, generation, and validation of an AAV library for multiplexed mutation of Kras. a. Sequence of the three sgRNAs targeting Kras exon 2. Cutting efficiency of each sgRNA was determined by sequencing DNA from Cas9-expressing MEFs 48 hours after transduction with lentiviral vectors encoding each sgRNA. All three sgRNAs induced indel formation at the targeted loci. Thus, the sgRNA targeting the sequence closest to Kras codons 12 and 13 (sgKras #3) was used for all subsequent experiments to increase the likelihood of HDR. (The sequence of sgKras #1 is set forth in SEQ ID NO: 66. The sequence of sgKras #2 is set forth in SEQ ID NO: 67. The sequence of sgKras #3 is set forth in SEQ ID NO: 68.) b. Synthesized library of dsDNA fragments containing wild type (WT) Kras sequence plus each of the 12 non-synonymous, single nucleotide Kras mutants at codons 12 and 13, silent mutations within the PAM and sgRNA homology region (PAM*), and an 8-nucleotide random barcode within the wobble positions of the downstream codons for barcoding of individual tumors. Each Kras allele can be associated with ~$2.4 \times 10^4$ unique barcodes. Fragments also contained restriction sites for cloning. (The sequence of exon 2 in (b) is set forth in SEQ ID NO: 133.) c. AAV vector library was generated by massively ligating synthesized regions into a parental AAV vector creating a barcoded pool with WT Kras and all 12 single-nucleotide, non-synonymous mutations in Kras codons 12 and 13. d. Position of Kras exon 2 within the Kras$^{HDR}$ template. The lengths of the homology arms are shown. e. Schematic of the experiment to test for HDR bias. A Cas9-expressing cell line was transduced with AAV-Kras$^{HDR}$/sgKras/Cre and then sequenced to quantify HDR events. f. Schematic of the PCR strategy to specifically amplify Kras$^{HDR}$ alleles introduced into the genome via HDR. Forward primer 1 (F1) binds to the sequence containing the 3 PAM* mutations, while reverse primer 1 (R1) binds the endogenous Kras locus, outside the sequence present in the homology arm of the Kras$^{HDR}$ template. F2 binds to the Illumina adaptor added by F1, R2 binds to a region near exon 2, and R3 binds to the Illumina adapter added in the same reaction by R2. g. Representation of each Kras allele within the endogenous Kras locus generated through HDR in Cas9-expressing cells in culture transduced with the AAV-Kras$^{HDR}$/sgKras/Cre vector library. h. Frequency of HDR events for each Kras$^{HDR}$ allele plotted against the initial frequency of each Kras mutant allele in the AAV-Kras$^{HDR}$/sgKras/Cre plasmid library used to generate the viral library. High-correlation between the initial plasmid library and the representation of mutant Kras alleles following HDR suggests little to no HDR bias.

Whereas current methods to assess gene function in autochthonous cancer models largely rely on manual quantification of tumor number and size, we established a simple yet high-throughput and multiplexed approach to link tumor cell number with tumor genotype directly from bulk tissue (FIGS. 23d and 4a). Since a unique DNA barcode introduced by HDR into a somatic cell will increase in number as the cell divides, the relative number of cancer cells in a given tumor can be determined by deep sequencing of the barcode region. Furthermore, the absolute number of cells in each tumor can be estimated by adding a normalization control to each sample prior to deep sequencing. To determine the genotype and estimate the absolute number of cancer cells in each tumor in whole lungs from T;H11$^{LSL-Cas9}$, PT;H11$^{LSL-Cas9}$, and LT;H11$^{LSL-Cas9}$ mice transduced with AAV-Kras$^{HDR}$/sgKras/Cre, we first added DNA from $5\times10^5$ cells with a known barcode to each sample (FIG. 26a and FIG. 34). We then extracted DNA from the bulk lung samples, PCR-amplified the Kras$^{HDR}$ alleles, and deep-sequenced the variant-barcode region of each allele (FIGS. 23d and 4a, and FIG. 34).

Following high-throughput sequencing, we corrected for recurrent sequencing errors and the possibility of individual tumors having identical barcodes. We then estimated the absolute number of cancer cells in each tumor by normalizing tumor barcode sequencing read counts to the number of reads from the normalization control DNA. This analysis pipeline was exceptionally reproducible with a high degree of concordance in tumor sizes across technical replicates (FIG. 35). By enabling quantitative analyses of individual tumors in parallel from bulk tissue, this HDR-based barcoding and deep sequencing approach provides an unprecedented picture of the tumor landscape in vivo.

High-throughput sequencing of the $Kras^{HDR}$ variant-barcode region uncovered many AAV-$Kras^{HDR}$/sgKras/Cre-induced lung tumors in T;H11$^{LSL-Cas9}$, PT;H11$^{LSL-Cas9}$, and LT;H11$^{LSL-Cas9}$ mice (FIG. 36a-c). Normalizing tumor number to the initial representation of each $Kras^{HDR}$ allele in the AAV-$Kras^{HDR}$/sgKras/Cre vector library allowed us to directly compare the in vivo oncogenicity of each Kras variant (FIG. 26b and FIG. 36d,e). Across more than 500 tumors, $Kras^{G12D}$ was the most common variant, consistent with $KRAS^{G12D}$ being the most frequent KRAS mutation in human lung adenocarcinoma in non-smokers. $Kras^{G12A}$, $Kras^{G12C}$, and $Kras^{G12V}$ (the most frequent KRAS variants in human lung adenocarcinoma after $KRAS^{G12D}$) as well as $Kras^{G13S}$ were identified as moderate drivers of lung tumorigenesis, but were present in significantly fewer tumors than KrasG12D (FIG. 26b). Interestingly, $Kras^{G12R}$ and $Kras^{G13R}$ were also identified as potent oncogenic variants, despite being infrequently mutated in human lung cancer (FIG. 26b).

We initiated tumors in PT;H11$^{LSL-Cas9}$, and LT;H11$^{LSL-Cas9}$ mice to directly assess whether concurrent tumor suppressor alterations modulate the ability of different Kras variants to initiate and drive tumor growth. Interestingly, although the overall spectrum of Kras oncogenicity changed significantly with Lkb1 inactivation, we did not observe dramatic differences in the relative tumorigenic potential of individual Kras variants in tumors with coincident inactivation of p53 or Lkb1 (FIG. 26c-e and FIG. 36). This data is consistent with a model in which the strength of signaling induced by these oncogenic Kras variants in vivo is insufficient to engage the p53-pathway; thus, while p53 functions to constrain tumor progression, it does not limit the initial expansion of tumors with certain Kras genotypes. Additionally, while Lkb1-deficiency increases tumor growth, the signaling induced by Lkb1-deficiency does not preferentially synergize with the downstream signals induced by specific mutant forms of Kras.

Since our tumor barcoding and sequencing platform allowed us to identify many individual lung tumors in parallel from bulk lungs, we anticipated that we could also use this approach to overcome the challenge of identifying and analyzing individual pancreas tumor clones in multifocal tumor masses initiated in autochthonous mouse models of human PDAC[31]. Therefore, we also analyzed bulk pancreatic tumor samples from PT;H11$^{LSL-Cas9}$ mice transduced with AAV-$Kras^{HDR}$/sgKras/Cre (FIG. 26f and FIG. 37a,b). Barcode sequencing of pancreatic tumor masses uncovered multiple primary tumor clones per mouse, each harboring a $Kras^{HDR}$ allele with a point mutation in Kras codon 12 or 13 and a unique DNA barcode. Pancreatic tumors demonstrated oncogenic Kras allele preferences with $Kras^{G12D}$, $Kras^{G12V}$, and $Kras^{G12R}$ being the most prevalent variants (FIG. 26f). Notably, these three Kras variants are also the most prevalent oncogenic KRAS mutations in human PDAC.

In addition to determining the in vivo oncogenicity of specific Kras variants, our barcode-sequencing approach allowed us to identify contiguous tumor clones from multi-region sequencing of PDAC masses, and uncover clonal relationships between primary tumors and their metastatic descendants (FIG. 26g and FIG. 37c).

The prevalence of a mutation in human cancer is a function of both the frequency with which the mutation is incurred and the degree to which the mutation drives tumorigenesis. By using AAV/Cas9-mediated somatic HDR to introduce point mutations into the endogenous Kras locus in an unbiased manner, we determined that Kras variants have quantitatively different abilities to drive lung tumorigenesis (FIG. 4b and FIG. 36). Furthermore, pancreatic tumors initiated in mice using our HDR-based approach demonstrated selection for the same dominant Kras variants as human PDACs, suggesting that the spectrum of KRAS mutations observed in human PDAC is likely driven by biochemical differences between KRAS mutants rather than by differences in their mutation rates (FIG. 26f and FIG. 37).

To begin to understand how the biochemical properties of each Kras variant influences its in vivo oncogenicity, we investigated the relationship between previously documented biochemical behaviors of Kras variants and their ability to drive lung or pancreatic tumor formation in our studies (FIG. 38). Notably, although KRAS mutations lead to dramatic differences in biochemical features thought to be critical to KRAS function (for example, GTPase activity and RAF kinase affinity), no single biochemical property predicted in vivo Kras variant oncogenicity. This result suggests that the in vivo oncogenicity of Kras variants may be best described by an alternate biochemical property, or perhaps more likely, through the integration of multiple biochemical outputs.

This work highlights our AAV/Cas9-mediated somatic HDR approach as a quantitative, scalable, and modular approach for cost-effective and systematic studies of the in vivo oncogenicities of panels of mutations in parallel. Multiplexed approaches that enable the genetic dissection of Kras function in vivo represent a critical complement to ongoing biochemical and cell culture studies of mutant forms of RAS proteins. This method will enable an unprecedented understanding of the function of diverse mutations in prevalent oncogenes as well as rare, putatively oncogenic mutations across many common cancer types. Finally, we envision that this platform will dramatically accelerate both the discovery and pre-clinical validation of targeted therapies for precisely defined genetic subtypes of cancer.

Methods

Design, Generation, and Screening of sgRNAs Targeting Kras

To obtain an sgRNA targeting Kras to enhance homology-directed repair (HDR) in somatic mouse cells, we identified all possible 20-bp sgRNAs (using the consensus Cas9 PAM: NGG) targeting Kras exon 2 and the flanking intronic sequences and scored them for predicted on-target cutting efficiency using an available sgRNA design/scoring algorithm. We then empirically determined the cutting efficiency of three sgRNAs targeting Kras (sgKras #1: GCAGCGT-TACCTCTATCGTA (SEQ ID NO: 66); sgKras #2: GCTAATTCAGAATCACTTTG (SEQ ID NO: 67); sgKras #3: GACTGAGTATAAACTTGTGG (SEQ ID NO: 68)) (FIG. 27a). Briefly, Lenti-U6-sgRNA/Cre vectors were generated for each sgRNA targeting Kras as previously described. Q5® site-directed mutagenesis (NEB) was used to insert the sgRNAs into a parental lentiviral vector containing a U6 promoter to drive sgRNA transcription as well as a PGK promoter driving Cre-recombinase. The cutting efficiency of each sgKras was determined via transduction of LSL-YFP;Cas9 cells in culture with each Lenti-sgKras/Cre virus. We isolated YFPP$^{positive}$ cells 48 hours post-infection (transduction) by FACS, extracted DNA, PCR-amplified the targeted Kras locus (forward primer: TCCCCTCTTGGTGCCTGTGTG (SEQ ID NO: 69); reverse primer: AAGCCCTTCCTGCTAATCTCGGAG (SEQ ID NO: 70)) and Sanger-sequenced the amplicons (sequencing primer: GCACGGATGGCATCTTGGACC (SEQ ID NO: 71)). Sequencing traces were analyzed by TIDE to determine percent indel induction. Since all three sgRNAs induced indels at the anticipated loci, the sgKras targeting the sequence closest to Kras codons 12 and 13 (sgKras #3) was used for all subsequent experiments as this was expected to best facilitate HDR at the desired locus (FIG. 27a).

Design, Construction, and Validation of AAV-Kras$^{HDR}$ Plasmid Libraries

Generation of the AAV-Kras$^{HDR}$/sgKras/Cre Backbone

The U6-sgKras/PGK-Cre cassette from pLL3.3;U6-sgKras/PGK-Cre was PCR-amplified with Q5® polymerase (NEB), TOPO-cloned (Invitrogen), and verified by sequencing. To generate the AAV-sgKras/Cre vector, the sequence between the ITRs of the 388-MCS AAV plasmid backbone was removed using XhoI/SpeI. The U6-sgKras/PGK-Cre cassette was digested from the TOPO vector with XhoI/XbaI and the 1.9-kb fragment was ligated into the XhoI/SpeI-digested 388-MCS backbone, destroying the SpeI site. A BGH polyA sequence was inserted 3' of Cre following MluI digestion. A ~2-kb region surrounding exon two of murine Kras was PCR-amplified from genomic DNA (forward primer: GCCGCCATGGCAGTTCTTTTGTATCCATTTGTCTCTTTATCTGC (SEQ ID NO: 72); reverse primer: GCCGCTCGAGCTCTTGTGTGTATGAAGACAGTGACACTG (SEQ ID NO: 73)). Amplicons were subsequently cloned into a TOPO vector (Invitrogen). AvrII/BsiWI sites were introduced into the TOPO-cloned 2-kb Kras sequence using Q5® site-directed mutagenesis (NEB) (AvrII forward primer: TGAGTGTTAAAATATTGATAAAGTTTTTG (SEQ ID NO: 74); AvrII reverse primer: CCTagGTGTGTAAAACTCTAAGATATTCC (SEQ ID NO: 75); BsiWI forward primer: CTTGTAAAGGACGGCAGCC (SEQ ID NO: 76); BsiWI reverse primer: CGtACGCAGACTGTAGAGCAGC (SEQ ID NO: 77); restriction sites are underlined with mismatching bases in lowercase). The Kras fragment harboring AvrII/BsiWI sites was released from TOPO with NcoI/XhoI and ligated into NcoI/XhoI-digested AAV-sgKras/Cre to produce the AAV-Kras$^{HDR}$/sgKras/Cre backbone.

Generation of the AAV-Kras$^{HDR}$/Cre Backbone

To generate an AAV-Kras$^{HDR}$ backbone without the sgRNA targeting Kras, PGK-Cre was excised from a TOPO clone with NotI/XbaI, and ligated into NotI/XbaI-digested 388-MCS AAV plasmid backbone. A BGH polyA sequence and the mouse Kras fragment were added as described above to produce the control AAV-Kras$^{HDR}$/Cre backbone.

Design and Synthesis of the Diverse Kras Variant/Barcode Region

To introduce a library of activating single point mutations and a DNA barcode into the Kras$^{HDR}$ sequence of the AAV backbones, we synthesized four 295-bp Kras fragments with a degenerate "N" base (A, T, C, or G) at each of the first two basepairs of Kras codons 12 and 13 (Integrated DNA Technologies) (FIG. 27b). By design, each of the four fragment pools consisted of three non-synonymous, single nucleotide mutations at codons 12 and 13 as well as the wild type Kras sequence to serve as a control. Thus, since each of the four pools contained wild type fragments, the overall representation of wild type Kras alleles was expected to be approximately four times higher than each of the mutant Kras alleles. The synthesized fragments also contained silent mutations within the sgKras target sequence and the associated protospacer adjacent motif (PAM*), and an eight-nucleotide random barcode created by introducing degenerate bases into the wobble positions of the downstream Kras codons for individual tumor barcoding (FIG. 27b). Finally, each fragment included flanking AvrII and BsiWI restriction sites for cloning into the AAV-Kras$^{HDR}$ backbones (FIG. 27b).

Ligation of Kras Mutant/Barcode Fragments into the AAV-Kras$^{HDR}$ Vectors

The four synthesized fragment pools were combined at equal ratios and PCR-amplified (forward primer: CACACCTAGGTGAGTGTTAAAATATTG (SEQ ID NO: 78); reverse primer: GTAGCTCACTAGTGGTCGCC (SEQ ID NO: 79)). Amplicons were digested with AvrII/BsiWI, purified by ethanol precipitation, and ligated into both AAV-Kras$^{HDR}$ backbones (FIG. 27c). Each ligated plasmid library was transformed into Stbl3 electro-competent cells (NEB) and plated onto 20 LB-Amp plates, which generated ~3×10$^5$ bacterial colonies per library. Colonies were scraped into LB-Amp liquid media and expanded for six hours at 37° C. to increase plasmid yields to obtain enough plasmid DNA for AAV production. Plasmid DNA was then extracted from bacterial cultures using a Maxiprep kit (Qiagen).

Validation of AAV-Kras$^{HDR}$ Plasmid Libraries

To determine the representation of each Kras variant and the distribution of barcode nucleotides within each AAV plasmid library, purified AAV plasmid libraries were PCR-amplified with primers tailed with Illumina adapters (lowercase) containing multiplexing tags (underlined N's) (forward primer: aatgatacggcgaccaccgagatctacactctttccctacacgacgctcttccgatctCTGCTGAAAATGACTGAGTATAAACTAGTAGTC (SEQ ID NO: 80); reverse primer: caagcagaagacggcatacgagatNNNNNNgtgactggagttcagacgtgtgctcttccgatc CTGCCGTCCTTTACAAGCGTACG (SEQ ID NO: 81)), and then deep-sequenced on a MiSeq (Illumina®).

AAV Capsid Serotype Lung Epithelial Cells Transduction Analysis

Recombinant AAV-GFP vectors were produced using a Ca$_3$(PO$_4$)$_2$ triple transfection protocol with pAd5 helper, ssAAV-RSV-GFP transfer vector and pseudotyping plasmids for each of nine capsids of interest: AAV1, 2, 3b, 4, 5, 6, 8, 9_hu14 and DJ. Viruses were produced in HEK293T cells (ATCC) followed by double cesium chloride density gradient purification and dialysis as previously described. rAAV vector preparations were titered by TaqMan qPCR for GFP (forward primer: GACGTAAACGGCCACAAGTT (SEQ ID NO: 82); reverse primers: GAACTTCAGGGTCAGCTTGC (SEQ ID NO: 83); probe: 6-FAM/CGAGGGCGATGCCACCTACG/BHQ-1 (SEQ ID NO: 84)). To identify an optimal AAV serotype for adult lung epithelial cell transduction, each mouse received 60 µl of pseudotyped AAV-GFP at maximal titer via intratracheal administration. Mice were analyzed 5 days after AAV administration. Lungs were dissociated into single-cell suspensions and prepared for FACS analysis of GFP$^{positive}$ cells as described previously. GFP$^{positive}$ percentages were determined by analyzing >10,000 live-gated cells (see FIG. 28).

Production and Titering of AAV-Kras$^{HDR}$ Plasmid Libraries

AAV libraries were produced using a Ca$_3$(PO$_4$)$_2$ triple transfection protocol with pAd5 helper, pAAV2/8 packaging plasmid and the barcoded Kras library transfer vector pools described above. Transfections were performed in HEK293T cells followed by double cesium chloride density gradient purification and dialysis as previously described. AAV libraries were titered by TaqMan qPCR for Cre (forward primer: TTTGTTGCCCTTTATTGCAG (SEQ ID NO: 85); reverse primer: CCCTTGCGGTATTCTTTGTT (SEQ ID NO: 86); probe: 6-FAM/TGCAGTTGTTGGCTC-CAACAC/BHQ-1 (SEQ ID NO: 87)).

In Vitro AAV/Cas9-Mediated HDR

The nucleotide changes surrounding the mutations at codon 12 and 13 (three nucleotide changes 5' of codons 12/13 to mutate the sgRNA recognition site and PAM motif, and up to 10 changes in the barcode sequence) made it unlikely that the point mutations at Kras codons 12 and 13 would differentially affect the rate of HDR. We nevertheless tested whether HDR efficiency might be influenced by differences in the sequence of individual Kras$^{HDR}$ alleles. To induce in vitro AAV/Cas9-mediated HDR, we transduced LSL-YFP/Cas9 cells with the purified AAV-Kras$^{HDR}$/sgKras/Cre library (FIG. 27e). Cells were maintained in cell culture media with 10 μM SCR7 (Xcessbio), an inhibitor of non-homologous end joining (NHEJ), to promote homology directed repair. 96 hours after transduction, DNA was isolated from the LSL-YFP/Cas9 cells by phenol/chloroform extraction followed by ethanol precipitation. The Kras locus was amplified from this DNA using a PCR strategy that we developed for the specific amplification of Kras$^{HDR}$ alleles integrated into the endogenous Kras locus. We then deep-sequenced these amplicons to determine the representation of Kras$^{HDR}$ alleles following in vitro HDR (see the "Illumina® library preparation and sequencing of tumor barcodes from bulk tissue" section below for details on PCR and sequencing).

Mice and Tumor Initiation

Lkb1$^{flox}$ (L), p53$^{flox}$ (P), R26$^{LSL-Tomato}$ (T), H11$^{LSL-Cas9}$, and Kras$^{LSL-G12D}$ (K) mice have been previously described. AAV administration by intratracheal inhalation to initiate lung tumors, retrograde pancreatic ductal injection to initiate pancreatic tumors, and intramuscular gastrocnemius injection to initiate sarcomas was performed as described. Lung tumors were initiated in PT;H11$^{LSL-Cas9}$, LT;H11$^{LSL-Cas9}$, and T;H11$^{LSL-Cas9}$ mice with 60 μl of AAV-Kras$^{HDR}$ Kras/Cre (1.4×10$^{12}$ vg/ml), in PT, LT, and T mice with 60 μl of AAV-Kras$^{HDR}$/Cre (2.4×10$^{12}$ vg/ml), or in KPT and KLT mice with 60 μl AAV-Kras$^{HDR}$/sgKras/Cre (1.4×10$^{12}$ vg/ml) diluted 1:10,000 in 1×PBS. Pancreatic tumors were initiated in PT;H11$^{LSL-Cas9}$ mice with 100-150 μl of AAV-Kras$^{HDR}$/sgKras/Cre (1.4×10$^{12}$ vg/ml) or in PT mice with 100-150 μl of AAV-Kras$^{HDR}$/Cre (2.4×10$^{12}$ vg/ml). A 1:10 dilution of AAV-Kras$^{HDR}$/sgKras/Cre in 1×PBS was also administered to the lungs or pancreata of mice where indicated. Sarcomas were initiated in PT;H11$^{LSL-Cas9}$ with 30 μl of AAV-Kras$^{HDR}$/sgKras/Cre (5.2×10$^{12}$ vg/ml). Mice were euthanized when they displayed symptoms of tumor development. The Institutional Animal Care & Use Committee of Stanford University approved all mouse procedures.

Analysis of Individual Tumors

Analysis of Individual Lung Tumors

Lung tumor-bearing mice displaying symptoms of tumor development were analyzed 4-10 months after viral administration. Lung tumor burden was assessed by lung weight and by quantification of macroscopic Tomato$^{positive}$ tumors under a fluorescence dissecting scope as indicated (a single LT;H11$^{LSL-Cas9}$ mouse had minimal Tomato$^{positive}$ signal that was restricted to a small region of one lung lobe, indicative of improper intratracheal administration of AAV, and was removed from the study). The largest individual lung tumors that were not visibly multifocal were dissected from bulk lungs under a fluorescence dissecting microscope for sequencing. For some lung tumors, the Tomato$^{positive}$ tumor cells were purified using FACS machines (Aria sorter; BD Biosciences) within the Stanford Shared FACS Facility. Several lung lobes from individual mice were also collected for histological analysis.

Analysis of Individual Pancreatic Tumor Masses

Pancreatic tumor-bearing mice displayed symptoms of tumor development and were analyzed 3-4 months after viral administration. Since pancreatic tumors largely appeared to be multifocal, individual regions of the pancreas containing Tomato$^{positive}$ tumor masses were dissected and FACS-purified for sequencing (a mouse treated with a 1:10 dilution of AAV-Kras$^{HDR}$/sgKras/Cre library also developed pancreatic tumor masses and therefore was included in these analyses). Regions of several pancreata were kept for histological analysis.

Analysis of Individual Sarcomas

Sarcoma-bearing mice with obvious tumor development and were analyzed 3-7 months after viral administration. A region of each sarcoma was kept for sequencing and an adjacent region was saved for histological analysis.

Characterization of Kras Alleles in Individual Tumors

DNA for sequencing was extracted from FACS-purified tumor cells and unsorted tumor samples with a DNeasy Blood and Tissue Extraction kit (Qiagen). To identify Kras point mutations and barcodes in tumors, we PCR-amplified and sequenced the Kras$^{HDR}$ alleles using two protocols that were optimized across several variables including annealing temperature, extension time, and primer sequences (Protocol 1—forward primer: CTGCTGAAAATGACTGAG-TATAAACTAGTAGTC (SEQ ID NO: 88); reverse primer: AGCAGTTGGCCTTTAATTGGTT (SEQ ID NO: 89); sequencing primer: AATGATACGGCGACCACCGA-GATCTACAC (SEQ ID NO: 90); annealing temperature 66° C.; Protocol 2—forward primer: GCTGAAAATGACT-GAGTATAAACTAGTAGTC (SEQ ID NO: 91); reverse primer: TTAGCAGTTGGCCTTTAATTGG (SEQ ID NO: 92); sequencing primer: GCACGGATGGCATCTTGGACC (SEQ ID NO: 93); annealing temperature: 64° C.). These protocols were used to specifically amplify integrated Kras$^{HDR}$ alleles from individual tumors as each incorporated a forward primer overlapping the engineered mutations in the PAM region upstream of codons 12 and 13, and a reverse primer outside the homology arm. Long extension times (2-3 minutes) were used to enable amplification of all Kras$^{HDR}$ alleles, even those containing insertions or duplications in intron 2 of the Kras locus (FIG. 31d).

Apart from introducing the desired point mutations into the endogenous Kras locus via HDR, targeting Kras exon 2 using CRISPR/Cas9 was also expected to result in indels at the cut site following DNA repair by NHEJ instead of HDR. To characterize these modifications, we used a generic PCR protocol to amplify both Kras alleles (forward primer: TCCCCTCTTGGTGCCTGTGTG (SEQ ID NO: 94; reverse primer: GGCTGGCTGCCGTCCTTTAC (SEQ ID NO: 95); sequencing primer: CAAGCTCATGCGGGTGT-GTC (SEQ ID NO: 96); annealing temperature: 72° C.). A spectrum of insertions and deletions at the site of DNA cleavage was identified by this approach (FIG. 31e,f). For some individual tumor samples, the sequence of both Kras alleles was not immediately obvious following the above PCR and sequencing strategies. PCR products from these samples were TOPO cloned (Invitrogen) and transformed, and several colonies from each sample were plasmid prepped and sequenced to characterize both Kras alleles in each tumor. This approach was reproducible and reliable across both biological and technical replicates, and a variety of HDR-induced oncogenic Kras alleles were identified. Indel-containing Kras alleles were identified in ~50 tumors (FIG. 31a,b).

These analyses also uncovered several other unexpected features in some of the Kras alleles from individual lung tumors. Three distinct missense mutations at codon 24 (I24L, I24N, I24M) were observed in a small subset of the individual lung tumors analyzed. The function of these alterations, if any, is unknown.

Furthermore, we initially anticipated that recombination of the Kras$^{HDR}$ template into the endogenous Kras locus would occur outside of the AvrII and BsiWI sites engineered into the Kras$^{HDR}$ template (FIG. 31c). However, the AvrII site, engineered by altering 2 base pairs 97 base pairs upstream of exon 2, was absent in 5 out of 25 tumors in which we directly analyzed this region of the Kras$^{HDR}$ allele. The BsiWI site, engineered by altering 1 base pair 20 base pairs downstream of exon 2, was absent in 11 out of 58 tumors. These findings indicated that while recombination of the Kras$^{HDR}$ template most often occurred within the larger, more distal homology arms, it also occurred at a detectable frequency within very short regions of homology that are flanked by 5' and 3' mismatches (including the PAM* mutation, a Kras codons 12 or 13 mutation, and 8 potential mismatches within the barcode).

After we initially identified the presence of duplications in the Kras$^{HDR}$ alleles in some tumors, we designed PCR primers to specifically amplify duplications of Kras exon 2 that occurred on either side of the HDR-integrated Kras locus (Right-hand duplication—forward primer: TGACCCTACGATAGAGGTAACG (SEQ ID NO: 97); reverse primer: CTCATCCACAAAGTGATTCTGA (SEQ ID NO: 98); sequencing primer: TGACCCTACGATAGAGG-TAACG (SEQ ID NO: 99); Left-hand duplication—forward primer: TGAGTGTTAAAATATTGATAAAGTTTTTG (SEQ ID NO: 100); reverse primer: TCCGAATTCAGT-GACTACAGATG (SEQ ID NO: 101); sequencing primer: TGAGTGTTAAAATATTGATAAAGTTTTTG (SEQ ID NO: 102)). Each of these duplication-specific PCR protocols used adjacent primer pairs in opposite orientations, ensuring that amplification would only occur if a duplication was present. Duplications of varying lengths were identified (FIG. 31d), including duplications of the second half of wild type exon 2 or the entire exon 2 (but lacking critical regions of the splice acceptor). Deletions and duplications of regions of intron 2 were also observed. Furthermore, we observed integrations of parts of the AAV vector, including the U6 promoter and viral ITR, into intron 2. Given the size and location of these alterations, none would be expected to change splicing of Kras mutant exon 2 to exon 3, consistent with the requirement of oncogenic Kras to drive tumorigenesis.

Generating a Normalization Control for High-Throughput Sequencing from a Cell Line with a Known Kras$^{HDR}$ Allele and Barcode To establish a cell line to use as a sequencing normalization control, a single large tumor was dissected from an PT;H11$^{LSL-Cas9}$ mouse, digested into a single cell suspension, and plated to generate a cell line. After expanding these cells and then extracting DNA, Kras exon 2 was PCR amplified (forward primer: TCCCCTCTTGGTGCCTGT-GTG (SEQ ID NO: 103); reverse primer: GGCTGGCTGC-CGTCCTTTAC (SEQ ID NO: 104)). The PCR product was sequenced (using specific and generic sequencing primers described above) to confirm the presence of a Kras$^{HDR}$ allele and a barcode. A single Kras$^{G12V}$ allele with a unique barcode (CGGGAAGTCGGCGCTTACGATC (SEQ ID NO: 105)) was identified. The genomic DNA from this cell lines was used as a normalization control for high-throughput sequencing for all bulk lung samples (FIG. 34).

Bulk Tissue Processing and DNA Extraction
Bulk Lung Tissue Processing and DNA Extraction
Bulk lung samples were dissected from infected (transdcued) mice and stored at −80° C. prior to processing. To extract DNA for sequencing, samples were thawed and transferred to 50 mL conical tubes. 20 mLs of lysis buffer (100 mM NaCl, 20 mM Tris pH7.6, 10 mM EDTA pH8.0, 0.5% SDS in H$_2$O) and 200 µL Proteinase K (20 mg/mL) were added to each sample. Next, 3 µg (~5×10$^5$ genomes) of normalization control DNA was added to each sample (FIG. 25a and FIG. 35b). Samples were then carefully homogenized using a tissue blender, which was cleaned between each sample by progressing through clean 10% bleach, 70% ethanol, and 1×PBS. Homogenized samples were lysed at 55° C. overnight. DNA was isolated from tissue lysates by phenol/chloroform extraction followed by ethanol precipitation (FIG. 37a,b).

Bulk Pancreatic Tissue Processing and DNA Extraction
Pancreatic tumor masses were dissected, digested, and viable (DAPI$^{negative}$), lineage (CD45, CD31, Ter119, F4/80)$^{negative}$, Tomato$^{positive}$ cells were isolated by FACS. No normalization control was added to the pancreatic cancer samples. DNA was isolated from the FACS isolated neoplastic cells using a DNeasy Blood and Tissue Extraction kit (Qiagen), and then further purified by ethanol precipitation.

Illumina® Library Preparation and Sequencing of Tumor Barcodes from Bulk Tissue
To uncover the number and size of tumors harboring each Kras variant in a massively parallel and quantitative manner, we developed a two-round PCR strategy that enabled multiplexed Illumina® sequencing of barcoded Kras$^{HDR}$ alleles (FIG. 27f). For the 1$^{st}$ round of PCR, we used a forward primer complementary to the Kras$^{HDR}$ sequence containing the three PAM and sgRNA target site mutations (PAM*; bold in the 1$^{st}$ round forward primer sequence) (1$^{st}$ round forward primer: GCTGAAAATGACTGAG-TATAAACTAGTAGTC) (SEQ ID NO: 2), and a reverse a primer complementary to a downstream region of the endogenous Kras locus not present in the HDR template in the AAV-Kras$^{HDR}$/sgKras/Cre vector (1$^{st}$ round reverse primer: TTAGCAGTTGGCCTTTAATTGG) (SEQ ID NO: 3). This primer pair was chosen to specifically amplify genomic Kras$^{HDR}$ alleles without amplifying abundant wild type Kras alleles or potential episomal AAV-Kras$^{HDR}$/sgKras/Cre vectors present in DNA purified from bulk tumor-bearing tissue. Additionally, a P5 adapter (italicized), 8-bp custom i5 index (N's), and Illumina® sequencing primer sequence (read 1) (underlined) was included at the 5' end of the 1$^{st}$ round forward primer to enable multiplexed Illumina® sequencing (1$^{st}$ round forward primer for Illumina sequencing:

(SEQ ID NO: 4)
*AATGATACGGCGACCACCGAGATCTACAC*NNNNNNNN<u>ACACTCTTTCCCTA</u>

<u>CACGACGCTCTTCCGATCT</u>GCTGAAAATGACTGAGTATAAACTAGTAGT

C).

Importantly, since the characterization of $Kras^{HDR}$ alleles in individual tumors uncovered some variability in HDR resulting in diverse indels in Kras intron 2 (FIG. 32d), only 4 (lung samples) or 6 (pancreas samples) cycles were performed in the $1^{st}$ round of PCR to minimize the potential for bias during the amplification of products of variable length. Furthermore, a high-efficiency polymerase (Q5® Hot Start High-Fidelity polymerase, NEB; 64° C. annealing temperature) and a long extension time (3:00 minutes) were used to ensure robust amplification of all $Kras^{HDR}$ alleles. $Kras^{HDR}$ alleles in genomic lung DNA were amplified using between 4 and 40 separate 100 µL PCR reactions and then pooled following amplification to reduce the effects of PCR jackpotting (FIG. 34a). Each of these 100-µL PCR reactions contained 4 µg of DNA template to amplify from a large initial pool of $Kras^{HDR}$ alleles. Following the $1^{st}$ round of amplification, all replicate PCR reactions were pooled and 100 µL of each sample was cleaned up using a QIAquick PCR Purification Kit (Qiagen).

Purified $1^{st}$ round PCR amplicons were used as template DNA for a 100 µL $2^{nd}$ round Illumina® library PCR (Q5® Hot Start High-Fidelity polymerase, NEB; 72° C. annealing temperature; 35 cycles for lung samples, 40 cycles for pancreas samples). The $2^{nd}$ round of PCR amplified a 112-bp region entirely within the Kras exon 2 sequence present in $1^{st}$ round PCR amplicons. The $2^{nd}$ round reverse primer contained a P7 adapter (italicized), reverse complemented 8-bp custom i7 index ("Ns"), and reverse complemented Illumina sequencing primer sequence (read 2) (underlined) at the 5' end to enable dual-indexed, paired-end sequencing of Illumina libraries ($2^{nd}$ round reverse primer #1: CAAGCAGAAGACGGCATACGAGATNNNNNNNN GTGACTGGACTTCAGACGTGTGCTCTTCCGAT CCGTAGGGTCATACTCATCCACA) (SEQ ID NO: 5). The $2^{nd}$ round PCR forward primer was complementary to the P5 Illumina adapter added to the amplified $Kras^{HDR}$ allele by the forward primer during the $1^{st}$ round PCR ($2^{nd}$ round forward primer: AATGATACGGCGACCACCGA-GATCTACAC) (SEQ ID NO: 6). This primer was used to amplify $1^{st}$ round PCR amplicons without amplifying any contaminating genomic DNA that may have been carried over from the $1^{st}$ round PCR reaction. Furthermore, a second reverse primer encoding the P7 adaptor sequence was added to the $2^{nd}$ round PCR reaction at the same concentration as the two other primers ($2^{nd}$ round reverse primer #2: CAAGCAGAAGACGGCATACGAGAT) (SEQ ID NO: 7). This primer binds the reverse complemented P7 adaptor sequence added to the $Kras^{HDR}$ amplicons by $2^{nd}$ round reverse primer #1. Since the $2^{nd}$ round PCR was performed over 35-40 cycles, the P7 adaptor ($2^{nd}$ round reverse primer #2) was added to limit the amount of non-specific amplification produced by the lengthy $2^{nd}$ round reverse primer #1.

After the $2^{nd}$ round of amplification, 100-µL PCR reactions were run on a 2.5% agarose gel and a band of the expected size was excised. DNA was extracted from gel fragments using a QIAquick Gel Extraction Kit (Qiagen). The quality and concentration of the purified Illumina® libraries was determined using a Bioanalyzer (Agilent). Individual Illumina® libraries with unique dual-indices were then pooled together such that libraries originally derived from mice with greater tumor burden were represented at a higher ratio in the final pool than those from mice with lower tumor burdens (FIG. 34a). A total of 35 individual samples were combined into two Illumina® library pools. The quality and concentration of each pool was confirmed on a Bioanalyzer (Agilent). Each final Illumina® library pool was then deep-sequenced on an Illumina® HiSeq lane using multiplexed, 150 bp paired-end Rapid Run sequencing program (Elim Biopharmaceuticals).

Analysis of Illumina Sequencing Data to Estimate the Size and Number of Barcoded Tumors We developed a pipeline to call tumors from our de-multiplexed Illumina® sequencing data. The pipeline tallies unique barcode sequences and eliminates recurrent sequencing errors using an algorithm designed to denoise deep-sequencing data of amplicons (DADA2). We tailored this algorithm to minimize the occurrence of spurious tumor calls, and minimize technical biases (including variation in read depth, variation in Illumina® sequencing machine error rates, and variation in barcode diversity). This pipeline, including modifications for the analysis of tumor genotypes and barcodes following AAV/Cas9-mediated somatic HDR-driven tumorigenesis, is described below.

Merging, Filtering, and Trimming Paired-End Reads

Although our Illumina® sequencing libraries contained a small 112-bp fragment of the $Kras^{HDR}$ alleles, we performed 150 bp paired-end sequencing of these fragments and merged the overlapping forward and reverse reads to reduce the likelihood of Illumina® sequencing errors in Kras codons 12 and 13 and the barcode region of the $Kras^{HDR}$ alleles. Overlapping paired end-reads were merged, quality-filtered, and trimmed using PANDAseq (fragment length: 60 bp; forward trimming primer: ATGACTGAGTATAAACT (SEQ ID NO: 106); reverse trimming primer: CTCATCCA-CAAAGTGA (SEQ ID NO: 107)).

Calling Unique Tumors

Even after merging forward and reverse reads to reduce sequencing errors, an average of ~1 error per 10,000 bases was detected, presumably from recurrent Illumina® sequencing errors (or less likely from recurrent PCR errors). Given this error rate, we expected that reads from a large, uniquely barcoded tumor containing single nucleotide mismatches would be called as small, spurious tumors of $\sim 1/10,000^{th}$ the size of the large real tumor. This phenomenon was discernible by eye, as we observed small clusters of spurious "tumors" that were ~3-4 orders of magnitude smaller and contained 1 nucleotide deviations relative to the largest tumor in specific mice. Additionally, each $Kras^{HDR}$ variant-barcode pair also generated recurrent sequencing errors in the mutant base in the oncogenic codon 12 or 13.

To accurately call tumors, we developed a computational and statistical pipeline for the analysis of tumor barcode sequencing data with the following steps:

Training an Error Model from Non-Barcode Regions of Reads and Clustering Unique Read Pileups into Tumors Using DADA2

We estimated the residual rate of sequencing/PCR error from the 7 nucleotides upstream of KRAS codon 12 and the 7 nucleotides downstream of the final barcode base. We then used our model of sequencing errors to cluster unique read pileups (truncated to within 7 nucleotides of the barcoded bases) into unique tumors via DADA2. A minimum confidence in unique origin of the clusters of 0.01 (i.e. omega_a=0.01) was used. A larger threshold increased the number of unique tumors called in a mouse sample. We chose this larger value because paired-end sequencing appeared to give us greater confidence that unique read pileups were truly distinct tumors. For example, we found that this threshold eliminated all unintended read sequences (e.g. reads with inappropriate nucleotides outside of the barcode), and that this threshold called a total number of lesions within each mouse that was more consistent between biological replicates. These were important considerations since without proper handling of read errors the number of called tumors can positively correlate with sequencing read depth. Finally, we removed any tumors with DNA sequences that deviated by only 1 nucleotide from a lesion that was 10,000× larger. This affected only 1.56% of tumor calls.

Normalizing Read Pileups to a Normalization Control to Get Approximate Tumor Size After generating the read pileups and performing the corrections described above, we normalized the number of reads from each called tumor to the number of reads from the normalization control that was spiked into each sample prior to DNA extraction from bulk tumor-bearing tissue lysates. This allowed us to generate a reasonable estimate of the number of cells in each tumor and allowed us to merge data from mice of the same genotype and treatment. However, there are several factors that impact our ability to accurately quantify the absolute number of cells within each tumor.

A first consideration is that some of the $Kras^{HDR}$ alleles in individual tumors harbored insertions or deletion in Kras intron 2, inside the PCR primers for Illumina® sequencing. Although the presence of different sized amplicons could generate a PCR bias, we attempted to reduce this by performing only 4-6 cycles in the $1^{st}$ round of Illumina library PCR, using a long extension time (~3 minutes), and using a fast (20-30 seconds/kb), high fidelity polymerase (Q5®; NEB). As the final Illumina® library PCR product in $2^{nd}$ round of amplification is short and uniform across all samples, PCR amplication should not be biased in this step.

Furthermore, given that the Kras variants and barcodes are knocked into the endogenous Kras locus, it is possible that in some tumors this region is genomically amplified (which has been documented in $Kras^{G12D}$-driven lung tumors initiated in mouse models of lung cancer). Although Kras amplifications do not typically result in very high Kras copy number, any amplification would lead to a slight overestimation of the number of cells in tumors with amplified $Kras^{HDR}$ alleles since our conversion from read count to cell number assumes that each cell contains a single copy of the barcoded $Kras^{HDR}$ allele.

Lastly, the normalization control itself was generated from cells from a tumor with a known duplication in Kras intron 2, which produces a larger PCR product in the $1^{st}$ round of the Illumina library preparation than tumors without a duplication. Thus, any PCR bias away from the Kras alleles in the normalization control would result in a systematic underestimation of the size of tumors without duplications.

Estimating the Barcode Overlap Rate and Correcting Tumor Size Distributions

Sequencing of tumor barcodes from 35 samples on two lanes of an Illumina® Hi-Seq Rapid Run, combined with our analysis pipeline, enabled the detection of unique barcodes with read counts covering over five orders of magnitude. Thus, the unprecedented resolution of this approach enables the detection of large lesions as well as small hyperplasias within bulk tissue. However, the ability to detect a large numbers of lesions within bulk tissue increases the probability of barcode collisions: the occurrence of two or more lesions with the same DNA barcode in the same mouse. Barcode collisions can overstate the size of observed tumors because two small "colliding" tumors would be identified as a single, larger tumor. Therefore, we developed a statistical model of barcode collisions to ensure that this issue was modest and did not overtly bias the estimated sizes of called tumors.

Our model of barcode collisions accounts for the likelihood $p_i$ of observing each of the 24,576 possible barcodes i for each Kras variant in our study. A majority of the reproducible variation between barcode frequencies in our pool derives from statistically independent variation in the nucleotide frequencies at each wobble base (i.e. each barcode is not equally likely in the pool because there was subtle variation in nucleotide concentrations during synthesis of the barcodes fragments) (FIG. 23g). Thus, we estimate the independent frequency $f_{b,n}$ of each nucleotide n at every base b in the barcode and use this table to predict barcode likelihoods based on each barcode's sequence $B_{i,b,n}$ (where B is 1 if barcode i possesses nucleotide n at position b and 0 otherwise) as follows:

$$p_i = \prod_b B_{i,b,n} \cdot f_b^n$$

Here, matrix notation is used to denote a dot product. This model predicts every barcode's frequency with only 21 free parameters. Because some residual over-representation of barcodes persisted in the lung samples, we simply discarded the 10% most frequently observed barcodes, after correcting for nucleotide frequencies, from all lung analyses. These most frequently observed barcodes were identified independent of our mouse experiments by Illumina® sequencing (MiSeq) of our AAV-$Kras^{HDR}$/sgKras/Cre plasmid pool prior to virus production. After this processing, we then renormalized $\Sigma_i p_i$ to one.

We then assumed that the occurrences of each barcode within each mouse was a Multinomial sampling process. The mean number of collisions $C_i$ for each observed barcode within each mouse is then:

$$C_i(p_i, N) = \sum_{k=1}^{\infty} (k-1) P(k; p_i, N)$$
$$= \mu_i - P(k=0; p_i, N) - 1$$
$$= N p_i + (1-p_i)^N - 1$$

Here, $\mu_i$ denotes the mean number of barcodes within each mouse, while N denotes the total number of tumors (both unknowns). N is determined from the observed number of tumors in each mouse $N^{(obs)}$ using the equation $N^{(obs)} = N - \Sigma_i C_i(p_i, N)$ and Brent's Method.

This model found that barcode collisions were generally rare in our mouse samples (on average 4.04%). However, the likelihood of collisions can vary by mouse and by Kras variant. For example, the average predicted number of collisions for WT $Kras^{HDR}$ alleles was 5.8% and as high as 12% in one mouse. WT $Kras^{HDR}$ alleles were expected to experience the highest number of collisions since WT Kras vectors were intentionally represented ~4 fold more than each mutant Kras vector in the initial AAV-$Kras^{HDR}$/sgKras/Cre plasmid pool) (FIG. 23f). Thus, we divided the size of each lesion by $1+C_i$ to minimize the bias that barcode collisions impart on tumor size distributions. Because collisions are rare events, the particular number of collisions within a particular mouse can differ substantially from C. Because of this limitation, we believe that this correction minimizes systematic bias in tumor size distributions resulting from barcode collisions; however, it cannot effectively identify the specific collisions that occurred.

Determining Illumina® Sequencing Quality and Reproducibility

To determine whether Kras variants had quantitatively different abilities to drive tumorigenesis, we elected to focus on tumors estimated to contain more than 100,000 cells (i.e. $\frac{1}{5}^{th}$ the "size" of the normalization control DNA added to each sample that was derived from ~5×10$^5$ cells). Regression analysis of tumors above this cell number cutoff from replicate samples (independent sample preparation, sequencing, and processing) demonstrated high correlation (all $R^2$ values were above 0.99; see FIG. 36). Furthermore, the estimated number of cells in tumors below this cutoff were more likely to be biased by barcode collisions and variability in PCR amplification and sequencing, all of which would have decreased our ability to accurately call the size and number of tumors harboring each Kras variant.

Analysis of Sequencing Data from Bulk Tumor-Bearing Lungs

We quantified the relative number of tumors harboring each Kras variant by counting tumors above 100,000 cells in all mouse genotypes with a $H11^{LSL-Cas9}$ allele (PT;$H11^{LSL-Cas9}$, LT;$H11^{LSL-Cas9}$, and T;$H11^{LSL-Cas9}$), and dividing each variant by its initial representation in the AAV-Kras$^{HDR}$/sgKras/Cre plasmid pool (for this analysis, the initial representation of each variant in the plasmid pool was calculated from the total number of reads associated with each Kras variant after removing barcodes above the 98$^{th}$ percentile of barcode abundance; this restriction did not appreciably alter results, and was simply applied to ensure that extremely abundant variant-barcode pairs did not overtly impact the overall representation of specific variants).

Relative tumor number was then scaled such that WT Kras variants had a representation of 1. There was a relatively small number of WT Kras$^{HDR}$ alleles that appeared to arise from tumors above 100,000 cells. These could represent tumors in which an HDR event created the non-oncogenic Kras WT genotype but which nonetheless evolved into a tumor for other reasons, or the WT Kras variant 'hitchhikes' with an oncogenic Kras variant by co-incident HDR in the same lung cell followed but expansion driven by the oncogenic variant.

A small number of residual cells from individual tumors that were dissected from bulk tissue (and analyzed as described above) were usually detectable in our bulk tumor sequencing data. In all analyses of tumor size these dissected tumors were excluded, as we could not infer their true size. However, when analyzing the number of tumors above 100,000 cells in each treated mouse genotype, we included data from individually dissected tumors since dissectible tumors were always among the largest observed within any mouse and, therefore, certainly above the 100,000 cell threshold.

Statistically significant differences in tumor number were determined using Fischer's Exact Test. For each variant two tests were performed, comparing to either the frequency of G12D or WT Kras$^{HDR}$ alleles. All p-values are Bonferroni-Corrected for the number of variants investigated and are two-sided. A two-sided "many cells" Pearson's Chi Squared Test was used to compare the distribution of tumor numbers across all Kras variants in PT;$H11^{LSL-Cas9}$ and LT;$H11^{LSL-Cas9}$ mice relative to T;$H11^{LSL-Cas9}$ mice.

Example 3. The Fitness Landscape of Tumor Suppression in Lung Adenocarcinoma In Vivo The functional impact of most genomic alterations found in cancer, alone or in combination, remains largely unknown. With experiments described herein, integration of tumor barcoding, CRISPR/Cas9-mediated genome editing, and ultra-deep barcode sequencing is demonstrated for interrogating pairwise combinations of tumor suppressor alterations in autochthonous mouse models of human lung adenocarcinoma. The tumor suppressive effects of 31 common lung adenocarcinoma genotypes are mapped, revealing a rugged landscape of context-dependence and differential effect strengths.

Results

Cancer growth is largely the consequence of multiple, cooperative genomic alterations. Cancer genome sequencing has catalogued a multitude of alterations within human cancers, however the combinatorial effects of these alterations on tumor growth is largely unknown. Most putative drivers are altered in less than ten percent of tumors, suggesting that these alterations may be inert, weakly-beneficial, or beneficial only in certain genomic contexts. Inferring genetic interactions through co-occurrence rates alone is practically impossible, as the number of possible combinations scales factorially with candidate gene number. Genetically engineered mouse models can provide insight into gene function in tumors growing within an autochthonous setting, however practical considerations have prevented broad studies of combinatorial tumor suppressor gene inactivation (FIG. 41). Hence, our understanding of the genetic interactions that drive tumor growth in vivo remains limited.

To address these practical challenges, a method was developed (described herein) to quantitatively measure the effect of many different tumor suppressor gene alterations in parallel using tumor barcoding coupled with deep-sequencing (Tuba-seq). Tuba-seq combines genetically engineered mouse models of lung adenocarcinoma with tumor suppressor inactivation (e.g., CRISPR/Cas9-mediated), tumor barcoding, and deep-sequencing. Because Tuba-seq measures the size of every tumor and is compatible with multiplexing tumor genotypes in individual mice, growth effects can be measured with unprecedented precision, sensitivity, and throughput. Here, this approach is employed eThe growth of oncogenic Kras$^{G12D}$-driven lung tumors with 31 common tumor suppressor genotypes is quantified (FIG. 39). Unexpected genetic interactions were identified, the effects of most tumor suppressors were found to be context-dependent, and several patterns of genetic alterations in human lung adenocarcinomas were explained.

The tumor suppressor TP53 is inactivated in more than half of human lung adenocarcinomas. To determine the effect of p53 deletion on the growth suppressive effects of ten other putative tumor suppressors, tumors were initiated in Kras$^{LSL-G12D}$;Rosa26$^{LSL-tdTomato}$;$H11^{LSL-Cas9}$ (KT;Cas9) and KT;p53$^{flox/flox}$;Cas9 (KPT;Cas9) mice using a pool of barcoded Lenti-sgRNA/Cre vectors targeting many common tumor suppressor genes and four barcoded Lenti-sgInert/Cre vectors (Lenti-sgTS-Pool/Cre; FIGS. 39, 41, and 42). Barcodes contained two components that uniquely identify each tumor and its sgRNA (sgID-BC; FIG. 42). The number of neoplastic cells in each tumor of each genotype was determined 15 weeks after tumor initiation when the lungs contained widespread hyperplasias, adenomas, and some early adenocarcinomas. The sgID-BC region was amplified from bulk tumor-bearing lung genomic DNA, the product was deep sequenced, and the Tuba-seq analysis pipeline (described herein) was applied.

Tuba-seq analysis of KT;Cas9 and KPT;Cas9 mice uncovered an altered spectrum of tumor suppressive effects for many of the genes in our survey (FIGS. 39 and 43). Tumor sizes were summarized by two previously-vetted measures: Log normal (LN) mean and the size of the 95$^{th}$ percentile tumor (FIG. 39). In p53-deficient tumors, inactivation of Rb1, Setd2, Lkb1/Stk11, Cdkn2a, or Apc still provided a growth advantage, while Smad4, Arid1a, and Atm emerged as tumor suppressors only in the absence of p53 (FIGS. 39 and 43). The emergence of additional tumor suppressors in this background suggests that p53-deficiency potentiates subsequent tumor evolution. By allowing more mutations to be adaptive, p53 loss may decrease the predictability of tumor evolution and facilitate future tumor evolution, including the emergence of treatment resistance and metastatic disease.

Coincident deletion of p53 not only allowed more alterations to be adaptive, but also significantly changed the magnitude of effect of tumor suppressor loss. In KT;Cas9 mice, Rb1-deficiency increased tumor size less than Lkb1- or Setd2-deficiency (FIG. 39 and FIG. 44a; P<0.0001 bootstrap test unless otherwise specified). In contrast, in the p53-deficient background, Rb1-deficiency conferred a growth advantage comparable to that of Lkb1- or Setd2-deficiency (P>0.05), consistent with a strong complementary interaction between the p53 and Rb1 tumor suppressor pathways (FIG. 39). Quantification of Cas9-generated indels at each targeted locus in bulk KPT;Cas9 lung DNA confirmed comparably high percentages of Lkb1, Setd2, and Rb1 alleles with indels (FIGS. 39 and 45). Finally, the effect of co-incident inactivation of p53 and Rb1 on lung cancer growth was confirmed using conventional Cre/LoxP-based mouse models (FIG. 44).

The quantitatively-different growth benefits of Rb1 inactivation in p53 proficient versus p53 deficient tumors presented the opportunity to investigate whether changes in the fitness strength of a driver alters the frequency of its alterations in human lung adenocarcinomas. Indeed, co-occurrence of RB1 alterations (SNVs and CNVs) and TP53 alterations were enriched in human lung adenocarcinoma (P=0.03; FIG. 39 and FIG. 44). Notably, despite a ~5-fold enrichment in the co-occurrence of these two alterations, this interaction would be statistically insignificant in a naïve survey of all potential pairwise driver interactions after correcting for multiple-hypothesis testing, thus illustrating the need to functionally study genetic interactions beyond co-occurrence patterns (P=0.32 after Bonferroni correction for 10 pairwise interactions).

Next, the effects of combinatorial loss of Lkb1 and other putative tumor suppressors was investigated by initiating tumors with Lenti-sgTS-Pool/Cre in KT;Lkb1$^{flox/flox}$;Cas9 (KLT;Cas9) mice (FIGS. 40 and 43). Lkb1 was investigated because it dramatically increases lung tumor growth in autochthonous models and is frequently inactivated in human lung adenocarcinoma (FIG. 41). Interestingly, both the number of adaptive tumor suppressor losses and the median growth benefit was attenuated in the already fast-growing Lkb1-deficient tumors (irrespective of changes in statistical power between mouse backgrounds, P<0.05, Methods). This once again demonstrates that a single alteration can change the entire fitness landscape of tumors. General attenuation of fitness benefits, termed diminishing returns epistasis, is common in evolution, and suggests that tumors may eventually reach a fitness plateau.

Apc and Rb1 inactivation were the only alterations that provided a significant growth advantage to Lkb1-deficient tumors (FIG. 40). The ability of Rb1-deficiency to increase tumor size, even with coincident Lkb1-deficiency, emphasizes the integral role of Rb1 in cell cycle regulation and fundamentally different mechanism of action from Lkb1 loss. Apc loss is also a key driver of lung cancer growth, and Apc was tumor suppressive in all three backgrounds studied.

Surprisingly, the effect of Setd2-deficiency on the growth of Lkb1-deficient tumors was modest and statistically insignificant (FIG. 40). This redundancy was striking because both Lkb1 and Setd2 inactivation strongly promote growth in KT;Cas9 and KPT;Cas9 mice and because there is no evidence that these genes function in the same pathway. Thus, the context dependence of Setd2 inactivation was tested and confirmed by initiating tumors with Lenti-sgNeo2/Cre and Lenti-sgSetd2/Cre in KPT, KPT;Cas9, and KLT;Cas9 mice. Setd2 inactivation enhanced Lkb1-proficient lung tumor growth, while conferring little, if any, growth advantage to Lkb1-deficient tumors (P<0.05 of (sgSetd2 in KPT;Cas9/KLT;Cas9)/(sgNeo2 in KPT;Cas9/ KLT;Cas9) for histological analysis, P<0.0001 for Tuba-seq analysis, FIGS. 40, and 46). This observation is also well supported by the mutual exclusivity of LKB1/STK11 and SETD2 alterations in human lung adenocarcinoma (P<0.001, FIGS. 40 and 46).

Most genes in these studies exhibited context-dependent growth effects, driving tumor growth only in the presence or absence of p53 or Lkb1 (FIG. 40). Even the tumor suppressor alterations that conferred advantage in all three contexts (Rb1 and Apc) still exhibited context-dependent magnitudes of tumor suppression. Such wide-spread context-dependency is overlooked by global surveys of drivers, where driver interactions are either ignored or presumed to be sufficiently rare and/or weak to justify considering only marginal correlations. Nonetheless, our fitness measurements overall agree with mutation co-occurrence patterns in human lung cancer, despite the limited statistical resolution of these data (Spearman R=0.50, P<0.05, FIG. 47). Furthermore, while lung cancers do not appear to be unique in their degree of context-dependency (FIG. 47) and the findings here suggest that direct measurement of context-dependency in other cancer types is warranted.

This rugged landscape of tumor evolution has several implications. First, to understand gene function, it can be important to investigate putative drivers in multiple genetic contexts, as most genes in the survey (8 of 11) were only adaptive in some contexts (FIG. 40). Second, broader fitness profiling is desirable. The power analyses here suggest that ~500 moderate-strength interactions could be surveyed using Tuba-seq with a one hundred-mouse cohort (FIG. 48). Larger genomic screens could survey more putative drivers, interactions with other oncogenic events, multiple sgRNAs targeting the same gene, or triplets of tumor suppressor alterations. Lastly, this extensive context-dependency suggests that most driver alterations sweep to fixation infrequently because they are beneficial only in specific genetic contexts.

The studies described herein of the fitness effects of combinatorial tumor suppressor losses in vivo identified unexpected genetic interactions that were validated by traditional methodologies as well as by human lung adenocarcinoma genomics data. The barcoded and multiplexed genome-editing approach described herein could easily be utilized to interrogate the functional consequences of these genetic interactions, including their impact on therapeutic response, cell signaling, and/or metastatic progression.

That which is claimed is:

1. A method of measuring population size for a plurality of clonal cell populations in the same tissue, the method comprising:
   (a) contacting a biological tissue with a plurality of cell markers comprising (i) barcoded nucleic acids providing unique identifiers and (ii) nucleotide sequences that induce neoplastic cell formation and/or tumor formation, wherein the cell markers are heritable and distinguishable from one another, to generate a plurality of distinguishable lineages of heritably marked cells within the contacted tissue;
   (b) after sufficient time has passed for at least a portion of the heritably marked cells to undergo at least one round of division, detecting and measuring quantities of at least two of the plurality of cell markers present in the contacted tissue, thereby generating a set of measured values; and
   (c) calculating, using the set of measured values as input, a number of heritably marked cells present in the contacted tissue for at least two of said distinguishable lineages of heritably marked cells.

2. The method of claim 1, wherein said detecting and measuring of step (b) is performed on a biological sample collected from the tissue.

3. The method of claim 1, wherein each cell marker of the plurality of cell markers corresponds to a known cell genotype for a lineage of heritably marked cells.

4. The method of claim 1, wherein said contacting comprises genetically altering cells of the tissue to generate the heritably marked cells.

5. The method of claim 1, wherein said method is a method of measuring tumor size for a plurality of tumors of the same tissue.

6. The method of claim 1, wherein said detecting and measuring is performed after sufficient time has passed for tumors to form in the contacted tissue as a result of said contacting.

7. The method of claim 1, wherein the plurality of cell markers comprises barcoded nucleic acids.

8. The method of claim 7, wherein said detecting and measuring comprises high-throughput sequencing and quantification of the number of sequence reads for each detected barcode.

9. The method of claim 1, wherein the plurality of cell markers comprises barcoded nucleic acids that induce neoplastic cell formation.

10. The method of claim 7, wherein the barcoded nucleic acids induce neoplastic cell formation and include one or more of: homology directed repair (HDR) DNA donor templates, nucleic acids encoding one or more oncogenes, nucleic acids encoding one or more wildtype proteins, nucleic acids encoding one or more mutant proteins, nucleic acids encoding one or more CRISPR/Cas guide RNAs, nucleic acids encoding one or more short hairpin RNAs (shRNAs), or nucleic acids encoding one or more genome editing proteins.

11. The method of claim 10, wherein the genome editing protein is selected from: a CRISPR/Cas RNA-guided protein, a CRISPR/Cas RNA-guided protein fused to a transcriptional activator or repressor polypeptide, a Cas9 protein, a Cas9 protein fused to a transcriptional activator or repressor polypeptide, a zinc finger nuclease (ZFN), a TALEN, a phage-derived integrase, a Cre protein, a Flp protein, and a meganuclease protein.

12. The method of claim 1, wherein the tissue is a vertebrate tissue.

13. The method of claim 1, wherein the tissue is a mammalian or a fish tissue.

14. The method of claim 1, wherein the tissue is a rat tissue, a mouse tissue, a pig tissue, a non-human primate tissue, or a human tissue.

15. The method of claim 1, wherein the tissue is part of a living animal.

16. The method of claim 1, wherein the tissue is an engineered tissue grown outside of an animal.

17. The method of claim 1, wherein the tissue is selected from: muscle, lung, bronchus, pancreas, breast, liver, bile duct, gallbladder, kidney, spleen, blood, gut, brain, bone, bladder, prostate, ovary, eye, nose, tongue, mouth, pharynx, larynx, thyroid, fat, esophagus, stomach, small intestine, colon, rectum, adrenal gland, soft tissue, smooth muscle, vasculature, cartilage, lymphatics, prostate, heart, skin, retina, reproductive system, and genital system.

18. The method of claim 1, wherein after sufficient time has passed for at least a portion of the heritably marked cells to undergo at least one round of division, the method further comprises: (i) detecting and/or measuring a biomarker of the heritably marked cells, and (ii) categorizing the heritably marked cells based on the results of said detecting and/or measuring of the biomarker.

19. The method of claim 18, wherein step (ii) comprises categorizing the hereditably marked cells according to one or more of the following, based on the results of said detecting and/or measuring of the biomarker: cell proliferation status, cell type, developmental cell lineage, cell death, or cellular signaling state.

20. The method of claim 1, wherein the cell markers are delivered to the tissue via viral vector.

21. The method of claim 1, wherein the plurality of cell markers comprise a plurality of different nucleotide sequences that induce neoplastic cell formation and/or tumor formation.

22. The method of claim 21, wherein the plurality of cell markers comprise at least one gRNA or shRNA directed against a tumor suppressor.

23. The method of claim 21, wherein the plurality of cell markers comprise at least one oncogene.

24. The method of claim 1, wherein the number of heritably marked cells present in the contacted tissue is measured by sequencing, high-throughput sequencing, next-generation sequencing, RNA sequencing, DNA sequencing, whole transcriptome sequencing, whole genome sequencing, or targeted DNA sequencing.

* * * * *